US006919338B2

(12) United States Patent
Mortlock et al.

(10) Patent No.: US 6,919,338 B2
(45) Date of Patent: Jul. 19, 2005

(54) SUBSTITUTED QUINAZOLINE DERIVATIVES AND THEIR USE AS INHIBITORS OF AURORA-2 KINASE

(75) Inventors: Andrew Mortlock, Cheshire (GB); Frederic Jung, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/311,916

(22) PCT Filed: Jun. 21, 2001

(86) PCT No.: PCT/SE01/01450

§ 371 (c)(1), (2), (4) Date: Dec. 16, 2002

(87) PCT Pub. No.: WO02/00649

PCT Pub. Date: Jan. 3, 2002

(65) Prior Publication Data

US 2003/0187002 A1 Oct. 2, 2003

(30) Foreign Application Priority Data

Jun. 28, 2000 (EP) .......................................... 00401842

(51) Int. Cl.[7] .................... C07D 403/12; C07D 409/12; A61K 31/505

(52) U.S. Cl. ................................ 514/234.5; 514/266.2; 514/266.23; 514/266.24; 544/119; 544/284; 544/293

(58) Field of Search ................................ 544/119, 284, 544/293; 514/234.5, 266.2, 266.23, 266.24

(56) References Cited

U.S. PATENT DOCUMENTS 5,710,158 A * 1/1998 Myers et al. ............ 514/266.2

FOREIGN PATENT DOCUMENTS

| | | | |
|---|---|---|---|
| WO | WO 92/20642 | | 11/1992 |
| WO | WO 95/15758 | | 6/1995 |
| WO | WO 97/03069 | | 1/1997 |
| WO | WO 99/09016 | | 2/1999 |
| WO | WO 99/35132 | | 7/1999 |
| WO | WO 99/35146 | | 7/1999 |
| WO | WO 00/21955 | * | 4/2000 |
| WO | WO 01/21597 | | 3/2001 |

OTHER PUBLICATIONS

Vinogradoff et al., CAPLUS Abstract 112:7444, 1990.*
Golovkin et al., CAPLUS Abstract 115:78820, 1991.*
Tanaka et al., PubMed Abstract (Cell 108(3):317–29), Feb. 2002.*
Rogers et al., PubMed Abstract (J. Cell Biol. 157(2):219–29), Apr. 2002.*
Simone, Oncology: Introduction, Cecil Textbook of Medicine, 20th Edition, vol. 1, pp. 1004–1010, 1996.*

* cited by examiner

*Primary Examiner*—Deepak Rao
(74) *Attorney, Agent, or Firm*—Ropes & Gray LLP

(57) ABSTRACT

The use of a compound of formula (I)

(I)

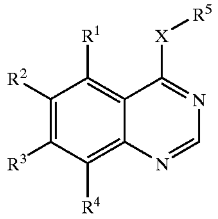

or a salt, ester or amide thereof;
where X is O, or S, S(O) or $S(O)_2$, or $NR^6$ where $R^6$ is hydrogen or $C_{1-6}$alkyl;
$R^5$ is an optionally substituted 5-membered heteroaromatic ring,
$R^1$, $R^2$, $R^3$, $R^4$ are independently selected from various specified moieties, in the preparation of a medicament for use in the inhibition of aurora 2 kinase.

Certain compounds are novel and these, together with pharmaceutical compositions containing them are also described and claimed.

12 Claims, No Drawings

SUBSTITUTED QUINAZOLINE DERIVATIVES AND THEIR USE AS INHIBITORS OF AURORA-2 KINASE

This application is a national stage filing under 35 U.S.C. 371 of International Application PCT/SE01/01450, filed Jun. 21, 2001, which claims priority from European Application No. 00401842.0, filed Jun. 28, 2000, the specifications of each of which are incorporated by reference herein. International Application PCT/SE01/01450 was published under PCT Article 21(2) in English.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672–1677; Pines, 1995, Seminars in Cancer Biology 6: 63–72). Other studies (Loda et al., 1997, Nature Medicine 3(2): 231–234; Gemma et al., 1996, International Journal of Cancer 68(5): 605–11; Elledge et al. 1996, Trends in Cell Biology 6; 388–392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ipl1 proteins. *Drosophila* aurora and S. cerevisiae Ipl1, which are highly homologous at the amino acid sequence level, encode serine/threonine protein kinases. Both aurora and Ipl1 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this amplicon, since aurora2 DNA is amplified and aurora2 mRNA overexpressed in greater than 50% of primary human colorectal cancers. In these tumours aurora2 protein levels appear greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052–3065). Other work (Zhou et al., 1998, Nature Genetics. 20(2): 189–93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/37788) eads to cell cycle arrest in the G2 phase of the cell cycle and exerts an antiproliferative effect in these tumour cell lines. This indicates that inhibition of the function of aurora2 will have an antiproliferative effect that may be useful in the treatment of human tumours and other hyperproliferative diseases.

A number of quinazoline derivatives have been proposed hitherto for use in the inhibition of various kinases. Examples of such proposals are included in WO 92/20642 and EP-B-584222 which relates to bicyclic compounds which inhibit epidermal growth factor (EGF) and platelet-derived growth factor (PDGF) receptor tyrosine kinase, WO 95/15758 which describes the use of bis ring systems for the selective inhibition of CSF-1R tyrosine kinase activity, and WO 99/09016, WO 97/03069 and U.S. Pat. No. 570,158 which describe the use of certain quinazoline compounds as tyrosine kinase inhibitors in other contexts.

The applicants have found a series of compounds which inhibit the effect of the aurora2 kinase and which are thus of use in the treatment of proliferative disease such as cancer, in particular in such diseases such as colorectal or breast cancer where aurora 2 kinase is known to be active.

The present invention provides the use of a compound of formula (I)

(I)

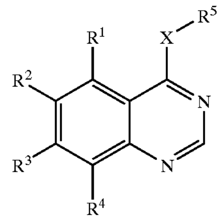

or a salt, ester or amide thereof;

where X is O, or S, S(O) or $S(O)_2$, or $NR^6$ where $R^6$ is hydrogen or $C_{1-6}$alkyl;

$R^5$ is an optionally substituted 5-membered heteroaromatic ring, $R^1$, $R^2$, $R^3$, $R^4$ are independently selected from, halo, Cyano, nitro, trifluoromethyl, $C_{1-3}$alkyl, —$NR^7R^8$ (wherein $R^7$ and $R^8$, which may be the same or different, each represents hydrogen or $C_{1-3}$alkyl), or —$X^1R^9$ (wherein $X^1$ represents a direct bond, —O—, —$CH_2$—, —OCO—, carbonyl, —S—, —SO—, —$SO_2$—, —$NR^{10}$CO—, —$CONR^{11}$—, —$SO_2NR^{12}$—, —$NR_3SO_2$— or —$NR^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following groups:

1) hydrogen or $C_{1-5}$alkyl which may be unsubstituted or which may be substituted with one or more groups selected from hydroxy, fluoro or amino, 2) $C_{1-5}$alkyl$X^2COR^{15}$ (wherein $X^2$ represents —O— or —$NR^{16}$—(in which $R^{15}$ represents hydrogen, $C_{1-3}$alkyl or $C_{1-3}$alkoxy$C_{2-3}$alkyl) and $R^{16}$ represents $C_{1-3}$alkyl, —$NR^{17}R^8$ or —$OR^{19}$ (wherein $R^{17}$, $R^{18}$ and $R^{19}$ which may be the same or different each represents hydrogen, $C_{1-3}$alkyl or $C_{1-3}$alkoxy$C_{2-3}$alkyl));

3) $C_{1-5}$alkyl$X^3R^{20}$ (wherein $X^3$ represents —O—, —S—, —SO—, —$SO_2$—, —OCO—, —$NR^{21}$CO—, —$CONR^{22}$—, $SO_2NR^{23}$—$NR^{24}SO_2$— or $NR^{25}$-(wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{26}$ (wherein $X^4$ and $X^5$ which may be the same or different are each —O—, —S—, —SO—, —$SO_2$—, —$NR^{27}$CO—, —$CONR^{28}$—, —$SO_2NR^{29}$—, —$NR^{30}SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_2$ $_3$alkyl) and $R^{26}$ represents hydrogen or $C_{1-3}$alkyl);

5) $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6) $C_{1-5}$alkyl $R^{32}$ (wherein $R^{32}$ is as defined hereinbefore);

7) $C_2$alkenyl$R^{32}$ (wherein $R^{32}$ is as defined hereinbefore);

8) $C_{2-5}$alkynyl$R^{32}$ (wherein $R^{32}$ is as defined hereinbefore);

9) $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{34}R^{35}$ and —$NR^{36}COR^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl));

10) $C_{1-5}$alkyl$R^{33}$ (wherein $R^{33}$ is as defined hereinbefore);

11) $C_{2-5}$alkeny$R^{33}$ (wherein $R^{33}$ is as defined hereinbefore);

12) $C_{2-5}$alkynyl$R^{33}$ (wherein $R^{33}$ is as defined hereinbefore);

13) $C_{1-5}$alkyl$X^6R^{33}$ (wherein $X^6$ represents —O—, —S—, —SO—, —$SO_2$—, —$NR_{38}$CO_, —$CONR^{39}$— $SO_2NR^{45}$—$NR^{46}$ $SO_2$— or —$NR^{42}$—(wherein $R^{43}$, $R^{44}$, $R^{45}$, $R^{46}$ and $R^{47}$ each in dependently represents hydrogen, $C_{1-3}$alkyl or $C_{1-3}$alkoxy$C_{2-3}$alkyl) and $R^{33}$ is as defined hereinbefore);

14) $C_{2-5}$alkenyl$X^7R^{33}$ (wherein $X^7$ represents —O—, —S—, —SO—, —$SO_2$—, —$NR^{43}$CO—, —$CONR^{44}$—, —$SO_2NR^{45}$—, —$NR^{46}SO_2$—or —$NR^{47}$—(wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15) $C_{2-5}$alkynyl$X^8R^{33}$ (wherein $X^8$ represents —O—, —S—, —SO—, —$SO_2$—, —$NR^{48}$CO—, —$CONR^{49}$—, —$SO_2NR^{50}$ —, —$NR^{51}SO_2$—or —$NR^{52}$ (wherein $R^{48}$, $R^{49}$, $R_{50}$, $R^{51}$ and $R^{52}$ each independently represents hydrogen, $C_{1-3}$alkyl or $C_{1-3}$alkoxy$C_{2-3}$alkyl) and $R^{33}$ is as defined hereinbefore);

16) $C_{1-3}$alkyl$X^9C_{1-3}$alkyl$R^{33}$ (wherein $X^9$ represents —O—, —S—, —SO—, $SO_2$—, —$NR^{53}$CO—, —$CONR^{54}$—, —$SO_2NR^{55}$—, —$NR^{56}SO_2$— or —$NR^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17) $C_{1-3}$alkyl$X^9C_{1-3}$alkyl$R^{12}$ (wherein $X^9$ and $R^{28}$ are as defined hereinbefore):

in the preparation of a medicament for use in the inhibition of aurora 2 kinase. In particular, such medicaments are useful in the treatment of proliferative disease such as cancer, and in particular cancers where aurora 2 is upregulated such as colon or breast cancers.

In this specification the term 'alkyl' when used either alone or as a suffix includes straight chained, branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents such as nitro, cyano, halo, oxo, $=CR^{78}R^{79}$, $C(O)_nR^{77}$, $OR^{77}$, $S(O)_yR^{77}$, $NR^{78}R^{79}$, $C(O)NR^{78}R^{79}$, $OC(O)NR^{78}R^{79}$, $NOR^{77}$, $—NR^{77}C(O)_nR^{78}$, $—NR^{77}CONR^{78}R^{79}$, $—N=CR^{78}$, $R^{79}$, $S(O)_yNR^{78}R^{79}$ or $—NR^{77}S(O)_yR^{78}$ where $R^{77}$, $R^{78}$ and $R^{79}$ are independently selected from hydrogen or optionally substituted hydrocarbyl, or $R^{78}$ and $R^{79}$ together form an optionally substituted ring which optionally contains further heteroatoms such as $S(O)_y$ oxygen and nitrogen, x is an integer of 1 or 2, y is 0 or an integer of 1–3.

Suitable optional substituents for hydrocarbyl groups $R^{77}$, $R^{78}$ and $R^{79}$ include halo, perhaloalkyl such as trifluoromethyl, mercapto, hydroxy, carboxy, alkoxy, aryl, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_y$ where y is as defined above.

Preferably $R^4$ is hydrogen.

Suitably $R^1$ is hydrogen or a group set out for $R^2$ or $R^3$ below. Frequently, $R^1$ is hydrogen.

In a preferred embodiment, at least one group $R^1$, $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Suitably $R^3$ is a group $X^1R^9$. Preferably in this case, $X^1$ is oxygen and $R^9$ is selected from a group of formula (I) or (10) above. Particular groups $R^9$ are those in group (1) above, especially alkyl such as methyl or halo substituted alkyl, or those in group (10) above. In one preferred embodiment, at least one of $R^2$ or $R^3$ is a group $—OC_{1-5}alkylR^{33}$ and $R^{33}$ is a heterocyclic ring such as an N-linked morpholine ring such as 3-morpholinopropoxy.

Suitably $R^2$ is selected from, halo, cyano, nitro, trifluoromethyl, $C_{1-3}$alkyl, $—NR^9R^{10}$ (wherein $R^9$ and $R^{10}$, which may be the same or different, each represents hydrogen or $C_{1-3}$alkyl), or a group $—X^1R^1$. Preferred examples of $—X^1R^{11\ for\ R2}$ include those listed above in relation to $R^3$.

Other examples for $R^2$ and $R^3$ include methoxy or 3,3,3-trifluoroethoxy.

Preferably X is NH or O and is most preferably NH.

Examples of 5-membered aromatic rings $R^5$ include rings containing one or more heteroatoms selected from sulphur, oxygen and nitrogen. Such rings include pyrrole, pyrazole, pyrazolone, imidazole, oxazole, furan, tetrazole, triazole, thiazole, thiophene, or to thiadiazole, any of which may be optionally substituted. In particular, $R^5$ includes at least one nitrogen or sulphur heteroatoms. Preferred rings for $R^5$ include pyrrole, pyrazole, imidazole, triazole, thiazole, thiophene, or thiadiazole.

In a particular embodiment, $R^5$ is a sulphur containing ring. Suitably $R^5$ is optionally substituted thiazole, optionally substituted thiophene or optionally substituted thiadiazole and preferably, optionally substituted thiazole or optionally substituted thiophene.

More preferably, $R^5$ is a substituted thiazole or substituted thiophene group.

In particular, $R^5$ is a group of formula (a), (b), (c) or (d) and preferably (a) or (b):

(a)

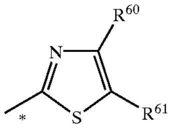

(b)

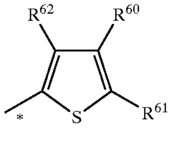

-continued (c)

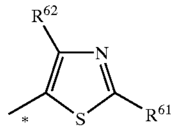

(d)

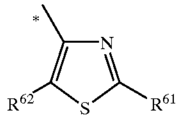

(e)

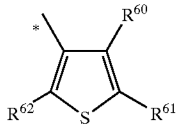

where $R^{60}$, $R^{61}$ and $R^{62}$ are independently selected from hydrogen or a substituent group and * indicates the point of attachment to the group X in formula (I). In particular, one of $R^{60}$, $R^{6'}$ or $R^{62}$ is a substituent group and the others are either hydrogen or a small substituent such as $C_{1-3}$ alkyl, for instance methyl. Suitably $R^{62}$ is hydrogen. Preferably $R^{61}$ is other than hydrogen, Alternatively, $R^5$ is an optionally substituted nitrogen containing ring such as a group of formula (f), (g), (h), (i) or (j):

(f)

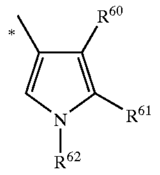

(g)

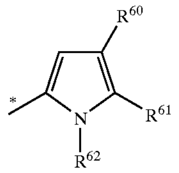

(h)

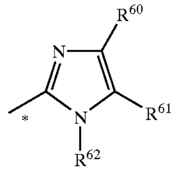

(i)

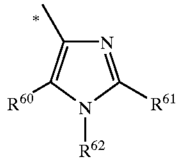

(j)

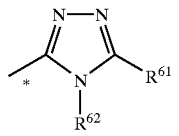

Suitable substituents for groups $R^5$ include optionally substituted hydrocarbyl, optionally substituted heterocylyl or a functional group as defined above.

In particular, $R^{60}$, $R^{61}$ or $R^{62}$ is a group of sub-formula (k)

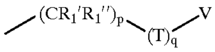

(k)

where p and q are independently 0 or 1 and wherein $R_1$' and $R_1$" are independently hydrogen, hydroxy, optionally substituted alkyl, optionally substituted cycloalkyl, halogen, cyano, optionally substituted alkyl, optionally substituted alkyenyl. The optionally substituted alkyl or alkynyl may be substituted with halo, nitro, cyano, hydroxy, trifluoromethyl, amino, carboxy, carbamoyl, mercapto, sulfamoyl, $C_{1-4}$ alkyl, $C_{2-4}$alkenyl, $C_{2-4}$ alkynyl, $C_{3-4}$ cycloalkyl, $C_{3-6}$ cycloalkenyl, $C_{1-4}$ alkoxy, $C_{1-4}$ alkanoyl, $C_{1-14}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$alkyl)carbamoyl, N,N-($C_{1-4}$)$_2$carbamoyl, $C_{1-4}$)S, $C_{1-4}$S(O), ($C_{1-4}$alkyl)S(O)$_2$, ($C_{1-4}$) alkoxycarbonyl, N-($C_{1-4}$ alkyl)sulfamoyl, N,N—$C_{1-4}$ alkyl)sulfamoyl, $C_{1-4}$ alkylsolfonylamino, or heterocyclyl. R is preferably $C_{1-4}$ alkyl, $C_{2-4}$alkenyl, or $C_{2-4}$ alkynyl, and $R_1$' can form with $R^1$ "a 3 to 6 membered ring.

T is C═O, $SO_n$, C(═NOR)CO, C(O)C(O), C═NCN, CV═NO or wherein n=0, 1 or 2 and V is independently $R^{63}$ or N($R^{63}$)$R^{64}$ wherein $R^{63}$ and $R^{64}$ are independently selected from hydrogen, optionally substituted hydrocarbyl or optionally substituted heterocyclyl, or $R^{63}$ and $R^{64}$ together with the nitrogen atom to which they are attached form an optionally substituted heterocyclic ring.

Examples of groups for $R^{63}$ and $R^{64}$ include the group —$(CH_2)_qR^{70}$ where q and $R^{70}$ are as defined below in relation to formula (II)

Suitably one of $R^{63}$ or $R^{64}$ is hydrogen, or methyl, ethyl or propyl optionally substituted with hydroxy and preferably one of $R^{63}$ or $R^{64}$ is hydrogen. In this case, the other is suitably a larger substituent for example of at least 4 carbon or heteroatoms, and is optionally substituted hydrocarbyl or optionally substituted heterocyclyl. Particular optionally substituted hydrocarbyl groups for $R^{63}$ or $R^{64}$ include alkyl, cycloalkyl, alkenyl, or aryl any of which is optionally substituted with a functional group as defined above, or in the case of aryl groups, with an alkyl group and in the case of alkyl group, with an aryl or heterocyclic group either of which may themselves be optionally substituted with alkyl or a functional group. Examples of optionally substituted aryl groups $R^{63}$ or $R^{64}$ include phenyl optionally substituted with one or more groups selected from $C_{1-4}$ alkyl group such as methyl or ethyl (either of which may be optionally substituted with a functional group such as hydroxy), or a functional group as defined above (such as halo like fluoro, chloro or bromo, hydroxy, alkoxy such as methoxy, trifluoromethyl, nitro, cyano, trifluromethoxy, $CONH_2$, $C(O)CH_3$, amino, or dimethylamino).

When $R^{63}$ or $R^{64}$ is an optionally substituted alkyl group, it is suitably a $C_{1-6}$alkyl group, optionally substituted with one or more functional groups (such as cyano, hydroxy, alkoxy, in particular methoxy, COOalkyl such as $COOCH_3$), or aryl optionally substituted with a functional group as defined above (in particular in relation to $R^{63}$ or $R^{64}$ themselves, or an optionally substituted heterocyclic group such as N-methylpyrrole.

When $R^{63}$ and $R^{64}$ is optionally substituted cycloalkyl, it is suitable cyclohexyl optionally substituted with a functional group such as hydroxy.

When $R^{63}$ and $R^{64}$ is optionally substituted alkenyl, it is suitably prop-2-enyl.

When $R^{63}$ or $R^{64}$ is optionally substituted heterocyclyl, or $R^{63}$ and $R^{64}$ together form a heterocyclic group, then this may be aromatic or non-aromatic and includes in particular, piperidine, piperazine, morpholino, pyrrolidine or pyridine any of which may be optionally substituted with a functional group such as hydroxy, alkoxy such as methoxy, or alkyl such as methyl which may itself be substituted with for instance a hydroxy group.

Alternatively at least one of $R^{60}$, $R^{61}$ or $R^{62}$ is a functional group, and in particular, one of $R^{60}$, $R^{61}$ or $R^{62}$ is a functional group a group of formula $(CR_2)_pC(O)R^{77}$ where R, p, x and $R^{77}$ are as defined above, and in particular x is 2 and $R^{77}$ is hydrogen or alkyl such as methyl.

Alternatively, $R^5$ is substituted by one or more groups selected from nitro, halo, $C_{1-6}$alkyl, optionally substituted $C_{1-6}$ alkoxy, $C_{1-4}$alkoxymethyl, di($C_{1-4}$alkoxy)methyl, $C_{1-6}$alkanoyl, trifluoromethyl, cyano, amino, $C_{2-6}$alkenyl, $C_{2-4}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl) carbamoyl, aminosulphonyl, N—$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl.

Suitably $R^5$ is substituted with at least one group which has at least 4 atoms which may be carbon or heteroatoms forming a chain. A particular example of such a substituent is optionally substituted alkoxy or alkoxy methyl. Suitable substituents for the alkoxy group include those listed above in relation to $R^{77}$, $R^{78}$ and $R^{79}$.

A further particular substituent group for $R^5$ is a group of sub-formula (II)

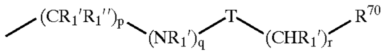

(II)

where p and q are independently 0 or 1, and r is 0, 1, 2, 3 or 4 and, R1', R1" and T are as previously defined above;

$R^{70}$ is hydrogen, hydroxy (other than where q is 0), $C_{1-6}$alkyl, $C_{1-6}$alkoxy, amino, N—$C_{1-6}$alkylamino, N,N-($C_{1-6}$alkyl)$_2$amino, hydroxy$C_{2-6}$alkoxy, $C_{1-6}$alkoxy$C_{2-6}$ alkoxy, amino$C_{2-6}$alkoxy, N—$C_{1-6}$alkylamino$C_{2-6}$ alkoxy, N,N-($C_{1-6}$alkyl)$_2$amino$C_{2-6}$alkoxy or $C_{3-7}$cycloalkyl, or $R^{70}$ is of the Formula (III):

—K—J (III)

wherein J is aryl, heteroaryl or heterocyclyl and K is a bond, oxy, imino, N-($C_{1-6}$alkyl)imino, oxy$C_{1-6}$alkylene, imino$C_{1-}$ ${}_6$alkylene, N-($C_{1-6}$alkyl)imino$C_{1-6}$alkylene, —NHC(O)—, —$SO_2$NH—, —$NHSO_2$— or —NHC(O)—$C_{1-6}$alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—, $C_{1-6}$alkylS$(O)_n$— (wherein n is 0–2), N—$C_{1-4}$alkylamino, N,N-$(C_{1-6}alkyl)_2$ amino, $C_{1-4}$alkoxycarbonyl, N—$C_{1-6}$alkylcarbamoyl, N,N-$(C_{1-6}alkyl)_2$carbamoyl, $C_{2-4}$alkanoyl, $C_{1-6}$alkanoyloxy, $C_{1-6}$alkanoylamino, N—$C_{1-6}$ alkylsulphamoyl, N,N-$(C_{1-6}alkyl)_2$sulphamoyl, $C_{1-4}$alkylsulphonylamino and $C_{1-6}$alkylsulphonyl-N-($C_{1-6}$ alkyl)amino, or any aryl, heteroaryl or heterocyclyl group in a $R^{70}$ group may be optionally substituted with one or more groups of the Formula (IV):

$$—B^1—(CH_2)_p—A^1 \quad (IV)$$

wherein $A^1$ is halo, hydroxy, $C_{1-6}$alkoxy, cyano, amino, N—$C_{1-6}$alkylamino, N,N-$(C_{1-6}alkyl)_2$amino, carboxy, $C_{1-6}$alkoxycarbonyl, carbamoyl, N—$C_{1-4}$alkylcarbamoyl or N,N-$(C_{1-6}alkyl)_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—; or any aryl, heteroaryl or heterocyclyl group in a $R^{70}$ group may be optionally substituted with one or more groups of the Formula (V):

$$—E^1—D^1 \quad (V)$$

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$ alkyl)imino, imino$C_{1-6}$alkylene, N-($C_{1-4}$alkyl)-imino$C_{1-6}$ alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$ alkylene, —NHC(O)—, —$NHSO_2$—, —$SO_2$NH— or —NHC(O)—$C_{1-6}$alkylene-, and any aryl, heteroaryl or heterocyclyl group in a substituent on $D^1$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N-$(C_{1-6}alkyl)_2$ carbamoyl, $C_{2-6}$alkanoyl, amino, N—$C_{1-6}$alkylamino and N,N-$(C_{1-6}alkyl)_2$amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N—$C_{1-6}$alkylamino, N,N-$(C_{1-6}alkyl)_2$amino and heterocyclyl.

A preferred example of a substituent of formula (II) is a group where q is 0.

A particular example of a group $R^{70}$ in formula (II) is phenyl.

Another preferred substituent group for $R^5$ is a group of formula (VI)

(VI)

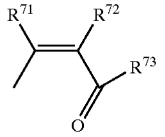

where $R^{71}$ and $R^{72}$ are independently selected from hydrogen or $C_{1-4}$alkyl, or $R^{71}$ and $R^{72}$ together form a bond, and R is a group $OR^{74}$, $NR^{75}R^{76}$ where $R^{74}$, $R^{75}$ and $R^{76}$ are independently selected from optionally substituted hydrocarbyl or optionally substituted heterocyclic groups, and $R^{75}$ and $R^{76}$ may additionally form together with the nitrogen atom to which they are attached, an aromatic or non-aromatic heterocyclic ring which may contain further heteroatoms.

Suitable optional substituents for hydrocarbyl or heterocyclic groups $R^{74}$, $R^{75}$ and $R^{76}$ include functional groups as defined above. Heterocyclic groups $R^{74}$, $R^{75}$ and $R^{76}$ may further be substituted by hydrocarbyl groups.

In particular, $R^{71}$ and $R^{72}$ in sub-formula (VI) are hydrogen.

Particular examples of $R^{73}$ are groups $OR^{74}$ where $R^{74}$ is $C_{1-4}$alkyl.

Further examples of $R^{73}$ are groups of formula $NR^{75}R^{76}$ where one of $R^{75}$ or $R^{76}$ is hydrogen and the other is optionally substituted $C_{1-6}$alkyl, optionally substituted aryl or optionally substituted heterocyclyl.

In particular, one of $R^{75}$ or $R^{76}$ is hydrogen and the other is $C_{1-4}$alkyl optionally substituted with trifluoromethyl, $C_{1-3}$ alkoxy such as methoxy, cyano, thio$C_{1-4}$alkyl such as methylthio, or heterocyclyl optionally substituted with hydrocarbyl, such as indane, furan optionally substituted with $C_{1-4}$ alkyl such as methyl.

In another embodiment, one of $R^{75}$ or $R^{76}$ is hydrogen and the other is an optionally substituted heterocyclic group such as pyridine, or a phenyl group optionally substituted with for example one or more groups selected from halo, nitro, alkyl such as methyl, or alkoxy such as methoxy.

Suitable pharmaceutically acceptable salts of compounds of Formula (I) or Formula (IA) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of Formula (I) or Formula (IA) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolysable ester of a compound of the Formula (I) or Formula (IA) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the Formula (I) or Formula (IA) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of Formula (I) or Formula (IA) which have a carboxy group which is derivatised into an amide such as a N—$C_{1-4}$alkyl and N,N-di-($C_{1-6}$alkyl)amide such as N-methyl, N-ethyl, N-propyl, N,N-dimethyl, N-ethyl-N-methyl or N,N-diethylamide.

Preferred compounds of Formula (I) or Formula (IA) are those that are stable in mouse, rat, or human serum, preferably those that are stable in human serum.

Esters which are not in vivo hydrolysable may be useful as intermediates in the production of the compounds of Formula (I) or Formula (IA).

Particular examples of compounds of Formula (I) or Formula (IA) are set out in Tables 1 to 30 below.

TABLE 1

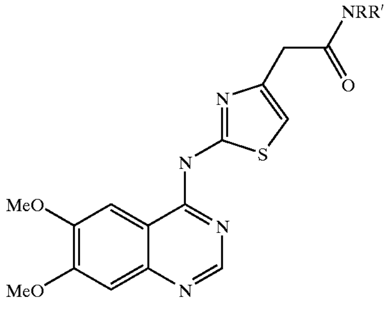

| Compound No | NRR' |
|---|---|
| 1 | 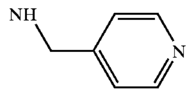 |
| 2 | 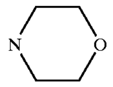 |
| 3 | 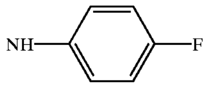 |
| 4 | 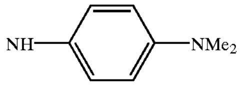 |

TABLE 1-continued

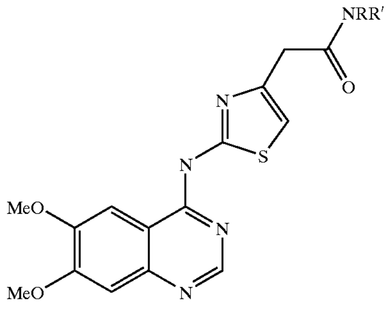

| Compound No | NRR' |
|---|---|
| 5 | 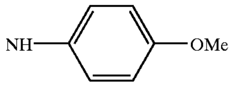 |
| 6 | 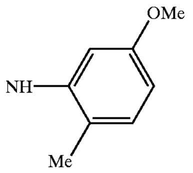 |
| 7 | 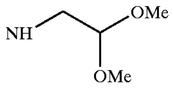 |
| 8 | 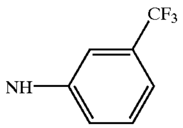 |
| 9 | 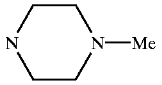 |
| 10 | 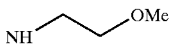 |
| 11 | 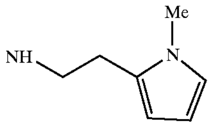 |
| 12 | 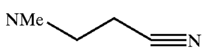 |
| 13 | 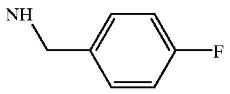 |
| 14 | 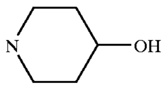 |

TABLE 1-continued
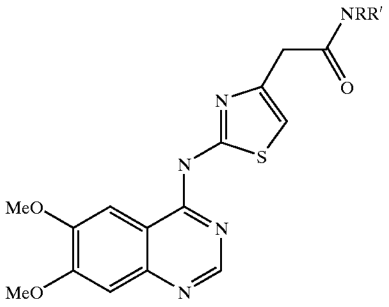
| Compound No | NRR' |
|---|---|
| 15 | 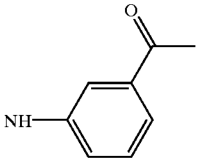 |
| 16 | 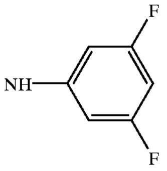 |
| 17 | 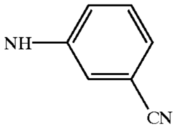 |
| 18 | 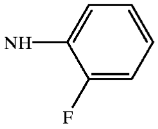 |
| 19 | 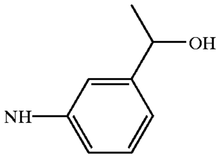 |
| 20 | 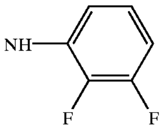 |
| 21 | 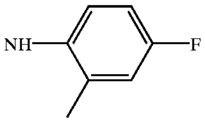 |
| 22 | 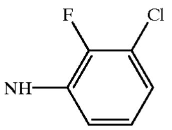 |
TABLE 1-continued
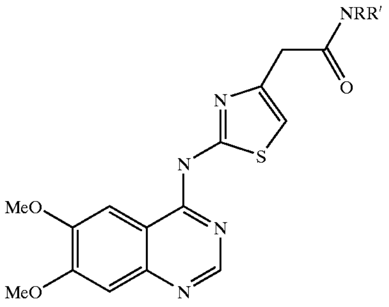
| Compound No | NRR' |
|---|---|
| 23 | 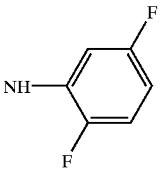 |
| 24 | 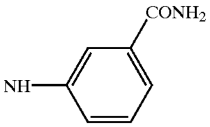 |
| 25 | 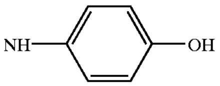 |
| 26 | 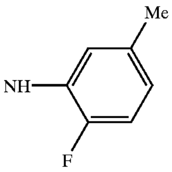 |
| 27 | 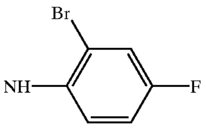 |
| 28 | 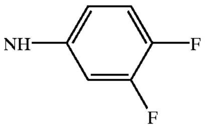 |
| 29 | 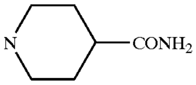 |
| 30 | 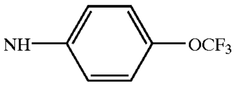 |
| 31 | 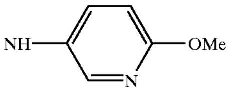 |

TABLE 1-continued
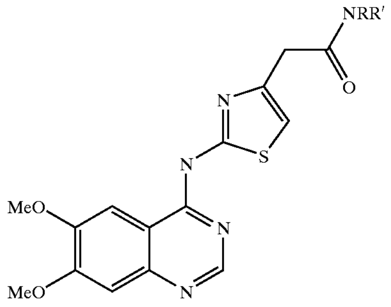
| Compound No | NRR' |
|---|---|
| 32 | 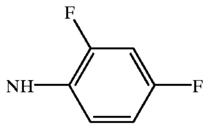 |
| 33 | 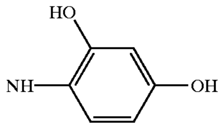 |
| 34 | 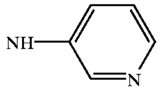 |
| 35 | 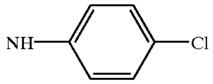 |
| 36 | 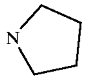 |
| 37 | 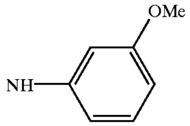 |
| 38 | 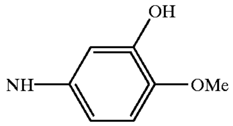 |
| 39 | 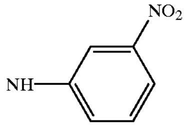 |
| 40 | 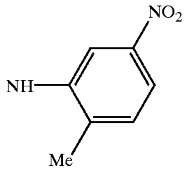 |
TABLE 1-continued
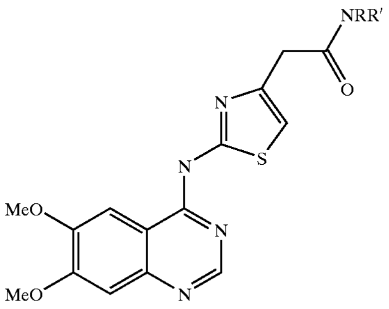
| Compound No | NRR' |
|---|---|
| 41 | 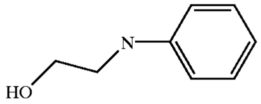 |
| 42 | 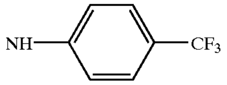 |
| 43 | 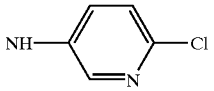 |
| 44 | 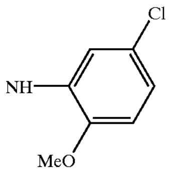 |
| 45 | 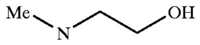 |
| 46 | 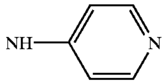 |
| 47 | 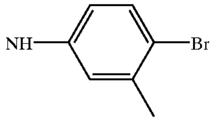 |
| 48 | 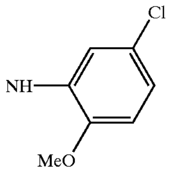 |
| 49 | 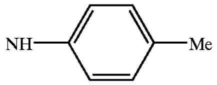 |
| 50 | 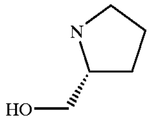 |

TABLE 2
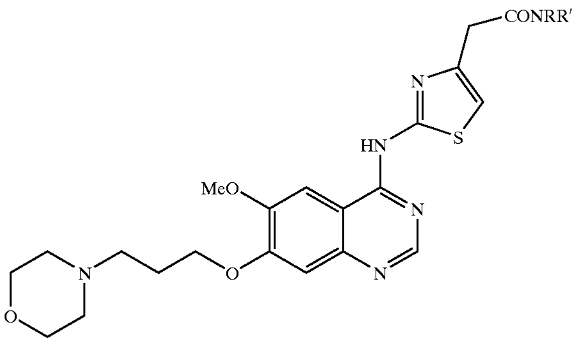
| Compound No | NRR' |
|---|---|
| 51 | 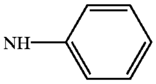 |
| 52 | 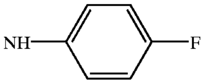 |
| 53 | 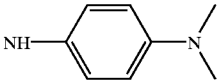 |
| 54 | 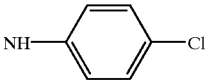 |
| 55 | 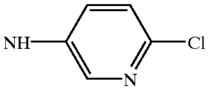 |
| 56 | 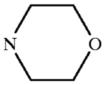 |
| 57 | 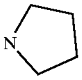 |
| 58 | 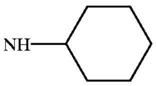 |
TABLE 3
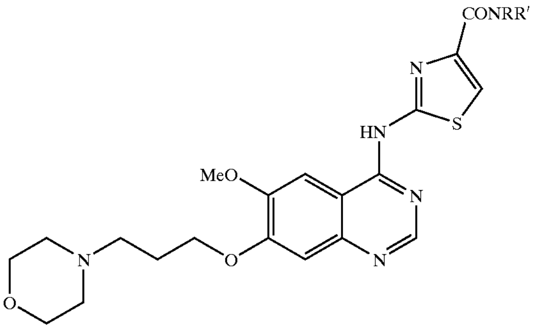
| Compound No | NRR' |
|---|---|
| 59 | 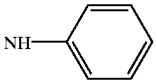 |
| 60 | 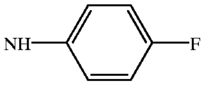 |
| 61 | 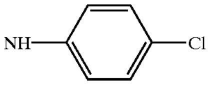 |
| 62 | 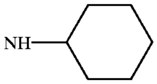 |
| 63 | 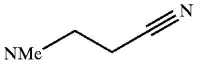 |
| 64 | 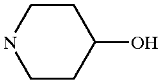 |
| 65 | 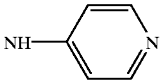 |
| 66 | 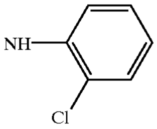 |

TABLE 4
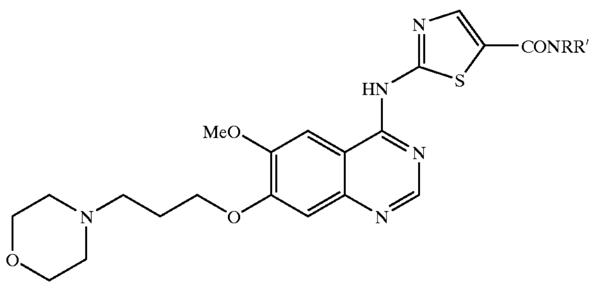
| Compound No | NRR' |
|---|---|
| 67 | 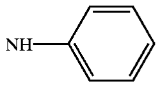 |
| 68 | 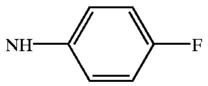 |
| 69 | 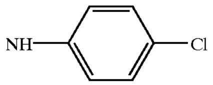 |
| 70 | 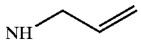 |
| 71 | 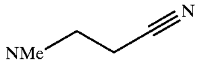 |
| 72 | 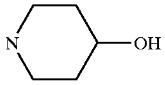 |
| 73 | 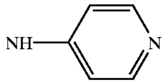 |

TABLE 5
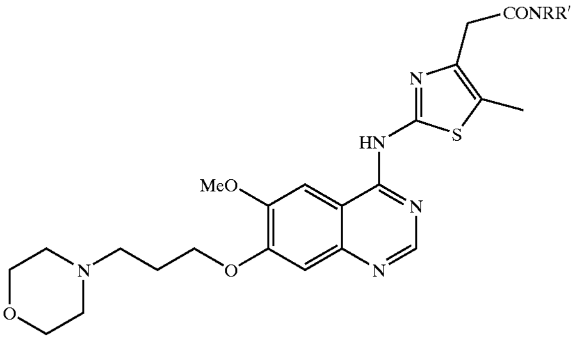
| Compound No | NRR' |
| --- | --- |
| 74 | 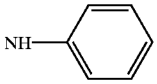 |
| 75 | 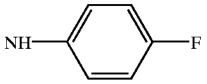 |
| 76 | 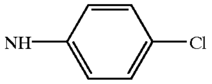 |
TABLE 5-continued
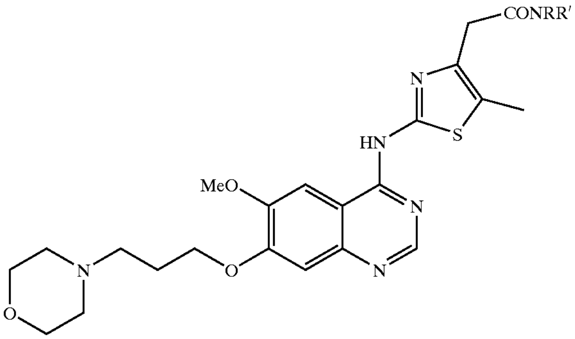
| Compound No | NRR' |
| --- | --- |
| 77 | 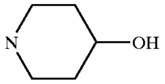 |
| 78 | 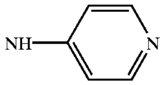 |
TABLE 6
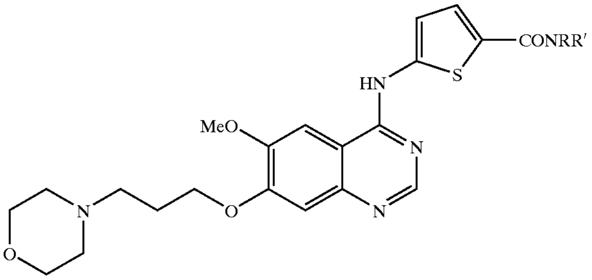
| Compound No. | NRR' |
| --- | --- |
| 79 | 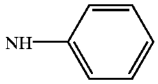 |
| 80 | 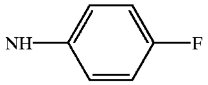 |
| 81 | 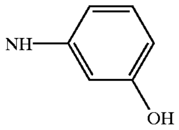 |

TABLE 6-continued

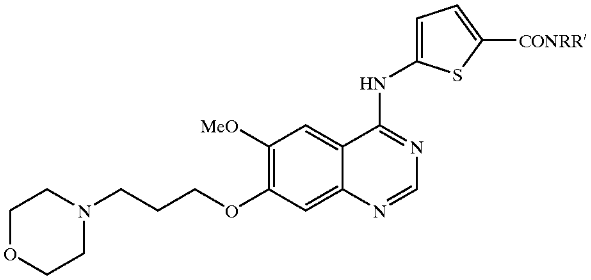

| Compound No. | NRR' |
|---|---|
| 82 | 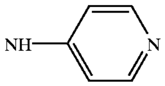 |
| 83 | 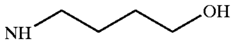 |
| 84 | 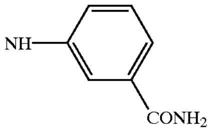 |
| 85 | 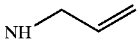 |
| 86 | 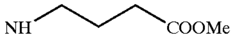 |

TABLE 7

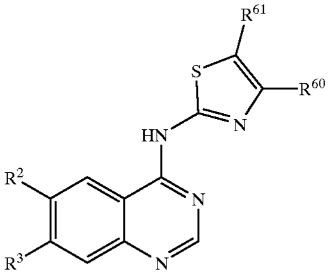

| No. | $R^2$ | $R^3$ | $R^{60}$ | $R^{61}$ |
|---|---|---|---|---|
| 200 | $OCH_3$ | $OCH_3$ | $CH_2COOCH_2CH_3$ | H |
| 201 | $OCH_3$ | $OCH_3$ | $CH_2COOH$ | H |
| 202 | $OCH_3$ | $OCH_3$ | $CH_3$ | $COOCH_2CH_3$ |
| 203 | $OCH_3$ | $O(CH_2)_3$-N-morpholino | $CH_3$ | $COOCH_2CH_3$ |
| 204 | $OCH_3$ | $O(CH_2)_3$-N-morpholino | $CH_3$ | COOH |
| 205 | $OCH_3$ | $O(CH_2)_3$-N-morpholino | $CH_2COOCH_2CH_3$ | H |
| 206[1] | $OCH_3$ | $O(CH_2)_3$-N-morpholino | $COOCH_2CH_3$ | H |
| 207 | $OCH_3$ | $O(CH_2)_3$-N-morpholino | COOH | H |

TABLE 7-continued

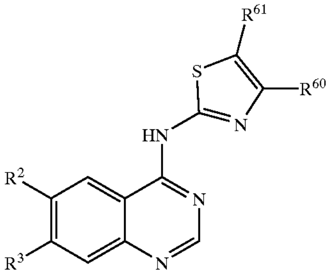

| No. | $R^2$ | $R^3$ | $R^{60}$ | $R^{61}$ |
|---|---|---|---|---|
| 208 | $OCH_3$ | $O(CH_2)_3$-N-morpholino | H | $COOCH_2CH_3$ |
| 209 | $OCH_3$ | $O(CH_2)_3$-N-morpholino | H | COOH |
| 210 | $OCH_3$ | $O(CH_2)_3$-N-morpholino | $CH_2COOCH_2CH_3$ | $CH_3$ |
| 211 | $OCH_3$ | $O(CH_2)_3$-N-morpholino | $CH_2COOH$ | $CH_3$ |

TABLE 8
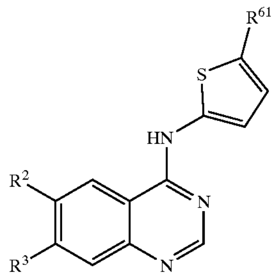
| No. | $R^2$ | $R^3$ | $R^{61}$ |
|---|---|---|---|
| 212 | $OCH_3$ | $O(CH_2)_3$-N-morpholino | COOH |
| 213 | 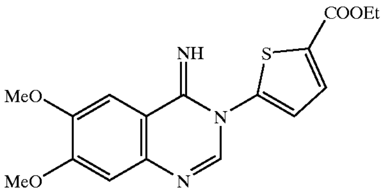 | | |
| 214 | $OCH_3$ | $OCH_3$ | COOH |
TABLE 9
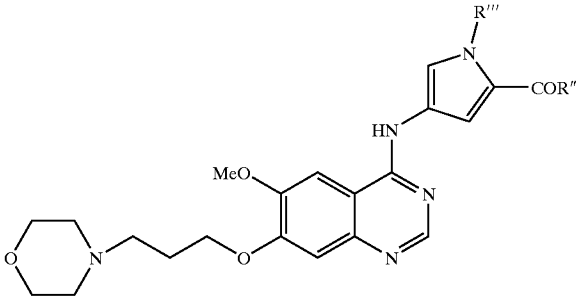
| Compound No | R''' | R" |
|---|---|---|
| 250 | $CH_3$ | $OCH_3$ |
| 251 | $CH_3$ | OH |
| 252 | $CH_3$ | 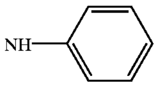 |
| 253 | $CH_3$ | 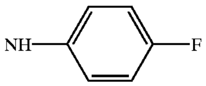 |
| 254 | $CH_3$ | 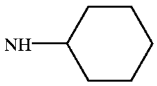 |
| 255 | $CH_3$ | 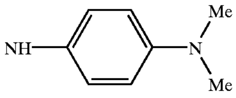 |
| 256 | H | $OCH_2CH_3$ |
| 257 | H | OH |
TABLE 9-continued
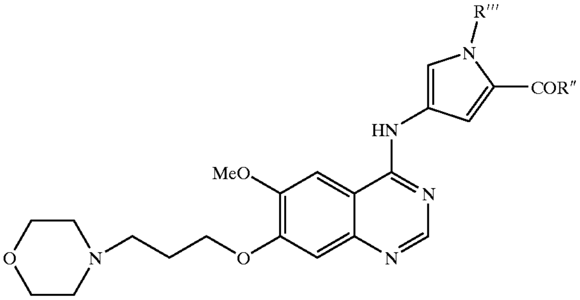
| Compound No | R''' | R" |
|---|---|---|
| 258 | H | 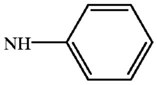 |
| 259 | H | 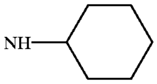 |
TABLE 10
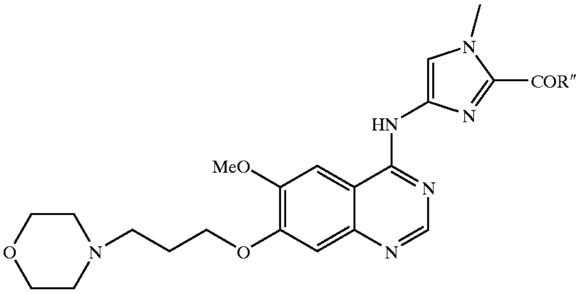
| Compound No | R" |
|---|---|
| 260 | $COOEt_3$ |
| 261 | COOH |
| 262 | 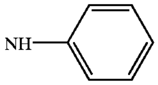 |
| 263 | 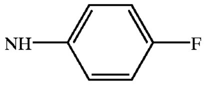 |
| 264 | 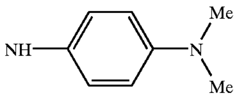 |

TABLE 10-continued

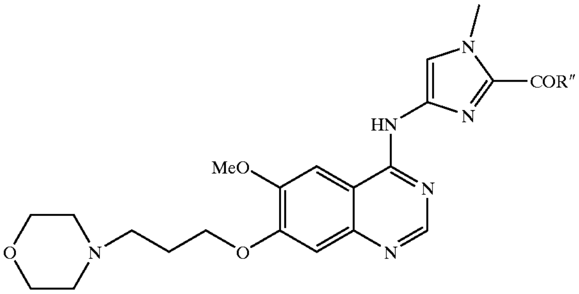

| Compound No | R" |
|---|---|
| 265 | 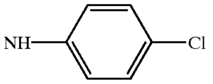 |
| 266 | 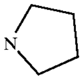 |
| 267 | 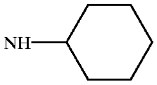 |

TABLE 11

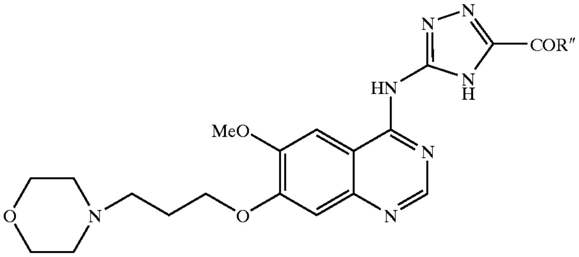

| Compound No | R" |
|---|---|
| 268 | $COOCH_2CH_3$ |
| 269 | COOH |
| 270 | 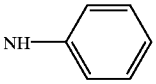 |
| 2 7 1 | 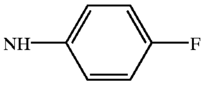 |

TABLE 11-continued

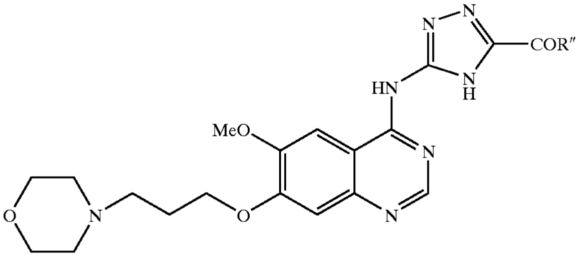

| Compound No | R" |
|---|---|
| 272 | 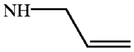 |

TABLE 12

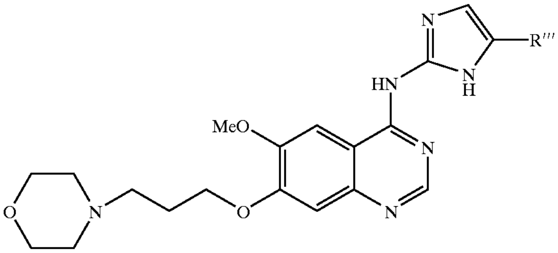

| Compound No. | R''' |
|---|---|
| 300 | H |
| 301 | $COOCH_2CH_3$ |

TABLE 13

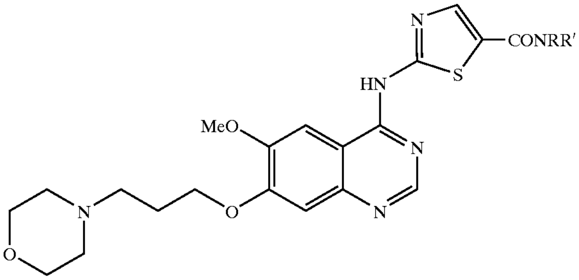

| N° | NRR' | N° | NRR' |
|---|---|---|---|
| 302 | 4-methoxyaniline | 320 | 2-methyl-4-fluoroaniline |
| 303 | 4-methylaniline | 321 | 2-fluoro-5-methylaniline |
| 304 | 2-aminopyridine | 322 | 4-fluorobenzylamine |
| 305 | 2-aminobenzyl alcohol | 323 | 3,4-difluorobenzylamine |
| 306 | 4-methoxybenzylamine | 324 | 3-methylaniline |
| 307 | 3-nitroaniline | 325 | 2-(methylthio)aniline |
| 308 | Aminoacetonitrile | 326 | 5-aminoindole |
| 309 | 2-methyl-5-nitroaniline | 327 | 3-aminobenzonitrile |
| 310 | Cyclopropylamine | 328 | 2,4-difluorobenzylamine |
| 311 | 4-nitrobenzylamine | 329 | 3-(2-aminoethyl)pyridine |
| 312 | 2-anilinoethanol | 330 | N-methylisobutylamine |

TABLE 13-continued

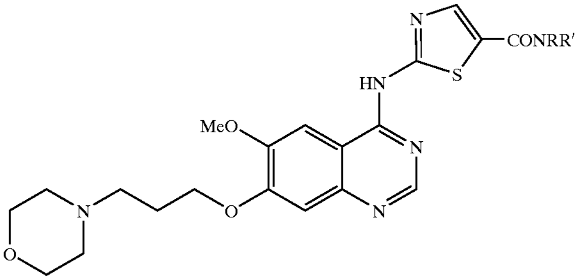

| N° | NRR' | N° | NRR' |
|---|---|---|---|
| 313 | Furfurylamine | 331 | 2-aminobenzylamine |
| 314 | 3-chloroaniline | 332 | 3-methylbutylamine |
| 315 | 2-methoxyaniline | 333 | 1-aminomethyl-1-cyclohexanol |
| 316 | thiophene-2-methylamine | 334 | 2-aminomethylpyrazine |
| 317 | Neopentylamine | 335 | 3-methoxyaniline |
| 318 | 2,6-difluorobenzylamine | 336 | 4-chlorobenzylamine |
| 319 | 2-methylallylamine | | |

TABLE 14

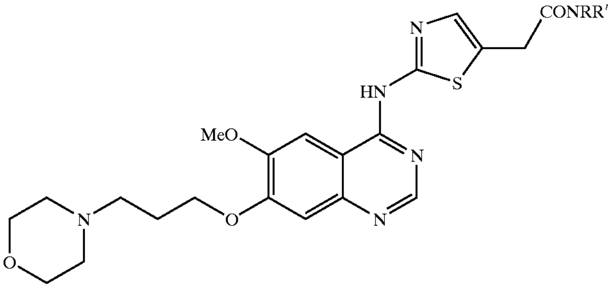

| N° | NRR' | N° | NRR' |
|---|---|---|---|
| 337 | Aniline | 357 | 2-methoxyaniline |
| 338 | 3-chloro-4-fluoroaniline | 358 | 2-fluoroaniline |
| 339 | 4-chloroaniline | 359 | thiophene-2-methylamine |
| 340 | 3,4-difluoroaniline | 360 | 2-amino-1-phenylethanol |
| 341 | 3-methoxyaniline | 361 | 3-(1-hydroxyethyl)aniline |
| 342 | 2-chloroaniline | 362 | neopentylamine |
| 343 | 4-methoxyaniline | 363 | 3-fluoro-4-methoxyaniline |
| 344 | 4-methylaniline | 364 | 2-methyl-4-fluoroaniline |
| 345 | 2-methylaniline | 365 | 2,5-difluoroaniline |
| 346 | 2-aminopyridine | 366 | 2-fluoro-4-chloroaniline |
| 347 | 2-aminobenzylalcohol | 367 | 2-fluoro-4-methylaniline |
| 348 | 2-amino-3-methyl-1-butanol | 368 | 3-methylaniline |
| 349 | 2-anilino ethanol | 369 | 2-(methylthio)aniline |
| 350 | 3-chloro-4-methylaniline | 370 | 5-aminoindole |
| 351 | 3-nitroaniline | 371 | 2,4-difluoroaniline |
| 352 | aminoacetonitrile | 372 | 2-fluoro-4-methylaniline |
| 353 | 2-methyl-5-nitroaniline | 373 | 3-cyanoaniline |
| 354 | 2-amino-5-chloropyridine | 374 | 2-methyl-5-fluoroaniline |
| 355 | 4-trifluoromethylaniline | 375 | 2-methyl-5-chloroaniline |
| 356 | 3-chloroaniline | | |

TABLE 15

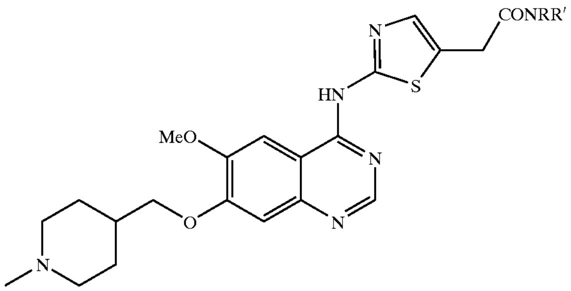

| N° | NRR' | N° | NRR' |
|---|---|---|---|
| 376 | aniline | 390 | 3-fluoro-4-methoxyaniline |
| 377 | 3-chloro-4-fluoroaniline | 391 | 2-methyl-4-fluoroaniline |
| 378 | 2-aminopyridine | 392 | 2-amino-4-methylpyridine |
| 379 | 3,4-difluoroaniline | 393 | 2,5-difluoroaniline |
| 380 | 2-chloroaniline | 394 | 2-fluoro-4-chloroaniline |
| 381 | 4-methylaniline | 395 | 2-fluoro-5-methylaniline |
| 382 | 2-methylaniline | 396 | 3-methylaniline |
| 383 | 4-chloroaniline | 397 | 2,4-difluoroaniline |
| 384 | 4-fluoroaniline | 398 | 2-fluoro-4-methylaniline |
| 385 | 2-amino-6-methylpyridine | 399 | 3-cyanoaniline |
| 386 | 3-methoxyaniline | 400 | 2-methyl-5-fluoroaniline |
| 387 | 2-amino-5-chloropyridine | 401 | 3,5-difluoroaniline |
| 388 | 3-chloroaniline | 402 | 3-fluoroaniline |
| 389 | 2-fluoroaniline | | |

TABLE 16

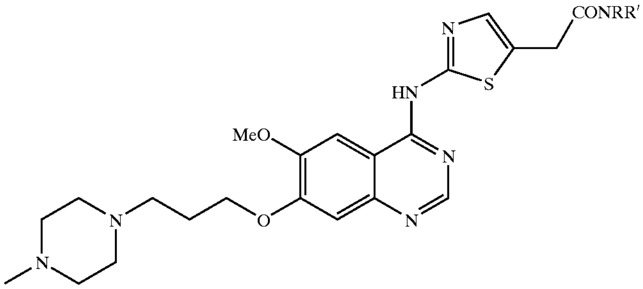

| N° | NRR' | N° | NRR' |
|---|---|---|---|
| 403 | Aniline | 418 | 2-fluoro-4-methylaniline |
| 404 | 3,4-dfifluoroaniline | 419 | 3-fluoro-4-methoxyaniline |
| 405 | 2-aminopyridine | 420 | 2-methyl-4-fluroaniline |
| 406 | 3-chloro-4-fluoroaniline | 421 | 2-amino-4-methylpyridine |
| 407 | 2-chloroaniline | 422 | 2,5-difluoraniline |
| 408 | 4-methylaniline | 423 | 2-fluoro-4-chloroaniline |
| 409 | 2-methylaniline | 424 | 2-fluoro-5-methylaniline |
| 410 | 4-chloroaniline | 425 | 3-methylaniline |
| 411 | 4-fluoroaniline | 426 | 2,4-difluoroaniline |
| 412 | 2-amino-6-methylpyridine | 427 | 2-methyl-5-fluoroaniline |
| 413 | 3-methoxyaniline | 428 | 3,5-difluoroaniline |
| 414 | 2-amino-5-chloropyridine | 429 | 3-fluoroaniline |
| 415 | 3-chloroaniline | | |
| 416 | 2-fluoroaniline | | |
| 417 | 3-cyanoaniline | | |

TABLE 17

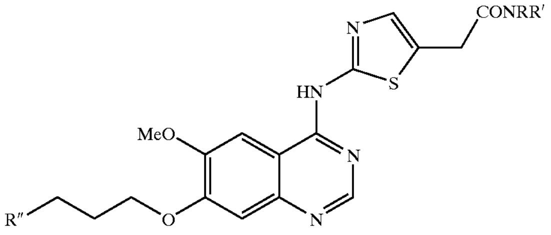

| N° | R" | NRR' |
|---|---|---|
| 430 | pyrrolidine | 3-chloroaniline |
| 431 | pyrrolidine | 3,4-difluoroaniline |
| 432 | dimethylamine | 3,5-difluoroaniline |
| 433 | 2-amino-2-methyl-1-propanol | 3-chloro-4-fluoroaniline |
| 434 | 2-amino-2-methyl-1-propanol | 3-fluoroaniline |
| 435 | 4-hydroxypiperidine | 3,4-difluoroaniline |
| 436 | N,N-dimethylethylenediamine | 3,4-difluoroaniline |
| 437 | piperidine | 3,4-difluoroaniline |
| 438 | 2-methylaminoethanol | 3,4-difluoroaniline |
| 439 | 1,2-diamino-2-methylpropane | 3,4-difluoroaniline |
| 440 | cyclohexylamine | 3,4-difluoroaniline |
| 441 | N,N,N'-trimethylethylenediamine | 3,4-difluoroaniline |
| 442 | D-prolinol | 3,4-difluoroaniline |
| 443 | L-prolinol | 3,4-difluoroaniline |
| 444 | 3-pyrrolidinol | 3,4-difluoroaniline |
| 445 | 1-(2-aminoethyl)pyrrolidine | 3,4-difluoroaniline |
| 446 | 1-acetylpiperazine | 3,4-difluoroaniline |
| 447 | 1-(2-morpholinoethyl)piperazine | 3,4-difluoroaniline |
| 448 | 2-(2-hydroxyethyl)piperidine | 3,4-difluoroaniline |
| 449 | 1-(2-hydroxyethyl)piperazine | 3,4-difluoroaniline |
| 450 | cyclopentylamine | 3,4-difluoroaniline |
| 451 | 4-(2-hydroxyethyl)piperidine | 3,4-difluoroaniline |
| 452 | L-alamine tert-butyester | 3,4-difluoroaniline |
| 453 | 3-hydroxypiperidine | 3,4-difluoroaniline |
| 454 | 4-hydroxymethylpiperidine | 3,4-difluoroaniline |
| 455 | 1-amino-2-propanol | 3,4-difluoroaniline |
| 456 | L-alanine-tert-butylester | 3-chloroaniline |
| 457 | 2-methylaminoethanol | 3-chloroaniline |
| 458 | 1,2-diamino-2-methylpropane | 3-chloroaniline |
| 459 | cyclohexylamine | 3-chloroaniline |
| 460 | N,N-dimethylethylenediamine | 3-chloroaniline |
| 461 | N,N,N'-trimethylethylenediamine | 3-chloroaniline |
| 462 | D-prolinol | 3-chloroaniline |
| 463 | L-prolinol | 3-chloroaniline |
| 464 | 4-hydroxypiperidine | 3-chloroaniline |
| 465 | 3-pyrrolidinol | 3-chloroaniline |
| 466 | 1-(2-aminoethyl)pyrrolidine | 3-chloroaniline |
| 467 | 4-hydroxymethylpiperidine | 3-chloroaniline |
| 468 | 1-(2-hydroxyethyl)piperazine | 3-chloroaniline |
| 469 | cyclopentylamine | 3-chloroaniline |
| 470 | 4-(2-hydroxyethyl)piperidine | 3-chloroaniline |
| 471 | 3-hydroxypiperidine | 3-chloroaniline |
| 472 | (S)-1-amino-2-porpanol | 3-chloroaniline |
| 473 | (R)-1-amino-2-propanol | 3-chloroaniline |
| 474 | piperazine | 3-chloroaniline |
| 475 | 2-(2-hydroxyethyl)piperidine | 3-chloroaniline |
| 476 | 2-amino-2-methyl-1-propanol | 3-chloroaniline |
| 477 | 1-(2-dimethylaminoethyl)piperazine | 3-chloroaniline |
| 478 | dimethylamine | 3-chloroaniline |
| 479 | aminomethylcyclopropane | 3-chloroaniline |
| 480 | piperidine | 3-chloroaniline |
| 481 | 1-(2-dimethylaminoethyl)piperazine | 3,5-difluoroaniline |
| 482 | (S)-(+)-2-Pyrrolidine methanol | 3,5-difluoroaniline |
| 483 | 4-hydroxypiperidine | 3,5-difluoroaniline |
| 484 | 3-pyrrolidinol | 3,5-difluoroaniline |
| 485 | 1-(2-aminoethyl)pyrrolidine | 3,5-difluoroaniline |
| 486 | 4-hydroxymethylpiperidine | 3,5-difluoroaniline |
| 487 | 2-(2-hydroxyethyl)piperidine | 3,5-difluoroaniline |

TABLE 17-continued

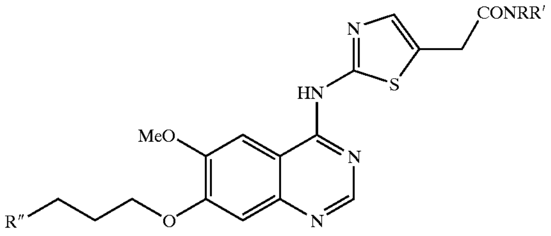

| N° | R" | NRR' |
|---|---|---|
| 488 | 1-(2-hydroxyethyl)piperazine | 3,5-difluoroaniline |
| 489 | 4-(2-hydroxyethyl)piperidine | 3,5-difluoroaniline |
| 490 | 3-hydroxypiperidine | 3,5-difluoroaniline |
| 491 | N,N,N'-trimethylethylenediamine | 3,5-difluoroaniline |
| 492 | piperidine | 3,5-difluoroaniline |
| 493 | pyrrolidine | 3,5-difluoroaniline |
| 494 | 2-amino-2-methyl-1-propanol | 3,5-difluoroaniline |
| 495 | 2-methylaminoethanol | 3,5-difluoroaniline |
| 496 | N,N-dimethylethylenediamine | 3,5-difluoroaniline |
| 497 | (S)-(+)-1-amino-2-propanol | 3,5-difluoroaniline |
| 498 | (R)-(−)-1-amino-2-propanol | 3,5-difluoroaniline |
| 499 | piperazine | 3,5-difluoroaniline |
| 500 | N-allylpiperazine | 3,5-difluoroaniline |
| 501 | (R)-(−)-2-pyrrolidinemethanol | 3,5-difluoroaniline |
| 502 | cyclopentylamine | 3,5-difluoroaniline |
| 503 | 2-methylaminoethanol | 3-chloro-4-fluoroaniline |
| 504 | N,N,N'-trimethylethylenediamine | 3-chloro-4-fluoroaniline |
| 505 | N-allylpiperazine | 3-chloro-4-fluoroaniline |
| 506 | 4-hydroxypiperidine | 3-chloro-4-fluoroaniline |
| 507 | 3-pyrrolidinol | 3-chloro-4-fluoroaniline |
| 508 | 1-(2-aminoethyl)pyrrolidine | 3-chloro-4-fluoroaniline |
| 509 | N-acetylpiperazine | 3-chloro-4-fluoroaniline |
| 510 | 2-(2-hydroxyethyl)piperidine | 3-chloro-4-fluoroaniline |
| 511 | 1-(2-hydroxyethyl)piperazine | 3-chloro-4-fluoroaniline |
| 512 | cyclopentylamine | 3-chloro-4-fluoroaniline |
| 513 | 4-(2-hydroxyethyl)piperidine | 3-chloro-4-fluoroaniline |
| 514 | 3-hydroxypiperidine | 3-chloro-4-fluoroaniline |
| 515 | 4-hydroxymethylpiperidine | 3-chloro-4-fluoroaniline |
| 516 | 1-amino-2-propanol | 3-chloro-4-fluoroaniline |
| 517 | piperazine | 3-chloro-4-fluoroaniline |
| 518 | 1-(2-morpholinoethyl)piperazine | 3-chloro-4-fluoroaniline |
| 519 | pyrrolidine | 3-chloro-4-fluoroaniline |
| 520 | 2-methylaminoethanol | 3-fluoroaniline |
| 521 | 1,2-diamino-2-methylpropane | 3-fluoroaniline |
| 522 | N,N-dimethylethylenediamine | 3-fluoroaniline |
| 523 | N,N,N'-trimethylethylenediamine | 3-fluoroaniline |
| 524 | N-allylpiperazine | 3-fluoroaniline |
| 525 | 4-hydroxypiperidine | 3-fluoroaniline |
| 526 | 3-pyrrolidinol | 3-fluoroaniline |
| 527 | 1-(aminoethyl)pyrrolidine | 3-fluoroaniline |
| 528 | N-acetylpiperazine | 3-fluoroaniline |
| 529 | 1-(2-hydroxyethyl)piperazine | 3-fluoroaniline |
| 530 | cyclopentylamine | 3-fluoroaniline |
| 531 | 4-(2-hydroxyethyl)piperidine | 3-fluoroaniline |
| 532 | 3-hydroxypiperidine | 3-fluoroaniline |

TABLE 17-continued

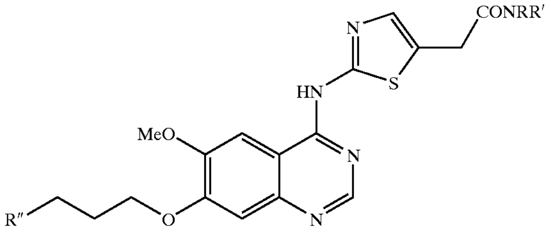

| N° | R" | NRR' |
|---|---|---|
| 533 | 4-hydroxymethylpiperidine | 3-fluoroaniline |
| 534 | 1-amino-2-propanol | 3-fluoroaniline |
| 535 | (R)-(−)-2-pyrrolidinemethanol | 3-fluoroaniline |
| 536 | (S)-(+)-2-pyrrolidinemethanol | 3-fluoroaniline |
| 537 | piperazine | 3-fluoroaniline |
| 538 | 1-(2-morpholinoethyl)piperazine | 3-fluoroaniline |
| 539 | 2-amino-2-methyl-1-propanol | 3-fluoroaniline |

TABLE 18

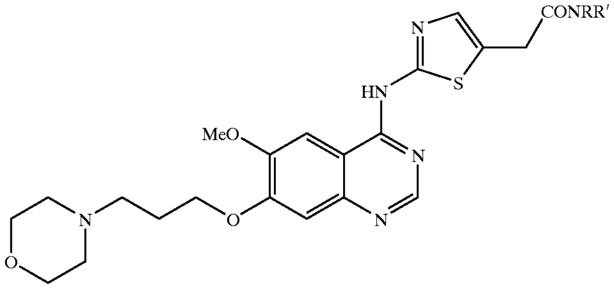

| N° | NRR' |
|---|---|
| 540 | N-ethylaniline |
| 541 | 3-chloro-4-fluoro-N-methylaniline |
| 542 | ethyl-2-(3-chloro-4-fluoroanilino)acetate |
| 543 | 2-anilinoacetronitrile |
| 544 | 3-anilinoproponitrile |
| 545 | N-(2-tert-butoxyethyl)-3-chloro-4-fluoroaniline |
| 546 | N-allylaniline |
| 547 | N-ethyl-3,4-(methylmedioxy)aniline |
| 548 | ethyl-4-(N-butylamino)benzate |
| 549 | N-ethyl-M-toluidine |
| 550 | N-(2-hydroxy"thyl)-3-chloro-4-fluoroaniline |

TABLE 19

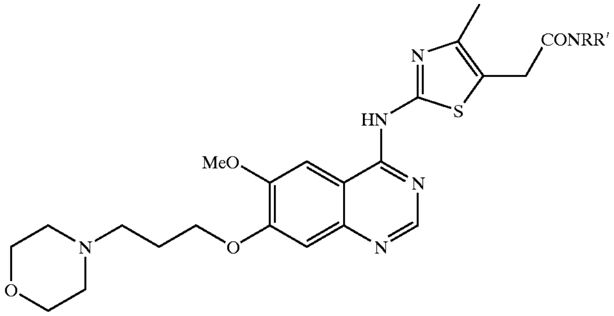

| N° | NRR' |
|---|---|
| 551 | aniline |

TABLE 19-continued

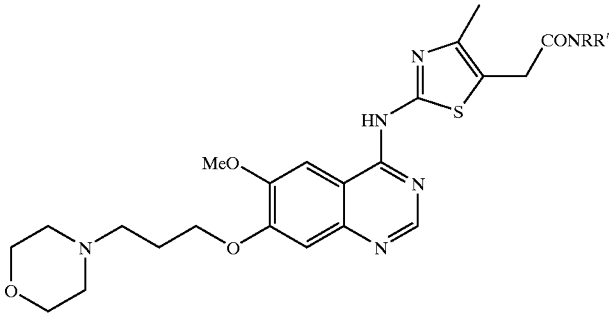

| N° | NRR' |
|---|---|
| 552 | 3-chloro-4-fluoroaniline |
| 553 | 2-aminopyridine |
| 554 | 3,4-difluoroaniline |

TABLE 20

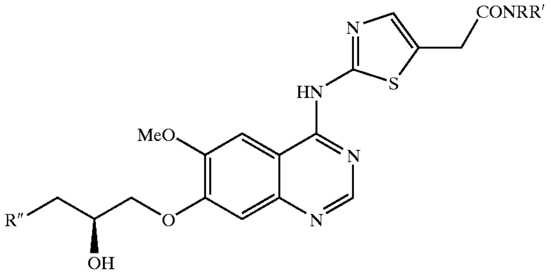

| N° | R" | NRR' |
|---|---|---|
| 555 | piperidine | 3-chloro-4-fluoroaniline |
| 556 | pyrrolidine | 3-chloro-4-fluoroaniline |
| 557 | 4-hydroxypiperidine | 3-chloro-4-fluoroaniline |
| 558 | piperazine | 3-chloro-4-fluoroaniline |
| 559 | cyclopentylamine | 3-chloro-4-fluoroaniline |
| 560 | 2-amino-2-methyl-1-propanol | 3-chloro-4-fluoroaniline |
| 561 | piperidine | 3,4-difluoroaniline |
| 562 | pyrrolidine | 3,4-difluoroaniline |
| 563 | 4-hydroxypiperidine | 3,4-difluoroaniline |
| 565 | cyclopentylamine | 3,4-difluoroaniline |
| 566 | pyrrolidine | 3-chloroaniline |
| 567 | 4-hydroxypiperidine | 3-chloroaniline |
| 568 | cyclopentylamine | 3-chloroaniline |
| 569 | 2-amino-2-methyl-1-propanol | 3-chloroaniline |
| 570 | piperazine | 3-chloroaniline |
| 571 | OMe | 3-chloroaniline |
| 572 | piperidine | 3-chloroaniline |
| 573 | piperidine | 3,5-difluoroaniline |
| 574 | pyrrolidine | 3,5-difluoroaniline |
| 575 | 2-amino-2-methyl-1-propanol | 3,5-difluoroaniline |
| 576 | piperazine (acetate) | 3,5-difluoroaniline |
| 577 | piperazine | 3,5-difluoroaniline |
| 578 | pyrrolidine | 3-fluoroaniline |
| 579 | piperidine | 3-fluoroaniline |
| 580 | piperazine | 3-fluoroaniline |
| 581 | piperazine (acetate) | 3-fluoroaniline |
| 582 | cyclopentylamine | 3-fluoroaniline |

TABLE 21

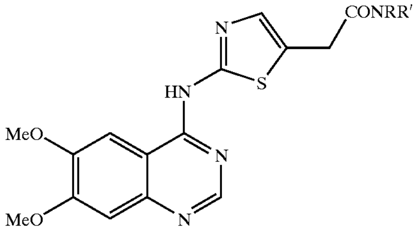

| N° | NRR' |
|---|---|
| 583 | 3,5-difluoroaniline |
| 584 | 3-chloroaniline |
| 585 | 3-chloro-4-fluoroaniline |
| 586 | 3,4-difluoroaniline |

TABLE 22

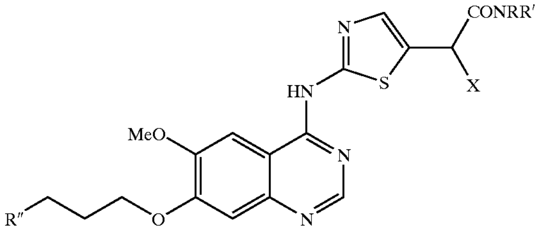

| N° | R" | X | NRR' |
|---|---|---|---|
| 587 | morpholine | OH | aniline |
| 588 | morpholine | OH | 3,4-difluoroaniline |
| 589 | N-Me-piperazine | OH | 3,4-difluoroaniline |
| 590 | piperidine | OH | 3-fluoroaniline |
| 591 | piperidine | OH | 3-chloroaniline |
| 592 | N-Me-piperazine | =N—OH | 3,4-difluoroaniline |

TABLE 23

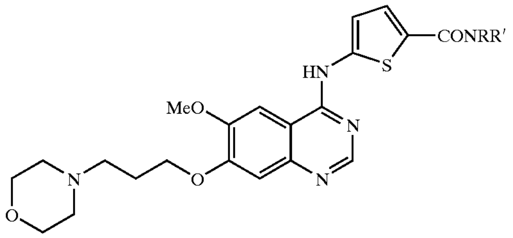

| N° | NRR' |
|---|---|
| 593 | 2-aminopyridine |
| 594 | 4-methylaniline |
| 595 | 2-methylaniline |
| 596 | 3-methoxyaniline |
| 597 | 2-hydroxymethylaniline |
| 598 | 3-nitroaniline |
| 599 | 4-trifluoromethylaniline |
| 600 | 3-chloroaniline |
| 601 | 2-methoxyaniline |
| 602 | 3-(2-hydroxyethyl)aniline |
| 603 | 3-fluoro-4-methoxyaniline |
| 604 | 2-methyl-4-fluoroaniline |
| 605 | 2-fluoro-5-methylailine |
| 606 | 3-cyanoaniline |
| 607 | isoamylamine |
| 608 | 2-chloroaniline |

TABLE 24

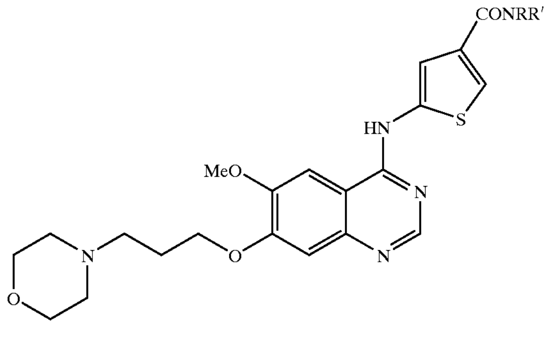

| N° | NRR' |
|---|---|
| 609 | aniline |
| 610 | 4-fluoroaniline |
| 611 | 3-hydroxyaniline |
| 612 | 3-(methylthio)aniline |
| 613 | 4-fluoro-3-chloroaniline |
| 614 | 2,4-difluorobenzylamine |
| 615 | 3-fluoroaniline |

TABLE 25

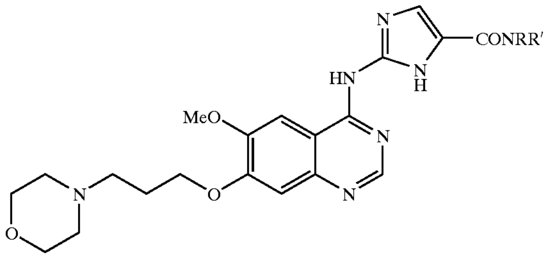

| N° | NRR' |
|---|---|
| 616 | aniline |
| 617 | 4-fluoroaniline |
| 618 | allylamine |

TABLE 26

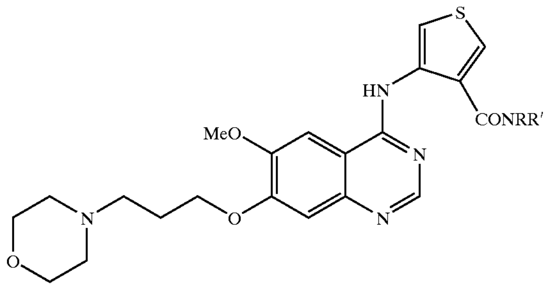

| N° | NRR' |
|---|---|
| 619 | aniline |
| 620 | allylamine |

TABLE 27

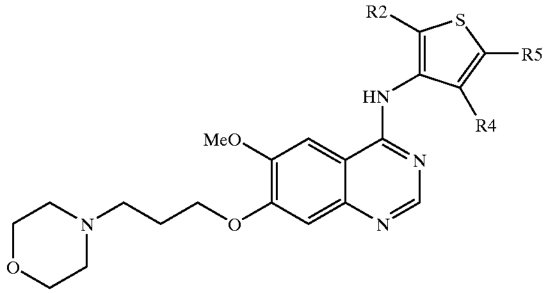

| N° | $R_2$ | $R_4$ | $R_5$ |
|---|---|---|---|
| 621 | COOMe | H | H |

TABLE 28

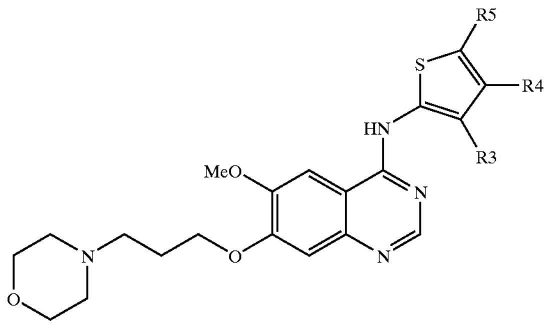

| N° | $R_3$ | $R_4$ | $R_5$ |
|---|---|---|---|
| 622 | CONH2 | H | isopropyl |
| 623 | H | H | COO allyl |
| 624 | CONH2 | H | H |
| 625 | CONH2 | H | ethyl |

TABLE 29

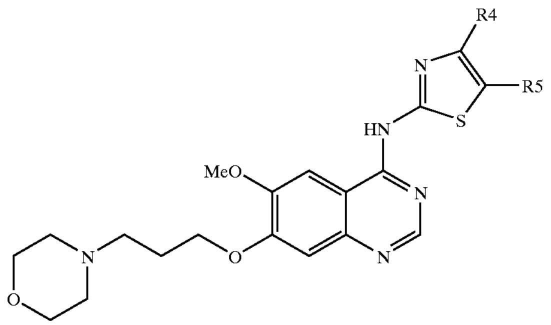

| | R4 | R5 |
|---|---|---|
| 626 | Ph | H |
| 627 | Me | COCH3 |
| 628 | CF3 | COOEt |
| 629 | Ph | COOEt |
| 630 | —(CH2)4— | |
| 631 | 4-acetylaminophenyl | H |
| 632 | CF3 | Ph |
| 633 | CF3 | H |
| 634 | tert-butyl | H |
| 635 | Me | Me |
| 636 | Me | H |
| 637 | Me | —C(=N—OH)-Me |
| 638 | H | —NHCOO-tert-butyl |
| 639 | Me | —C(=NOMe)-Me |
| 640 | Me | —C(=NOPh)-Me |
| 641 | H | 4-methoxyphenyl |
| 642 | H | Ph |
| 643 | H | Et |
| 644 | H | isopropyl |
| 645 | H | —CH2Ph |
| 646 | H | Me |
| 647 | H | n-butyl |
| 648 | H | CHO |
| 649 | H | —CH=N—OH |

TABLE 30

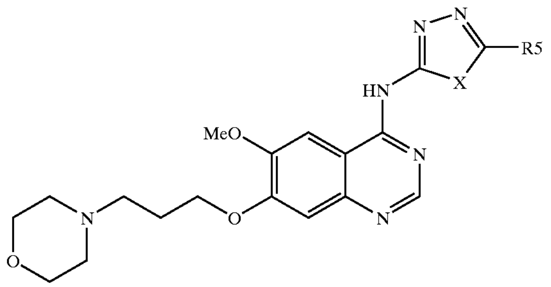

| | X | R5 |
|---|---|---|
| 650 | S | tert-butyl |
| 651 | S | cyclopropyl |
| 652 | S | —S—CH2—CH3 |
| 653 | S | -Ph |
| 654 | NH | —NH-Ph |

Other compounds of Formula (I) or Formula (IA), in particular those in which $R^5$ carries a carboxy or carboxyl ester substituent are described below in the Examples.

Compounds of Formula (I) or Formula (IA) may be prepared by various methods which would be apparent from the literature. For example compounds of formula (I) where X is NH may be prepared by reacting a compound of formula (VII)

(VII)

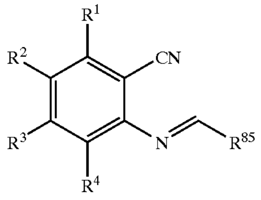

where $R^1$, $R^2$, $R^3$, and $R^4$ are as defined in relation to formula (I) and $R^{85}$ is a group $NR^{86}R^{87}$ where $R^{86}$ and $R^{87}$ are independently selected from alkyl such as methyl, with a compound of formula (VIII)

$$H_2N—R^{5'}$$ (VIII)

where $R^{5'}$ is a group $R^5$ as defined in relation to formula (I) or a precursor group thereof; and thereafter if desired or necessary, converting a precursor group $R^{5'}$ to a group $R^5$ and/or modifying substituents on the group $R^5$. The reaction is suitably effected in an organic solvent such as an acetic acid at elevated temperatures, conveniently at the reflux temperature of the solvent.

Examples of reactions in which a precursor group $R^5$ is converted to a group $R^5$ and/or substituents on the group $R^5$ are modified are standard chemical reactions, such as conversion of esters to acids, and thereafter, if required to the preferred amides. Examples of such reactions are provided hereinafter.

Compounds of formula (VII) are suitably prepared by reacting a compound of formula (IX)

(IX)

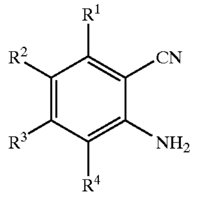

(IX)

with an appropriate acetal such as N,N-dimethylformamide dimethyl acetal. The reaction is suitably effected in an organic solvent such as benzene, at elevated temperature, conveniently at the reflux temperature of the solvent.

Alternatively, compounds of formula (I) where X is NH may be prepared by rearranging a compound of formula (X)

(X)

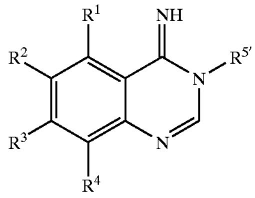

(X)

where $R^1$, $R^2$, $R^3$ and $R^4$ are as defined in relation to formula (I) and $R^{5'}$ is as defined in relation to formula (VIII) above, and thereafter if desired or necessary, converting a precursor group $R^{5'}$ to a group $R^5$ and/or modifying substituents on the group $R^5$, for example as described generally above.

The rearrangement reaction is suitably effected in an organic solvent such as an alkyl alcohol, in particular methanol, ethanol or cyclohexanol, acetic acid, or dimethylformamide, using a strong base such as sodium hydroxide, sodium acetate, sodium methylate, or dimethylamine. Elevated temperatures, for example of from 20°–120° C. and preferably at about 75° C. are employed.

Compounds of formula (X) are suitably obtained by reacting a compound of formula (XI)

(XI)

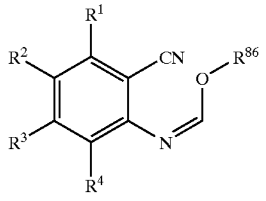

(XI)

where $R^1$, $R^2$, $R^3$ and $R^4$ are as defined in relation to formula (I) and $R^{86}$ is an alkyl group such as methyl; with a compound of formula (XIII)

$$H_2N—R^{5'} \quad (XII)$$

where $R^{5'}$ is as defined in relation to formula (VIII). The reaction is suitably effected in an organic solvent such as methylene chloride, in the presence of a salt such as pyridinium hydrochloride. Moderate temperatures for example of from 0°–50° C. and conveniently ambient temperature are employed.

Compounds of formula (XI) are suitably prepared by reacting a compound of formula (IX) as defined above, with a trialkylorthoformate such as trimethylorthoformate. The reaction is suitably effected at elevated temperature, for example of from 50° C. to 120° C., and preferably at about 100° C., in the presence of a catalytic amount of an acid such as p-toluene sulphonic acid.

Compounds of formula (IX) are either known compounds or they can be prepared by conventional methods. In particular, compounds of formula (IX) may be prepared by reduction of the corresponding nitro compound of formula (XIII)

(XIII)

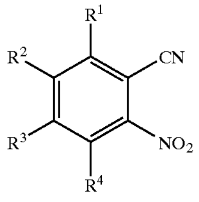

(XIII)

where $R^1$, $R^2$, $R^3$ and $R^4$ are as defined in relation to formula (I). Suitable reaction conditions the illustrated hereinafter.

Compounds of formula (XIII) may be obtained by nitration of a compound of formula (XIV)

(XIV)

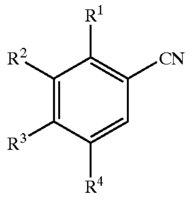

(XIV)

for example, using nitric acid as the nitrating agent. Again, suitable reaction conditions are illustrated hereinafter.

The nitrile of formula (XIV) may be derived by reaction of the corresponding formamide with hydroxylamine as illustrated hereinafter.

Compounds of Formula (I) and Formula (IA) are inhibitors of aurora 2 kinase. As a result, these compounds can be used to treat disease mediated by these agents, in particular proliferative disease.

According to a further aspect of the present invention there is provided a method for inhibiting aurora 2 kinase in a warm blooded animal, such as man, in need of such treatment, which comprises administering to said animal an effective amount of a compound of Formula (I) or Formula (IA), or a pharmaceutically acceptable salt, or an in vivo hydrolysable ester thereof.

Certain compounds of formula (I) are novel and these form a further aspect of the invention. Thus the invention further comprises a compound of formula (IA)

(IA)

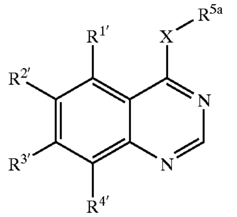

or a salt, ester or amide thereof;

where X is as defined in relation to formula (I);

$R^{1'}$, $R^{2'}$, $R^{3'}$, $R^{4'}$ are equivalent to $R^1$, $R^1$, $R^3$, $R^4$ as defined in relation to formula (I) and $R^{5a}$ is an optionally substituted 5-membered heteroaromatic ring, subject to the following provisos:

(i) that where $R^{5a}$ is a pyrazole group, it carries a substitutent of formula (k), (II) of (VI) above, (ii) that where X is NH and $R^{5a}$ is a substituted pyrazolone or tetrazolyl group, at least one of $R^{1'}$, $R^{2'}$, $R^{3'}$ and $R^{4'}$ is other than hydrogen; or (iii) that where X is O and $R^{5a}$ is 1-methyl-4-nitro-1H-imidazol-5-yl, at least one of $R^{1'}$, $R^{2'}$, $R^{3'}$ and $R^{4'}$ is other than hydrogen.

Preferably at least one of $R^{1'}$, $R^{2'}$, $R^{3'}$ and $R^{4'}$ is other than hydrogen.

Suitably $R^{5a}$ is selected from the groups of sub-formulae (a)–(j) as set out above.

Preferably $R^{5a}$ is pyrrole, imidazole, triazole, thiazole, thiophene, or thiadiazole, any of which may be optionally substituted.

In particular, $R^{5a}$ is substituted by at least one group of formula (k), (U) of (VI) above.

Other preferred or particular groups and substitutents in formula (IA) are as set out for the equivalent groups in formula (I) above.

According to a further aspect of the invention there is provided a compound of the formula (IA) as defined herein, or a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where aurora 2 is upregulated.

The invention also provides a pharmaceutical composition comprising a compound of formula (IA) as defined herein, or a pharmaceutically acceptable salt, or an in vivo hydrolysable ester thereof, in combination with at pharmaceutically acceptable carrier. Preferred or particular compounds of formula (IA) for use in the compositions of the invention are as described above in relation to preferred compounds of formula (I).

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insulation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

A further aspect of the invention comprises a compound of Formula (I) or Formula (IA) as defined above, or a pharmaceutically acceptable salt or in vivo hydrolysable ester thereof, for use in the preparation of a medicament for the treatment of proliferative disease. Preferred compounds of Formula (I) or Formula (IA) for this purpose are as described above.

The following Examples illustrate the invention.

General Scheme 1

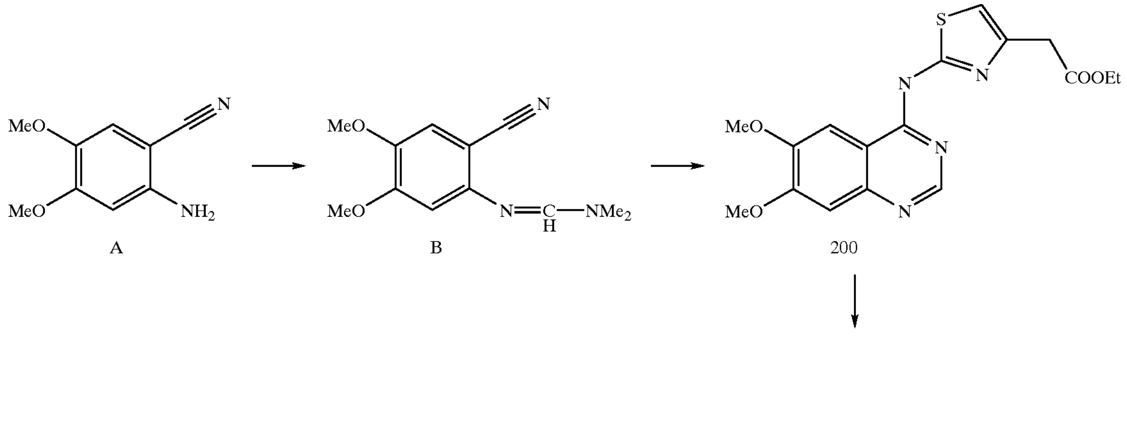

A B 200

-continued

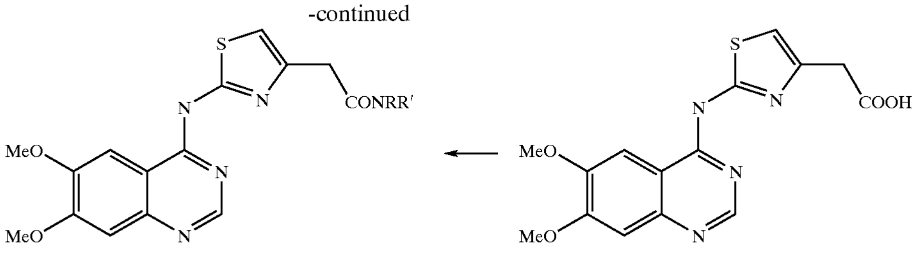

C 201

Compound B

The amino nitrile A (534 mg, 3 mmol) in benzene (15 ml) was reacted with N,N-dimethylformamide dimethyl acetal (535 mg, 4.5 mmol) at 90° C., in a Dean Stark equipped flask. After 4.5 hours reflux, the solution was concentrated, and the residual oil triturated with ether to give the title compound as a solid (680 mg, 90%).

$^1$HNMR ($CDCl_3$): 3.08 (s, 6H); 3.86 (s, 3H); 3.91 (s, 3H); 6.48 (s, 1H); 6.94 (s, 1H); 7.58 (s, 1H).

MS ES$^+$: 234 $(M_+H)^+$

Compound 200

A mixture of amidine B (1.4 g, 6 mmol), ethyl 2-amino-4-thiazoleacetate (1.4 g, 7.5 mmol) in acetic acid (14 ml) was heated at 130° C. for 3 hours. The solvent was removed under vacuum, the residue was triturated in ethanol (5 ml) and a solution of $NaHCO_3$ (pH 8) for 10 minutes. The solid was recovered by filtration, washed with water, dissolved in $CH_2Cl_2$, and dried over $MgSO_4$. $CH_2Cl_2$ was evaporated, the residual oil treated with ether and pet. ether to give title compound (1.8 g, 80%).

$^1$H NMR (DMSO-$d_6$): 1.2 (t, 3H); 3.74 (s, 2H); 3.95 (s, 6H); 4.1 (q, 2H); 7.02 (s, 1H) 7.26 (s, 1H); 8.14 (s, 1H); 8.68 (s, 1H).

Compound 201

Ester 200 (1.8 g, 4.8 mmol) was reacted with 2N NaOH (4.8 ml, 9.6 mmol) in ethanol (20 ml) at room temperature for 2 hours. The mixture was cooled to room temperture, acidified with EtOH, HCl (2N) to pH 3. Stirring was carried on for 15 minutes, and a yellow solid of title compound was recovered by filtration (1.7 g, 100%).

$^1$HNMR (DMSO-$d_6$): 3.71 (s, 2H); 3.96 (s, 3H); 3.97 (s, 3H); 7.11 (s, 1H); 7.28 (s, 1H); 8.3 (brs, 1H); 8.88 (s, 1H).

Synthesis of Amide c, General Procedure

The acid 201 (86.5 mg, 0.25 mmol) in DMF (1 ml) was reacted with various amines (2.6 mmol) in presence of O-(7-azabenzotriazol-lyl) N,N,N',N',-tetramethyluronium hexafluorophosphate (98 mg, 0.26 mmol), DIEA (33 mg, 0.26 mmol) at room temperature for 0.5 hour. A solution of $NaHCO_3$ (1 ml) and water (7 ml) was added to the mixture. The mixture was left overnight, and the precipitated solid was then recovered by filtration, washed with water and dried under vacuum in presence of $P_2O_5$, to give compounds of formula C as listed below.

EXAMPLE 1

Using the reaction described in the General Scheme 1, starting with 4-aminomethyl pyridine (27 mg, 0.25 mmol) yielded Compound No. 1 in Table 1 (50 mg, 46%).

$^1$HNMR (DMSO-$d_6$): 3.64 (s, 2H); 3.95 (s, 3H); 3.96 (s, 3H); 4.32 (d, 2H); 6.98 (s, 1H); 7.26 (m, 3H); 8.15 (s, 1H); 8.49 (m, 3H); 8.68 (s, 1H).

EXAMPLE 2

An analogous reaction to that described in the General Scheme 1, starting with morpholine (23 mg, 0.26 mmol) yielded Compound No 2 in Table 1 (70 mg, 67%).

$^1$HNMR (DMSO-$d_6$, TFA): 3.55 (br m, 8H); 3.88 (s, 2H); 3.97 (s, 3H); 4.0 (s, 3H); 7.15 (s, 1H); 7.27 (s, 1H); 7.92 (s, 1H); 9.07 (s, 1H).

EXAMPLE 3

An analogous reaction to that described in the General Scheme 1, starting with 4-fluoroaniline (29 mg, 0.26 mmol) yielded the Compound No. 3 in Table 1 (75 mg, 68%).

$^1$H NMR (DMSO-$d_6$): 3.74 (s, 2H); 3.93 (s, 6H); 7.00 (s, 1H); 7.15 (t, 2H); 7.25 (s, 1H); 7.64 (m, 2H); 8.12 (s, 1H); 8.67 (s, 1H); 10.20 (s, 1H).

MS ES$^+$: 440 $(M_+H)^+$

EXAMPLE 4

An analogous reaction to that described in the General Scheme 1, starting with N,N-dimethyl-1,4-phenylenediamine (35 mg, 0.26 mmol) yielded Compound 4 in Table 1 (65 mg, 56%).

$^1$HNMR (DMSO-$d_4$, TFA): 3.2 (s, 6H); 3.9 (s, 2H); 3.97 (s, 3H); 4.0 (s, 3H); 7.27 (s, 1H); 7.3 (s, 1H); 7.65 (d, 2H); 7.8 (d, 2H); 7.99 (s, 1H).

MS ES$^+$: 465 $(M_+H)^+$

EXAMPLE 5

An analogous reaction to that described in the General Scheme 1, starting with 4-methoxy-aniline (32 mg, 0.26 mmol) yielded Compound 5 in Table 1 (80 mg, 71%).

$^1$HNMR (DMSO-$d_6$): 3.71 (s, 5H); 3.93 (s, 3H); 3.94, (s, 3H); 6.88 (d, 2H); 6.99 (s, 1H); 7.25 (s, 1H); 7.53 (d, 2H); 8.13 (s, 1H); 8.67 (s, 1H); 9.99 (s, 1H).

MS ES$^+$: 452 $(M_+H)^+$

EXAMPLE 6

An analogous reaction to that described in the General Scheme 1, starting with 5-methoxy-2-methylaniline (36 mg, 0.26 mmol) yielded Compound 6 in Table 1 (87 mg, 75%).

$^1$HNMR (DMSO-$d_6$) 2.13 (s, 3H); 3.69 (s, 3H); 3.81 (s, 2H); 3.96 (s, 6H); 6.65 (m, 1H); 7.05 (m, 1H); 7.09 (d, 1H); 7.21 (s, 1H); 7.26 (s, 1H); 8.13 (s, 1H); 8.68 (s, 1H); 9.3 (s, 1H).

MS ES$^+$: 466 $(M_+H)^+$

EXAMPLE 7

An analogous reaction to that described in the General Scheme 1, starting with aminoacetaldehyde dimethyl acetal (27 mg, 0.26 mmol) yielded Compound 7 in Table 1 (80 mg, 74%).

$^1$HNMR (DMSO-$d_6$): 3.2 (t, 2H); 3.29 (s, 3H); 3.31 (s, 3H); 3.55 (s, 2H); 3.94 (s, 6H); 4.37 (t, 1H); 6.92 (s, 1H); 7.26 (s, 1H); 8.02 (t, 1H); 8.14 (s, 1H); 8.67 (s, 1H).

MS ES$^+$: 434 $(M_+H)^+$

EXAMPLE 8

An analogous reaction to that described in the General Scheme 1, starting with 3-trifluoromethylaniline (42 mg, 0.26 mmol) yielded Compound 8 in Table 1 (72 mg, 59%).

$^1$HNMR (DMSO-$d_6$): 3.80 (s, 2H); 3.93 (s, 3H); 3.94 (s, 3H); 7.04 (s, 1H); 7.26 (s, 1H) 7.41 (d, 1H); 7.55 (t, 1H); 7.81 (d, 1H); 8.13 (s, 1H); 8.69 (s, 1H); 10.50 (s, 1H).

MS ES$^+$: 490 $(M_+H)^+$

EXAMPLE 9

An analogous reaction to that described in General Scheme 1, starting with N-methylpiperazine (26 mg, 0.26 mmol) yielded Compound 9 in Table 1 (65 mg, 61%).

$^1$HNMR (DMSO-$d_6$): 2.73 and 2.77 (two t, 4H); 2.86 and 3.10 (two s, 3H); 3.56 and 3.74 (two t, 4H); 3.79 and 3.84 (two s, 2H); 3.95 (s, 6H); 6.95 (m, 1H); 7.26 (s, 1H); 8.14 (s, 1H); 8.68 (s, 1H).

MS ES$^+$: 429 $(M_+H)^+$

EXAMPLE 10

An analogous reaction to that described in General Scheme 1, starting with 2-methoxyethylamine (20 mg, 0.26 mmol) yielded Compound 10 in Table 1 (68 mg, 67%).

$^1$HNMR (DMSO-$d_6$): 3.25 (s, 3H); 3.3 (m, 6H); 3.54 (s, 2H); 3.94 (s, 6H); 6.92 (s, 1H); 7.26 (s, 1H); 8.0 (t, 1H); 8.14 (s, 1H); 8.67 (s, 1H).

MS ES$^+$: 404 $(M_+H)^+$

EXAMPLE 11

An analogous reaction to that described in General Scheme 1, starting with 2-(2-aminoethyl)-N-methylpyrrole (32 mg, 0.26 mmol) yielded Compound 11 in Table 1 (93 mg, 82%).

$^1$HNMR (DMSO-$d_6$): 3.3 (m, 4H); 3.5 (s, 2H); 3.94 (s, 6H); 5.78 (s, 1H); 5.84 (m, 1H); 6.58 (s, 1H); 6.89 (s, 1H); 7.24 (s, 1H); 8.01 (t, 1H); 8.13 (s, 1H); 8.66 (s, 1H).

MS ES$^+$: 453 $(M_+H)^+$

EXAMPLE 12

An analogous reaction to that described in the General Scheme 1, starting with 3-(methylamino)propionitrile (22 mg, 0.26 mmol) yielded Compound 12 in Table 1 (60 mg, 58%).

$^1$HNMR (DMSO-$d_6$): 2.15 (s, 3H); 3.45 (m, 4H); 3.77 (s, 2H); 3.96 (s, 6H); 6.91 (s, 1H); 7.25 (s, 1H); 8.14 (s, 1H); 8.67 (s, 1H).

MS ES$^+$: 413 $(M_+H)^+$

EXAMPLE 13

An analogous reaction to that described in General Scheme 1, starting with 4-fluorobenzylamine (33 mg, 0.26 mmol) yielded Compound 13 in Table 1 (81 mg, 81%).

$^1$HNMR (DMSO-$d_6$) 3.59 (s, 2H); 3.95 (m, 6H); 4.27 (d, 2H); 6.94 (s, 1H); 7.15 (m, 2H); 7.26 (s, 1H); 7.31 (m, 2H); 7.95 (s, 1H); 8.14 (s, 1H); 8.41 (t, 1H); 8.67 (s, 1H).

MS ES$^+$: 454 $(M_+H)$+

EXAMPLE 14

An analogous reaction to that described in General Scheme 1, starting with 4-hydroxypiperidine (26 mg, 0.26 mmol) yielded Compound 14 in Table 1 (86 mg, 80%).

$^1$HNMR (DMSO-$d_6$): 1.21 (m, 2H); 1.65 (m, 2H); 3.02 (m, 1H); 3.16 (m, 1H); 3.65 (m, 1H); 3.78 (m, 3H); 4.71 (d, 1H); 6.91 (s, 1H); 7.26 (s, 1H); 8.14 (s, 1H); 9.67 (s, 1H).

MS ES$^+$: 430 $(M_+H)^+$

EXAMPLE 15

An analogous reaction to that described in General Scheme 1, starting with 3-aminoacetophenone (35 mg, 0.26 mmol) yielded Compound 15 in Table 1 (92 mg, 79%).

$^1$HNMR (DMSO-$d_6$): 2.59 (s, 3H); 3.78 (s, 2H); 3.90 (s, 3H); 3.93 (s, 3H); 7.02 (s, 1H); 7.26 (s, 1H); 7.47 (t, 1H); 7.67 (d, 1H); 7.89 (d, 1H); 8.12 (s, 1H); 8.2 (s, 1H); 8.68 (s, 1H); 10.36 (s, 1H).

MS ES$^+$: 464 $(M_+H)^+$.

EXAMPLE 16

An analogous reaction to that described in General Scheme 1, starting with 3,5-difluoroaniline (34 mg, 0.26 mmol) yielded Compound 16 in Table 1 (71 mg, 64%).

$^1$HNMR (DMSO-$d_6$, TFA): 3.90 (s, 2H); 3.93 (s, 3H); 3.97 (s, 3H); 6.89 (m, 1H); 7.27 (s, 1H); 7.29 (s, 1H); 7.35 (m, 2H); 7.96 (m, 1H) 9.10 (s, 1H).

MS ES$^+$: 458 $(M_+H)^+$

EXAMPLE 17

An analogous reaction to that described in General Scheme 1, starting with 3-cyanoaniline (31 mg, 0.26 mmol) yielded Compound 17 in Table 1 (90 mg, 84%).

MS ES$^+$: 447 $(M_+H)^+$

EXAMPLE 18

An analogous reaction to that described in General Scheme 1, starting with 2-fluoroaniline (29 mg, 0.26 mmol) yielded Compound 18 in Table 1 (86 mg, 82%).

MS ES$^+$: 440 $(M_+H)^+$

EXAMPLE 19

An analogous reaction to that described in General Scheme 1, starting with 3-(1-hydroxyethyl)aniline (36 mg, 0.26 mmol) yielded Compound 19 in Table 1 (92 mg, 82%).

MS ES$^+$: 466 $(M_+H)^+$

EXAMPLE 20

An analogous reaction to that described in General Scheme 1, starting with 2,3-difluoroaniline (34 mg, 0.26 mmol) yielded Compound 20 in Table 1 (51 mg, 47%).

$^1$HNMR (DMSO-$d_6$, TFA): 3.98 (s, 3H); 4.01 (s, 3H); 4.03 (s, 2H) 7.19 (m, 2H); 7.27 (s, 1H); 7.29 (s, 1H); 7.73 (m, 1H); 7.99 (s, 1H); 9.11 (s, 1H).

MS ES$^+$: 458 $(M_+H)^+$

EXAMPLE 21

An analogous reaction to that described in General Scheme 1, starting with 2-methyl-4 fluoroaniline (33 mg, 0.26 mmol) yielded Compound 21 in Table 1 (94 mg, 86%).

MS ES$^+$: 454 $(M_+H)^+$

EXAMPLE 22

An analogous reaction to that described in General Scheme 1, starting with 2-fluoro-3-chloroaniline (38 mg, 0.26 mmol) yielded Compound 22 in Table 1 (60 mg, 53%).

$^1$HNMR (DMSO-$d_6$, TFA): 3.95 (s, 3H); 3.98 (s, 3H); 4.01 (s, 2H); 7.20 (m, 1H); 7.24 (s, 1H); 7.26 (s, 1H); 7.31 (m, 1H); 7.88 (m, 1H); 7.96 (s, 1H); 9.08 (s, 1H).

MS $ES^+$: 474 $(M_+H)^+$

EXAMPLE 23

An analogous reaction to that described in General Scheme 1, starting with 2,5-difluoroaniline (34 mg, 0.26 mmol) yielded Compound 23 in Table 1 (52 mg, 48%).

$^1$HNMR (DMSO-$d_6$, TFA): 3.97 (s, 3H); 4.00 (s, 2H); 4.01 (s, 3H); 6.97 (m, 1H); 7.26 (s, 1H); 7.29 (s, 1H); 7.33 (m, 1H); 7.94 (m, 1H); 7.98 (s, 1H); 9.11 (s, 1H).

MS $ES^+$: 458 $(M_+H)$+

EXAMPLE 24

An analogous reaction to that described in General Scheme 1, starting with 3-aminobenzamide (36 mg, 0.26 mmol) yielded Compound 24 in Table 1 (94 mg, 84%).

MS $ES^+$: 465 $(M_+H)^+$

EXAMPLE 25

An analogous reaction to that described in General Scheme 1, starting with 4-aminophenol (29 mg, 0.26 mmol) yielded Compound 25 in Table 1 (89 mg, 84%).

$^1$HNMR (DMSO-$d_6$, TFA): 3.81 (s, 2H); 3.97 (s, 3H); 4.00 (s, 3H); 6.71 (d, 2H); 7.23 (s, 1H); 7.27 (s, 1H); 7.40 (d, 2H); 7.95 (s, 1H); 9.09 (s, 1H).

MS $ES^+$: 438 $(M_+H)^+$

EXAMPLE 26

An analogous reaction to that described in General Scheme 1, starting with 2-fluoro-5-methylaniline (33 mg, 0.26 mmol) yielded Compound 26 in Table 1 (88 mg, 81%).

MS $ES^+$: 454 $(M_+H)^+$

EXAMPLE 27

An analogous reaction to that described in General Scheme 1, starting with 2-bromo-4-fluoroaniline (50 mg, 0.26 mmol) yielded Compound 27 in Table 1 (68 mg, 55%).

$^1$HNMR (DMSO-$d_6$, TFA): 3.89 (s, 2H); 3.94 (s, 3H); 3.97 (s, 3H); 7.21 (m, 1H); 7.25 (s, 1H); 7.6 (s, 1H); 7.61 (m, 1H); 7.92 (m, 1H); 7.95 (s, 1H); 9.07 (s, 1H).

MS $ES^+$: 518, 520 $(M_+H)^+$

EXAMPLE 28

An analogous reaction to that described in General Scheme 1, starting with 3,4-difluoroaniline (34 mg, 0.26 mmol) yielded Compound 28 in Table 1 (81 mg, 74%).

MS $ES^+$: 458 $(M_+H)^+$

EXAMPLE 29

An analogous reaction to that described in General Scheme 1, starting with isonipecotamide (34 mg, 0.26 mmol) yielded Compound 29 in Table 1 (96 mg, 88%).

MS $ES^+$: 457 $(M_+H)^+$

EXAMPLE 30

An analogous reaction to that described in General Scheme 1, starting with 4-trifluoromethoxyaniline (47 mg, 0.26 mmol) yielded Compound 30 in Table 1 (105 mg, 87%).

MS $ES^+$: 506 $(M_+H)^+$

EXAMPLE 31

An analogous reaction to that described in General Scheme 1, starting with 5-amino-2-methoxypyridine (33 mg, 0.26 mmol) yielded Compound 31 in Table 1 (86 mg, 79%).

MS $ES^+$: 453 $(M_+H)^+$

EXAMPLE 32

An analogous reaction to that described in General Scheme 1, starting with 2,4-difluoroaniline (34 mg, 0.26 mmol) yielded Compound 32 in Table 1 (81 mg, 74%).

MS $ES^+$: 458 $(M_+H)^+$

EXAMPLE 33

An analogous reaction to that described in General Scheme 1, starting with 4-aminoresorcinol hydrochloride (43 mg, 0.26 mmol) yielded Compound 33 in Table 1 (84 mg, 77%).

MS $ES^+$: 454 $(M_+H)^+$

EXAMPLE 34

An analogous reaction to that described in General Scheme 1, starting with 3-aminopyridine (25 mg, 0.26 mmol) yielded Compound 34 in Table 1 (101 mg, 100%).

MS $ES^+$: 423 $(M_+H)^+$

EXAMPLE 35

An analogous reaction to that described in General Scheme 1, starting with 4-chloroaniline (34 mg, 0.26 mmol) yielded Compound 35 in Table 1 (109 mg, 100%).

MS $ES^+$: 456, 458 $(M_+H)^+$.

EXAMPLE 36

An analogous reaction to that described in General Scheme 1, starting with pyrrolidine (19 mg, 0.26 mmol) yielded Compound 36 in Table 1 (33 mg, 35%).

MS $ES^+$: 400 $(M_+H)^+$

EXAMPLE 37

An analogous reaction to that described in General Scheme 1, starting with 3-methoxyaniline (33 mg, 0.26 mmol) yielded Compound 37 in Table 1 (94 mg, 87%).

$^1$HNMR (DMSO-$d_6$, TFA): 3.72 (s, 3H); 3.87 (s, 2H); 3.96 (s, 3H); 4.0 (s, 3H); 6.64 (m, 1H); 7.14 (d, 1H); 7.21 (d, 1H); 7.22 (s, 1H); 7.24 (s, 1H); 7.27 (s, 1H); 7.95 (s, 1H); 9.09 (s, 1H).

MS $ES^+$: 452 $(M_+H)^+$

EXAMPLE 38

An analogous reaction to that described in General Scheme 1, starting with 3-hydroxy-4 methoxyaniline (37 mg, 0.26 mmol) yielded Compound 38 in Table 1 (95 mg, 85%).

MS $ES^+$: 468 $(M_+H)^+$

EXAMPLE 39

An analogous reaction to that described in General Scheme 1, starting with 3-nitroaniline (36 mg, 0.26 mmol) yielded Compound 39 in Table 1 (87 mg, 78%).

MS $ES^+$: 467 $(M_+H)^+$

EXAMPLE 40

An analogous reaction to that described in General Scheme 1, starting with 1-methyl-3-nitroaniline (40 mg, 0.26 mmol) yielded Compound 40 in Table 1 (50 mg, 44%).

MS $ES^+$: 481 $(M_+H)^+$

EXAMPLE 41

An analogous reaction to that described in General Scheme 1, starting with 2-anilinoethanol (36 mg, 0.26 mmol) yielded Compound 41 in Table 1 (45 mg, 41%).

MS $ES^+$: 466 $(M_+H)^+$

EXAMPLE 42

An analogous reaction to that described in General Scheme 1, starting with 4-trifluoromethylaniline (43 mg, 0.26 mmol) yielded Compound 42 in Table 1 (86 mg, 73%).

MS $ES^+$: 490 $(M_+H)^+$

EXAMPLE 43

An analogous reaction to that described in General Scheme 1, starting with 3-amino-6-chloropyridine (33 mg, 0.26 mmol) yielded Compound 43 in Table 1 (90 mg, 82%).

$^1$HNMR (DMSO-$d_6$, TFA): 3.92 (s, 2H); 3.96 (s, 3H); 4.0 (s, 3H); 7.27 (s, 1H); 7.28 (s, 1H); 7.46 (d, 1H); 7.98 (s, 1H); 8.1 (d, 1H); 8.65 (d, 1H); 9.1 (s, 1H).

MS $ES^+$: 457,459 $(M_+H)^+$

EXAMPLE 44

An analogous reaction to that described in General Scheme 1, starting with 2-methoxy-5-chloroaniline (42 mg, 0.26 mmol) yielded Compound 44 in Table 1 (90 mg, 77%).

MS $ES^+$: 486, 488 $(M_+H)^+$

EXAMPLE 45

An analogous reaction to that described in General Scheme 1, starting with 2-methylaminoethanol (20 mg, 0.26 mmol) yielded Compound 45 in Table 1 (83 mg, 86%).

MS $ES^+$: 404 $(M_+H)^+$

EXAMPLE 46

An analogous reaction to that described in General Scheme 1, starting with 4-aminopyridine (25 mg, 0.26 mmol) yielded Compound 46 in Table 1 (101 mg, 100%).

MS $ES^+$: 423 $(M_+H)^+$

EXAMPLE 47

An analogous reaction to that described in General Scheme 1, starting with 3-methyl-4-bromoaniline (49 mg, 0.26 mmol) yielded Compound 47 in Table 1 (120 mg, 97%).

MS $ES^+$: 516,517 $(M_+H)^+$

EXAMPLE 48

An analogous reaction to that described in General Scheme 1, starting with 2-chloro-5-methoxyaniline (42 mg, 0.26 mmol) yielded Compound 48 in Table 1 (65 mg, 56%).

$^1$HNMR (DMSO-$d_6$, TFA): 3.73 (s, 2H); 3.98 (m, 9H); 6.78 (m, 1H); 7.28 (s, 2H); 7.39 (d, 1H); 7.50 (d, 1H); 7.98 (s, 1H); 9.10 (s, 1H).

MS $ES^+$: 486, 488 $(M_+H)^+$

EXAMPLE 49

An analogous reaction to that described in General Scheme 1, starting with 4-aminotoluene (28 mg, 0.26 mmol) yielded Compound 49 in Table 1 (89 mg, 85%).

MS $ES^+$: 436 $(M_+H)^+$

EXAMPLE 50

An analogous reaction to that described in General Scheme 1, starting with R(−)-2-pyrrolidinemethanol (27 mg, 0.26 mmol) yielded Compound 50 in Table 1 (81 mg, 78%).

MS $ES^+$: 430 $(M_+H)^+$

EXAMPLE 50A

Preparation of Compound 202

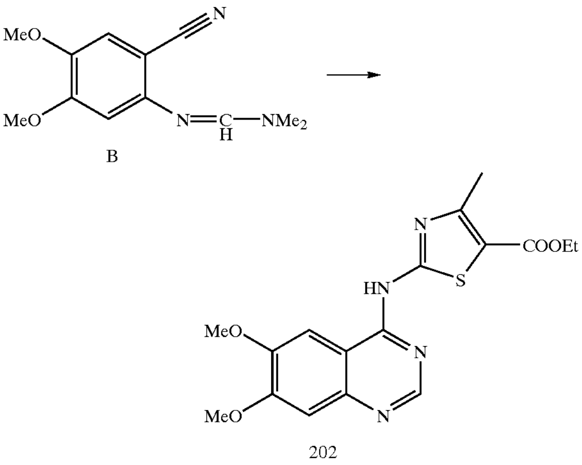

Amidine B (117 mg, 0.5 mmol) in acetic acid (12 ml) was reacted with ethyl-2-amino-4-methylthiazol-5-carboxylate (112 mg, 0.6 mmol) at 130° C. for 3 hours. The solvent was evaporated, the residue was taken up into ethanol, and stirred for 10 minutes with a solution of $NaHCO_3$. The solid was recovered by filtration, washed with water, ether and dried under vacuum, to give title compound as a yellow solid (157 mg, 84%).

$^1$HNMR (DMSO-$d_6$): 1.31 (t, 31); 2.6 (s, 3H); 3.96 (s, 6H); 4.27 (q, 2H); 7.28 (s, 1H); 8.11 (s, 1H); 8.77 (s, 1H).

MS $ES^+$: 375 $(M_+H)^+$

General Scheme 2

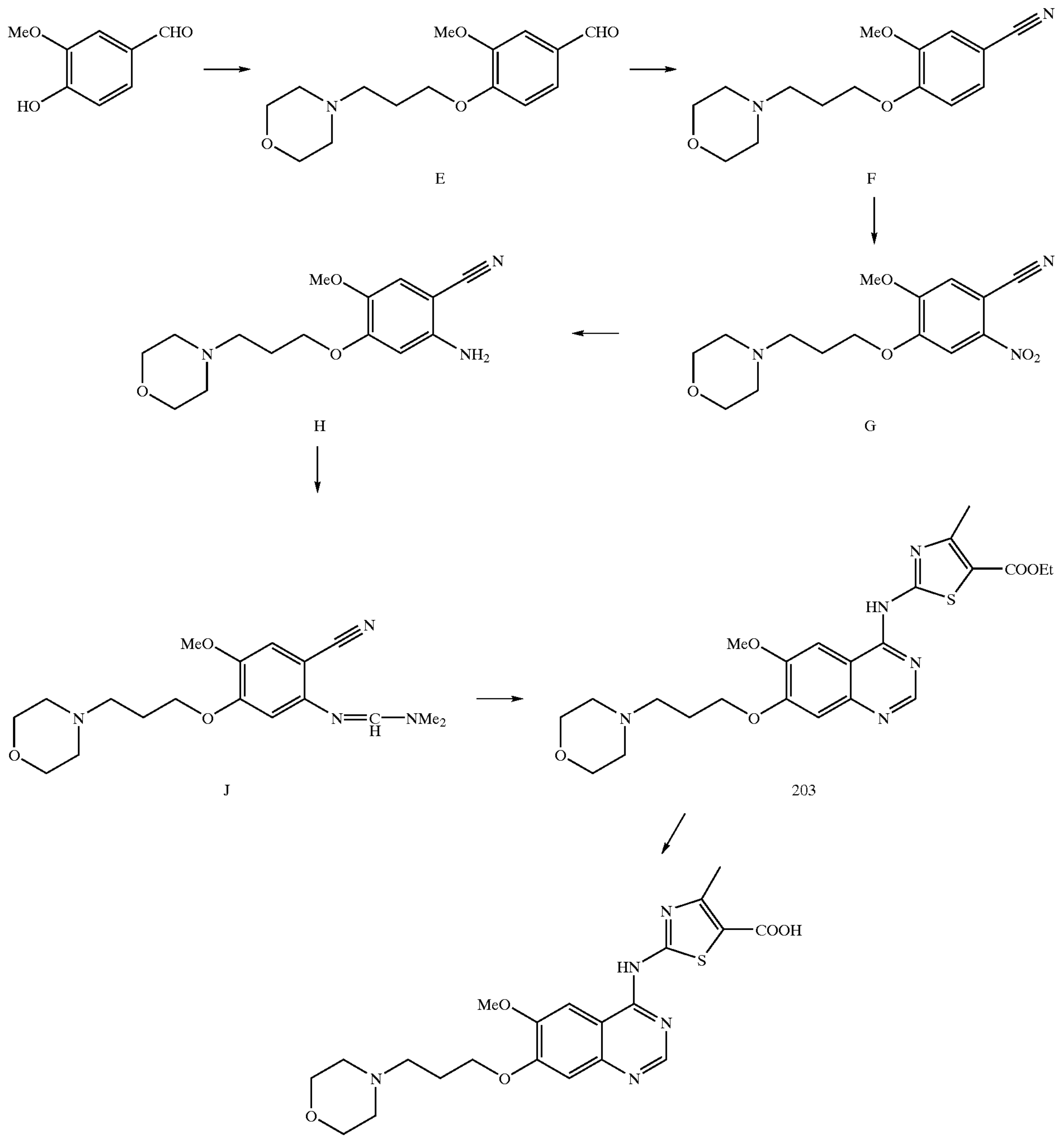

E F G H J 203 204

Compound E

Vanilline (30.4 g, 0.2 mol) was solubilized in DMF (200 ml) in presence of $K_2CO_3$ at 50° C. N-(3-chloropropyl) morpholine was slowly added over 30 minutes to this mixture, which was heated over night at 80° C. Formed KCl was removed by filtration, the solvent was evaporated, and the residual orange oil dissolved in AcOEt, washed with water 2×, dried over $MgSO_4$, filtered and concentrated. The residual oil crystallises to give title compound as a white solid (45.6 g, 82%).

$^1$HNMR (DMSO-$d_6$, TFA): 2.22 (m, 2H); 3.13 (t, 2H); 3.32 (t, 2H); 3.52 (d, 2H); 3.67 (t, 2H); 3.84 (s, 3H); 4.02 (d, 2H); 4.18 (t, 2H); 7.20 (d, 1H); 7.43 (d, 1H); 7.58 (d, 1H); 9.90 (s, 1H).

MS ES$^+$: 280 $(M_+H)^+$

Compound F

The aldehyde E (5.6 g, 20 mmol) was added to a solution of sodium acetate (3.3 g, 40 mmol) and hydroxylamine hydrochloride (2.8 g, 40 mmol) in acetic acid (25 ml). The mixture was refluxed for 18 hours, cooled, diluted with water and extracted with methylene chloride, dried over $MgSO_4$, filtered, concentrated, to give title compound (5.1 g, 93%).

$^1$HNMR ($DMSO-d_6$, TFA): 2.19 (m, 2H); 3.12 (t, 2H); 3.29 (t, 2H); 3.50 (d, 2H); 3.67 (t, 2H); 3.81 (s, 3H); 4.01 (d, 2H); 4.15 (t, 2H); 7.12 (d, 1H); 7.39 (s, 1H); 7.41 (d, 1H).

MS $ES^+$: 277 $(M_+H)^+$

Compound G

The nitrile F (37.2 g, 135 mmol) in acetic acid (100 ml) was added to a solution of nitric acid (d=1.42) 180 ml, at such a rate to maintain the temperature below 30° C. The mixture was stirred at room temperature over night. A solution of potassium hydroxide (10N, 370 ml) was then added slowly to the solution at 0° leading to a final pH of 11–12. The reaction was extracted with $CH_2Cl_2$, the organic phases were dried over $MgSO_4$, filtered, evaporated to give a yellow solid which was washed with ether, dried to give title compound (22 g, 50%).

$^1$HNMR ($DMSO-d_6$, TFA): 2.2 (m, 2H); 3.13 (t, 2H); 3.3 (t, 2H); 3.53 (d, 2H); 3.67 (t, 2H); 3.99 (s, 3H); 4.01 (d, 2H); 4.31 (t, 2H); 7.74 (s, 1H); 7.90 (s, 1H).

Compound H

Compound G (21 g, 65 mmol) in solution in $CH_2Cl_2$ (250 ml), was reacted with sodium hydrosulfite (92 g, 458 mmol) in solution in water (250 ml) in presence of tetrabutyl ammonium chloride (12.7 g, 45.8 mmol) at room temperature, over night. Sodium hydroxide (2N) was then added, and the reaction mixture was extracted with $CH_2Cl_2$, the organic phase was washed with water, dried over $MgSO_4$, filtered, evaporated. The residue was purified by silica gel chromatography, eluent: AcOEt/$CH_2Cl_2$: 50/50 followed by MeOH/AcOEt/$CH_2Cl_2$ 5/45/1950 to 20/30/50 to give title compound (12.5 g, 66%).

$^1$HNMR ($DMSO-d_6$, TFA): 2.2 (m, 2H); 3.13 (t, 2H); 3.31 (t, 2H); 3.53 (d, 2H); 3.68 (t, 2H); 3.71 (s, 3H); 4.05 (m, 4H); 6.56 (s, 1H); 7.02 (s, 1H).

MS $ES^+$: 292 $(M_+H)^+$

Compound J

The amino nitrile H (2.91 g, 10 mmol) in solution in toluene (50 ml) was reacted with N,N-dimethylformamide dimethyl acetal (1.79 g, 15 mmol), at 105° C. for 5 hours, in a Dean Stark equipped flask. The solvent was evaporated, the residue triturated with ether to give title compound (3.4 g, 98%).

$^1$HNMR ($DMSO-d_6$): 1.87 (m, 2H); 2.36 (m, 6H); 2.95 (s, 3H); 3.04 (s, 3H); 3.56 (t, 4H); 3.72 (s, 3H); 4.06 (t, 2H); 6.72 (s, 1H); 7.07 (s, 1H); 7.89 (s, 1H).

MS $ES^+$: 347 $(M_+H)^+$

Compound 203

Amidine J (173 mg, 0.5 mmol) was dissolved in AcOH (1.7 ml) in presence of ethyl-2-amino-4-methyl thiazole-5-carboxylate (112 mg, 0.6 mmol) and heated at 130° C. for 3 hours. The solvent was removed by evaporation, and the residual solid was stirred in ethanol and a diluted solution of $NaHCO_3$ for 10 minutes. The solid was washed with water, dried over $P_2O_5$ under vacuum, to give a yellow powder of title compound (170 mg, 70%).

$^1$HNMR ($DMSO-d_6$, TFA) 1.32 (t, 3H); 2.30 (m, 2H); 2.68 (s, 3H); 3.16 (t, 2H); 3.35 (t, 2H); 3.54 (d, 2H); 3.68 (t, 2H); 3.99 (s, 3H); 4.03 (d, 2H); 4.32 (m, 4H); 7.38 (s, 1H); 8.01 (s, 1H); 9.26 (s, 1H).

MS $ES^+$: 488 $(M_+H)$+

Compound 204

The ester 203 (122 mg, 0.25 mmol) was suspended in ethanol (5 ml) and reacted with sodium hydroxide (10N, 0.5 ml) at 80° C. for 1 hour. The reaction mixture was cooled, acidified (pH 3.5), the yellow precipitate was filtered, washed with water, dried under vacuum, to give title compound (100 mg, 87%).

$^1$HNMR ($DMSO-d_6$, TFA): 2.32 (m, 2H); 2.62 (s, 3H); 3.16 (t, 2H); 3.36 (t, 2H); 3.57 (d, 2H); 3.71 (t, 2H); 3.99 (s, 3H); 4.03 (d, 2H); 4.33 (t, 2H); 7.35 (s, 1H); 7.98 (s, 1H); 9.23 (s, 1H).

MS $ES^+$: 460 $(M_+H)^+$

General Scheme 3

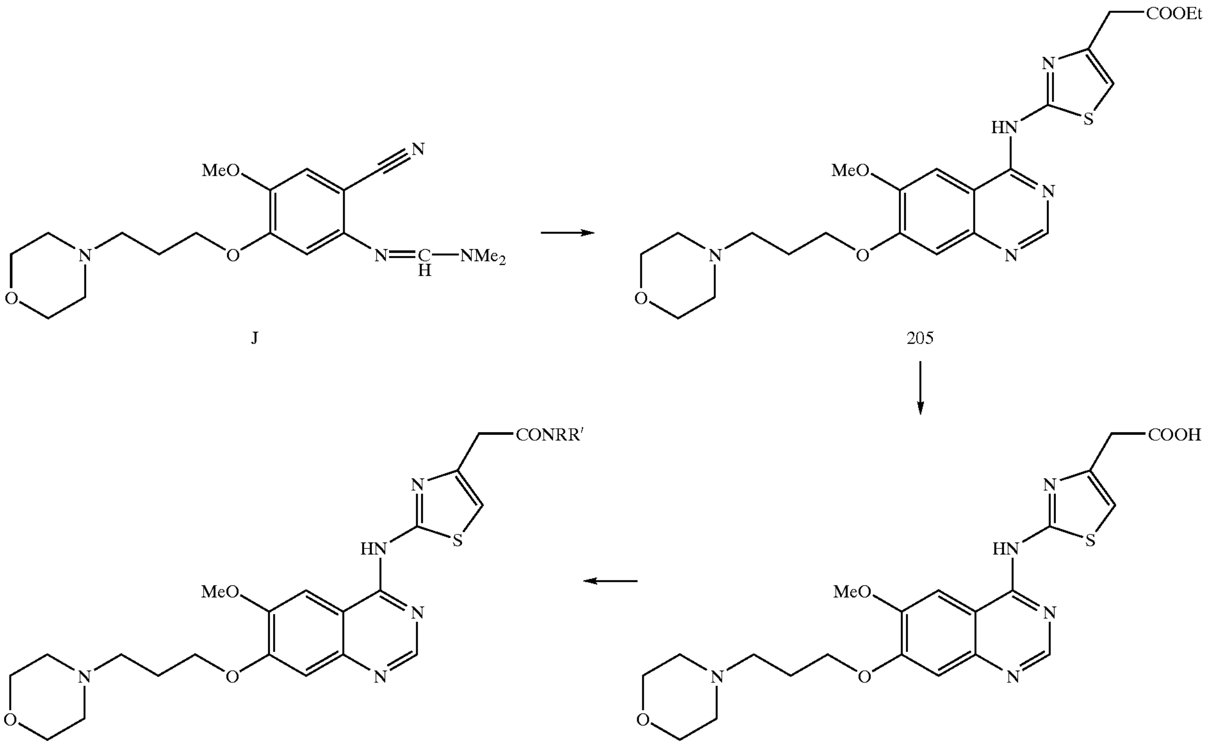

J

205

206

K

Compound 205

Amidine J (2.08 g, 6 mmol) was reacted with ethyl 2-amino-4-thiazolacetate (1.34 g, 7.2 mmol) in acetic acid (2 ml) at 130° C. for 4 hours, under argon. The solvent was evaporated, the residual oil was triturated in ether/petr. ether, and the solid filtered. This solid was suspended in water at pH 9 ($NaHCO_3$) and extracted with $CH_2Cl_2$, dried, evaporated, to give title compound (2 g, 68%).

$^1$HNMR (DMSO-$d_6$, TFA): 2.3 (m, 2H); 3.16 (t, 2H); 3.36 (t, 2H); 3.56 (d, 2H); 3.69 (t, 2H); 3.87 (s, 2H); 4.0 (s, 3H); 4.04 (d, 2H); 4.15 (q, 2H); 4.31 (t, 2H); 7.28 (s, 1H); 7.34 (s, 1H); 8.06 (s, 1H); 9.15 (s, 1H).

MS ES$^+$: 488 ($M^+H$)+

Compound 206

Ester 205 (2 g, 4.1 mmol) was suspended in ethanol (20 ml). 2N sodium hydroxide (4.1 ml, 8.2 mmol) was added to the suspension which was stirred for 3 hours at room temperature. HCl 2N was added to the solution, the yellow precipitate was filtered, washed with water, ethanol, ether and dried under vacuum, to give title compound (1.98 g, 99%).

$^1$HNMR (DMSO-$d_6$, TFA): 2.31 (m, 2H); 3.16 (t, 2H); 3.55 (d, 2H); 3.71 (t, 2H); 3.79 (s, 2H); 4.0 (s, 3H); 4.03 (d, 2H); 4.31 (t, 2H); 7.25 (s, 1H); 7.34 (s, 1H); 8.01 (s, 1H); 9.12 (s, 1H).

MS ES$^+$: 460 ($M_+H$)$^+$

Synthesis of Amides K, General Procedure

The acid 206 (83 mg, 0.17 mmol) in DMF (0.8 ml) was reacted with amine (0.17 mmol) in presence of O-(7-azabenzotriazol-1-yl)N,N,N',N'-tetramethyluronium hexafluorophosphate (78 mg, 0.204 mmol), DIEA (52 mg, 0.4 mmol), for 6 hours at room temperature. The reaction mixture was then treated with a solution of $NaHCO_3$ (6 ml) with stirring for 2 hours, washed with water, cooled to 5° C., and the solid filtered, triturated with ether, dried under vacuum over P2O5 to give title compounds.

EXAMPLE 51

An analogous reaction to that described in General Scheme 3, starting with aniline (19 mg, 0.2 mmol) yielded Compound 51 in Table 2 (73 mg, 81%).

$^1$HNMR (DMSO-$d_6$, TFA): 2.29 (m, 2H); 3.16 (t, 2H); 3.35 (t, 2H); 3.54 (d, 2H); 3.68 (t, 2H); 3.88 (s, 2H); 3.98 (s, 3H); 4.03 (d, 2H); 4.3 (t, 2H); 7.09 (t, 1H); 7.27 (s, 1H); 7.33 (m, 3H); 7.63 (d, 2H); 7.99 (s, 1H); 9.12 (s, 1H).

MS ES$^+$: 535 ($M_+H$)$^+$.

EXAMPLE 52

An analogous reaction to that described in General Scheme 3, starting with 4-fluoroaniline (23 mg, 0.2 mmol) yielded Compound 52 in Table 2 (79 mg, 84%).

$^1$HNMR (DMSO-$d_6$-TFA): 2.29 (m, 2H); 3.15 (t, 2H); 3.34 (t, 2H); 3.54 (d, 2H); 3.67 (t, 2H); 3.87 (s, 2H); 3.98 (s, 3H); 4.02 (d, 2H); 4.3 (t, 2H); 7.17 (t, 2H); 7.27 (s, 1H); 7.32 (s, 1H); 7.63 (m, 2H); 7.99 (s, 1H); 9.11 (s, 1H).

MS ES$^+$: 553 ($M_+H$)$^+$.

EXAMPLE 53

An analogous reaction to that described in General Scheme 3, starting with 4-dimethylaminoaniline (28 mg, 0.2 mmol) yielded Compound 53 in Table 2 (52 mg, 53%).

$^1$HNMR (DMSO-$d_6$-TFA): 2.3 (m, 2H); 3.15 (t, 2H); 3.19 (s, 6H); 3.34 (t, 2H); 3.54 (d, 2H); 3.68 (t, 2H); 3.91 (s, 2H); 3.98 (s, 3H); 4.03 (d, 2H); 4.30 (t, 2H); 7.28 (s, 1H); 7.33 (s, 1H); 7.64 (d, 1H); 7.77 (d, 1H); 8.01 (s, 1H); 9.12 (s, 1H).

MS ES$^+$: 578 ($M_+H$)$^+$

EXAMPLE 54

An analogous reaction to that described in General Scheme 3, starting with 4-chloroaniline (26 mg, 0.2 mmol) yielded Compound 54 in Table 2 (72 mg, 75%).

$^1$HNMR (DMSO-$d_6$, TFA): 2.31 (m, 2H); 3.14 (t, 2H); 3.35 (t, 2H); 3.54 (d, 2H); 3.68 (t, 2H); 3.89 (s, 2H); 3.98 (s, 3H); 4.03 (d, 2H); 4.3 (t, 2H); 7.27 (s, 1H); 7.32 (s, 1H); 7.38 (d, 1H); 7.65 (d, 1H); 8.0 (s, 1H); 9.12 (s, 1H).

MS ES$^-$: 567, 569 ($M^-H$)$^-$.

EXAMPLE 55

An analogous reaction to that described in General Scheme 3, starting with 3-amino-6-chloropyridine (26 mg, 0.2 mmol) yielded Compound 55 in Table 2 (80 mg, 83%).

$^1$HNMR (DMSO-$d_6$, TFA): 2.28 (m, 2H); 3.16 (t, 2H) 3.35 (t, 2H); 3.55 (d, 2H); 3.68 (t, 2H); 3.93 (s, 2H); 3.98 (s, 3H); 4.04 (d, 2H); 4.3 (t, 2H); 7.29 (s, 1H); 7.33 (s, 1H); 7.49 (d, 1H); 8.01 (s, 1H); 8.09 (d, 1H); 8.66 (d, 1H); 9.13 (s, 1H).

MS ES$^+$: 570, 572 ($M_+H$)$^+$.

EXAMPLE 56

An analogous reaction to that described in General Scheme 3, starting with morpholine (18 mg, 0.2 mmol) yielded Compound 56 in Table 2 (14 mg, 16%).

$^1$HNMR (DMSO-$d_6$, TFA): 2.3 (m, 2H); 3.17 (t, 2H); 3.37 (t, 2H); 3.6 (m, 12H); 3.9 (s, 2H); 3.99 (s, 3H); 4.03 (d, 2H); 4.3 (t, 2H); 7.17 (s, 1H); 7.3 (s, 1H); 7.95 (s, 1H); 9.09 (s, 1H).

MS ES$^+$: 529 ($M_+H$)+

EXAMPLE 57

An analogous reaction to that described in General Scheme 3, starting with pyrrolidine (14 mg, 0.2 mmol) yielded Compound 57 in Table 2 (73 mg, 84%).

$^1$HNMR (DMSO-$d_6$, TFA): 1.82 (m, 2H); 1.93 (m, 2H); 2.28 (m, 2H); 3.16 (t, 2H); 3.36 (m, 4H); 3.55 (m, 4H); 3.68 (t, 2H); 3.71 (s, 2H); 3.99 (s, 3H); 4.04 (d, 2H); 4.3 (t, 2H); 7.17 (s, 1H); 7.3 (s, 1H); 7.94 (s, 1H); 9.08 (s, 1H).

MS ES$^+$: 513 ($M_+H$)$^+$

EXAMPLE 58

An analogous reaction to that described in General Scheme 3, starting with cyclohexylamine (20 mg, 0.2 mmol) yielded Compound 58 in Table 2 (80 mg, 87%).

$^1$HNMR (DMSO-$d_6$, TFA): 1.25 (m, 4H); 1.75 (m, 4H); 2.3 (m, 2H) 3.15 (t, 2H); 3.35 (t, 2H); 3.56 (d, 2H); 3.6 (s, 2H); 3.69 (t, 2H); 3.99 (s, 3H); 4.04 (d, 2H); 4.3 (t, 2H); 7.15 (s, 1H); 7.97 (s, 1H); 9.09 (s, 1H);

MS ES$^+$: 541 ($M_+H$)$^+$

General Scheme 4

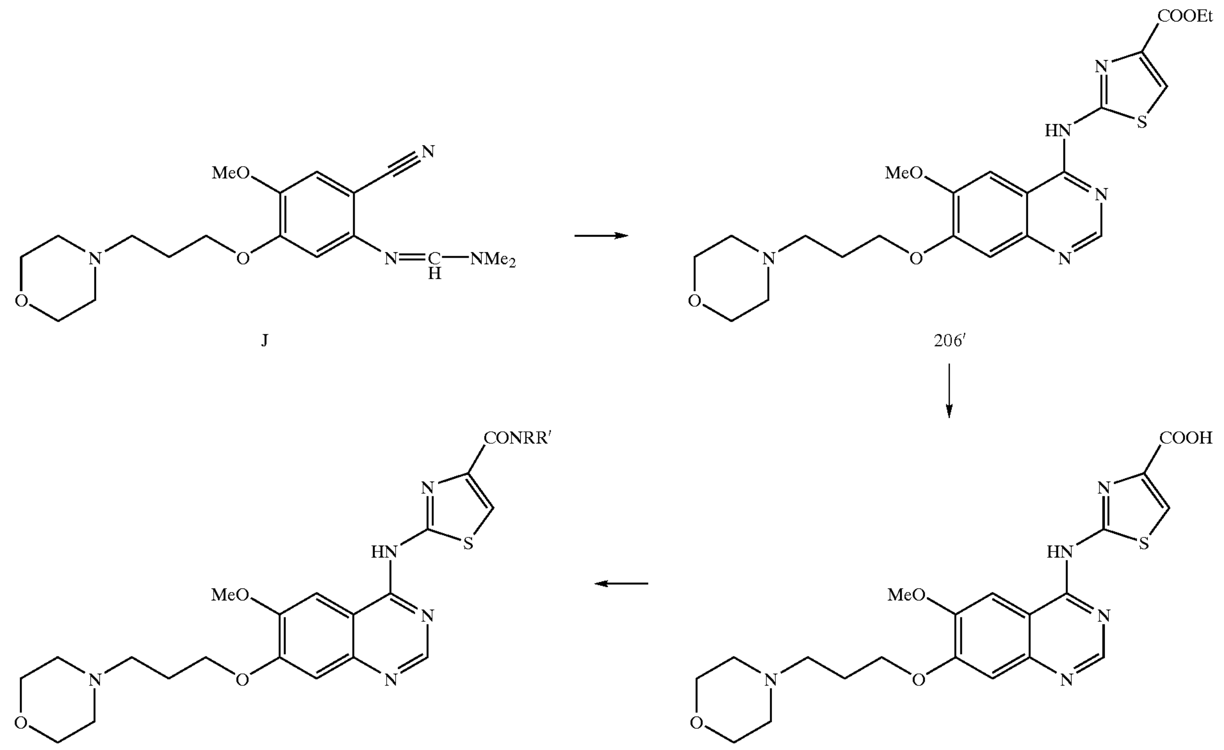

J, 206', 207, M

Compound 206[1]

The amidine J (1.38 g, 4 mmol) in acetic acid (14 ml) was reacted with ethyl 2-amino-4-thiazolcarboxylate (0.72 g, 4.2 mmol) at 130° C. for 6 hours. The solvent was evaporated, the residue dissolved in ethanol, and stirred with a saturated solution of $NaHCO_3$. The mixture was extracted with $CH_2Cl_2$, dried, and purified by silica gel chromatography, eluent $CH_2Cl_2$% MeOH 98/2→90/10, to give title compound (0.738 g, 52%).

$^1$HNMR (DMSO-$d_6$, TFA): 1.34 (t, 3H); 2.28 (m, 2H); 3.16 (t, 2H); 3.35 (t, 2H); 3.55 (d, 2H); 3.68 (t, 2H); 4.03 (s, 3H); 4.04 (d, 2H); 4.34 (m, 4H); 7.45 (s, 1H); 8.33 (s, 1H); 8.44 (s, 1H); 9.26 (s, 1H).

MS $ES^+$: 474 $(M_+H)^+$

Compound 207

Ester 206[1] (946 mg, 2 mmol) in suspension in ethanol (20 ml) was treated with sodium hydroxide (6N, 4 ml) at 75° C. for 45 minutes. The reaction mixture was then cooled to room temperature, acidified (pH 3) with 6N HCl. The precipitate was filtered, washed with ethanol, triturated with ether, dried under vacuum, to give title compound (795 mg, 80%).

$^1$HNMR (DMSO-$d_6$, TFA): 2.34 (m, 2H); 3.15 (t, 2H); 3.35 (t, 2H); 3.54 (d, 2H); 3.76 (t, 2H); 4.03 (m, 5H); 4.35 (t, 2H); 7.48 (s, 1H); 8.26 (s, 1H); 8.41 (s, 1H); 9.29 (s, 1H).

Synthesis of Amides of General Structure M, General Procedure

The acid 207 (79 mg, 0.16 mmol) in DMF (1 ml) was reacted with amine (0.19 mmol) in presence of O-(7-azabenzotriazol-1-yl)N,N,N',N'-tetramethyluronium hexafluorophosphate (73 mg, 0.19 mmol), DIEA (52 mg, 0.4 mmol), for 1 hour at room temperature. The reaction mixture was then treated with a solution of $NaHCO_3$ (5 ml) with stirring for 0.5 hour, and the solid filtered, dried under vacuum over $P_2O_5$. For the compounds which did not precipitate, the solution was concentrated to dryness, the residues were washed with methylene chloride/methanol, filtered. Alumine was added to the methylene chloride/methanol solution and the solvent evaporated. Purification of the compounds was carried out by chromatography over alumine, eluent $CH_2Cl_2$; $CH_2Cl_2$/MeOH: 95/5, to give title compounds.

EXAMPLE 59

An analogous reaction to that described in General Scheme 4, starting with aniline (18 mg, 0.19 mmol) yielded Compound 59 in Table 3 (50 mg, 60%).

$^1$HNMR (DMSO-$d_6$, TFA): 2.3 (m, 2H); 3.16 (t, 2H); 3.36 (t, 2H); 3.55 (d, 2H); 3.69 (t, 2H); 4.03 (d, 2H); 4.05 (s, 3H); 4.34 (t, 2H); 7.14 (t, 1H); 7.39 (t, 2H); 7.45 (s, 1H); 7.8 (d, 2H); 8.29 (s, 1H); 8.41 (s, 1H); 9.29 (s, 1H).

MS $ES^+$: 521 $(M_+H)^+$.

EXAMPLE 60

An analogous reaction to that described in General Scheme 4, starting with 4-fluoroaniline (21 mg, 0.19 mmol) yielded Compound 60 in Table 3 (70 mg, 82%).

$^1$HNMR (DMSO-$d_6$, TFA): 2.3 (m, 2H); 3.16 (t, 2H); 3.33 (t, 2H); 3.56 (d, 2H); 3.68 (t, 2H); 4.03 (d, 2H); 4.04 (s, 3H); 4.35 (t, 2H); 7.22 (t, 2H); 7.45 (s, 1H); 7.83 (m, 2H); 8.28 (s, 1H); 8.4 (s, 1H); 9.27 (s, 1H).

MS $ES^+$: 539 $(M_+H)^+$

EXAMPLE 61

An analogous reaction to that described in General Scheme 4, starting with 4-chloroaniline (24 mg, 0.19 mmol) yielded Compound 61 in Table 3 (70 mg, 79%).

$^{1}$HNMR (DMSO-$d_6$, TFA): 2.3 (m, 2H); 3.15 (t, 2H); 3.36 (t, 2H); 3.56 (d, 2H); 3.68 (t, 2H); 4.04 (m, 5H); 4.35 (t, 2H); 7.45 (m, 3H); 7.84 (d, 2H); 8.29 (s, 1H); 8.4 (s, 1H); 9.27 (s, 1H).

MS ES$^+$: 555, 557 $(M_+H)^+$

EXAMPLE 62

An analogous reaction to that described in General Scheme 4, starting with cyclohexylamine (19 mg, 0.19 mmol) yielded Compound 62 in Table 3 (60 mg, 72%).

$^{1}$HNMR (DMSO-$d_6$, TFA): 1.32 (m, 5H); 1.62 (m, 1H); 1.73 (m, 2H); 1.87 (m, 2H); 2.33 (m, 2H); 3.15 (t, 2H); 3.35 (t, 2H); 3.54 (d, 2H); 3.68 (t, 2H); 3.75 (m, 1H); 4.03 (s, 3H); 4.05 (d, 2H); 4.33 (t, 2H); 7.42 (s, 1H); 8.07 (s, 1H); 8.32 (s, 1H); 9.24 (s, 1H).

MS ES$^+$: 527 $(M_+H)^+$

EXAMPLE 63

An analogous reaction to that described in General Scheme 4, starting with 3-(methylamino)-propionitrile (16 mg, 0.19 mmol) yielded Compound 63 in Table 3 (40 mg, 49%).

$^{1}$HNMR (DMSO-$d_6$, TFA): 2.3 (m, 2H); 2.88 Sm, 3H); 3.14 (m, 4H); 3.35 (t, 2H); 3.54 (d, 2H); 3.71 (t, 2H); 3.75 (m, 2H); 4.02 (s, 3H); 4.04 (d, 2H); 4.33 (t, 2H); 7.44 (s, 1H); 7.85 (s, 1H); 8.37 (s, 1H); 9.27 (s, 1H).

MS ES$^+$: 512 $(M_+H)^+$

EXAMPLE 64

An analogous reaction to that described in General Scheme 4, starting with 4-hydroxypiperidine (19 mg, 0.19 mmol) yielded Compound 64 in Table 3 (45 mg, 54 M).

$^{1}$HNMR (DMSO-$d_6$, TFA): 1.36 (m, 2H); 1.78 (m, 2H); 2.3 (m, 2H); 3.15 (t, 2H); 3.29 (m, 2H); 3.37 (t, 2H); 3.54 (d, 2H); 3.68 (t, 2H); 3.77 (m, 2H); 3.84 (m, 1H); 4.02 (s, 3H); 4.04 (d, 2H); 4.33 (t, 2H); 7.42 (s, 1H); 7.75 (s, 1H); 8.35 (s, 1H); 9.27 (s, 1H).

MS ES$^+$: 529 $(M_+H)^+$.

EXAMPLE 65

An analogous reaction to that described in General Scheme 4, starting with 4-aminopyridine (18 mg, 0.19 mmol) yielded Compound 65 in Table 3 (35 mg, 42%).

$^{1}$HNMR (DMSO-$d_6$, TFA): 2.29 (m, 2H); 3.15 (t, 2H); 3.34 (t, 2H); 3.55 (d, 2H); 3.68 (t, 2H); 4.03 (m, 5H); 4.34 (t, 2H); 7.48 (s, 1H) 8.41 (d, 2H); 8.43 (s, 1H); 8.52 (s, 1H); 8.81 (d, 2H); 9.24 (s, 1H).

MS ES$^+$: 522 $(M_+H)^+$

EXAMPLE 66

An analogous reaction to that described in General Scheme 4, starting with 2-chloroaniline (24 mg, 0.19 mmol) yielded Compound 66 in Table 3 (25 mg, 28%).

$^{1}$HNMR (DMSO-$d_6$, TFA) 2.3 (m, 2H); 3.17 (t, 2H); 3.36 (t, 2H); 3.55 (d, 2H); 3.69 (t, 2H); 4.04 (d, 2H); 4.05 (s, 3H); 4.35 (t, 2H); 7.24 (t, 1H); 7.42 (t, 1H); 7.47 (s, 1H); 7.6 (d, 1H) $(M_+H)^+$.

General Scheme 5

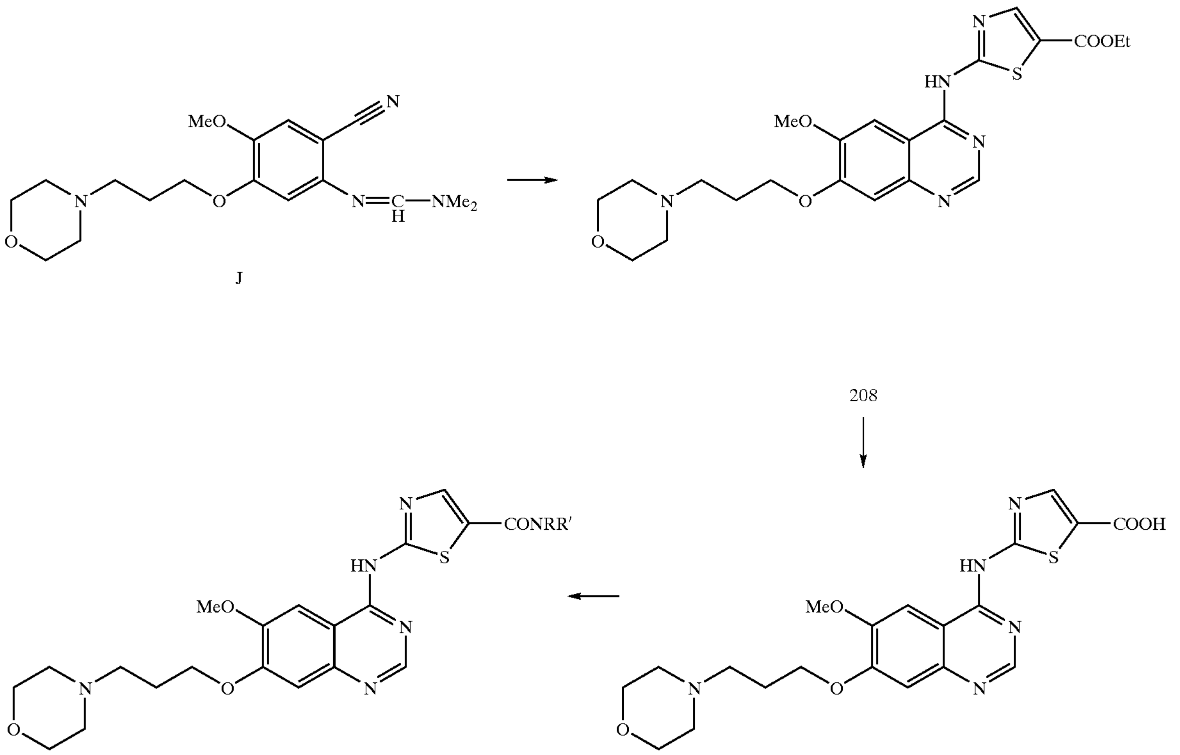

J

208

209

P

Compound 208

The amidine J (1.52 g, 4.4 mmol) in AcOH (15 ml) was reacted with ethyl 2-amino-5-thiazolcarboxylate (757 mg, 4.4 mmol) at 130° C. under argon for 3 hours. The solvent was evaporated, the residual oil was dissolved in methyl ene chloride and purified by silica gel chromatography, eluent $CH_2Cl_2$, $CH_2Cl_2$/MeOH: 95/5, to give title compound as a yellow solid (1.44 g, 70%).

$^1$HNMR (DMSO-$d_6$, TFA): 1.33 (t, 3H); 2.3 (m, 2H); 3.15 (t, 2H); 3.36 (t, 2H); 3.55 (d, 2H); 3.68 (t, 2H); 4.01 (s, 3H); 4.03 (d, 2H); 4.35 (m, 4H); 7.41 (s, 1H); 8.14 (s, 1H); 8.44 (s, 1H); 9.3 (s, 1H).

MS ES$^+$: 474 ($M_{30}$H)+

Compound 209

Ester 208 (1.6 g, 3.4 mmol) in suspension in ethanol (32 ml) was reacted with sodium hydroxide (6N, 6 ml) at 75° C. for 1 hour. The cooled solution was acidified with HCl (6N) to pH 4. The solid was filtered, washed with EtOH, ether, dried, to give a yellow solid (1.65 g, 86%).

$^1$HNMR (DMSO-$d_6$, TFA): 2.28 (m, 2H); 3.2 (t, 2H); 3.32 (t, 2H); 3.51 (d, 2H); 3.66 (t, 2H); 3.97 (s, 3H); 3.99 (d, 2H); 4.31 (t, 2H); 7.37 (s, 4H); 8.06 (s, 1H); 8.32 (s, 1H); 9.24 (s, 1H).

MS ES$^+$: 446 ($M_+H$)$^+$

Synthesis of Amides of General Structure P, General Procedure

The acid 209 (95 mg, 0.17 mmol) in DMF, 1 ml was reacted with amine (0.2 mmol) in presence of O-(7-azabenzotriazol-1-yl)N,N,N',N'-tetramethyluronium hexafluorophosphate (91 mg, 0.24 mmol), DIEA (110 mg, 0.85 mmol) for 14 hours at room temperature and 5 hours at 50° C. The reaction mixture was then treated with a solution of $NaHCO_3$ (1 ml) with stirring for 0.5 hour, and concentrated. The residue was washed with methylene chloride/methanol (1/1, 25 ml). Alumine was added to the organic phase, which was then evaporated. Purification of the compound was carried out by chromatography over alumine, eluent $CH_2Cl_2$, $CH_2Cl_2$/MeOH/95/5, to give title compounds.

EXAMPLE 67

An analogous reaction to that described in General Scheme 5, starting with aniline (19 mg, 0.2 mmol) yielded Compound 67 in Table 4 (30 mg, 34%).

$^1$HNMR (DMSO-$d_6$, TFA): 2.31 (m, 2H); 3.16 (t, 2H); 3.36 (t, 2H); 3.56 (d, 2H); 3.69 (t, 2H); 4.02 (s, 3H); 4.04 (d, 2H); 4.33 (t, 2H); 7.14 (t, 1H); 7.39 (m, 3H); 7.73 (d, 2H); 8.05 (s, 1H); 8.61 (s, 1H); 9.28 (s, 1H). MS ES: 521 ($M_+H$)+

EXAMPLE 68

An analogous reaction to that described in General Scheme 5, starting with 4-fluoroaniline (23 mg, 0.2 mmol) yielded Compound 68 in Table 4 (58 mg, 64%).

$^1$HNMR (DMSO-$d_6$, TFA) 2.31 (m, 2H); 3.16 (t, 2H); 3.36 (t, 2H); 3.56 (d, 2H); 3.69 (t, 2H); 4.01 (s, 3H); 4.03 (d, 2H); 4.32 (t, 2H); 7.20 (t, 1H); 7.38 (s, 1H); 7.73 (m, 1H); 8.05 (s, 1H); 8.57 (s, 1H); 9.28 (s, 1H).

MS ES$^+$: 539 ($M_+H$)$^+$

EXAMPLE 69

An analogous reaction to that described in General Scheme 5, starting with 4-chloroaniline (26 mg, 0.2 mmol) yielded Compound 69 in Table 4 (32 mg, 34%).

$^1$HNMR (DMSO-$d_6$, TFA): 2.32 (m, 2H); 3.16 (t, 2H); 3.36 (t, 2H); 3.56 (d, 2H); 3.69 (t, 2H); 4.01 (s, 3H); 4.03 (d, 2H); 4.33 (t, 2H); 7.39 (s, 1H); 7.44 (d, 2H); 7.76 (d, 2H). 8.06 (s, 1H); 8.6 (s, 1H); 9.29 (s, 1H).

MS ES$^+$: 555, 557 ($M_+H$)+

EXAMPLE 70

An analogous reaction to that described in General Scheme 5, starting with allylamine (12 mg, 0.2 mmol) yielded Compound 70 in Table 4 (32 mg, 39%).

$^1$HNMR (DMSO-$d_6$, TFA): 2.3 (m, 2H); 3.16 (t, 2H); 3.36 (t, 2H); 3.56 (d, 2H); 3.7 (t, 2H) 3.92 (d, 2H); 4.0 (s, 3H); 4.03 (d, 2H); 4.33 (t, 2H); 5.16 (d, 1H); 5.25 (d, 1H); 5.9 (m, 1H); 7.38 (s, 1H); 8.02 (s, 1H); 8.36 (s, 1H); 9.24 (s, 1H).

MS ES$^+$: 485 ($M_+H$)$^+$

EXAMPLE 71

An analogous reaction to that described in General Scheme 5, starting with 3-(methylamino)-propionitrile (17 mg, 0.2 mmol) yielded Compound 71 in Table 4 (32 mg, 39%).

$^1$HNMR (DMSO-$d_6$, TFA): 2.3 (m, 2H); 2.89 (m, 3H); 3.15 (t, 2H); 3.34 (m, 4H); 3.55 (d, 2H); 3.69 (t, 2H); 3.8 (m, 2H); 4.01 (s, 3H); 4.03 (d, 2H); 4.33 (t, 2H); 7.38 (s, 1H); 8.07 (s, 1H); 8.22 (s, 1H); 9.25 (s, 1H).

MS ES$^+$: 512 ($M_+H$)$^+$.

EXAMPLE 72

An analogous reaction to that described in General Scheme 5, starting with 4-hydroxypiperidine (20 mg, 0.2 mmol) yielded Compound 72 in Table 4 (12 mg, 13%).

$^1$HNMR (DMSO-$d_6$, TFA): 1.45 (m, 2H); 1.82 (m, 2H); 2.31 (m, 2H); 3.15 (m, 4H); 3.35 (t, 2H); 3.4 (m, 2H); 3.54 (d, 2H); 3.7 (t, 2H); 3.79 (m, 1H); 4.01 (s, 3H); 4.03 (d, 2H); 4.32 (t, 2H); 7.38 (s, 1H); 8.06 (s, 1H); 8.09 (s, 1H); 9.23 (s, 1H).

MS ES$^+$: 529 ($M_+H$)$^+$

EXAMPLE 73

An analogous reaction to that described in General Scheme 5, starting with 4-aminopyridine (19 mg, 0.2 mmol) yielded Compound 73 in Table 4 (50 mg, 57%).

$^1$HNMR (DMSO-$d_6$-TFA): 2.29 (m, 2H); 3.17 (t, 2H); 3.36 (t, 2H); 3.56 (d, 2H); 3.7 (t, 2H); 4.02 (s, 3H); 4.03 (d, 2H); 4.34 (t, 2H); 7.46 (s, 1H); 8.15 (s, 1H); 8.27 (d, 2H); 8.78 (s, 1H); 8.8 (d, 2H); 9.31 (s, 1H).

MS ES$^+$: 522 ($M_+H$)$^+$

General Scheme 6

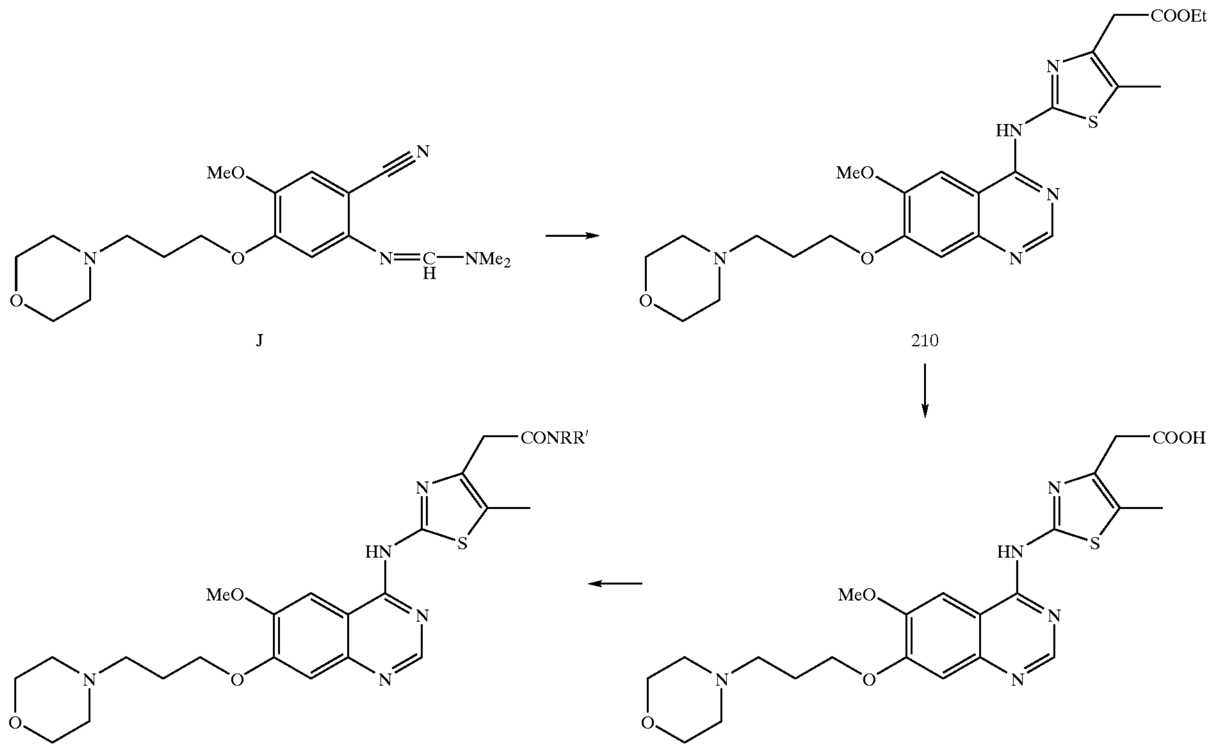

J

210

211

Q

Compound 210

Amidine J (450 mg, 1.3 mmol) was reacted with methyl 2-amino-5-methyl-4-thiazolacetate (242 mg, 1.3 mmol) in acetic acid (5 ml) at 130° C. for 3 hours, under argon. The solvent was evaporated, ethylacetate and water were added to the residual oil, the pH adjusted to 9 with a saturated solution of sodium bicarbonate and the mixture extracted with ethylacetate. The organic phase was washed with a saturated solution of sodium chloride, dried over magnesium sulphate, filtered, concentrated. The residual oil was purified by silica gel chromatography, eluent $CH_2Cl_2$/MeOH:98/2 to 95/5 to give title compound (380 mg, 60%).

$^1$HNMR (DMSO-$d_6$, TFA) 2.3 (m, 2H); 2.35 (s, 3H); 3.15 (t, 2H); 3.34 (t, 2H); 3.55 (d, 2H); 3.68 (t, 2H); 3.68 (s, 3H); 3.83 (s, 2H); 3.98 (s, 3H); 4.03 (d, 2H); 4.29 (t, 2H); 7.31 (s, 1H); 7.96 (s, 1H); 9.06 (s, 1H).

MS $ES^+$: 488 $(M_+H)^+$

Compound 211

Ester 210 (360 mg, 0.74 mmol) in ethanol (10 ml) was reacted with sodium hydroxide (6N, 1 ml) at room temperature for 1 hour. HCl (6N) was then added to the solution cooled to 0° C., and the pH adjusted to 3–4. The solid was recovered by filtration, washed with ethanol, ether, dried under vacuum, to give title compound as a dihydrochloride (550 mg, 83%).

$^1$HNMR (DMSO-$d_6$, TFA): 2.34 (m, 5H); 3.13 (t, 2H); 3.32 (t, 2H); 3.52 (d, 2H); 3.74 (s, 2H); 3.78 (t, 2H); 3.98 (s, 3H); 4.01 (d, 2H); 4.31 (t, 2H); 7.37 (s, 1H); 7.91 (s, 1H); 9.03 (s, 1H).

MS $ES^+$: 474 $(M_+H)^+$

Synthesis of Amides of General Structure Q, General Procedure

The acid 211 (87 mg, 0.13 mmol) in DMF (1 ml) was reacted with amine (0.169 mmol) in presence of O-(7-azabensotriazol-1-yl)N,N,N',N'-tetramethyluronium hexafluorophosphate (69 mg, 0.182 mmol), diisopropylethylamine (84 mg, 0.65 mmol) over night, at room to temperature. The reaction mixture was diluted with water (5 ml) and a concentrated solution of sodium bicarbonate (1 ml). The solid was filtered, washed with water, ethanol, ether, and dried under vacuum, to give title compounds. For the compounds which did not precipitate, the solution was concentrated to dryness, the residues were washed with methylene chloride, methanol, filtered. Alumine was added to the methylene chloride/methanol solution, and the solvent was evaporated. Purification of the compounds was carried out by chromatography over alumine, eluent $CH_2Cl_2$/MeOH: 98/2 to 95/5, to give title compounds.

EXAMPLE 74

An analogous reaction to that described in General Scheme 6, starting with aniline (16 mg, 0.17 mmol) yielded Compound 74 in Table 5 (50 mg, 70%).

$^1$HNMR (DMSO-$d_6$, TFA): 2.28 (m, 2H); 2.37 (s, 3H) 3.15 (t, 2H); 3.34 (t, 2H); 3.56 (d, 2H); 3.68 (t, 2H); 3.84 (s, 2H); 3.96 (s, 3H); 4.03 (d, 2H); 4.28 (t, 2H); 7.07 (t, 1H); 7.29 (s, 1H); 7.3 (t, 2H); 7.61 (d, 2H); 7.89 (s, 1H); 9.02 (s, 1H).

MS $ES^+$: 549 $(M_+H)$+

EXAMPLE 75

An analogous reaction to that described in General Scheme 6, starting with 4-fluoroaniline (19 mg, 0.17 mmol) yielded Compound 75 in Table 5 (50 mg, 67%).

$^1$HNMR (DMSO-$_6$, TFA): 2.3 (m, 2H); 2.38 (s, 3H); 3.16 (t, 2H); 3.34 (t, 2H); 3.54 (d, 2H); 3.68 (t, 2H); 3.84 (s, 2H);

3.97 (s, 3H); 4.03 (d, 2H); 4.29 (t, 2H); 7.16 (t, 2H); 7.29 (s, 1H); 7.64 (m, 2H); 7.9 (s, 1H); 9.03 (s, 1H).

MS $ES^+567$ $(M_+H)^+$.

EXAMPLE 76

An analogous reaction to that described in General Scheme 6, starting with 4-chloroaniline (22 mg, 0.17 mmol) yielded Compound 76 in Table 5 (45 mg, 59%).

$^1$HNMR (DMSO-$d_6$, TFA): 2.28 (m, 2H); 2.37 (s, 3H); 3.15 (t, 2H); 3.34 (t, 2H); 3.55 (d, 2H); 3.68 (t, 2H); 3.85 (s, 2H); 3.97 (s, 3H); 4.03 (d, 2H); 4.29 (t, 2H); 7.29 (s, 1H); 7.37 (d, 2H); 7.65 (d, 2H); 7.9 (s, 1H); 9.03 (s, 1H).

MS $ES^+$: 583 $(M_+H)^+$

EXAMPLE 77

An analogous reaction to that described in General Scheme 6, starting with 4-hydroxypiperidine (17 mg, 0.17 mmol) yielded Compound 77 in Table 5 (45 mg, 62%).

EXAMPLE 78

An analogous reaction to that described in General Scheme 6, starting with 4-aminopyridine (16 mg, 0.17 mmol) yielded Compound 78 in Table 5 (35 mg, 49%).

$^1$HNMR (DMSO-d6, TFA): 2.29 (m, 2H); 2.39 (s, 3H); 3.15 (t, 2H); 3.34 (t, 2H); 3.55 (d, 2H); 3.68 (t, 2H); 3.96 (s, 3H); 4.02 (d, 2H); 4.04 (s, 2H); 4.29 (t, 2H); 7.33 (s, 1H); 7.92 (s, 1H); 8.1 (d, 2H); 8.76 (d, 2H); 9.06 (s, 1H).

MS $ES^+$: 550 $(M_+H)^+$.

General Scheme 7

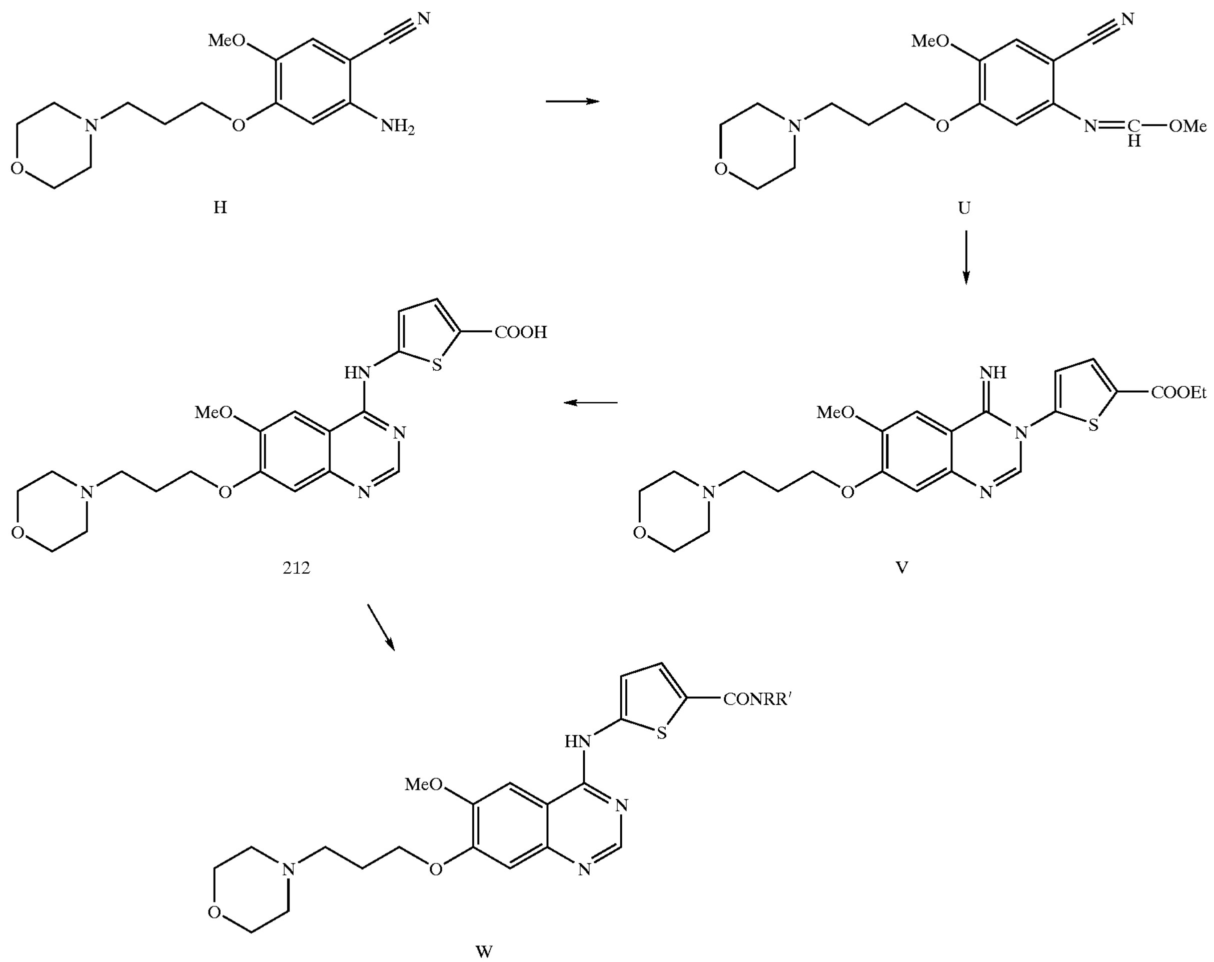

H U V 212 W $^1$HNMR (DMSO-$d_6$, TFA): 1.42 (m, 2H); 1.82 (m, 2H); 2.31 (m, 5H); 3.08 (m, 1H); 3.16 (t, 2H); 3.27 (m, 1H); 3.35 (t, 2H); 3.54 (d, 2H); 3.68 (t, 2H); 3.78 (m, 2H); 3.83 (s, 2H) 3.92 (m, 1H); 3.97 (s, 3H); 4.03 (d, 2H); 4.29 (t, 2H); 7.28 (s, 1H); 7.85 (s, 1H); 9.0 (s, 1H).

MS $ES^+$: 557 $(M_+H)^+$.

Compound U

The amino nitrile H (2.91 g, 10 mmol) was reacted with trimethylorthoformate (10 ml) in presence of p-toluenesulfonic acid (38 mg, 2 mmol) at 80° C. for 6 hours. The solvent was evaporated, the residue crystallised from ether to give title compound (3.01 g, 90.4%).

$^1$HNMR (DMSO-$d_6$): 1.9 (t, 2H); 2.4 (m, 6H); 3.58 (t, 4H); 3.78 (s, 3H); 3.85 (s, 3H); 4.08 (t, 2H); 6.88 (s, 1H); 7.28 (s, 1H); 8.2 (s, 1H).

MS ES$^+$: 334 $(M_+H)^+$

Compound V

Imidate U (0.25 g, 0.75 mmol) in $CH_2Cl_2$ (5 ml) was reacted with ethyl 2-amino-5-thiophenecarboxylate (0.13 g, 0.79 mmol) in presence of pyridinium hydrochloride (0.09 g, 0.75 mmol), at room temperature over night. Ethyl acetate was then added, and the solid was recovered by filtration, washed with ethyl acetate, dried under vacuum, to give product (0.23 g, 65%).

$^1$HNMR (DMSO-$d_6$, TFA): 1.33 (t, 3H); 2.28 (m, 2H); 3.12 (t, 2H); 3.32 (t, 2H); 3.53 (d, 2H); 3.73 (t, 2H); 3.96 (s, 3H); 4.02 (d, 2H); 4.37 (m, 4H); 7.45 (s, 1H); 7.67 (d, 1H); 7.95 (d, 1H); 8.12 (s, 1H); 8.52 (s, 1H).

MS ES$^+$473 $(M_+H)^+$

Compound 212

Ester V (1.1 g, 2.3 mmol) in methanol (20 ml) was treated with sodium hydroxide (2N, 20 ml) at 75° C. for 4 hours, and at room temperature over night. Methanol was evaporated, and the remaining aqueous solution was kept for 24 hours at 5° C. The solid was filtered, washed with water, MeOH/$CH_2Cl_2$:1/1, dried under vacuum to give title compound (0.9 g, 87%).

$^1$HNMR (DMSO-$d_6$, TFA): 2.31 (m, 2H); 3.14 (t, 2H); 3.33 (t, 2H); 3.53 (d, 2H); 3.76 (t, 2H); 4.01 (d, 2H); 4.07 (s, 3H); 4.33 (t, 2H); 7.44 (s, 1H); 7.54 (d, 1H); 7.68 (d, 1H); 8.54 (s, 1H); 9.22 (s, 1H).

MS ES$^+$: 445 $(M_+H)^+$

Synthesis of Amides of General Structure W, General Procedure

Acid 212 (80 mg, 0.18 mmol) in DMF (1.5 ml) was reacted with amine (0.216 mmol) in presence of 0-(7-azabenzotriazol-1-yl)N,N,N',N'-tetramethyluronium hexafluorophosphate (80 mg, 0.21 mmol), DIEA (80 $\mu$l, 0.46 mmol), for 3 hours at room temperature. The reaction mixture was then treated with a solution of $NaHCO_3$ (2 ml) with stirring for 0.5 hour, the solid filtered, washed with water, ether, dried under vacuum over $P_2O_5$, to give title compound.

EXAMPLE 79

An analogous reaction to that described in General Scheme 7, starting with aniline (17 $\mu$l, 0.186 mmol) yielded Compound 79 in Table 6 (80 mg, 86%).

$^1$HNMR (DMSO-$d_6$, TFA): 2.32 (m, 2H); 3.15 (t, 2H); 3.35 (t, 2H); 3.53 (d, 2H); 3.69 (t, 2H); 4.01 (d, 2H); 4.03 (s, 3H); 4.3 (t, 2H); 7.7 (t, 1H); 7.32 (m, 4H); 7.73 (d, 2H); 7.98 (d, 1H); 8.18 (s, 1H); 9.22 (s, 1H).

MS ES$^+$: 520 $(M_+H)^+$

EXAMPLE 80

An analogous reaction to that described in General Scheme 7, starting with 4-fluoroaniline (24 mg, 0.216 mmol) yielded Compound 80 in Table 6 (62 mg, 64%).

$^1$HNMR (DMSO-$d_6$, TFA): 2.3 (m, 2H); 3.15 (t, 2H); 3.35 (t, 2H); 3.55 (d, 2H); 3.68 (t, 2H); 4.05 (m, 5H); 4.33 (t, 2H); 7.21 (t, 2H); 7.33 (d, 1H); 7.4 (s, 1H); 7.77 (m, 2H); 7.98 (d, 1H); 8.2 (s, 1H); 9.25 (s, 1H).

MS ES$^+$: 538 $(M_+H)^+$.

EXAMPLE 81

An analogous reaction to that described in General Scheme 7, starting with 3-aminophenol (24 mg, 0.216 mmol) yielded Compound 81 in Table 6 (60 mg, 66%).

$^1$HNMR (DMSO-$d_6$, TFA): 2.3 (m, 2H); 3.15 (t, 2H); 3.35 (t, 2H); 3.55 (d, 2H); 3.7 (t, 2H); 4.04 (d, 2H); 4.06 (s, 3H); 4.33 (t, 2H); 6.53 (m, 1H); 7.13 (m, 2H); 7.3 (d, 1H); 7.36 (d, 1H); 7.4 (s, 1H); 7.96 (s, 1H); 8.0 (d, 1H); 8.26 (s, 1H); 9.25 (s, 1H).

MS ES$^+$: 536 $(M_+H)^+$.

EXAMPLE 82

An analogous reaction to that described in General Scheme 7, starting with 4-aminopyridine (20 mg, 0.216 mmol) yielded Compound 82 in Table 6 (16 mg, 19%).

$^1$HNMR (DMSO-$d_6$, TFA): 2.3 (m, 2H); 3.15 (t, 2H); 3.35 (t, 2H); 3.54 (d, 2H); 3.68 (t, 2H); 4.03 (d, 2H); 4.05 (s, 3H); 4.32 (t, 2H); 7.01 (d, 1H); 7.03 (s, 1H); 8.18 (d, 1H); 8.22 (s, 1H); 8.3 (d, 2H); 8.76 (d, 2H); 9.3 (s, 1H).

MS ES$^+$: 521 $(M_+H)^+$.

EXAMPLE 83

An analogous reaction to that described in General Scheme 7, starting with 4-amino-1-butanol (19 mg, 0.216 mmol) yielded Compound 83 in Table 6 (22 mg, 28+%).

$^1$HNMR (DMSO-$d_6$, TFA): 1.46 (m, 2H); 1.58 (m, 2H); 2.3 (m, 2H); 3.16 (t, 2H); 3.26 (t, 2H); 3.36 (t, 2H); 3.44 (t, 2H); 3.55 (d, 2H); 3.69 (t, 2H); 4.04 (m, 5H); 4.32 (t, 2H); 7.26 (d, 1H); 7.39 (s, 1H); 7.7 (d, 1H); 8.19 (s, 1H); 9.21 (s, 1H).

MS ES$^+$: 516 $(M_+H)^+$

EXAMPLE 84

An analogous reaction to that described in General Scheme 7, starting with 3-aminobenzamide (29 mg, 0.216 mmol) yielded Compound 84 in Table 6 (60 mg, 77%).

$^1$HNMR (DMSO-$d_6$, TFA): 2.3 (m, 2H); 3.15 (t, 2H); 3.35 (t, 2H); 3.55 (d, 2H); 3.67 (t, 2H); 4.03 (d, 2H); 4.05 (s, 3H); 4.32 (t, 2H); 7.34 (d, 1H); 7.39 (s, 1H); 7.42 (t, 1H); 7.62 (d, 1H); 7.96 (d, 1H); 8.05 (d, 1H); 8.21 (m, 2H); 9.27 (s, 1H).

MS ES$^+$: 563 $(M+)^+$.

EXAMPLE 85

An analogous reaction to that described in General Scheme 7, starting with allylamine (12 mg, 0.216 mmol) yielded title Compound 85 in Table 6 (20 mg, 43%).

$^1$HNMR (DMSO-$d_6$, TFA): 2.3 (m, 2H); 3.15 (t, 2H); 3.35 (t, 2H); 3.55 (d, 2H); 3.68 (t, 2H); 3.91 (d, 2H); 4.04 (m, 5H); 4.32 (t, 2H); 5.12 (d, 1H); 5.2 (d, 1H); 5.91 (m, 1H); 7.26 (d, 1H); 7.38 (s, 1H); 7.75 (d, 1H); 8.19 (s, 1H); 9.22 (s, 1H).

MS ES$^+$: 484 $(M_+H)^+$.

EXAMPLE 86

An analogous reaction to that described in General Scheme 7, starting with Methyl-4 aminobutyrate (25 mg, 0.216 mmol) yielded Compound 86 in Table 6 (18 mg, 23%).

$^1$HNMR: 1.8 (t, 2H); 2.3 (m, 2H); 2.39 (t, 2H); 3.16 (t, 2H); 3.28 (t, 2H); 3.35 (t, 2H); 3.56 (d, 2H); 3.6 (s, 3H); 3.67 (t, 2H); 4.04 (m, 5H); 4.32 (t, 2H); 7.26 (d, 1H); 7.38 (s, 1H); 7.69 (d, 1H); 8.19 (s, 1H); 9.22 (s, 1H).

MS ES$^+$: 544 $(M_+H)^+$.

General Scheme 8

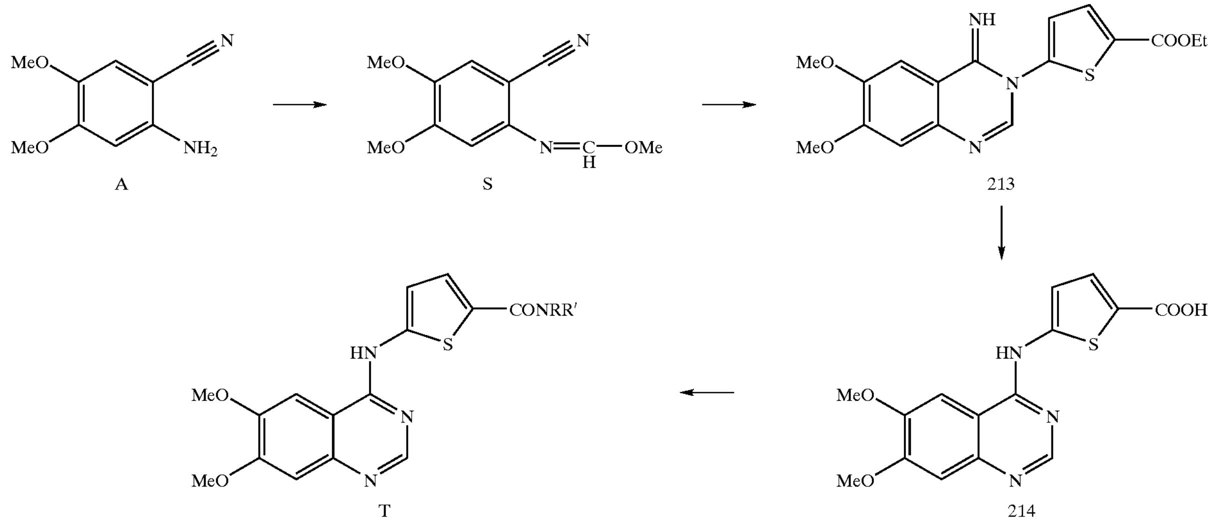

A S 213 214 T

Compound S

Aminonitrile A (1.78 g, 10 mmol) was treated with trimethylorthoformate (10 ml) and a catalytic amount of p-toluene sulfonic acid at 100° C. for 1 hour. The mixture was cooled to room temperature, ethyl acetate was added, and the insoluble solid removed by filtration, the solvent was then evaporated, the residue triturated with ether to give title compound as a yellow solid (1.56 g, 71%).

$^1$HNMR (DMSO-$d_6$): 3.77 (s, 3H); 3.83 (s, 3H); 3.84 (s, 3H); 6.87 (s, 1H); 7.26 (s, 1H) 8.19 (s, 1H).

MS $ES^+$: 221 $(M_+H)^+$.

Compound 213

Imidate S (0.165 g, 0.75 mmol) was reacted with ethyl 2-amino-5-thiophenecarboxylate (0.13 g, 0.79 mmol) in methylene chloride (4 ml) in presence of pyridinium hydrochloride (88 mg, 0.75 mmol) at room temperature for 4 hours. The solvent was evaporated, and the residue was purified by silica gel chromatography, eluent: AcOEt/$CH_2Cl_2$, 1/1; followed by MeOH/AcOEt/$CH_2Cl_2$, 1/4/5, to give title compound (0.135 g, 50%).

$^1$HNMR (DMSO-$d_6$, TFA): 1.33 (t, 3H); 3.95 (s, 3H); 4.03 (s, 3H); 4.38 (q, 2H); 7.43 (s, 1H); 7.67 (d, 1H); 7.95 (d, 1H); 8.05 (s, 1H); 8.52 (s, 1H).

MS $ES^+$: 360 $(M_+H)^+$

Compound 214

The ester 213 (72 mg, 0.2 mmol) in methanol (2 ml) was treated with sodium hydroxide (2N, 2 ml) at 75° C. for 1.5 hour. The reaction mixture was cooled to room temperature, and the pH adjusted to 3 by addition of HCl 2N. The solid was recovered by filtration, washed with water, dried under vacuum in presence of $P_2O_5$, to give title compound (83 mg, 100%).

$^1$HNMR (DMSO-$d_6$, TFA): 4.02 (s, 3H); 4.04 (s, 3H); 7.38 (s, 1H); 7.42 (d, 1H); 7.68 (d, 1H); 8.35 (s, 1H); 9.21 (s, 1H).

MS $ES^+$: 332 $(M_+H)^+$.

EXAMPLE 87

Synthesis of Compound of General Formula T where NRR'═NHPh (Compound 87)

Quinazoline 214 (45 mg, 0.108 mmol) in DMF (1 ml) was reacted with aniline (12 μl, 0.13 mmol) in presence of (7-azabenzotriazol-1-yl)N,N,N',N'-tetramethyluronium hexafluorophosphate (50 mg, 0.13 mmol), DIEA (75 μl, 0.43 mmol) for 1.5 hour at room temperature. A saturated solution of sodium bicarbonate (2 ml) was added to the mixture which was stirred for 0.5 hour. The solid was filtered, washed with water, and purified by chromatography over alumine, eluent AcOEt/$CH_2Cl_2$:1/1 to MeOH/AcOEt/$CH_2Cl_2$:1/4/5, to give title compound (15 mg, 34%).

$^1$HNMR (DMSO-$d_6$): 3.97 (s, 3H); 4.01 (s, 3H); 7.05 (d, 1H); 7.09 (t, 1H); 7.29 (s, 1H); 7.36 (t, 2H); 7.74 (d, 2H); 7.91 (d, 1H); 7.92 (s, 1H); 8.72 (s, 1H).

MS $ES^+$: 406 $(M_+H)^+$

EXAMPLE 88

Synthesis of Compound 88 of General Formula T where NRR' is NHPh(4-F)

An analogous reaction to that described in the Example 87, starting with quinazoline 213 (60 mg, 0.14 mmol), 4-fluoroaniline (17 ll, 0.17 mmol) yielded title compound (15 mg, 24%).

$^1$HNMR (DMSO-$d_6$, TFA): 4.04 (s, 3H); 4.06 (s, 3H); 7.18 (t, 2H); 7.32 (d, 1H); 7.35 (s, 1H); 7.75 (t, 2H); 7.98 (d, 1H); 8.17 (s, 1H); 9.23 (s, 1H).

MS $ES^+$: 425 $(M_+H)^+$.

EXAMPLE 89

Preparation of Compound 250 in Table 9

Amidine J (1.04 g, 3 mmol) in acetic acid (10 ml) was reacted with methyl 4-amino-1-methyl-2-pyrrolecarboxylate hydrochloride (686 mg, 3.6 mmol) and dimethylamine in methanol (1.25 M 2.9 ml, 3.6 mmol) at 130° C. for 5.5 hours. The solvent was evaporated, water and an aqueous solution of sodium bicarbonate were added to the residue, the precipitate was filtered, dried under vacuum over $P_2O_5$. The solid was redissolved in a large volume of tetrahydrofuran, methylene chloride, methanol, the solution was concentrated, the solid filtered, washed with ether, dried, to give title compound (1.18 g, 86%).

$^1$HNMR (DMSO-$d_6$, TFA): 2.31 (m, 2H); 3.16 (t, 2H); 3.35 (t, 2H); 3.55 (d, 2H); 3.69 (t, 2H); 3.8 (s, 3H); 3.95 (s, 3H); 4.01 (s, 3H); 4.03 (d, 2H); 4.29 (t, 2H); 7.26 (d, 1H); 7.32 (s, 1H); 7.69 (d, 1H); 8.06 (s, 1H); 8.94 (s, 1H).

MS $ES^+$: 456 $[H_+H]^+$

General Scheme 9

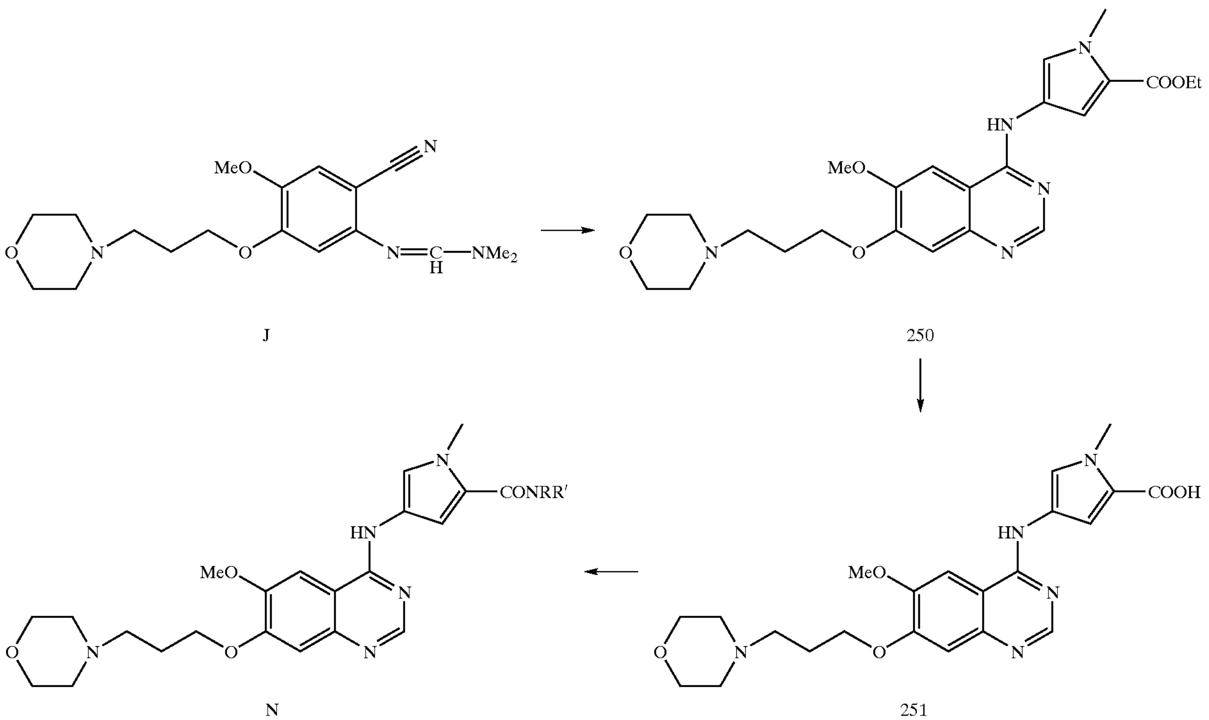

J, 250, 251, N

EXAMPLE 90

Preparation of Compound 251 in Table 9

Ester 250 (1.34 g, 3 mmol) was treated with sodium hydroxide (6N, 3 ml) in ethanol (25 ml) at 75° for 2 hours. The solution was then cooled to room temperature, acidified to pH 3 with HCl (6N), the precipitate was recovered by filtration, washed with ethanol, ether, dried under vacuum to give title compound (636 mg, 42%).

$^1$HNMR (DMSO-$d_6$, TFA): 2.3 (m, 2H); 3.15 (t, 2H); 3.34 (t, 2H); 3.54 (d, 2H); 3.72 (t, 2H); 4.02 (m, 5H); 4.3 (t, 2H); 7.19 (s, 1H); 7.32 (s, 1H); 7.62 (s, 1H); 8.17 (s, 1H); 8.93 (s, 1H).

MS ES$^+$: 428 [$M_+H$]$^+$

EXAMPLE 91

Synthesis of Amides N, General Procedure

Acid 251 (79 mg, 0.15 mmol) in DMF (1 ml) was reacted with O-(Benzotriazol-1-yl)-N,N,N',N'-tetramethyluronium hexafluorophosphate (62 mg, 0.165 mmol), the appropriate amine (1.65 mmol) and DIEA (68 mg, 0.525 mmol) at room temperature for 1.5 hour. The reaction mixture was then diluted with water (4 ml) and an aqueous solution of sodium bicarbonate (1 ml). The solid was recovered by filtration, redissolved in tetrahydrofuran, methylene chloride, and concentrated, the precipitated solid was recovered, washed with ether, dried under vacuum, to give title compound.

EXAMPLE 92

Preparation of Compound 252 in Table 9

Compound 252 was obtained by reaction of the N-hydroxybenzotriazol ester of 251 (56 mg, 0.1 mmol) with aniline (11 mg, 0.12 mmol) in DMF (1 ml) at 105° C. for 3 hours. Water was added to the cooled reaction mixture, which was extracted with ethylacetate, the organic phase was washed with water, dried over $MgSO_4$, filtered and concentrated to give title compound (12 mg, 23%). The N-hydroxybenzotriazol ester was obtained as described in the general procedure of Example 91.

$^1$HNMR (DMSO-$d_6$, TFA): 2.3 (m, 2H); 3.15 (t, 2H); 3.35 (t, 2H); 3.55 (d, 2H); 3.68 (t, 2H) 3.97 (s, 3H); 4.02 (s, 3H); 4.04 (d, 2H); 4.29 (t, 2H); 7.08 (t, 1H); 7.33 (m, 3H); 7.4 (s, 1H); 7.63 (s, 1H); 7.74 (d, 2H); 8.1 (s, 1H); 8.93 (s, 1H).

MS ES$^+$: 517 [$M_+H$]$^+$

EXAMPLE 93

Preparation of Compound 253 in Table 9

An analogous reaction to that described in Example 92, but starting with 4-fluoroaniline (22 mg, 0.195 mmol) yielded title compound (40 mg, 57%).

$^1$H NMR (DMSO-$d_6$, TFA): 2.3 (m, 2H); 3.17 (t, 2H); 3.36 (t, 2H); 3.55 (d, 2H); 3.72 (t, 2H); 3.97 (s, 3H); 4.02 (s, 3H); 4.04 (d, 2H); 4.3 (t, 2H); 7.18 (t, 2H); 7.34 (s, 1H); 7.4 (d, 1H); 7.63 (d, 1H); 7.76 (m, 1H); 8.11 (s, 1H); 8.94 (s, 1H).

MS ES$^+$: 535 [$M_+H$]$^+$

EXAMPLE 94

Preparation of Compound 254 in Table 9

An analogous reaction to that described in Example 92, but starting with cyclohexylamine (16 mg, 0.17 mmol) yielded title compound (60 mg, 76%).

$^1$HNMR (DMSO-$d_6$, TFA): 1.14 (m, 1H); 1.3 (m, 4H); 1.62 (m, 1H); 1.8 (m, 4H); 2.29 (m, 2H); 3.15 (t, 2H); 3.34

(t, 2H); 3.54 (d, 2H); 3.68 (m, 3H); 3.9 (s, 3H); 4.0 (s, 3H); 4.03 (d, 2H); 4.28 (t, 2H); 7.14 (d, 1H); 7.31 (s, 1H); 7.49 (d, 1H); 8.07 (s, 1H); 8.9 (s, 1H).

MS ES$^+$: 523 $[H_+H]^+$

EXAMPLE 95

Preparation of Compound 255 in Table 9

An analogous reaction to that described in the Example 92, but starting with N,N-dimethyl-1,4-phenylenediamine (23 mg, 0.17 mmol) yielded title compound (61 mg, 73%).

$^1$HNMR (DMSO-$d_6$, TFA): 2.3 (m, 2H); 3.15 (t, 2H); 3.21 (s, 6H); 3.35 (t, 2H); 3.55 (d, 2H); 3.69 (t, 2H); 3.97 (s, 3H); 4.01 (s, 3H); 4.03 (d, 2H); 4.29 (t, 2H); 7.35 (s, 1H); 7.45 (d, 1H); 7.66 (m, 3H); 7.93 (d, 2H); 8.1 (s, 1H); 8.93 (s, 1H).

MS ES$^+$: 560 $[H_+H]^+$

EXAMPLE 96[1]

Preparation of Compound 257 in Table 9

Ester 256 (1.34 g, 3 mmol) in ethanol (25 ml) was treated with sodium hydroxide (6N, 3 ml) at 75° C. for 2 hours. The solution was cooled, and acidified with hydrochloric acid (6N) to pH 3. The precipitate was filtered, washed with ethanol, ether, dried under vacuum over $P_2O_5$, to give title compound (0.63 g, 42%).

$^1$HNMR (DMSO-$d_6$, TFA): 2.3 (m, 2H); 3.15 (t, 2H); 3.34 (t, 2H); 3.54 (d, 2H); 3.72 (t, 2H); 4.02 (s, 3H); 4.03 (d, 2H); 4.3 (t, 2H); 7.19 (d, 1H); 7.32 (s, 1H); 7.62 (d, 1H); 8.17 (s, 1H); 8.93 (s, 1H).

MS ES$^+$: 428 $[H_+H]^+$

General Scheme 10

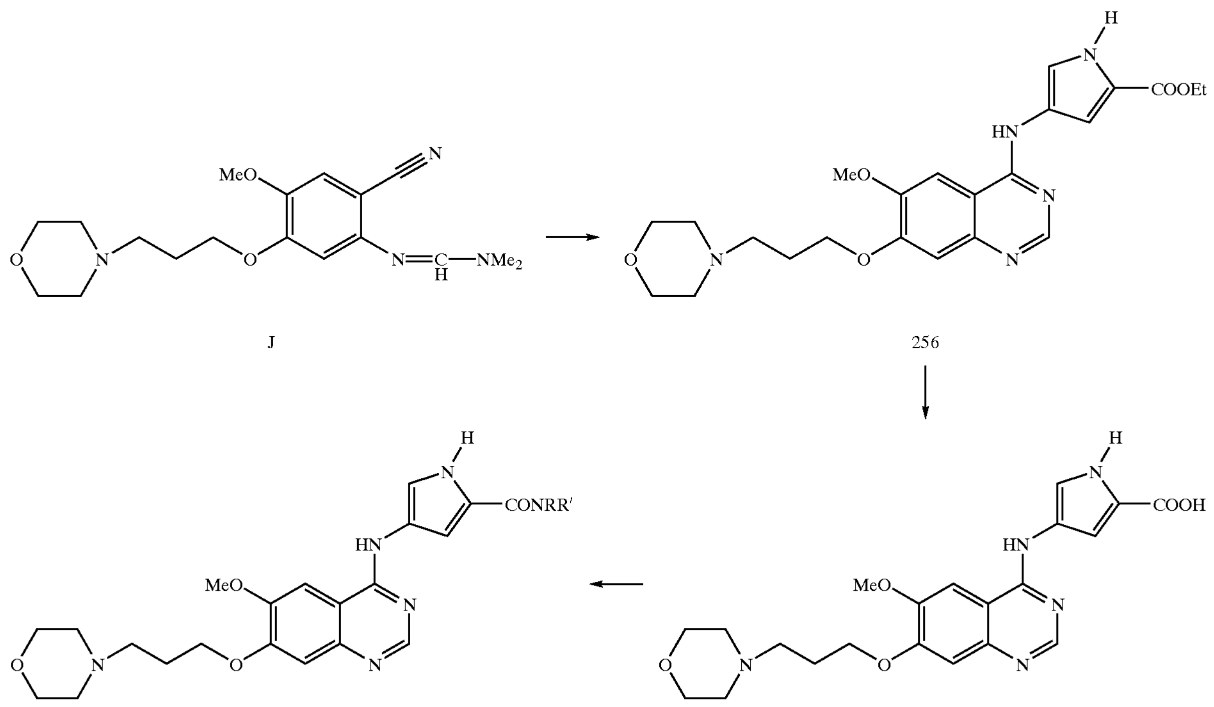

J, 256, 257, R

EXAMPLE 96

Preparation of Compound 256 in Table 9

Amidine J (1.38 g, 4 mmol) in acetic acid (14 ml) was reacted with ethyl 4-amino-2-pyrrolecarboxylate (0.702 g, 4.56 mmol) at 130° C. for 5 hours. The solution was concentrated, the solid recovered by filtration and washed with ether. This solid was then treated with a diluted solution of sodium bicarbonate, filtered, washed with water and dried under vacuum over $P_2O_5$ to give title compound (1.34 g, 73%).

$^1$H NMR (DMSO-$d_6$): 1.3 (t, 3H); 1.95 (t, 2H); 2.38 (m, 4H); 2.44 (t, 2H); 3.58 (m, 4H); 3.94 (s, 3H); 4.16 (d, 2H); 4.23 (q, 2H); 7.05 (d, 1H); 7.14 (s, 1H); 7.59 (d, 1H); 7.75 (s, 1H); 8.46 (s, 1H); 9.53 (s, 1H); 11.72 (s, 1H).

MS ES$^+$: 456 $[M_+H]^+$

EXAMPLE 97

Preparation of Compound 258 in Table 9

Acid 257 (75 mg, 0.15 mmol) in DMF (0.7 ml) was reacted with O-(Benzotriazol-1-yl)-N,N,N',N'-tetramethyluronium hexafluorophosphate (68 mg, 0.18 mmol), aniline (17 mg, 0.18 mmol) and DIEA (62 mg, 0.48 mmol) at room temperature over night. The reaction mixture was then diluted with a saturated solution of sodium bicarbonate (5 ml), and stirred for 1 hour. The solid was filtered, washed with water, dried under vacuum over $P_2O_5$, to give title compound (30 mg, 40%).

$^1$HNMR (DMSO-$d_6$, TFA): 2.3 (m, 2H); 3.16 (t, 2H); 3.37 (t, 2H); 3.54 (d, 2H); 3.69 (t, 2H); 4.01 (s, 3H); 4.03 (d, 2H); 4.31 (t, 2H); 7.08 (t, 1H); 7.35 (m, 3H); 7.46 (d, 1H); 7.56 (d, 1H); 7.77 (d, 1H); 8.1 (s, 1H); 8.93 (s, 1H).

MS ES$^+$: 503 $[H_+H]^+$

EXAMPLE 98

Preparation of Compound 259 in Table 9

An analogous reaction to that described for the Example 97, but starting with cyclohexylamine (18 mg, 0.18 mmol) yielded title compound (30 mg, 39%).

$^1$HNMR (DMSO-$d_6$, TFA): 1.13 (m, 1H); 1.3 (m, 4H); 1.63 (m, 1H); 1.8 (m, 4H); 2.3 (m, 2H); 3.15 (t, 2H); 3.35 (t, 2H); 3.54 (d, 2H); 3.68 (t, 2H); 3.76 (m, 1H); 4.0 (s, 1H); 4.03 (d, 2H); 4.3 (t, 2H); 7.2 (d, 1H); 7.3 (s, 1H); 7.43 (d, 1H); 8.0 (s, 1H); 8.9 (s, 1H).

MS $ES^+$: 509 $[H_+H]^+$

General Scheme 11

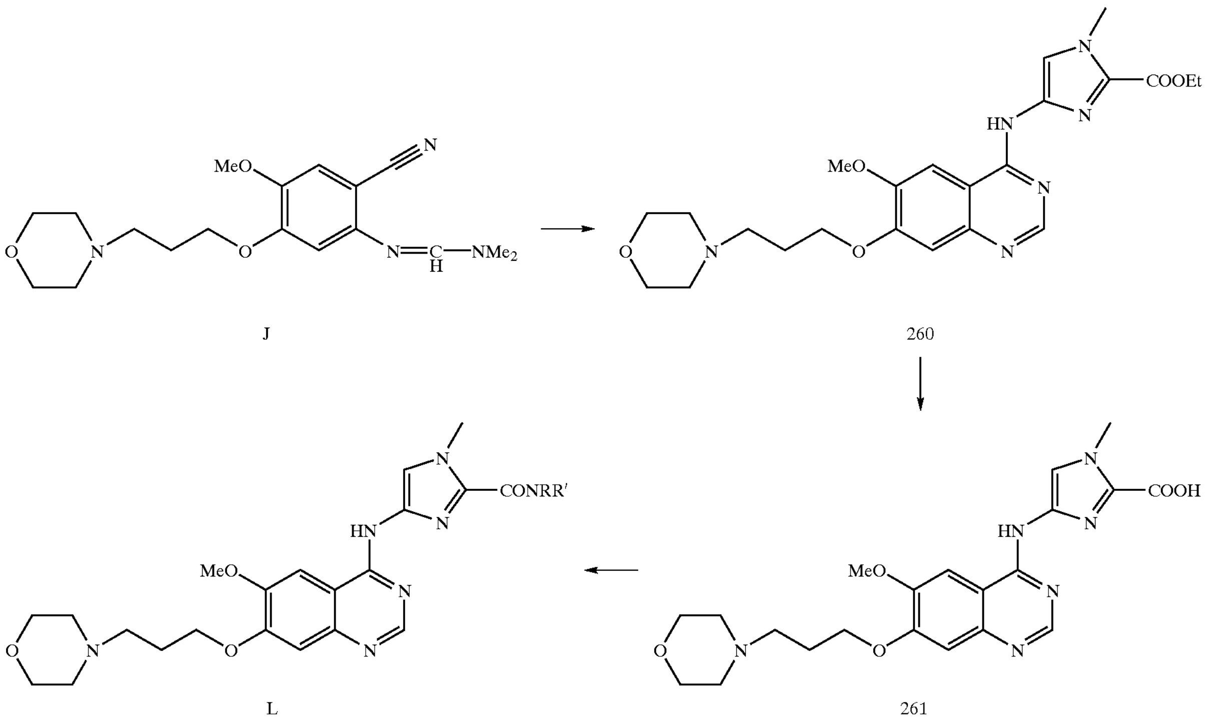

EXAMPLE 99

Preparation of Compound 260 in Table 10

Amidine J (1.04 g, 3 mmol) in acetic acid (10 ml) was reacted with ethyl 4-amino-1-methyl-2-imidazolecarboxylate hydrochloric acid (0.74 g, 3.6 mmol) in presence of dimethylamine/MeOH (1.25N, 2.9 ml, 3.6 mmol) at 130° C. for 3 hours. The solvent was evaporated, the residue triturated with ether and filtered. The solid was suspended in water, the pH adjusted to 9 with an aqueous solution of sodium bicarbonate, the suspension was filtered, washed with water, dried under vacuum over $P_2O_5$, to give title compound (1.1 g, 78%).

$^1$HNMR (DMSO-$d_6$): 1.32 (t, 3H); 1.96 (m, 2H); 2.37 (m, 4H); 2.44 (t, 2H); 3.58 (m, 4H); 3.94 (s, 3H); 4.0 (s, 3H); 4.17 (t, 2H); 4.28 (q, 2H); 7.16 (s, 1H); 7.99 (s, 1H); 8.07 (s, 1H); 8.53 (s, 1H); 10.55 (s, 1H).

EXAMPLE 100

Preparation of Compound 261 in Table 10

Ester 260 (1.1 g, 2.34 mmol) in ethanol (23 ml) was reacted with sodium hydroxyde (6N, 2.3 ml) at 80° C. for 2.5 hours. The mixture was cooled, and acidified with hydrochloric acid (6N) to pH 3. The suspension was recovered by centrifugation, washed with ethanol, ether, dried under vacuum over $P_2O_5$, to give title compound (930 mg, 73%).

$^1$HNMR (DMSO-$d_6$, TFA): 2.31 (m, 2H); 3.16 (t, 2H); 3.35 (t, 2H); 3.54 (d, 2H); 3.76 (t, 2H); 4.01 (s, 3H); 4.05 (m, 5H); 4.32 (t, 2H); 7.41 (s, 1H); 8.03 (s, 1H); 8.38 (s, 1H); 9.0 (s, 1H).

MS $ES^+$: 443 $[H_+H]^+$

EXAMPLE 101

Preparation of Compounds of General Structure L

Acid 261 (88 mg, 0.16 mmol) in DMF (1 ml) was reacted with O-(Benzotriazol-1-yl)-N,N,N',N'-tetramethyluroniumhexafluorophosphate (73 mg, 0.19 mmol), the appropriate amine (0.18 mmol) and DIEA (82 mg, 0.4 mmol) at room temperature for 3 hours. The solution was then diluted with a saturated solution of sodium bicarbonate (4 ml) and stirred at room temperature for 3 hours. The precipitate was filtered, washed with water, dried under vacuum over $P_2O_5$, to give title compound.

EXAMPLE 102

Preparation of Compound 262 in Table 10

An analogous reaction to that described in Example 101, but starting with aniline (17 mg, 0.18 mmol) yielded title compound (37 mg, 44%).

$^1$HNMR (DMSO-$d_6$, TFA): 2.3 (m, 2H); 3.16 (t, 2H); 3.35 (t, 2H); 3.55 (d, 2H); 3.69 (t, 2H); 4.02 (m, 5H); 4.06 (s, 3H); 4.31 (t, 2H); 7.13 (t, 1H); 7.38 (m, 3H); 7.78 (d, 2H); 7.99 (s, 1H); 8.27 (s, 1H); 9.01 (s, 1H).

MS $ES^+$: 518 $[H_+H]^+$

EXAMPLE 103

Preparation of Compound 263 in Table 10

An analogous reaction to that described in Example 101, but starting with 4-fluoroaniline (20 mg, 0.18 mmol) yielded title compound (84 mg, 97%).

$^1$HNMR (DMSO-$d_6$, TFA): 2.3 (m, 2H); 3.16 (t, 2H); 3.36 (t, 2H); 3.56 (d, 2H); 3.69 (t, 2H); 4.02 (s, 3H); 4.04 (d, 2H); 4.1 (s, 3H); 4.31 (t, 2H); 7.21 (t, 2H); 7.39 (s, 1H); 7.82 (m, 2H); 7.98 (s, 1H); 8.32 (s, 1H); 9.01 (s, 1H).

MS ES$^+$: 536 [$H_+H$]$^+$

EXAMPLE 104

Preparation of Compound 264 in Table 10

An analogous reaction to that described in Example 101, but starting with N,N-dimethyl-1,4-phenylenediamine (24 mg, 0.18 mmol) yielded title compound (80 mg, 88%).

$^1$HNMR (DMSO-$d_6$, TFA): 2.3 (m, 2H); 3.17 (t, 2H); 3.21 (s, 6H); 3.35 (t, 2H); 3.55 (d, 2H); 3.69 (t, 2H); 4.02 (m, 5H); 4.1 (s, 3H); 4.31 (t, 2H); 7.4 (s, 1H); 7.66 (d, 2H); 7.98 (d, 2H); 8.01 (s, 1H); 8.32 (s, 1H); 9.01 (s, 1H).

MS ES$^+$: 561 [$H_+H$]$^+$

EXAMPLE 105

Reparation of Compound 265 in Table 10

An analogous reaction to that described in Example 101, but starting with 4-chloroaniline (23 mg, 0.18 mmol) yielded title compound (55 mg, 62%).

$^1$HNMR (DMSO-$d_6$, TFA): 2.3 (m, 2H); 3.17 (t, 2H); 3.35 (t, 2H); 3.55 (d, 2H); 3.69 (t, 2H) 4.02 (s, 3H); 4.04 (d, 2H); 4.1 (s, 3H); 4.32 (t, 2H); 7.39 (s, 1H); 7.43 (d, 2H); 7.84 (d, 2H); 7.99 (s, 1H); 8.32 (s, 1H); 9.01 (s, 1H).

MS ES$^+$: 552, 554 [$H_+H$]$^+$

EXAMPLE 106

Preparation of Compound 266 in Table 10

An analogous reaction to that described in Example 101, but starting with pyrrolidine (13 mg, 0.18 mmol) yielded title compound (50 mg, 62%).

$^1$HNMR (DMSO-$d_6$, TFA): 1.85 (m, 4H); 2.28 (m, 2H); 3.15 (t, 2H); 3.32 (t, 2H); 3.5 (m, 4H); 3.66 (t, 2H); 3.89 (m, 5H); 3.98 (m, 5H); 4.27 (t, 2H); 7.33 (s, 1H); 7.85 (s, 1H); 8.29 (s, 1H); 8.96 (s, 1H).

MS ES$^+$: 496 [$H_+H$]$^+$

EXAMPLE 107

Preparation of Compound 267 in Table 10

An analogous reaction to that described in Example 101, but starting with cyclohexylamine (18 mg, 0.18 mmol) yielded title compound (54 mg, 64%).

$^1$HNMR (DMSO-$d_6$, TFA): 1.19 (m, 1H); 1.35 (m, 4H); 1.61 (m, 1H); 1.71 (m, 2H); 1.85 (m, 2H); 2.31 (m, 2H); 3.16 (t, 2H); 3.34 (t, 2H); 3.54 (d, 2H); 3.69 (t, 2H); 3.75 (m, 1H); 4.01 (s, 3H); 4.04 (m, 5H); 4.3 (t, 2H); 7.37 (s, 1H); 7.9 (s, 1H); 8.29 (s, 1H); 8.99 (s, 1H).

MS ES$^+$: 524 [$M_+H$]$^+$

General Scheme 12

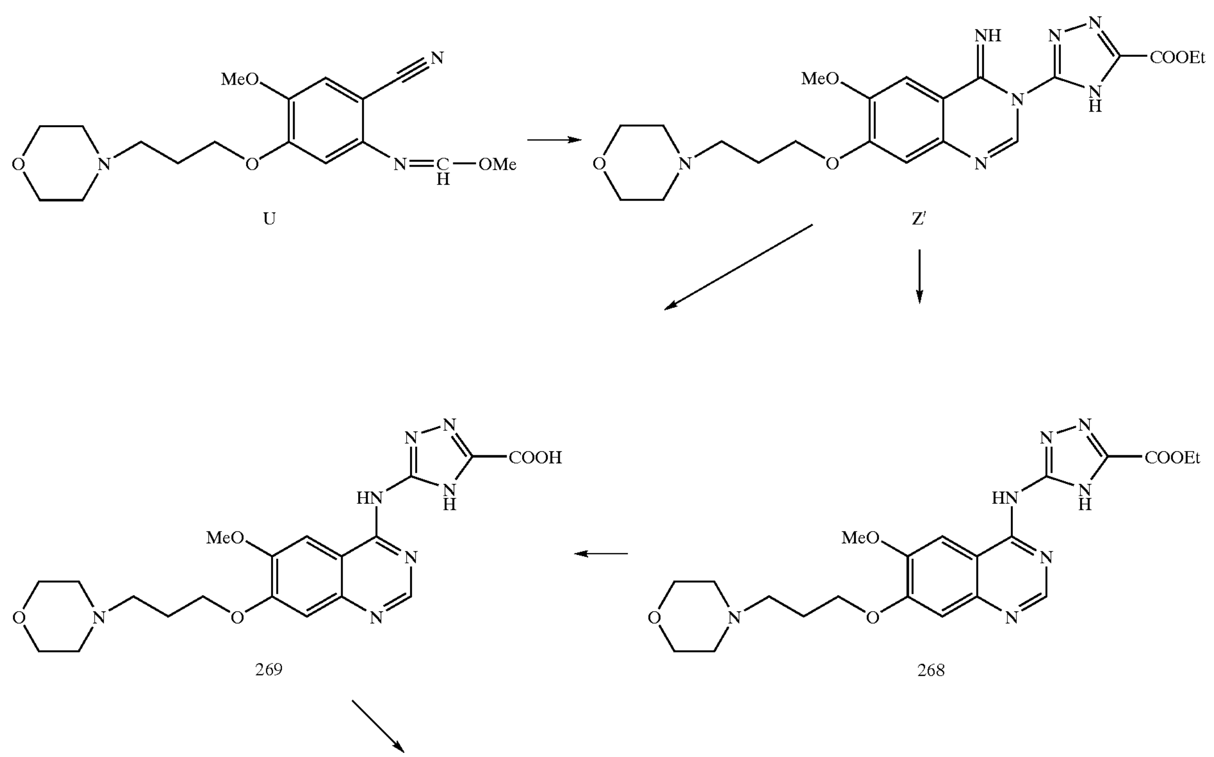

U

Z'

269

268

-continued

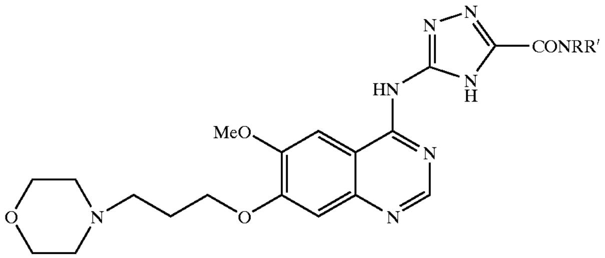

Z

EXAMPLE 108

Step (a) Preparation of Intermediates of General formula $Z^1$

Imidate U (2 g, 6 mmol) in dimethylformamide (40 ml) was reacted with ethyl 5-amino-4H-1,2,4-triazole-3-carboxylate hydrochloric acid (1.16 g, 6 mmol) in presence of sodium hydride (60%, 504 mg, 12.6 mmol) at 110° C. for 7 hours, under argon. The mixture was then cooled to room temperature, and acetic acid (1.03 ml, 18 mmol) was added, the solvent was evaporated under vacuum, the residue purified by silica gel chromatography, eluent: $CH_2Cl_2$/MeOH, 90/10 to give title compound (1.07 g, 39%).

$^1$H NMR (DMSO-$d_6$, TFA): 0.39 (t, 3H); 2.28 (m, 2H); 3.15 (t, 2H); 3.32 (t, 2H); 3.56 (d, 2H); 3.68 (t, 2H); 3.98 (s, 3H); 4.05 (d, 2H); 4.37 (t, 2H); 4.52 (q, 2H); 7.49 (s, 1H); 8.12 (s, 1H); 8.71 (s, 1H).

MS ES$^+$: 458 $[M_+H]^+$

Step (b): Preparation of Compound 268 in Table 11

Triazole ester $Z^1$ (80 mg, 0.17 mmol) in dimethylformamide (3 ml) was treated with dimethylamine acetate (0.52 mmol) at 70° C. for 20 minutes. The mixture was cooled, the solvent evaporated, and the residue purified by silica gel chromatography, eluent $CH_2Cl_2$/MeOH/NH3, 90/10/1 to give title product (60 mg, 75%).

$^1$H NMR (DMSO-$d_6$, TFA): 1.34 (t, 3H); 2.3 (m, 2H); 3.15 (t, 2H); 3.35 (t, 2H); 3.54 (d, 2H); 3.68 (t, 2H); 4.0 (s, 3H); 4.04 (d, 2H); 4.36 (m, 4H); 7.48 (s, 1H); 8.26 (s, 1H); 9.01 (s, 1H).

MS ES$^+$: 458 $[H_+H]^+$

EXAMPLE 109

Preparation of Compound 269 in Table 11

Triazole ester 268 (900 mg, 1.97 mmol) in methanol (20 ml), was treated with sodium hydroxyde (2N, 20 ml) at 80° C. for 1.5 hour. The mixture was cooled, and acidified to pH 2.5 with hydrochloric acid (6N), the solid was recovered by filtration dried under vacuum over $P_2O_5$ to give title compound (843 mg, 100%).

$^1$HNMR (DMSO-$d_6$, TFA): 2.37 (m, 2H); 3.12 (t, 2H); 3.3 (t, 2H); 3.5 (d, 2H); 3.87 (t, 2H); 3.97 (d, 2H); 4.01 (s, 3H); 4.35 (t, 2H); 7.63 (s, 1H); 8.32 (s, 1H); 8.97 (s, 1H).

MS ES$^+$: 430 $(M+H)^+$.

EXAMPLE 110

Preparation of Compound 270 in Table 11

Acid 269 (120 mg, 0.28 mmol) in DMF (2 ml) was reacted with aniline (0.025 ml, 0.28 mmol) in presence of O-(7-azabenzotriazol-1-yl)N,N,N',N',-tetramethyluronium hexafluorophosphate (106 mg, 0.28 mmol) and DIEA (0.12 ml, 0.7 mmol) at room temperature for 4 hours. The solvent was evaporated, the residue dissolved in methylene chloride/methanol, and treated with a methanolic solution of dimethylamine (2M, 1 ml) at room temperature over night. The solvent was evaporated, and the residue purified by flash silica gel chromatography, eluent $CH_2Cl_2$/MeOH, 90/10 to give title compound (12 mg, 9%).

$^1$H NMR (DMSO-$d_6$, TFA): 2.3 (m, 2H); 3.18 (t, 2H); 3.35 (t, 2H); 3.54 (d, 2H); 3.68 (t, 2H); 4.01 (s, 3H); 4.03 (d, 2H); 4.33 (t, 2H); 7.16 (t, 1H); 7.39 (t, 2H); 7.45 (s, 1H); 7.83 (d, 2H); 8.2 (s, 1H); 8.95 (s, 1H).

MS ES$^+$: 505 $[H_+H]^+$

EXAMPLE 111

Preparation of Compound 271 in Table 11

An analogous reaction to that described in Example 110, but starting with 4-fluoroaniline (0.13 ml, 1.4 mmol) yielded title compound (44 mg, 18%).

$^1$H NMR (DMSO-$d_6$, TFA): 2.3 (m, 2H); 3.15 (t, 2H); 3.35 (t, 2H); 3.54 (d, 2H); 3.68 (t, 2H); 4.0 (s, 3H); 4.04 (d, 2H); 4.33 (t, 2H); 7.23 (t, 2H); 7.44 (s, 1H); 7.86 (m, 1H); 8.18 (s, 1H); 8.93 (s, 1H).

MS ES$^+$: 523 $[M_+H]^+$

EXAMPLE 112

Preparation of Compound 272 in Table 11

An analogous reaction to that described in Example 110 but starting with allylamine (0.13 ml, 1.75 mmol) yielded the title compound (26 mg, 10%).

$^1$H NMR (DMSO-$d_6$, TFA): 2.3 (m, 2H); 3.16 (t, 2H); 3.34 ((, 2H); 3.54 (d, 2H); 3.68 (t, 2H); 3.94 (d, 2H); 3.99 (s, 3H); 4.03 (d, 2H); 4.32 (t, 2H); 5.13 (d, 1H); 5.18 (d, 1H); 5.92 (m, 1H); 7.41 (s, 1H); 8.17 (s, 1H); 8.91 (s, 1H).

MS ES$^+$: 469 $[M_+H]^+$

General Scheme 13

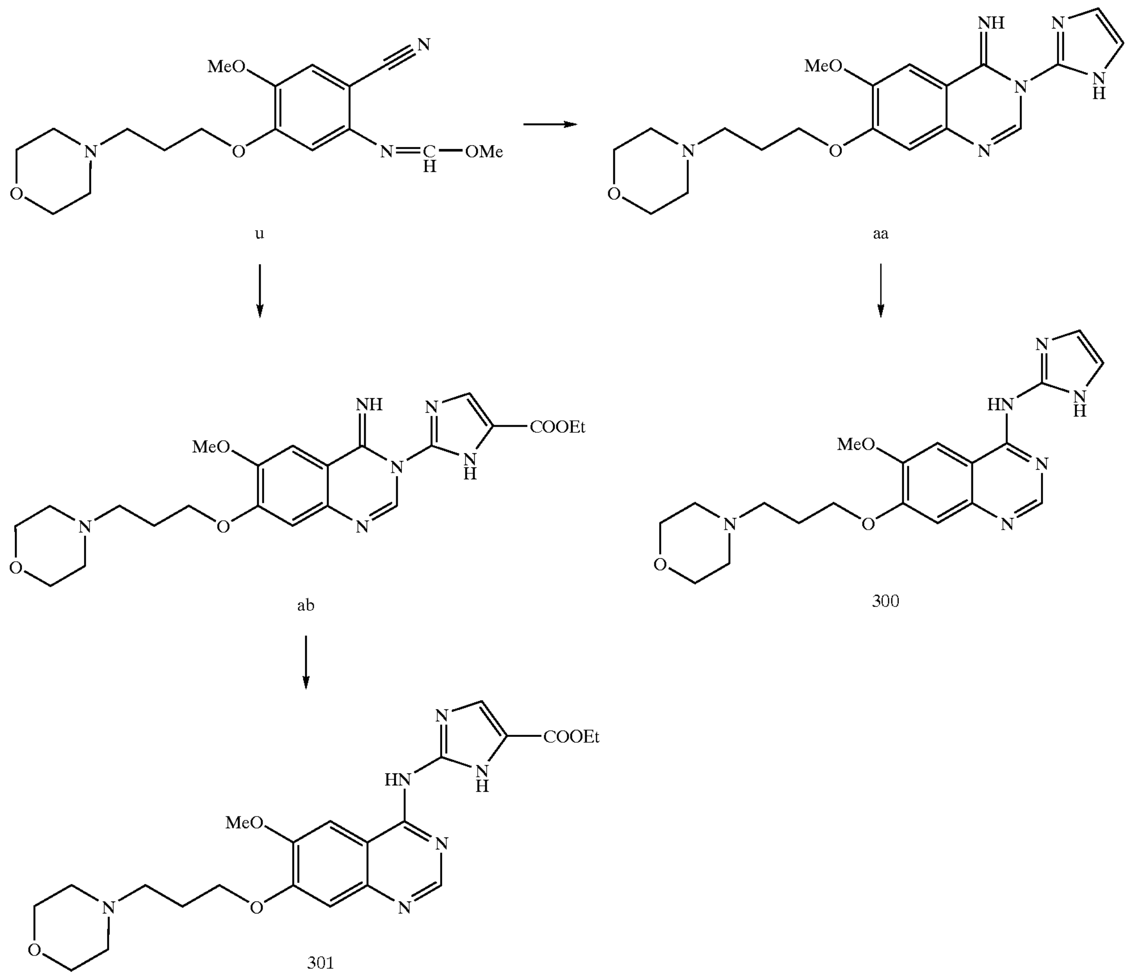

u aa ab 300 301

EXAMPLE 113

Preparation of Compound 300 in Table 12

Step 1 Preparation of Compound aa

Imidate u, (200 mg, 0.6 mmol) in DMF (4 ml) was condensed with 2-aminoimidazole, sulfate (160 mg, 0.6 mmol) in presence of sodium hydride (60%, 50 mg, 1.26 mmol) at 90° C. for 2 hours. The mixture was cooled, acetic acid (0.01 ml, 1.8 mmol) was added, the solvent was evaporated, and the residue purified by silica gel chromatography, eluent $CH_2Cl_2$/MeOH, 90/10 to give title compound (112 mg, 48%).

$^1$HNMR (DMSO-$d_6$, TFA): 2.3 (m, 2H); 3.15 (t, 2H); 3.33 (t, 2H); 3.54 (d, 2H); 3.68 (t, 2H); 3.97 (s, 3H); 4.03 (d, 2H); 4.36 (t, 2H); 7.41 (s, 2H); 7.47 (s, 1H); 8.13 (s, 1H); 8.66 (s, 1H).

MS $ES^+$: 385 $[H_+H]^+$

Step 2: Preparation of Compound 300

Imidazole aa (105 mg, 0.273 mmol) in DMF (2 ml) was heated at 80° C. for 0.3 hour in presence of dimethylamine acetate (0.819 mmol), the solvent was evaporated, and the residue was purified by silica gel chromatography, eluent $CH_2Cl_2$/MeOH sat. NH3, 90/10 to give title compound (78 mg, 74%).

$^1$HNMR (DMSO): 1.96 (m, 2H); 2.39 (m, 4H); 2.46 (t, 2H); 3.6 (m, 4H); 3.9 (s, 3H); 4.18 (t, 2H). 6.9 (s, 2H); 7.14 (s, 1H); 7.84 (s, 1H); 8.39 (s, 1H).

MS $ES^+$: 385 $[H_+H]^+$

EXAMPLE 114

Preparation of Compound 301 in Table 12

Step 1: Preparation of Compound ab

Imidate u (250 mg, 0.751 mmol) in DMF (4 ml) was reacted with ethyl 2-aminoimidazole-4-carboxylate (117 mg, 0.751 mmol) in presence of sodium hydride (60%, 30 mg, 0.826 mmol) at 100° C. for 3 hours. The mixture was cooled, acetic acid (0.13 ml, 2.25 mmol) was added, the solvent was evaporated, and the residue purified by silica gel chromatography to give title compound (125 mg, 36%).

$^1$HNMR (DMSO-$d_6$, TFA): 1.32 (t, 3H); 2.3 (m, 2H); 3.15 (t, 2H); 3.34 (t, 2H); 3.55 (d, 2H); 3.68 (t, 2H); 3.98 (s, 3H); 4.03 (d, 2H); 4.33 (q, 2H); 4.37 (t, 2H); 7.49 (s, 1H); 8.11 (s, 1H); 8.2 (s, 1H); 8.65 (s, 1H).

MS $ES^+$: 457 $[H_+H]^+$

Step 2: Preparation of Compound 301 in Table 12

Imidazole 3 (122 mg, 0.268 mmol) in DMF (2 ml) was heated at 80° C. for 0.3 hour in presence of dimethylamine acetate (0.802 mmol). The solvent was evaporated, and the residue was purified by silica gel chromatography, eluent $CH_2Cl_2$/MeOH sat. $NH_3$ 95/5 to 90/10 to give title compound (105 mg, 86%).

$^1$HNMR (DMSO-$d_6$, TFA): 1.32 (t, 3H); 2.3 (m, 2H); 3.15 (t, 2H); 3.34 (t, 2H); 3.54 (d, 2H); 3.68 (t, 2H); 3.94 (s, 3H);

4.03 (d, 2H); 4.27 (t, 2H); 4.33 (q, 2H); 7.27 (s, 1H); 7.84 (s, 1H); 7.92 (s, 1H); 8.76 (s, 1H).

MS ES$^+$: 457 $[H_+H]^+$

EXAMPLE 115

Preparation of Compound 302 in Table 13

An analogous reaction to that described in general scheme 5, starting with 4-methoxyaniline (32 mg, 0.26 mmol) yielded compound 302 in Table 13 (24 mg, 21%).

MS ES$^+$: 551 $(M+H)^+$ $^1$H NMR (DMSO-$d_6$, TFA): 2.31 (t, 2H); 3.16 (t, 2H); 3.36 (t, 2H); 3.55 (d, 2H); 3.69 (t, 2H); 3.76 (s, 3H); 4.02 (s, 3H); 4.04 (d, 2H); 4.33 (t, 2H); 6.96 (d, 2H); 7.38 (s, 1H); 7.62 (d, 2H); 8.04 (s, 1H); 8.55 (s, 1H) 9.27 (s, 1H).

EXAMPLE 116

Preparation of Compound 303 in Table 13

An analogous reaction to that described in general scheme 5, starting with 4-methylaniline (28 mg, 0.26 mmol) yielded compound 303 in Table 13 (23 mg, 22%).

MS ES$^+$: 535 $(M+H)^+$ $^1$H NMR (DMSO-$d_6$, TFA): 2.29 (s, 3H); 2.33 (t, 2H); 3.17 (t, 2H); 3.36 (t, 2H); 3.55 (d, 2H); 3.69 (t, 2H); 4.01 (s, 3H); 4.04 (d, 2H); 4.33 (t, 2H); 7.19 (d, 2H); 7.38 (s, 1H); 7.60 (d, 2H); 8.05 (s, 1H); 8.58 (s, 1H); 9.28 (s, 1H).

EXAMPLE 117

Preparation of Compound 304 in Table 13

An analogous reaction to that described in general scheme 5, starting with 2-aminopyridine (24 mg, 0.26 mmol) yielded compound 304 in Table 13 (12 mg, 11%).

MS ES$^+$: 522 $(M+H)^+$ $^1$H NMR (DMSO-$d_6$, TFA): 2.32 (t, 2H); 3.16 (t, 2H); 3.36 (t, 2H); 3.55 (d, 2H); 3.69 (t, 2H); 4.02 (s, 3H); 4.04 (d, 2H); 4.34 (t, 2H); 7.33 (m, 1H); 7.41 (s, 1H); 8.07 (m, 2H); 8.09 (s, 1H); 8.46 (d, 1H); 8.81 (s, 1H); 9.30 (s, 1H).

EXAMPLE 118

Preparation of Compound 305 in Table 13

An analogous reaction to that described in general scheme 5, starting with 2-aminobenzyl alcohol (32 mg, 0.26 mmol) yielded compound 305 in Table 13 (54 mg, 60%).

MS ES$^+$: 551 $(M+H)^+$ $^1$H NMR (DMSO-$d_6$, TFA): 2.33 (t, 2H); 3.18 (t, 2H); 3.37 (t, 2H); 3.56 (d, 2H); 3.70 (t, 2H); 3.78 (s, 2H); 4.02 (s, 3H); 4.05 (d, 2H); 4.34 (t, 2H); 6.73 (d, 1H); 7.30 (m, 2H); 7.39 (s, 1H); 7.40 (m, 1H); 8.07 (s, 1H); 8.62 (s, 1H); 9.3 (s, 1H).

EXAMPLE 119

Preparation of Compound 306 in Table 13

An analogous reaction to that described in general scheme 5, starting with 4-methoxybenzylamine (36 mg, 0.26 mmol) yielded compound 306 in Table 13 (29 mg, 26%).

MS ES$^+$: 565 $(M+H)^+$ $^1$H NMR (DMSO-$d_6$, TFA): 2.28 (t, 2H); 3.14 (t, 2H); 3.31 (t, 2H); 3.50 (d, 2H); 3.68 (t, 2H); 3.69 (s, 3H); 3.94 (s, 3H); 3.98 (d, 2H); 4.26 (t, 2H); 4.37 (s, 2H); 6.89 (m, 2H); 7.12 (m, 2H); 7.35 (s, 1H); 7.90 (s, 1H); 8.31 (s, 1H); 9.15 (s, 1H).

EXAMPLE 120

Preparation of Compound 307 in Table 13

An analogous reaction to that described in general scheme 5, starting with 3-nitroaniline (36 mg, 0.26 mmol) yielded compound 307 in Table 13 (27 mg, 24%).

MS ES$^+$: 566 $(M+H)^+$ $^1$H NMR (DMSO-$d_6$, TFA): 2.30 (t, 2H); 3.17 (t, 2H); 3.36 (t, 2H); 3.56 (d, 2H); 3.69 (t, 2H); 4.02 (s, 3H); 4.04 (d, 2H); 4.33 (t, 2H); 7.40 (s, 1H); 7.71 (t, 1H); 7.99 (d, 1H); 8.08 (s, 1H); 8.14 (d, 1H); 8.64 (s, 1H); 8.71 (s, 1H); 9.31 (s, 1H).

EXAMPLE 121

Preparation of Compound 308 in Table 13

An analogous reaction to that described in general scheme 5, starting with aminoacetonitrile (24 mg, 0.26 mmol) yielded compound 308 in Table 13 (29 mg, 30%).

MS ES$^+$: 484 $(M+H)^+$ $^1$H NMR (DMSO-$d_6$, TFA): 2.31 (t, 2H); 3.16 (t, 2H); 3.35 (t, 2H); 3.55 (d, 2H); 3.68 (t, 2H); 4.00 (s, 3H); 4.02 (d, 2H); 4.32 (t, 2H); 4.37 (s, 2H); 7.39 (s, 1H); 8.06 (s, 1H); 8.36 (s, 1H); 9.27 (s, 1H).

EXAMPLE 122

Preparation of Compound 309 in Table 13

An analogous reaction to that described in general scheme 5, starting with 2-methyl-5-nitroaniline (40 mg, 0.26 mmol) yielded compound 309 in Table 13 (14 mg, 12%).

MS ES$^+$: 580 $(M+H)^+$ $^1$H NMR (DMSO-$d_6$, TFA): 2.31 (t, 2H); 3.16 (t, 2H); 3.36 (t, 2H); 3.54 (d, 2H); 3.68 (t, 2H); 4.01 (s, 3H); 4.03 (d, 2H); 4.32 (t, 2H); 7.39 (s, 1H); 7.58 (d, 1H); 8.04 (d, 1H); 8.08 (s, 1H); 8.34 (d, 1H); 8.62 (s, 1H); 9.29 (s, 1H).

EXAMPLE 123

Preparation of Compound 310 in Table 13

An analogous reaction to that described in general scheme 5, starting with cyclopropylamine (15 mg, 0.26 mmol) yielded compound 310 in Table 13 (6 mg, 6%).

MS ES$^+$: 485 $(M+H)^+$ $^1$H NMR (DMSO-$d_6$, TFA): 0.68 (m, 2H); 0.74 (m, 2H); 2.27 (t, 2H); 2.67 (m, 1H); 3.12 (t, 2H); 3.31 (t, 2H); 3.51 (d, 2H); 3.69 (t, 2H); 3.95 (s, 3H); 3.98 (d, 2H); 4.29 (t, 2H); 7.32 (s, 1H); 7.96 (s, 1H); 8.24 (s, 1H); 9.20 (s, 1H).

EXAMPLE 124

Preparation of Compound 311 in Table 13

An analogous reaction to that described in general scheme 5, starting with 4-nitrobenzylamine (49 mg, 0.26 mmol) yielded compound 311 in Table 13 (5 mg, 4%).

MS ES$^+$: 580 $(M+H)^+$ $^1$H NMR (DMSO-$d_6$, TFA): 2.31 (t, 2H); 3.17 (t, 2H); 3.36 (t, 2H); 3.55 (d, 2H); 3.69 (t, 2H); 4.00 (s, 3H); 4.03 (d, 2H); 4.32 (t, 2H); 4.63 (s, 2H); 7.38 (s, 1H); 7.62 (d, 2H); 8.04 (s, 1H); 8.23 (d, 2H); 8.40 (s, 1H); 9.25 (s, 1H).

EXAMPLE 125

Preparation of Compound 312 in Table 13

An analogous reaction to that described in general scheme 5, starting with 2-anilinoethanol (36 mg, 0.26 mmol) yielded compound 312 in Table 13 (49 mg, 44%).

MS ES$^+$: 565 $(M+H)^+$ $^1$H NMR (DMSO-$d_6$, TFA) 2.31 (t, 2H); 3.17 (t, 2H); 3.36 (t, 2H); 3.55 (d, 2H); 3.7 (m, 4H); 4.01 (s, 3H); 4.03 (d, 2H); 4.33 (t, 2H) 4.49 (t, 2H); 7.15 (t, 1H); 7.26 (d, 2H); 7.41 (t, 2H); 7.43 (s, 1H); 8.15 (s, 1H); 8.48 (s, 1H); 9.31 (s, 1H).

EXAMPLE 126

Preparation of compound 313 in Table 13

An analogous reaction to that described in general scheme 5, starting with furfurylamine (25 mg, 0.26 mmol) yielded compound 313 in Table 13 (20 mg, 19%).

MS ES$^+$: 525 $(M+H)^+$ $^1$H NMR (DMSO-$d_6$, TFA): 2.32 (t, 2H); 3.16 (t, 2H); 3.35 (t, 2H); 3.54 (d, 2H); 3.69 (t, 2H); 3.99 (s, 3H); 4.02 (d, 2H); 4.32 (t, 2H); 4.48 (s, 2H); 6.33 (d, 1H); 6.41 (d, 1H); 7.37 (s, 1H); 7.59 (s, 1H); 8.01 (s, 1H); 8.37 (s, 1H); 9.24 (s, 1H).

EXAMPLE 127

Preparation of Compound 314 in Table 13

An analogous reaction to that described in general scheme 5, starting with 3-chloroaniline (33 mg, 0.26 mmol) yielded compound 314 in Table 13 (21 mg, 19%).

MS ES$^+$: 555, 557 $(M+H)^+$ $^1$H NMR (DMSO-$d_6$, TFA): 2.31 (t, 2H); 3.17 (t, 2H); 3.36 (t, 2H); 3.54 (d, 2H); 3.69 (t, 2H); 4.02 (s, 3H); 4.04 (d, 2H); 4.32 (t, 2H); 7.20 (d, 1H); 7.39 (s, 1H); 7.42 (t, 1H); 7.63 (d, 1H); 7.91 (s, 1H); 8.07 (s, 1H); 8.61 (s, 1H); 9.30 (s, 1H).

EXAMPLE 128

Preparation of Compound 315 in Table 13

An analogous reaction to that described in general scheme 5, starting with 2-methoxyaniline (32 mg, 0.26 mmol) yielded compound 315 in Table 13 (67 mg, 61%).

MS ES$^+$: 551 $(M+H)^+$ $^1$H NMR (DMSO-$d_6$, TFA): 2.32 (t, 2H); 3.16 (t, 2H); 3.36 (t, 2H); 3.56 (d, 2H); 3.69 (t, 2H); 3.87 (s, 3H); 4.02 (s, 3H); 4.04 (d, 2H); 4.33 (t, 2H); 6.99 (t, 1H); 7.13 (d, 1H); 7.23 (t, 1H); 7.40 (s, 1H); 7.66 (d, 1H); 8.04 (s, 1H); 8.64 (s, 1H); 9.27 (s, 1H).

EXAMPLE 139

Preparation of Compound 316 in Table 13

An analogous reaction to that described in general scheme 5, starting with thiophene-2-methylamine (29 mg, 0.26 mmol) yielded compound 316 in Table 13 (25 mg, 23%).

MS ES$^+$: 541 $(M+H)^+$ $^1$H NMR (DMSO-$d_6$, TFA): 2.31 (t, 2H); 3.18 (t, 2H); 3.37 (t, 2H); 3.56 (d, 2H); 3.70 (t, 2H); 4.01 (s, 3H); 4.04 (d, 2H); 4.34 (t, 2H); 4.67 (s, 2H); 6.99 (m, 1H); 7.08 (m, 1H); 7.39 (s, 1H); 7.41 (d, 1H); 8.04 (s, 1H); 8.36 (s, 1H); 9.27 (s, 1H).

EXAMPLE 140

Preparation of Compound 317 in Table 13

An analogous reaction to that described in general scheme 5, starting with neopentylamine (23 mg, 0.26 mmol) yielded compound 317 in Table 13 (31 mg, 30%)

MS ES$^+$: 515 $(M+H)^+$ $^1$H NMR (DMSO-$d_6$, TFA): 0.91 (s, 9H); 2.31 (t, 2H); 3.10 (s, 2H); 3.17 (t, 2H); 3.35 (t, 2H); 3.56 (d, 2H); 3.69 (t, 2H); 4.00 (s, 3H); 4.03 (d, 2H); 4.32 (t, 2H); 7.35 (s, 1H); 8.00 (s, 1H); 8.45 (s, 1H); 9.23 (s, 1H).

EXAMPLE 141

Preparation of Compound 318 in Table 13

An analogous reaction to that described in general scheme 5, starting with 2,6-difluorobenzylamine (37 mg, 0.26 mmol) yielded compound 318 in Table 13 (35 mg, 31%0).

MS ES$^+$: 571 $(M+H)^+$ $^1$H NMR (DMSO-$d_6$, TFA): 2.31 (t, 2H); 3.17 (t, 2H); 3.35 (t, 2H); 3.55 (d, 2H); 3.68 (t, 2H); 3.99 (s, 3H); 4.03 (d, 2H); 4.31 (t, 2H); 4.54 (s, 2H); 7.11 (t, 2H); 7.36 (s, 1H); 7.42 (m, 1H); 8.00 (s, 1H); 8.35 (s, 1H); 9.24 (s, 1H).

EXAMPLE 142

Preparation of Compound 319 in Table 13

An analogous reaction to that described in general scheme 5, starting with 2-methylallylamine (28 mg, 0.26 mmol) yielded compound 319 in Table 13 (16 mg, 16%).

MS ES$^+$: 499 $(M+H)^+$ $^1$H NMR (DMSO-$d_6$, TFA): 1.72 (s, 3H); 2.31 (t, 1H); 3.15 (t, 2H); 3.36 (t, 2H); 3.55 (d, 2H); 3.69 (t, 2H); 3.72 (s, 2H); 3.99 (s, 3H); 4.02 (d, 2H); 4.31 (t, 2H); 4.82 (s, 1H); 4.86 (s, 1H); 7.36 (s, 1H); 8.01 (s, 1H); 8.37 (s, 1H); 9.23 (s, 1H).

EXAMPLE 143

Preparation of Compound 320 in Table 13

An analogous reaction to that described in general scheme 5, starting with 2-methyl-4-fluoroaniline (33 mg, 0.26 mmol) yielded compound 320 in Table 13 (47 mg, 43%).

MS ES$^+$: 553 $(M+H)^+$ $^1$H NMR (DMSO-$d_6$, TFA): 2.26 (s, 3H); 2.31 (t, 1H); 3.16 (t, 2H); 3.36 (t, 2H); 3.55 (d, 2H); 3.68 (t, 2H); 4.01 (s, 3H); 4.03 (d, 2H); 4.33 (t, 2H); 7.07 (m, 1H); 7.18 (d, 1H); 7.36 (m, 1H); 7.38 (s, 1H); 8.06 (s, 1H); 8.53 (s, 1H); 9.27 (s, 1H).

EXAMPLE 144

Preparation of Compound 321 in Table 13

An analogous reaction to that described in general scheme 5, starting with 2-fluoro-5-methylaniline (33 mg, 0.26 mmol) yielded compound 321 in Table 13 (60 mg, 54%).

MS ES$^+$: 553 $(M+H)^+$

EXAMPLE 145

Preparation of Compound 322 in Table 13

An analogous reaction to that described in general scheme 5, starting with 4-fluorobenzylamine (33 mg, 0.26 mmol) yielded compound 322 in Table 13 (33 mg, 30%).

MS ES$^+$: 553 $(M+H)^+$ $^1$H NMR (DMSO-$d_6$, TFA): 2.31 (t, 1H); 3.15 (t, 2H); 3.35 (t, 2H); 3.55 (d, 2H); 3.69 (t, 2H); 3.99 (s, 3H); 4.02 (d, 2H); 4.33 (t, 2H); 4.47 (s, 2H); 7.15 (t, 2H); 7.36 (s, 1H); 7.37 (m, 2H); 8.02 (s, 1H); 8.36 (s, 1H); 9.24 (s, 1H).

EXAMPLE 146

Preparation of Compound 323 in Table 13

An analogous reaction to that described in general scheme 5, starting with 3,4-difluorobenzylamine (37 mg, 0.26 mmol) yielded compound 323 in Table 13 (17 mg, 15%).

MS $ES^+$: 571 $(M+H)^+$ $^1H$ NMR (DMSO-$d_6$, TFA): 2.32 (t, 2H); 3.16 (t, 2H); 3.35 (t, 2H); 3.55 (d, 2H); 3.69 (t, 2H); 4.00 (s, 3H); 4.04 (d, 2H); 4.33 (t, 2H); 4.48 (s, 2H); 7.21 (m, 1H); 7.38 (s, 1H); 7.38 (m, 2H); 8.03 (s, 1H); 8.38 (s, 1H); 9.24 (s, 1H).

EXAMPLE 147

Preparation of Compound 324 in Table 13

An analogous reaction to that described in general scheme 5, starting with 3-methylaniline (28 mg, 0.26 mmol) yielded compound 324 in Table 13 (57 mg, 53%).

MS $ES^+$: 535 $(M+H)^+$ $^1H$ NMR (DMSO-$d_6$, TFA): 2.32 (m, 5H); 3.17 (t, 2H); 3.36 (t, 2H); 3.56 (d, 2H); 3.69 (t, 2H); 4.01 (s, 3H); 4.04 (d, 2H); 6.95 (d, 1H); 7.24 (t, 1H); 7.38 (s, 1H); 7.53 (m, 2H); 8.04 (s, 1H); 8.59 (s, 1H); 9.28 (s, 1H).

EXAMPLE 148

Preparation of Compound 325 in Table 13

An analogous reaction to that described in general scheme 5, starting with 2-(methylthio)aniline (36 mg, 0.26 mmol) yielded compound 325 in Table 13 (73 mg, 64%).

MS $ES^+$: 567 $(M+H)^+$ $^1H$ NMR (DMSO-$d_6$, TFA): 2.31 (t, 2H); 2.44 (s, 3H); 3.16 (t, 2H); 3.36 (t, 2H); 3.55 (d, 2H); 3.68 (t, 2H); 4.01 (s, 3H); 4.03 (d, 2H); 4.32 (t, 2H); 7.22 (t, 1H); 7.37 (m, 4H); 8.06 (s, 1H); 8.52 (s, 1H); 9.27 (s, 1H).

EXAMPLE 149

Preparation of Compound 326 in Table 13

An analogous reaction to that described in general scheme 5, starting with 5-aminoindole (34 mg, 0.26 mmol) yielded compound 326 in Table 13 (16 mg, 15%).

MS $ES^+$: 560 $(M+H)^+$ $^1H$ NMR (DMSO-$d_6$, TFA): 2.31 (t, 2H); 3.16 (t, 2H); 3.37 (t, 2H); 3.55 (d, 2H); 3.69 (t, 2H); 4.02 (s, 3H); 4.04 (d, 2H); 4.32 (t, 2H); 7.36 (m, 5H); 7.94 (s, 1H); 8.04 (s, 1H); 8.28 (s, 1H); 9.28 (s, 1H).

EXAMPLE 150

Preparation of Compound 327 in Table 13

An analogous reaction to that described in general scheme 5, starting with 3-aminobenzonitrile (31 mg, 0.26 mmol) yielded compound 327 in Table 13 (30 mg, 28%).

MS $ES^+$: 546 $(M+H)^+$ $^1H$ NMR (DMSO-$d_6$, TFA): 2.31 (t, 2H); 3.17 (t, 2H); 3.36 (t, 2H); 3.55 (d, 2H); 3.67 (t, 2H); 4.02 (s, 3H); 4.04 (d, 2H); 4.33 (t, 2H); 7.40 (s, 1H); 7.60 (m, 2H); 7.97 (m, 1H); 8.08 (s, 1H); 8.21 (s, 1H); 8.61 (s, 1H); 9.30 (s, 1H).

EXAMPLE 151

Preparation of Compound 328 in Table 13

An analogous reaction to that described in general scheme 5, starting with 2,4-difluorobenzylamine (37 mg, 0.26 mmol) yielded compound 328 in Table 13 (27 mg, 24%).

MS $ES^+$: 571 $(M+H)^+$ $^1H$ NMR (DMSO-$d_6$, TFA): 2.31 (t, 2H); 3.16 (t, 2H); 3.35 (t, 2H); 3.55 (d, 2H); 3.70 (t, 2H); 4.00 (s, 3H); 4.03 (d, 2H); 4.32 (t, 2H); 4.49 (s, 2H); 7.09 (m, 1H); 7.21 (m, 1H); 7.38 (s, 1H); 8.02 (s, 1H); 8.38 (s, 1H); 9.24 (s, 1H).

EXAMPLE 152

Preparation of Compound 329 in Table 13

An analogous reaction to that described in general scheme 5, starting with 3-(2-aminoethyl)pyridine (32 mg, 0.26 mmol) yielded compound 329 in Table 13 (33 mg, 30%).

MS $ES^+$: 550 $(M+H)^+$ $^1H$ NMR (DMSO-$d_6$, TFA): 2.33 (t, 2H); 3.11 (t, 2H); 3.18 (t, 2H); 3.35 (t, 2H); 3.57 (d, 2H); 3.66 (t, 2H); 3.68 (t, 2H); 4.01 (s, 3H); 4.05 (d, 2H); 4.34 (t, 2H); 7.41 (s, 1H); 8.05 (s, 1H); 8.08 (dd, 2H); 8.28 (s, 1H); 8.59 (d, 1H); 8.87 (d, 1H); 8.95 (s, 1H); 9.25 (s, 1H).

EXAMPLE 153

Preparation of Compound 330 in Table 13

An analogous reaction to that described in general scheme 5, starting with N-methylisobutylamine (23 mg, 0.26 mmol) yielded compound 330 in Table 13 (23 mg, 22%).

MS $ES^+$: 515 $(M+H)^+$ $^1H$ NMR (DMSO-$d_6$, TFA): 0.88 (d, 6H); 2.02 (m, 1H); 2.31 (t, 2H); 3.16 (t, 2H); 3.27 (m, 5H); 3.36 (t, 2H); 3.56 (d, 2H); 3.69 (t, 2H); 4.00 (s, 3H); 4.03 (d, 2H); 4.32 (t, 2H); 7.37 (s, 1H); 8.03 (s, 1H); 8.18 (s, 1H); 9.23 (s, 1H).

EXAMPLE 154

Preparation of Compound 331 in Table 13

An analogous reaction to that described in general scheme 5, starting with 2-aminobenzylamine (32 mg, 0.26 mmol) yielded compound 331 in Table 13 (6 mg, 6%).

MS $ES^+$: 550 $(M+H)^+$ $^1H$ NMR (DMSO-$d_6$, TFA): 2.31 (t, 2H); 3.16 (t, 2H); 3.37 (t, 2H); 3.56 (d, 2H); 3.70 (t, 2H); 4.00 (s, 3H); 4.03 (d, 2H); 4.32 (t, 2H); 4.47 (s, 2H); 7.41 (s, 1H); 7.46 (m, 4H); 8.06 (s, 1H); 8.42 (s, 1H); 9.24 (s, 1H).

EXAMPLE 155

Preparation of Compound 332 in Table 13

An analogous reaction to that described in general scheme 5, starting with 3-methylbutylamine (23 mg, 0.26 mmol) yielded compound 332 in Table 13 (48 mg, 47%).

MS $ES^+$: 515 $(M+H)^+$ $^1H$ NMR (DMSO-$d_6$, TFA): 0.90 (d, 6H); 1.43 (q, 2H); 1.62 (m, 1H); 2.31 (t, 2H); 3.15 (t, 2H); 3.28 (t, 2H); 3.35 (t, 2H); 3.54 (d, 2H); 3.68 (t, 2H); 3.99 (s, 3H); 4.02 (d, 2H); 4.31 (t, 2H); 7.35 (s, 1H); 8.00 (s, 1H); 8.31 (s, 1H); 9.23 (s, 1H).

EXAMPLE 156

Preparation of Compound 333 in Table 13

An analogous reaction to that described in general scheme 5, starting with 1-aminomethyl-1-cyclohexanol (43 mg, 0.26 mmol) yielded compound 333 in Table 13 (7 mg, 6%).

MS $ES^+$: 557 $(M+H)^+$ $^1$H NMR (DMSO-$d_6$, TFA): 1.37 (m, 1H); 2.28 (t, 2H); 3.11 (t, 2H); 3.23 (s, 2H); 3.32 (t, 2H); 3.51 (d, 2H); 3.65 (t, 2H); 3.96 (s, 3H); 3.99 (d, 2H); 4.28 (t, 2H); 7.32 (s, 1H); 7.95 (s, 1H); 8.43 (s, 1H); 9.19 (s, 1H).

EXAMPLE 157

Preparation of Compound 334 in Table 13

An analogous reaction to that described in general scheme 5, starting with 2-aminomethylpyrazine (38 mg, 0.26 mmol) yielded compound 334 in Table 13 (25 mg, 24%).

MS ES$^+$: 537 (M+H)$^+$ $^1$H NMR (DMSO-$d_6$, TFA): 2.33 (t, 2H); 3.13 (t, 2H); 3.36 (t, 2H); 3.55 (d, 2H); 3.69 (t, 2H); 4.00 (s, 3H); 4.05 (d, 2H); 4.30 (t, 2H); 4.65 (s, 2H); 7.38 (s, 1H); 8.03 (s, 1H); 8.40 (s, 1H); 8.57 (d, 1H); 8.62 (d, 1H); 8.70 (s, 1H); 9.24 (s, 1H).

EXAMPLE 158

Preparation of Compound 335 in Table 13

An analogous reaction to that described in general scheme 5, starting with 3-methoxyaniline (32 mg, 0.26 mmol) yielded compound 335 in Table 13 (60 mg, 54%).

MS ES$^+$: 551 (M+H)$^+$ $^1$H NMR (DMSO-d6, TFA): 2.31 (t, 2H); 3.17 (t, 2H); 3.37 (t, 2H); 3.58 (d, 2H); 3.70 (t, 2H); 3.79 (s, 3H); 4.03 (s, 3H); 4.06 (d, 2H); 4.34 (t, 2H); 6.73 (d, 1H); 7.29 (d, 1H); 7.32 (d, 1H); 7.41 (m, 2H); 8.07 (s, 1H); 8.62 (s, 1H); 9.30 (s, 1H).

EXAMPLE 159

Preparation of Compound 336 in Table 13

An analogous reaction to that described in general scheme 5, starting with 4-chlorobenzylamine (19 mg, 0.26 mmol) yielded compound 336 in Table 13 (31 mg, 54%).

MS ES$^+$: 569, 571 (M+H)$^+$ $^1$H NMR (DMSO-$d_6$, TFA): 2.31 (t, 2H); 3.15 (t, 2H); 3.35 (t, 2H); 3.55 (d, 2H); 3.69 (t, 2H); 4.00 (s, 3H); 4.03 (d, 2H); 4.32 (t, 1H); 4.48 (s, 2H); 7.42 (m, 5H); 8.02 (s, 1H); 8.37 (s, 1H); 9.24 (s, 1H).

EXAMPLE 160

Preparation of Compound 337 in Table 14

4-((2-amino-1,3-thiazole-5-yl)acetic acid)-6-methoxy-7-(3-morpholinopropoxy)quinazoline (78 mg, 0.17 mmol) in DMF (1 ml), was reacted with aniline (19 mg, 0.2 mmol) in presence of 0-(7-azabenzotriazol-1-yl)-N,N,N',N'-tetramethyluronium hexafluorophosphate (76 mg, 0.2 mmol) and DIEA (44 mg, 0.34 mmol) at 50° C. over night. The reaction mixture was cooled, treated with $NaHCO_3$ (1 ml), concentrated. The yellow solid was recovered, dissolved in a mixture of $CH_2Cl_2$/MeOH (60/40) 20 ml. Alumina (3 g) was added to the mixture, the solvent was evaporated, and the solid was added on top of an alumina column which was eluted with $CH_2Cl_2$/MeOH (10/0 to 9/1) to give title compound (43 mg, 47%).

MS ES$^+$: 535 (M+H)$^+$ $^1$HNMR (DMSO-$d_6$, TFA): 2.31 (t, 2H); 3.16 (t, 2H); 3.37 (t, 2H); 3.55 (d, 2H); 3.69 (t, 2H); 3.99 (m, 5H); 4.04 (d, 2H); 4.30 (t, 2H); 7.08 (t, 1H); 7.32 (m, 3H); 7.62 (m, 3H); 7.91 (s, 1H); 9.09 (s, 1H).

4-(ethyl(2-amino-1,3-thiazole-5-yl)acetate)-6-methoxy-7-(3-morpholinopropoxy)quinazoline Amidine J of scheme. 2 (4.5 g, 13 mmol) in acetic acid (45 ml) was reacted with ethyl (2-amino-1,3-thiazole-5-yl) acetate (2.54 g, 13.65 mmol) at reflux for 5.5 hour under argon. The mixture was concentrated, and the residue was purified over silicagel chromatography, eluant $CH_2Cl_2$/MeOH, 95/5 to 90/10 to give title compound (4.5 g, 63%).

$^1$HNMR (DMSO-$d_6$): 1.22 (t, 3H); 1.96 (t, 2H); 2.37 (m, 4H); 2.35 (t, 2H); 3.58 (m, 4H); 3.91 (s, 2H); 3.95 (s, 3H); 4.13 (q, 2H); 4.20 (t, 2H); 7.25 (s, 1H); 7.36 (s, 1H); 8.10 (s, 1H); 8.66 (s, 1H).

4-((2-amino-1,3-thiazole-5-yl)acetic acid)$_6$-methoxy-7-(3-morpholinopropoxy)quinazoline 4-(ethyl(2-amino-1,3-thiazole-5-yl)acetate)-$_6$-methoxy-7-(3-morpholinopropoxy)quinazoline (4.38 g, 8 mmol) in ethanol (44 ml) was treated with sodium hydroxyde (2N, 10 ml) at 50° C. for 4 hours. The mixture was cooled to room temperature and the pH adjusted to 3.5 with 2N HCl. The residue was dissolved in $CH_2Cl_2$/MeOH, 60/40, DIEA (3 g, 24 mmoles) was added, the mixture was stirred for 10 minutes, filtered, and the solution was concentrated to give an oily residue. This residue was dissolved in ethanol, and the solvent was partially evaporated. A cristalin solid was recovered, suspended in ethanol, washed with ether and dried under vacuum to give title compound (3.7 g, 100%).

$^1$HNMR (DMSO-$d_6$, TFA): 2.28 (t, 2H); 3.16 (t, 2H); 3.35 (t, 2H); 3.54 (d, 2H); 3.70 (t, 2H); 3.92 (s, 2H); 3.99 (s, 3H); 4.03 (d, 2H); 4.30 (t, 2H); 7.32 (s, 1H); 7.60 (s, 1H); 7.90 (s, 1H); 9.08 (s, 1H).

EXAMPLE 161

Preparation of Compound 338 in Table 14

An analogous reaction to that described in example 160 but starting with 3-chloro-4-fluoroaniline (30 mg, 0.2 mmol) yielded the title compound (24 mg, 24%).

MS ES$^+$: 587 (M+H)$^+$ $^1$HNMR (DMSO-$d_6$, TFA): 2.31 (t, 2H); 3.16 (t, 2H); 3.34 (t, 2H); 3.56 (d, 2H); 3.69 (t, 2H); 3.99 (m, 5H); 4.03 (d, 2H); 4.30 (t, 2H); 7.30 (s, 1H); 7.39 (t, 1H); 7.50 (m, 1H); 7.65 (s, 1H); 7.85 (s, 1H); 7.97 (d, 1H); 9.09 (s, 1H).

EXAMPLE 162

Preparation of Compound 339 in Table 14

An analogous reaction to that described in example 160 but starting with 4-chloroaniline (26 mg, 0.2 mmol) yielded title compound (73 mg, 76%).

MS ES$^+$: 569 (M+H)$^+$ $^1$HNMR (DMSO-$d_6$, TFA): 2.32 (t, 2H); 3.16 (t, 2H); 3.36 (t, 2H); 3.55 (d, 2H); 3.69 (t, 2H); 3.89 (m, 5H); 4.04 (d, 2H); 4.30 (t, 2H); 7.30 (s, 1H); 7.39 (d, 2H); 7.64 (s, 1H); 7.65 (d, 2H); 7.91 (s, 1H); 9.09 (s, 1H).

EXAMPLE 163

Preparation of Compound 340 in Table 14

An analogous reaction to that described in example 160 but starting with 3,4-difluoroaniline (26 mg, 0.2 mmol) yielded title compound (75 mg, 77%).

MS ES$^+$: 571 (M+H)$^+$ $^1$HNMR (DMSO-$d_6$, TFA) 2.31 (t, 2H); 3.17 (t, 2H); 3.36 (t, 2H); 3.55 (d, 2H); 3.72 (t, 2H); 3.99 (m, 5H); 4.04 (d,

2H); 4.30 (t, 2H); 7.31 (s, 1H); 7.32 (m, 1H); 7.41 (q, 1H); 7.65 (s, 1H); 7.81 (m, 1H); 7.92 (s, 1H); 9.09 (s, 1H).

EXAMPLE 164

Preparation of Compound 341 in Table 14

An analogous reaction to that described in example 160 but starting with 3-methoxyaniline (25 mg, 0.2 mmol) yielded title compound (40 mg, 42%).

MS $ES^+$: 565 $(M+H)^+$ $^1$HNMR (DMSO-$d_6$, TFA): 2.31 (t, 2H); 3.16 (t, 2H); 3.36 (t, 2H); 3.55 (d, 2H); 3.70 (t, 2H) 3.74 (s, 3H); 3.97 (s, 2H); 3.99 (s, 3H); 4.04 (d, 2H); 4.31 (t, 2H); 6.68 (d, 1H); 7.15 (d, 1H); 7.23 (t, 1H); 7.29 (s, 1H); 7.33 (s, 1H); 7.64 (s, 1H); 7.91 (s, 1H); 9.09 (s, 1H).

EXAMPLE 165

Preparation of Compound 342 in Table 14

An analogous reaction to that described in example 160 but starting with 2-chloroaniline (26 mg, 0.2 mmol) yielded title compound (15 mg, 16%).

MS $ES^+$: 569 $(M+H)^+$ $^1$HNMR (DMSO-$d_6$, TFA): 2.30 (t, 2H); 3.16 (t, 2H); 3.36 (t, 2H); 3.56 (d, 2H); 3.69 (t, 2H); 3.99 (s, 3H); 4.05 (m, 4H); 4.31 (t, 2H); 7.22 (t, 1H); 7.30 (s, 1H); 7.35 (t, 1H); 7.51 (d, 1H); 7.65 (s, 1H); 7.75 (d, 1H); 7.91 (s, 1H); 9.08 (s, 1H).

EXAMPLE 166

Preparation of Compound 343 in Table 14

An analogous reaction to that described in example 160 but starting with 4-methoxyaniline (26 mg, 0.21 mmol) yielded title compound (55 mg, 57%).

MS $ES^+$: 565.6 $(M+H)^+$ $^1$HNMR (DMSO-$d_6$, TFA): 2.32 (t, 2H); 3.19 (t, 2H); 3.39 (t, 2H); 3.58 (d, 2H); 3.73 (t, 2H); 3.80 (s, 3H); 3.97 (s, 2H); 4.02 (s, 3H); 4.07 (d, 2H); 4.33 (t, 2H); 6.93 (d, 2H); 7.09 (s, 1H); 7.33 (s, 1H); 7.56 (d, 2H); 7.66 (s, 1H); 7.94 (s, 1H); 9.12 (s, 1H).

EXAMPLE 167

Preparation of Compound 344 in Table 14

An analogous reaction to that described in example 160 but starting with 4-methylaniline (23 mg, 0.21 mmol) yielded title compound (51 mg, 54%).

MS $ES^+$: 549.7 $(M+H)^+$ $^1$HNMR (DMSO-$d_6$, TFA): 2.29 (s, 3H); 2.31 (t, 2H); 3.19 (t, 2H); 3.38 (t, 2H); 3.58 (d, 2H); 3.72 (t, 2H); 3.99 (s, 2H); 4.02 (s, 3H); 4.04 (d, 2H); 4.33 (t, 2H); 7.16 (d, 2H); 7.33 (s, 1H); 7.54 (d, 2H); 7.67 (s, 1H); 7.94 (s, 1H); 9.12 (s, 1H).

EXAMPLE 168

Preparation of Compound 345 in Table 14

An analogous reaction to that described in example 160 but starting with 2-methylaniline (23 mg, 0.21 mmol) yielded title compound (42 mg, 45%).

MS $ES^+$: 549.6 $(M+H)^+$ $^1$HNMR (DMSO-$d_6$, TFA): 2.24 (s, 3H); 2.31 (t, 2H); 3.16 (t, 2H); 3.36 (t, 2H); 3.56 (d, 2H); 3.69 (t, 2H); 3.99 (s,

2H); 4.02 (s, 3H); 4.04 (d, 2H); 4.30 (t, 2H); 7.12 (t, 1H); 7.19 (t, 1H); 7.24 (d, 1H); 7.31 (s, 1H); 7.43 (t, 1H); 7.66 (s, 1H); 7.92 (s, 1H); 9.08 (s, 1H).

EXAMPLE 169

Preparation of Compound 346 in Table 14

An analogous reaction to that described in example 160 but starting with 2-aminopyridine (20 mg, 0.21 mmol) yielded title compound (12 mg, 13%).

MS $ES^+$: 536.6 $(M+H)^+$ $^1$HNMR (DMSO-$d_6$, TFA): 2.31 (t, 2H); 3.18 (t, 2H); 3.37 (t, 2H); 3.56 (d, 2H); 3.70 (t, 2H); 4.00 (m, 5H); 4.04 (d, 2H); 4.33 (, 2H); 7.34 (s, 1H); 7.37 (t, 1H); 7.68 (s, 1H); 7.93 (d, 1H); 7.94 (s, 1H); 8.10 (t, 1H); 8.42 (d, 1H); 9.10 (s, 1H).

EXAMPLE 170

Preparation of Compound 347 in Table 14

An analogous reaction to that described in example 160 but starting with 2-aminobenzylalcohol (26 mg, 0.21 mmol) yielded title compound (24 mg, 24%).

MS $ES^+$: 565.7 $(M+H)^+$ $^1$HNMR (DMSO-$d_6$): 1.97 (t, 2H); 2.41 (m, 6H); 3.59 (m, 4H); 3.91 (s, 2H); 3.97 (s, 3H); 4.21 (t, 2H); 4.50 (d, 2H); 5.27 (t, 1H); 7.18 (t, 1H); 7.25 (d, 1H); 7.26 (s, 1H); 7.42 (m, 2H); 7.52 (d, 1H); 8.67 (s, 1H); 9.59 (s, 1H).

EXAMPLE 171

Preparation of Compound 348 in Table 14

An analogous reaction to that described in example 160 but starting with 2-amino-3-methyl-1-butanol (22 mg, 0.21 mmol) yielded title compound (25 mg, 27%).

MS $ES^+$: 545.7 $(M+H)^+$ $^1$HNMR (DMSO-$d_6$, TFA): 0.87 (d, 3H); 0.89 (d, 3H); 1.86 (m, 1H); 2.31 (t, 2H); 3.18 (t, 2H); 3.37 (t, 2H); 3.44 (2s, 2H); 3.57 (d, 2H); 3.63 (q, 1H); 3.70 (t, 2H); 3.80 (d, 2H); 4.01 (t, 3H); 4.07 (d, 2H); 4.31 (t, 2H); 7.32 (s, 1H); 7.58 (s, 1H); 7.92 (s, 1H); 9.09 (s, 1H).

EXAMPLE 172

Preparation of Compound 349 in Table 14

An analogous reaction to that described in example 160 but starting with 2-anilinoethanol (29 mg, 0.21 mmol) yielded title compound (11 mg, 11%).

MS $ES^+$: 579.7 $(M+H)^+$ $^1$HNMR (DMSO-$d_6$, TFA): 2.31 (t, 2H); 3.17 (t, 2H); 3.38 (t, 2H); 3.40 (m, 2H); 3.50 (t, 2H); 3.54 (d, 2H); 3.67 (m, 2H); 3.75 (t, 2H); 3.98 (s, 3H); 4.07 (d, 2H); 4.31 (t, 2H); 7.30 (s, 1H); 7.40 (s, 1H); 7.45 (m, 2H); 7.52 (m, 3H); 7.89 (s, 1H); 9.08 (s, 1H).

EXAMPLE 173

Preparation of Compound 350 in Table 14

An analogous reaction to that described in example 160 but starting with 3-chloro-4-methylamine (30 mg, 0.21 mmol) yielded title compound (3 mg, 3%).

MS $ES^+$: 583.6 $(M+H)^+$ $^1$HNMR (DMSO-$d_6$, TFA): 2.32 (m, 5H); 3.20 (t, 2H); 3.40 (t, 2H); 3.60 (d, 2H); 3.72 (t, 2H); 4.01 (s, 2H); 4.02 (s,

3H); 4.07 (d, 2H); 4.33 (t, 2H); 7.32 (m, 2H); 7.42 (d, 1H); 7.68 (s, 1H); 7.87 (s, 1H); 7.95 (s, 1H); 9.13 (s, 1H).

EXAMPLE 174

Preparation of Compound 351 in Table 14

An analogous reaction to that described in example 160 but starting with 3-nitroaniline (29 mg, 0.21 mmol) yielded title compound (20 mg, 21%).

MS $ES^+$: 580.6 $(M+H)^+$ $^1$HNMR (DMSO-$d_6$, TFA): 2.33 (t, 2H); 3.20 (t, 2H); 3.39 (t, 2H); 3.60 (d, 2H); 3.73 (t, 2H); 4.02 (s, 3H); 4.06 (d, 2H); ‘; 4.09 (s, 2H); 4.34 (t, 2H); 7.34 (s, 1H); 7.67 (d, 1H); 7.70 (s, 1H); 7.95 (s, 1H); 7.98 (m, 2H); 8.74 (s, 1H); 9.15 (s, 1H).

EXAMPLE 175

Preparation of Compound 352 in Table 14

An analogous reaction to that described in example 160 but starting with aminoacetonitrile (19 mg, 0.21 mmol) yielded title compound (28 mg, 31%).

MS $ES^+$: 498.6 $(M+H)^+$ $^1$HNMR (DMSO-$d_6$, TFA): 2.31 (t, 2H); 3.18 (t, 2H); 3.36 (t, 2H); 3.56 (d, 2H); 3.70 (t, 2H) 3.84 (s, 2H); 3.99 (s, 3H); 4.04 (d, 2H); 4.21 (s, 2H); 4.31 (t, 2H); 7.31 (s, 1H); 7.60 (s, 1H); 9.10 (s, 1H).

EXAMPLE 176

Preparation of Compound 353 in Table 14

An analogous reaction to that described in example 160 but starting with 2-methyl-5-nitroaniline (32 mg, 0.21 mmol) yielded title compound (11 mg, 11%).

MS $ES^+$: 594.6 $(M+H)^+$ $^1$HNMR (DMSO-$d_6$, TFA): 2.32 (t, 2H); 2.44 (s, 3H); 3.19 (t, 2H); 3.40 (t, 2H); 3.59 (d, 2H); 3.73 (t, 2H); 4.03 (s, 3H); 4.07 (d, 2H); 4.16 (s, 2H); 4.34 (t, 2H); 7.34 (s, 1H); 7.57 (d, 1H); 7.71 (s, 1H); 7.95 (s, 1H); 8.01 (d, 1H); 8.58 (s, 1H); 9.13 (s, 1H).

EXAMPLE 177

Preparation of Compound 354 in Table 14

An analogous reaction to that described in example 160 but starting with 2-amino-5-chloropyridine (27 mg, 0.21 mmol) yielded title compound (13 mg, 13%).

MS $ES^+$: 570.6 $(M+H)^+$ $^1$HNMR (DMSO-$d_6$, TFA): 2.31 (t, 2H); 3.17 (t, 2H); 3.37 (t, 2H); 3.57 (d, 2H); 3.70 (t, 2H) 3.99 (s, 3H); 4.04 (d, 2H); 4.07 (s, 2H); 4.31 (t, 2H); 7.02 (d, 1H); 7.36 (s, 1H); 7.64 (s, 1H); 7.92 (s, 1H); 7.98 (dd, 1H); 8.21 (d, 1H); 9.1 (s, 1H).

EXAMPLE 178

Preparation of Compound 355 in Table 14

An analogous reaction to that described in example 160 but starting with 4-trifluoromethylaniline (34 mg, 0.21 mmol) yielded title compound (26 mg, 25%);

MS $ES^+$: 603.7 $(M+H)^+$ $^1$H NMR (DMSO-$d_6$, TFA): 2.30 (t, 2H); 3.17 (t, 2H); 3.36 (t, 2H); 3.56 (d, 2H); 3.72 (t, 2H); 3.99 (s, 3H); 4.05 (m, 4H); 4.31 (t, 2H); 7.31 (s, 1H); 7.66 (s, 1H); 7.70 (d, 2H); 7.84 (d, 2H); 7.92 (s, 1H); 9.10 (s, 1H).

EXAMPLE 179

Preparation of Compound 356 in Table 14

An analogous reaction to that described in example 160 but starting with 3-chloroaniline (27 mg, 0.21 mmol) yielded title compound (47 mg, 48%).

MS $ES^+$: 569.7 $(M+H)^+$ $^1$H NMR (DMSO-$d_6$ TFA): 2.31 (t, 2H); 3.16 (t, 2H); 3.37 (t, 2H); 3.56 (d, 2H); 3.69 (t, 2H); 3.99 (s, 3H); 4.00 (s, 2H); 4.04 (d, 2H); 4.31 (t, 2H); 7.14 (d, 1H); 7.30 (s, 1H); 7.37 (t, 1H); 7.47 (d, 1H); 7.65 (s, 1H); 7.87 (s, 1H); 7.92 (s, 1H); 9.10 (s, 1H).

EXAMPLE 180

Preparation of Compound 357 in Table 14

An analogous reaction to that described in example 160 but starting with 2-methoxyaniline (26 mg, 0.21 mmol) yielded title compound (44 mg, 46%).

MS $ES^+$: 565.7 $(M+H)^+$ $^1$H NMR (DMSO-$d_6$, TFA): 2.33 (t, 2H); 3.20 (t, 2H); 3.40 (t, 2H); 3.60 (d, 2H); 3.73 (t, 2H); 3.91 (s, 3H); 4.03 (s, 3H); 4.08 (d, 2H); 4.11 (s, 2H); 4.34 (t, 2H); 6.96 (t, 1H); 7.12 (m, 2H); 7.34 (s, 1H); 7.66 (s, 1H); 7.95 (s, 1H); 8.01 (d, 1H); 9.12 (s, 1H).

EXAMPLE 181

Preparation of Compound 358 in Table 14

An analogous reaction to that described in example 160 but starting with 2-fluoroaniline (23 mg, 0.21 mmol) yielded title compound (43 mg, 46%).

MS $ES^+$: 553.7 $(M+H)^+$ $^1$H NMR (DMSO-$d_6$, TFA): 2.31 (t, 2H); 3.18 (t, 2H); 3.37 (t, 2H); 3.57 (d, 2H); 3.70 (t, 2H) 4.00 (s, 3H); 4.05 (d, 2H); 4.08 (s, 2H); 4.31 (t, 2H); 7.19 (m, 2H); 7.28 (m, 1H); 7.31 (s, 1H); 7.64 (s, 1H); 7.93 (m, 2H); 9.06 (, 1H).

EXAMPLE 182

Preparation of Compound 359 in Table 14

An analogous reaction to that described in example 160 but starting with thiphene-2-methylamine (24 mg, 0.21 mmol) yielded title compound (50 mg, 53%).

MS $ES^+$: 555.7 $(M+H)^+$ $^1$H NMR (DMSO-$d_6$, TFA): 2.32 (t, 2H); 3.18 (t, 2H); 3.38 (t, 2H); 3.58 (d, 2H); 3.72 (t, 2H) 3.80 (s, 2H); 4.01 (s, 3H); 4.06 (d, 2H); 4.33 (t, 2H); 4.52 (s, 2H), 6.98 (dd, 1H); 7.02 (dd, 1H); 7.32 (s, 1H); 7.41 (dd, 1H); 7.60 (sq, 1H); 7.93 (s, 1H); 9.11 (s, 1H).

EXAMPLE 183

Preparation of Compound 360 in Table 14

An analogous reaction to that described in example 160 but starting with 2-amino-1-phenylethanol (29 mg, 0.21 mmol) yielded title compound (32 mg, 33%).

MS $ES^+$: 579.7 $(M+H)^+$ $^1$H NMR (DMSO-$d_6$, TFA): 2.31 (t, 2H); 3.18 (m, 3H); 3.36 (m, 3H); 3.56 (d, 2H); 3.69 (t, 2H); 3.74 (s, 2H); 3.99 (s, 3H); 4.05 (d, 2H); 4.30 (t, 2H); 4.66 (m, 1H); 7.3 (m, 6H); 7.53 (s, 1H); 7.90 (s, 1H); 9.09 (s, 1H).

EXAMPLE 184

Preparation of Compound 361 in Table 14

An analogous reaction to that described in example 160 but starting with 3-(1-hydroxyethyl)aniline (29 mg, 0.21 mmol) yielded title compound (50 mg, 50%).

MS ES$^+$: 579.7 (M+H)$^+$ $^1$H NMR (DMSO-$d_6$, TFA): 1.34 (d, 3H); 2.31 (t, 2H); 3.18 (t, 2H); 3.38 (t, 2H); 3.58 (d, 2H); 3.72 (t, 2H); 4.00 (s, 2H); 4.02 (s, 3H); 4.07 (d, 2H); 4.33 (t, 2H); 4.72 (q, 1H); 7.07 (d, 1H); 7.29 (t, 1H); 7.33 (s, 1H); 7.53 (d, 1H); 7.67 (s, 2H); 7.93 (s, 1H); 9.12 (s, 1H).

EXAMPLE 185

Preparation of Compound 362 in Table 14

An analogous reaction to that described in example 160 but starting with neopentylamine (18 mg, 0.21 mmol) yielded title compound (57 mg, 64%).

MS ES$^+$: 529.7 (M+H)$^+$ $^1$H NMR (DMSO-$d_6$, TFA): 0.89 (s, 9H); 2.33 (t, 2H); 2.97 (s, 2H); 3.19 (t, 2H); 3.39 (t, 2H); 3.59 (d, 2H); 3.80 (s, 2H); 4.02 (s, 3H); 4.07 (d, 2H); 4.32 (t, 2H); 7.33 (s, 1H); 7.60 (s, 1H); 7.93 (s, 1H); 9.11 (s, 1H).

EXAMPLE 186

Preparation of Compound 363 in Table 14

An analogous reaction to that described in example 160 but starting with 3-fluoro-4-methoxyaniline (30 mg, 0.21 mmol) yielded title compound (64 mg, 65%).

MS ES$^+$: 583.7 (M+H)$^+$ $^1$H NMR (DMSO-d6, TFA): 2.31 (t, 2H); 3.17 (t, 2H); 3.37 (t, 2H); 3.57 (d, 2H); 3.70 (t, 2H); 3.82 (s, 3H); 3.96 (s, 2H); 4.00 (s, 3H); 4.04 (d, 2H); 4.31 (t, 2H); 7.15 (t, 1H); 7.30 (d, 1H); 7.31 (s, 1H); 7.61 (s, 1H); 7.64 (s, 1H); 7.91 (s, 1H); 9.10 (s, 1H).

EXAMPLE 187

Preparation of Compound 364 in Table 14

An analogous reaction to that described in example 160 but starting with 2-methyl-4-fluoroaniline (26 mg, 0.21 mmol) yielded title compound (60 mg, 62%).

MS ES$^+$: 567.7 (M+H)$^+$ $^1$H NMR (DMSO-$d_6$, TFA): 2.31 (t, 2H); 3.17 (t, 2H); 3.37 (t, 2H); 3.56 (d, 2H); 3.70 (t, 2H) 4.00 (s, 3H); 4.01 (s, 2H); 4.04 (d, 2H); 4.31 (t, 2H); 7.02 (t, 1H); 7.10 (d, 1H); 7.31 (s, 1H); 7.41 (q, 1H); 7.66 (s, 1H); 7.92 (s, 1H); 9.09 (s, 1H).

EXAMPLE 188

Preparation of Compound 365 in Table 14

An analogous reaction to that described in example 160 but starting with 2,5-difluoroaniline (27 mg, 0.21 mmol) yielded title compound (14 mg, 14%).

MS ES$^+$: 571.7 (M+H)$^+$ $^1$H NMR (DMSO-$d_6$, TFA): 2.31 (t, 2H); 3.19 (t, 2H); 3.39 (t, 2H); 3.58 (d, 2H); 3.72 (t, 2H); 4.01 (s, 3H); 4.06 (d, 2H); 4.12 (s, 2H); 4.33 (t, 2H); 7.00 (m, 1H); 7.33 (m, 2H); 7.65 (s, 1H); 7.95 (m, 2H); 9.11 (s, 1H).

EXAMPLE 189

Preparation of Compound 366 in Table 14

An analogous reaction to that described in example 160 but starting with 2-fluoro-4-chloroaniline (31 mg, 0.21 mmol) yielded title compound (12 mg, 12%).

MS ES$^+$: 587.6 (M+H)$^+$ $^1$H NMR (DMSO-$d_6$, TFA): 2.31 (t, 2H); 3.17 (t, 2H); 3.37 (t, 2H); 3.56 (d, 2H); 3.70 (t, 2H) 3.99 (s, 3H); 4.04 (m, 4H); 4.31 (t, 2H); 7.29 (d, 1H); 7.52 (dd, 1H); 7.64 (s, 1H); 7.97 (d, 1H); 9.09 (s, 1H).

EXAMPLE 190

Preparation of Compound 367 in Table 14

An analogous reaction to that described in example 160 but starting with 2-fluoro-4-methylaniline (26 mg, 0.21 mmol) yielded title compound (20 mg, 20%).

MS ES": 567.7 (M+H)$^+$ $^1$H NMR (DMSO-$d_6$, TFA): 2.31 (s, 3H); 2.32 (t, 2H); 3.20 (t, 2H); 3.39 (t, 2H); 3.59 (d, 2H); 3.73 (t, 2H); 4.03 (s, 3H); 4.07 (d, 2H); 4.09 (s, 2H); 4.34 (t, 2H); 7.02 (m, 1H); 7.18 (dd, 1H); 7.34 (s, 1H); 7.67 (s, 1H); 7.77 (d, 1H); 7.95 (s, 1H); 9.12 (s, 1H).

EXAMPLE 191

Preparation of Compound 368 in Table 14

An analogous reaction to that described in example 160 but starting with 3-methylaniline (23 mg, 0.21 mmol) yielded title compound (45 mg, 48%).

MS ES$^+$: 549.7 (M+H)$^+$ $^1$H NMR (DMSO-$d_6$, TFA): 2.31 (in, 5H); 3.19 (t, 2H); 3.39 (t, 2H); 3.58 (d, 2H); 3.72 (t, 2H); 4.00 (s, 2H); 4.02 (s, 3H); 4.07 (d, 2H); 4.33 (t, 2H); 6.93 (d, 1H); 7.24 (t, 1H); 7.33 (s, 1H); 7.43 (d, 1H); 7.51 (s, 1H); 7.67 (s, 1H); 7.94 (s, 1H); 9.12 (s, 1H).

EXAMPLE 192

Preparation of Compound 369 in Table 14

An analogous reaction to that described in example 160 but starting with 2-(methylthio)aniline (29 mg, 0.21 mmol) yielded title compound (13 mg, 13%).

MS ES$^+$: 581.7 (M+H)$^+$ $^1$H NMR (DMSO-$d_6$, TFA): 2.31 (t, 2H); 2.46 (s, 3H); 3.19 (t, 2H); 3.39 (t, 2H); 3.59 (d, 2H); 3.72 (t, 2H); 3.99 (s, 3H); 4.02 (s, 2H); 4.07 (d, 2H); 4.33 (t, 2H); 7.22 (t, 1H); 7.27 (t, 1H); 7.34 (s, 1H); 7.39 (d, 1H); 7.45 (d, 1H); 7.68 (s, 1H); 7.93 (s, 1H); 9.10 (s, 1H).

EXAMPLE 193

Preparation of Compound 370 in Table 14

An analogous reaction to that described in example 160 but starting with 5-aminoindole (28 mg, 0.21 mmol) yielded title compound (33 mg, 34%).

MS ES$^+$: 574.7 (M+H)$^+$ $^1$H NMR (DMSO-$d_6$, TFA): 2.31 (t, 2H); 3.18 (t, 2H); 3.36 (t, 2H); 3.57 (d, 2H); 3.70 (t, 2H); 3.97 (s, 2H); 4.00 (s, 3H); 4.03 (d, 2H); 4.31 (t, 2H); 7.32 (m, 6H); 7.65 (s, 1H); 7.91 (s, 1H); 9.10 (s, 1H).

EXAMPLE 194

Preparation of Compound 371 in Table 14

An analogous reaction to that described in example 160 but starting with 2,4-difluoroaniline (27 mg, 0.21 mmol) yielded title compound (28 mg, 29%).

MS ES$^+$: 571.7 (M+H)$^+$ $^1$H NMR (DMSO-$d_6$, TFA): 2.32 (t, 2H); 3.19 (t, 2H); 3.39 (t, 2H); 3.59 (d, 2H); 3.72 (t, 2H); 4.02 (s, 3H); 4.07 (d,

2H); 4.08 (s, 2H); 4.34 (t, 2H); 7.12 (t, 1H); 7.34 (s, 1H); 7.36 (m, 1H); 7.89 (m, 1H); 7.95 (s, 1H); 9.12 (s, 1H).

EXAMPLE 195

Preparation of Compound 372 in Table 14

An analogous reaction to that described in example 160 but starting with 2-fluoro-4-methylaniline (26 mg, 0.21 mmol) yielded title compound (35 mg, 37%).

MS ES$^+$: 567.7 (M+H)$^+$ $^1$H NMR (DMSO-d$_6$, TFA): 2.33 (s, 5H); 3.19 (t, 2H); 3.39 (t, 2H); 3.58 (d, 2H); 3.72 (t, 2H); 4.02 (s, 3H); 4.07 (s, 2H); 4.08 (d, 2H); 4.33 (t, 2H); 7.04 (d, 1H); 7.12 (d, 1H); 7.34 (s, 1H); 7.66 (s, 1H); 7.78 (t, 1H); 7.94 (s, 1H); 9.12 (s, 1H).

EXAMPLE 196

Preparation of Compound 373 in Table 14

An analogous reaction to that described in example 160 but starting with 3-cyanoaniline (25 mg, 0.21 mmol) yielded title compound (21 mg, 22%).

MS ES$^+$: 560.7 (M+H)$^+$ $^1$H NMR (DMSO-d$_6$, TFA): 2.31 (t, 2H); 3.19 (t, 2H); 3.39 (t, 2H); 3.58 (d, 2H); 3.72 (t, 2H) 4.02 (s, 3H); 4.06 (s, 2H); 4.07 (d, 2H); 4.33 (t, 2H); 7.34 (s, 1H); 7.6 (m, 2H); 7.69 (s, 1H); 7.85 (m, 1H); 7.95 (s, 1H); 8.18 (s, 1H); 9.13 (s, 1H).

EXAMPLE 197

Preparation of Compound 374 in Table 14

An analogous reaction to that described in example 160 but starting with 2-methyl-5-fluoroaniline (26 mg, 0.21 mmol) yielded title compound (15 mg, 16%).

MS ES$^+$: 567.7 (M+H)$^+$ $^1$H NMR (DMSO-d$_6$, TFA): 2.27 (s, 3H); 2.32 (t, 2H); 3.20 (t, 2H); 3.39 (t, 2H); 3.59 (d, 2H); 3.72 (t, 2H); 4.02 (s, 3H); 4.07 (d, 2H); 4.09 (s, 2H); 4.33 (t, 2H); 6.96 (t, 1H); 7.29 (t, 1H); 7.34 (s, 1H); 7.48 (d, 1H); 7.69 (s, 1H); 7.95 (s, 1H); 9.12 (s, 1H).

EXAMPLE 198

Preparation of Compound 375 in Table 14

An analogous reaction to that described in example 160 but starting with 2-methyl-5-chloroaniline (30 mg, 0.21 mmol) yielded title compound (20 mg, 21%).

MS ES$^+$: 583.6 (M+H)$^+$ $^1$H NMR (DMSO-d$_6$, TFA): 2.26 (s, 3H); 2.32 (t, 2H); 3.17 (t, 2H); 3.38 (t, 2H); 3.58 (d, 2H); 3.71 (t, 2H); 4.01 (s, 3H); 4.05 (d, 2H); 4.07 (s, 2H); 4.32 (t, 2H); 7.16 (dd, 1H); 7.27 (d, 1H); 7.31 (s, 1H); 7.65 (d, 1H); 7.65 (s, 1H); 7.93 (s, 1H); 9.10 (s, 1H).

EXAMPLE 199

Preparation of Compound 376 in Table 15

4-((2-amino-1,3-thiazole-5-yl)acetic acid)-6-methoxy-7-((1-methyl-piperidine-4-yl)methoxy)quinazoline (89 mg, 0.2 mmol) in DMF (1.5 ml), was reacted with aniline (22 mg, 0.24 mmol) in presence of 047-azabenzotriazol-1-yl)-N,N,N',N'-tetramethyluronium hexafluorophosphate (99 mg, 0.26 mmol) and DIEA (50 mg, 0.4 mmol) at 60° C. over night. After cooling to room temperature the reaction mixture was diluted with dichloromethane, and purified by silicagel chromatography, eluting successively with $CH_2Cl_2$, $CH_2Cl_2$/MeOH 90/10, and $CH_2Cl_2$/MeOH sat. $NH_3$ 90/10 to give title compound (50 mg, 42%).

MS ES$^+$: 519.6 (M+H)$^+$ $^1$HNMR (DMSO-d$_6$, TFA): 1.58 (m, 2H); 2.02 (m, 2H); 2.13 (m, 1H); 2.80 (s, 3H); 3.03 (t, 2H); 3.52 (d, 2H); 3.98 (s, 2H); 3.98 (s, 3H); 4.10 (d, 2H); 7.06 (t, 1H); 7.29 (s, 1H); 7.33 (t, 2H); 7.60 (d, 2H); 7.61 (s, 1H); 7.90 (s, 1H); 9.08 (s, 1H).

The NMR spectrum of example 199 in presence of acid shows the existence of 2 forms in a ratio of approximately 9:1. Signals due to the minor form are seen at 1.95 (m) 3.23 (m) 3.32 (m) 4.28 (d) 9.38 (m).

4-benzyloxy-3-methoxybenzonitrile 4-benzyloxy-3-methoxybenzaldehyde (4.84 g, 20 mmol) in acetic acid (25 ml) and sodium acetate (3.3 g, 40 mmol) was reacted with hydroxylamine hydrochloride (2.8 g, 40 mmol) at reflux for 6 hours. The mixture was cooled, diluted with water, extracted with methylene chloride, dried over $MgSO_4$, concentrated to give title compound (4.8 g, 100%).

$^1$HNMR (DMSO-d$_6$): 3.83 (s, 3H); 5.20 (s, 2H); 7.21 (d, 1H); 7.40 (m, 7H).

2-nitro-4-benzyloxy-5-methoxybenzonitrile 4-benzyloxy-3-methoxybenzonitrile (4.78 g, 20 mmol) in acetic acid (10 ml) was slowly added to nitric acid (25 ml) at 20° C. to 30° C. The mixture was stirred at room temperature for 6 hours, basified (pH 10–11) with cooling (KOH 10N), extracted with methylene chloride, dried over $MgSO_4$ evaporated. The solid was recristallysed in hot EtOAc, a yellow solid of title compound was obtained (3.62 g, 64%).

MS ES$^+$: 285 (M+H)$^+$ $^1$HNMR (DMSO-d$_6$): 3.97 (s, 3H); 5.33 (s, 2H); 7.40 (m, 5H); 7.71 (s, 1H); 8.01 (s, 1H).

2-nitro-4-hydroxy-5-methoxybenzonitrile 2-nitro-4-benzyloxy-5-methoxybenzonitrile (3 g, 10.6 mmol) was treated with trifluoroacetic acid (30 ml) at reflux for 0.5 hour. The solvent was evaporated, the residue triturated with ether to give a yellow solid of title compound (1.27 g, 62%).

$^1$HNMR (DMSO-d$_6$): 3.95 (s, 3H); 7.63 (s, 1H); 7.70 (s, 1H).

2-nitro-4-((1-tert-butyloxycarbonylpiperidin-4-yl)methoxy)-5-methoxybenzonitrile 2-nitro-4-hydroxy-5-methoxybenzonitrile (388 mg, 2 mmol) in DMF (5 ml) and acetonitrile (5 ml) was reacted with 4-(4-tolylsulphonyloxymethyl)-1-tert-butyloxycarbonyl-piperidine (738 mg, 2 mmol) and $K_2CO_3$ (414 mg, 3 mmol) at 110° C. for 3.5 hours. The mixture was diluted with water, extracted with ethylacetate, washed HCl (2N), dried over $MgSO_4$, evaporated to give title compound (630 mg, 80%).

$^1$HNMR ($CDCl_3$): 1.31 (m, 2H); 1.47 (s, 9H); 1.85 (m, 2H); 2.07 (m, 1H); 2.77 (m, 2H); 3.96 (d, 2H); 3.99 (s, 3H); 4.19 (m, 2H); 7.19 (s, 1H); 7.75 (s, 1H).

2-nitro-4-(1-piperidin-4-ylmethoxy)-5-methoxybenzonitrile 2-nitro-4-((1-tert-butyloxycarbonylpiperidin-4-yl)methoxy)-5-methoxybenzonitrile (1.17 g, 3 mmol) in $CH_2Cl_2$ (12 ml) was treated with TFA (2.4 ml) for 1 hour at room temperature. The solvent was evaporated, the residue was taken up in a mixture of $CH_2Cl_2$ and concentrated sodium bicarbonate, extracted with $CH_2Cl_2$. The organic phase was dried over $MgSO_4$, concentrated to give title compound as a solid (770 mg, 88%).

$^1$HNMR ($CDCl_3$): 1.33 (m, 2H); 1.86 (d, 2H); 2.03 (m, 1H); 2.71 (t, 2H); 3.15 (d, 2H) 3.96 (d, 2H); 3.99 (s, 3H); 7.18 (s, 1H); 7.76 (s, 1H).

2-nitro-4-(1-methylpiperidin-4-ylmethoxy)-5-methoxybenzonitrile 2-nitro-4-(1-piperidin-4-ylmethoxy)$_5$-methoxybenzonitrile (771 mg, 2.65 mmol) in $CH_2Cl_2$ (8 ml) and MeOH (4 ml) was reacted for 0.5 hour with formaldehyde (13.3 M, 300 μl, 4 mmol), acetic acid (191 mg, 3.18 mmol) and $NaBH(OAc)_3$ (674 mg, 3.18 mmol) slowly added over 15 minutes. The solution was evaporated, the oily residue was taken up in a mixture of $Na_2CO_3$ and ethylacetate, extracted with ethylacetate. The organic phase was dried over $MgSO_4$, evaporated to give title compound as a yellow solid (698 mg, 86%).

$^1$HNMR ($CDCl_3$): 4.7 (m, 2H); 1.88 (d, 2H); 1.90 (m, 1H); 2.0 (m, 2H); 2.3 (s, 3H); 2.91 (d, 2H); 2.95 (d, 2H); 2.99 (s, 3H); 7.18 (s, 1H); 7.76 (s, 1H).

2-amino-4-(1-methylpiperidin-4-ylmethoxy)-5-methoxybenzonitrile 2-nitro-4-(1-methylpiperidin-4-ylmethoxy)-5-methoxybenzonitrile (1.1 g, 3.6 mmol) in THF (20 ml) in presence of benzyltrimethylammonium chloride (334 mg, 1.8 mmol) was treated by a slow addition of $Na_2S_2O_4$ (3.1 g, 18 mmol) in water (20 ml). After 0.5 h, HCl (6N, 20 ml) was added to the mixture, which was stirred at 60° C. for 5 h. The mixture was cooled to room temperature, extracted with ethylacetate. The aqueous phase was made basic with $Na_2$ $CO_3$ (solid), and extracted with ethylacetate. The organic phase was dried over $MgSO_4$, concentrated, to give a yellow solid (748 mg, 75%) of title compound.

$^1$HNMR (DMSO-$d_6$): 1.29 (m, 2H); 1.70 (m, 3H); 1.85 (t, 2H); 2.14 (s, 3H); 2.76 (d, 2H); 3.64 (s, 3H); 3.75 (d, 2H); 5.57 (s, 2H); 6.40 (s, 1H); 6.87 (s, 1H).

N'-(2-cyano-4-methoxy-5(1-methylpiperidin-4-ylmethoxy)phenyl)-N,N-dimethylimidoformamide 2-amino-4-(1-methylpiperidin-4-ylmethoxy)$_5$-methoxybenzonitrile (710 mg, 2.58 mmol) was reacted with DMF DMA (414 mg, 3.5 mmol) in toluene (15 ml) at reflux for 5 hours. The solution was concentrated, the oily residue triturated with ether to give a yellow solid of title compound (680 mg, 80%).

$^1$HNMR (DMSO-$d_6$): 1.28 (m, 2H); 1.72 (m, 3H); 1.85 (t, 2H); 2.14 (s, 3H); 2.76 (d, 2H); 2.95 (s, 3H); 3.05 (s, 3H); 3.72 (s, 3H); 3.86 (d, 2H); 6.71 (s, 1H); 7.07 (s, 1H); 7.89 (s, 1H).

4-(methyl(2-amino-1,3-thiazole-5-yl)acetate)-6-methoxy-7-((1-methylpiperidin-4-yl)methoxy) quinazoline N'-(2-cyano-4-methoxy-5-(1-methylpiperidin-4-ylmethoxy)phenyl)-N,N-diemethylimidoformamide (627 mg, 1.9 mmol) was reacted with methyl-2-amino 1,3-thiazol-5-acetate (360 mg, 2.1 mmol) in acetic acid (6.3 ml) at reflux for 4.5 hour under nitrogen. The mixture was concentrated, and the oily residue purified by silicagel chromatography, Eluant: $CH_2Cl_2$/MeOH 90/10 and $CH_2Cl_2$/MeOH sat. $NH_3$ 90/10 to give title compound (552 mg, 63%).

$^1$HNMR (DMSO-$d_6$): 1.35 (m, 2H); 1.76 (m, 3H); 1.87 (t, 2H); 2.16 (d, 2H); 2.78 (d, 2H); 3.67 (s, 3H); 3.93 (s, 2H); 3.96 (s, 3H); 4.01 (d, 2H); 7.24 (s, 1H); 7.36 (s, 1H); 8.10 (s, 1H); 8.66 (s, 1H).

4-((2-amino-1,3-thiazole-5-yl)acetic acid)-6-methoxy-7-((1-methylpiperidin-4-yl)methoxy) quinazoline 4-(methyl(2-amino-1,3-thiazole-5-yl)acetate)-6-methoxy-7-((1-methylpiperidin-4-yl)methoxy)quinazoline (137 mg, 0.3 mmol) in ethanol (1.4 ml) was treated with NaOH (2N, 3.75 ml, 7.5 mmol) at room temperature for 0.5 hour. HCl (2N) was added to adjust the pH to 3. The solution was evaporated, the solid solubilized in $CH_2Cl_2$ (6 ml) MeOH (4 ml) DIEA (excess) was added. The insoluble was filtered, the filtrate was concentrated, ethanol was added, the solid filtered, washed with ether, to give title compound (102 mg, 77%).

MS ES$^+$: 444.6 $(M+H)^+$ $^1$HNMR (DMSO-$d_6$, TFA): 1.61 (m, 2H); 2.03 (d, 2H); 2.16 (m, 1H); 2.80 (s, 3H); 3.03 (t, 2H); 3.5 (d, 2H); 3.92 (s, 2H); 3.98 (s, 3H); 4.10 (d, 2H); 7.32 (s, 1H); 7.59 (s, 1H); 7.89 (s, 1H); 9.07 (s, 1H).

EXAMPLE 200

Preparation of Compound 377 in Table 15

An analogous reaction to that described in example 199 but starting with 3-chloro-4-fluoroaniline (44 mg, 0.3 mmol) yielded compound 377 in table 15 (63 mg, 60%)

MS ES$^+$: 571 $(M+H)^+$ $^1$HNMR (DMSO-$d_6$, TFA): 1.64 (m, 2H); 2.04 (m, 2H); 2.15 (m, 1H); 2.8 (s, 3H); 3.04 (t, 2H); 3.51 (d, 2H); 3.99 (s, 3H); 4.0 (s, 2H); 4.11 (d, 2H); 7.34 (s, 1H); 7.39 (t, 1H); 7.5 (m, 1H); 7.65 (s, 1H); 7.91 (dd, 1H); 9.09 (s, 1H).

EXAMPLE 201

Preparation of Compound 378 in Table 15

An analogous reaction to that described in example 199 but starting with 2-aminopyridine (40 mg, 0.42 mmol) yielded compound 378 in table 15 (100 mg, 53%)

MS ES$^+$: 520 $(M+H)^+$ $^1$HNMR (DMSO-$d_6$, TFA): 1.65 (m, 2H); 2.02 (m, 2H); 2.15 (m, 1H); 2.78 (s, 3H); 3.02 (t, 2H); 3.48 (d, 2H); 3.99 (s, 3H); 4.1 (d, 2H); 4.14 (s, 2H); 7.32 (m, 1H); 7.39 (s, 1H); 7.66 (s, 1H); 7.91 (s, 1H); 7.97 (d, 1H); 8.16 (t, 1H); 8.4 (d, 1H); 9.079 (s, 1H).

EXAMPLE 202

Preparation of Compound 379 in Table 15

An analogous reaction to that described in example 199 but starting with 3,4-difluoroaniline (54 mg, 0.42 mmol) yielded compound 379 in table 15 (120 mg, 72%)

MS ES$^+$: 555 $(M+H)^+$ $^1$HNMR (DMSO-$d_6$, TFA): 1.63 (m, 2H); 2.02 (m, 2H); 2.15 (m, 1H); 2.79 (s, 3H); 3.03 (t, 2H); 3.49 (d, 2H); 3.99 (s, 3H); 4.0 (s, 2H); 4.10 (d, 2H); 7.35 (s, 1H); 7.39 (m, 2H); 7.64 (s, 1H); 7.82 (dd., 1H); 7.90 (s, 1H) 9.08 (s, 1H).

EXAMPLE 203

Preparation of Compound 380 in Table 15

An analogous reaction to that described in example 199 but starting with 2-chloroaniline (54 mg, 0.42 mmol) yielded compound 380 in table 15 (29 mg, 16%)

MS $ES^+$: 553 $(M+H)^+$ $^1$HNMR (DMSO-$d_6$, TFA): 1.62 (m, 2H); 2.03 (m, 2H); 2.15 (m, 1H); 2.81 (s, 3H); 3.04 (t, 2H); 3.51 (d, 2H); 4.0 (s, 3H); 4.08 (s, 2H); 4.11 (d, 2H); 7.24 (t, 1H); 7.31 (s, 1H); 7.34 (dd, 1H); 7.53 (d, 1H); 7.66 (s, 1H); 7.75 (d, 1H); 7.91 (s, 1H); 9.09 (s, 1H).

EXAMPLE 204

Preparation of Compound 381 in Table 15

An analogous reaction to that described in example 199 but starting with 4-methylaniline (45 mg, 0:42 mmol) yielded compound 381 in table 15 (155 mg, 85%)

MS $ES^+$: 533 $(M+H)^+$ $^1$HNMR (DMSO-$d_6$, TFA): 1.65 (m, 2H); 2.02 (m, 2H); 2.16 (m, 1H); 2.27 (s, 3H); 2.8 (s, 3H); 3.05 (t, 2H); 3.50 (d, 2H); 3.97 (s, 2H); 3.99 (s, 3H); 4.11 (d, 2H); 7.14 (d, 2H); 7.34 (s, 1H); 7.52 (d, 2H); 7.63 (s, 1H); 7.91 (s, 1H); 9.08 (s, 1H).

EXAMPLE 205

Preparation of Compound 382 in Table 15

An analogous reaction to that described in example 199 but starting with 2-methylaniline (45 mg, 0.42 mmol) yielded compound 382 in table 15 (126 mg, 69%)

MS $ES^+$: 533 $(M+H)^+$ $^1$HNMR (DMSO-$d_6$, TFA): 1.62 (m, 2H); 2.02 (m, 1H); 2.15 (m, 1H); 2.24 (s, 3H); 2.8 (s, 3H); 3.04 (t, 2H); 3.51 (d, 2H); 3.99 (s, 3H); 4.02 (s, 2H); 4.10 (d, 2H); 7.11 (t, 1H); 7.19 (t, 1H); 7.24 (d, 1H); 7.33 (s, 1H); 7.43 (d, 1H); 7.65 (s, 1H); 7.91 (s, 1H); 9.07 (s, 1H).

EXAMPLE 206

Preparation of Compound 383 in Table 15

An analogous reaction to that described in example 199 but starting with 4-chloroaniline (54 mg, 0.42 mmol) yielded compound 383 in table 15 (128 mg, 68%)

MS $ES^+$: 553 $(M+H)^+$ $^1$HNMR (DMSO-$d_6$, TFA): 1.65 (m, 2H); 2.04 (m, 2H); 2.15 (m, 1H); 2.79 (s, 3H); 3.04 (t, 2H); 3.50 (d, 2H); 3.99 (s, 3H); 4.0 (s, 2H); 4.1 (d, 2H); 7.36 (s, 1H); 7.38 (d, 2H); 7.64 (s, 1H); 7.68 (d, 2H); 7.9 (s, 1H); 9.08 (s, 1H).

EXAMPLE 207

Preparation of Compound 384 in Table 15

An analogous reaction to that described in example 199 but starting with 4-fluoroaniline (47 mg, 0.42 mmol) yielded compound 384 in table 15 (136 mg, 84%)

MS $ES^+$: 537 $(M+H)^+$ $^1$HNMR (DMSO-$d_6$, TFA): 1.62 (m, 2H); 2.02 (m, 2H); 2.15 (m, 1H); 2.79 (s, 3H); 3.03 (t, 2H); 3.50 (d, 2H); 3.97 (s, 2H); 3.98 (s, 3H); 4.1 (d, 2H); 7.16 (t, 2H); 7.34 (s, 1H); 7.63 (s, 1H); 7.65 (m, 2H); 7.9 (s, 1H); 9.07 (s, 1H).

EXAMPLE 208

Preparation of Compound 385 in Table 15

An analogous reaction to that described in example 199 but starting with 2-amino-6-methylpyrimidine (45 mg, 0.42 mmol) yielded compound 385 in table 15 (91 mg, 57%)

MS $ES^+$: 534 $(M+H)^+$ $^1$HNMR (DMSO-$d_6$, TFA): 1.61 (m, 2H); 2.05 (m, 2H); 2.15 (m, 1H); 2.50 (s, 3H); 2.8 (s, 3H); 3.03 (t, 2H); 3.52 (d, 2H); 4.02 (s, 3H); 4.1 (s, 2H); 4.11 (d, 2H); 7.15 (m, 1H); 7.33 (s, 1H); 7.65 (s, 1H); 7.8 (m, 2H); 7.91 (s, 1H); 9.07 (s, 1H).

EXAMPLE 209

Preparation of Compound 386 in Table 15

An analogous reaction to that described in example 199 but starting with 3-methoxyaniline (52 mg, 0.42 mmol) yielded compound 386 in table 5 (125 mg, 67%)

MS $ES^+$: 549 $(M+H)^+$ $^1$HNMR (DMSO-$d_6$, TFA): 1.63 (m, 2H); 2.04 (m, 2H); 2.15 (m, 1H); 2.8 (s, 3H); 3.04 (t, 2H); 3.52 (d, 2H); 3.75 (s, 3H); 3.98 (s, 2H); 3.99 (s, 3H); 4.11 (d, 2H); 6.68 (m, 1H); 7.17 (d, 1H); 7.24 (t, 1H); 7.33 (s, 1H); 7.35 (d, 1H); 7.64 (s, 1H); 7.92 (s, 1H); 9.09 (s, 1H).

EXAMPLE 210

Preparation of Compound 387 in Table 15

An analogous reaction to that described in example 199 but starting with 2-amino-5-chloropyridine (54 mg, 0.42 mmol) yielded compound 387 in table 15 (22 mg, 11%)

MS $ES^+$: 554 $(M+H)^+$ $^1$HNMR (DMSO-$d_6$, TFA): 1.61 (m, 2H); 2.03 (m, 2H); 2.15 (m, 1H); 2.8 (s, 3H); 3.03 (t, 2H); 3.5 (d, 2H); 3.98 (s, 3H); 4.07 (s, 2H); 4.11 (d, 2H); 7.30 (s, 1H); 7.63 (s, 1H); 7.9 (s, 1H); 7.93 (dd, 1H); 8.12 (d, 1H); 8.41 (d, 1H).

EXAMPLE 211

Preparation of Compound 388 in Table 15

An analogous reaction to that described in example 199 but starting with 3-chloroaniline (54 mg, 0.42 mmol) yielded compound 388 in Table 15 (130 mg, 69%).

MS $ES^+$: 553 $(M+H)^+$ $^1$HNMR (DMSO-$d_6$, TFA): 1.62 (m, 2H); 2.02 (m, 2H); 2.15 (m, 1H); 2.78 (s, 3H); 3.02 (t, 2H); 3.49 (d, 2H); 3.97 (s, 3H); 3.99 (s, 2H); 4.08 (d, 2H); 7.13 (d, 1H); 7.3 (s, 1H); 7.38 (t, 1H); 7.64 (s, 1H); 7.86 (s, 1H); 7.90 (s, 1H); 9.07 (s, 1H).

EXAMPLE 212

Preparation of Compound 389 in Table 15

An analogous reaction to that described in example 199 but starting with 2-fluoroaniline (47 mg, 0.42 mmol) yielded compound 389 in Table 15 (116 mg, 63%).

MS $ES^+$: 537 $(M+H)^+$ $^1$HNMR (DMSO-$d_6$, TFA): 1.64 (m, 2H); 2.04 (m, 2H); 2.15 (m, 1H); 2.79 (s, 3H); 3.03 (t, 2H); 3.50 (d, 2H); 3.99 (s, 3H); 4.07 (s, 2H); 4.10 (d, 2H); 7.19 (m, 2H); 7.25 (m, 1H); 7.35 (s, 1H); 7.63 (s, 1H); 7.90 (s, 1H); 7.91 (m, 1H); 9.07 (s, 1H).

EXAMPLE 213

Preparation of compound 390 in Table 15

Analogous reaction to that described in example 199 but starting with 3-dluoro-4-methoxyaniline (59 mg, 0.42 mmol) yielded compound 390 in Table 15 (151 mg, 85%).

MS $ES^+$: 567 $(M+H)^+$ $^1$HNMR (DMSO-$d_6$, TFA): 1.62 (m, 2H); 2.01 (m, 2H); 2.15 (m, 1H); 2.79 (s, 3H); 3.03 (t, 2H); 3.51 (d, 2H); 3.81 (s, 3H); 3.96 (s, 2H); 3.98 (s, 3H); 4.10 (d, 2H); 7.14 (t, 1H); 7.28 (d, 1H); 7.34 (s, 1H); 7.59 (dd, 1H); 7.6 (s, 1H); 7.90 (s, 1H); 9.07 (s, 1H).

EXAMPLE 214

Preparation of Compound 391 in Table 15

An analogous reaction to that described in example 199 but starting with 2-methyl-4-fluoroaniline (53 mg, 0.42 mmol) yielded compound 391 in Table 15 (151 mg, 81%).

MS ES$^+$: 551 (M+H)$^+$ $^1$HNMR (DMSO-$d_6$, TFA): 1.62 (m, 2H); 2.02 (m, 2H); 2.15 (m, 1H); 2.33 (s, 3H); 2.79 (s, 3H); 2.93 (t, 2H); 3.48 (d, 2H); 3.97 (s, 3H); 3.99 (s, 2H), 4.09 (d, 2H); 7.01 (dt, 1H); 7.1 (dd, 1H); 7.37 (s, 1H); 7.39 (m, 1H); 7.64 (s, 1H); 7.89 (s, 1H); 9.05 (s, 1H).

EXAMPLE 215

Preparation of Compound 392 in Table 15

An analogous reaction to that described in example 199 but starting with 2-amino-4-methylpyridine (45 mg, 0.42 μmmol) yielded compound 392 in Table 15 (119 mg, 66%).

MS ES$^+$: 534 (M+H)$^+$ $^1$HNMR (DMSO-$d_6$, TFA): 1.66 (m, 2H); 2.05 (in, 2H); 2.15 (m, 1H); 2.77 (s, 3H); 3.03 (t, 2H); 3.48 (d, 2H); 3.97 (s, 3H); 4.09 (d, 2H); 4.21 (s, 2H); 7.35 (m, 1H); 7.45 (s, 1H) 7.69 (s, 1H); 7.70 (s, 1H); 7.90 (s, 1H); 8.31 (d, 1H); 9.06 (s, 1H).

EXAMPLE 216

Preparation of Compound 393 in Table 15

An analogous reaction to that described in example 199 but starting with 2,5-difluoroaniline (54 mg, 0.42 mmol) yielded compound 393 in Table 15 (42 mg, 22%).

MS ES$^+$: 555 (M+H)$^+$ $^1$HNMR (DMSO-$d_6$, TFA): 1.60 (in, 2H); 2.02 (m, 2H); 2.15 (m, 1H); 2.81 (s, 3H); 3.04 (t, 2H); 3.52 (d, 2H); 3.99 (s, 3H); 4.10 (s, 2H); 4.11 (d, 2H); 7.02 (in, 2H); 7.32 (s, 1H); 7.34 (m, 1H); 7.64 (s, 1H); 7.91 (s, 1H); 7.92 (m, 1H); 9.08 (s, 1H).

EXAMPLE 217

Preparation of Compound 394 in Table 15

An analogous reaction to that described in example 199 but starting with 2-fluoro-4-chloroaniline (61 mg, 0.42 mmol) yielded compound 394 in Table 15 (97 mg, 50%).

MS ES$^+$: 571 (M+H)$^+$ $^1$HNMR (DMSO-$d_6$, TFA): 1.63 (in, 2H); 2.04 (m, 2H); 2.15 (m, 1H); 2.77 (s, 3H); 3.03 (t, 2H); 3.48 (d, 2H); 3.98 (s, 3H); 4.07 (s, 2H); 4.09 (d, 2H); 7.26 (d, 1H); 7.38 (s, 1H); 7.5 (dd, 1H); 7.62 (s, 1H); 7.89 (s, 1H); 7.96 (t, 1H); 9.06 (s, 1H).

EXAMPLE 218

Preparation of Compound 395 in Table 15

An analogous reaction to that described in example 199 but starting with 2-fluoro-5-methylaniline (53 mg, 0.42 mmol) yielded compound 395 in Table 15 (119 mg, 63%).

MS ES$^+$: 551 (M+H)$^+$ $^1$HNMR (DMSO-$d_6$, TFA): 1.63 (in, 2H); 2.03 (m, 2H); 2.15 (m, 1H); 2.28 (s, 3H); 2.77 (s, 3H); 3.03 (t, 2H); 3.49 (d, 2H); 3.98 (s, 3H); 4.05 (s, 2H); 4.09 (d, 2H); 6.98 (m, 1H); 7.15 (dd, 1H); 7.38 (s, 1H); 7.62 (s, 1H); 7.72 (m, 1H); 7.89 (s, 1H); 9.06 (s, 1H).

EXAMPLE 219

Preparation of Compound 396 in Table 15

An analogous reaction to that described in example 199 but starting with 3-methylaniline (45 mg, 0.42 mmol) yielded compound 396 in Table 15 (144 g, 79%).

MS ES$^+$: 533 (M+H)$^+$ $^1$HNMR (DMSO-$d_6$; TFA): 1.64 (m, 2H); 2.04 (m, 2H); 2.15 (m, 1H); 2.3 (s, 3H); 2.79 (s, 3H); 3.04 (t, 2H); 3.51 (d, 2H); 3.98 (s, 2H); 3.99 (3H); 4.10 (d, 2H); 6.90 (d, 1H); 7.21 (t, 1H); 7.36 (s, 1H); 7.42 (d, 1H); 7.49 (s, 1H); 7.63 (s, 1H); 7.9 (s, 1H); 9.07 (s, 1H).

EXAMPLE 220

Preparation of Compound 397 in Table 15

An analogous reaction to that described in example 199 but starting with 2,4-difluoroaniline (54 mg, 0.42 mmol) yielded compound 397 in Table 15 (121 mg, 74%).

MS ES$^+$: 555 (M+H)$^+$ $^1$HNMR (DMSO-$d_6$, TFA): 1.63 (m, 2H); 2.03 (m, 2H); 2.15 (m, 1H); 2.78 (s, 3H); 3.03 (t, 2H); 3.5 (d, 2H); 3.98 (s, 3H); 4.04 (s, 2H); 4.1 (d, 2H); 7.08 (m, 1H); 7.33 (m, 1H); 7.36 (s, 1H); 7.63 (s, 1H); 7.86 (m, 1H); 7.90 (s, 1H); 9.07 (s, 1H).

EXAMPLE 221

Preparation of Compound 398 in Table 15

An analogous reaction to that described in example 199 but starting with 2-fluoro-4-methylaniline (53 mg, 0.42 mmol) yielded compound 398 in Table 15 (147 mg, 79%).

MS ES$^+$: 551 (M+H)$^+$ $^1$HNMR (DMSO-$d_6$, TFA): 1.63 (m, 2H); 2.04 (m, 2H); 2.15 (m, 1H); 2.3 (s, 3H); 2.79 (s, 3H); 3.04 (t, 2H); 3.51 (d, 2H); 3.99 (s, 3H); 4.04 (s, 2H); 4.1 (d, 2H); 6.99 (d, 1H); 7.10 (d, 1H); 7.35 (s, 1H); 7.62 (s, 1H); 7.75 (t, 1H); 7.90 (s, 1H); 9.07 (s, 1H).

EXAMPLE 222

Preparation of Compound 399 in Table 15

An analogous reaction to that described in example 199 but starting with 3-cyanoaniline (50 mg, 0.42 mmol) yielded compound 399 in Table 15 (118 mg, 71%).

MS ES$^+$: 544 (M+H)$^+$ $^1$HNMR (DMSO-$d_6$, TFA): 1.66 (m, 2H); 2.07 (m, 2H); 2.17 (m, 1H); 2.81 (s, 3H); 3.06 (t, 2H); 3.53 (d, 2H); 4.0 (s, 3H); 4.05 (s, 2H); 4.11 (d, 2H); 7.36 (s, 1H); 7.54 (m, 2H); 7.65 (s, 1H); 7.86 (dd, 1H); 7.92 (s, 1H); 8.18 (s, 1H); 9.09 (s, 1H).

EXAMPLE 223

Preparation of Compound 400 in Table 15

An analogous reaction to that described in example 199 but starting with 2-methyl-5-fluoroaniline (53 mg, 0.42 mmol) yielded compound 400 in Table 15 (107 mg, 57%).

MS $ES^+$: 551 $(M+H)^+$ $^1$HNMR (DMSO-$d_6$, TFA): 1.65 (m, 2H); 2.04 (m, 2H); 2.15 (m, 1H); 2.24 (s, 3H); 2.76 (s, 3H); 3.02 (t, 2H); 3.47 (d, 2H); 3.98 (s, 3H); 4.07 (s, 2H); 4.08 (d, 2H); 6.92 (m, 1H); 7.25 (t, 1H); 7.4 (s, 1H); 7.43 (m, 1H); 7.64 (s, 1H); 7.88 (s, 1H); 9.04 (s, 1H).

EXAMPLE 224

Preparation of Compound 401 in Table 15

An analogous reaction to that described in example 199 but starting with 3,5-difluoroaniline (54 mg, 0.42 mmol) yielded compound 401 in Table 15 (83 mg, 44%).

MS $ES^+$: 555 $(M+H)^+$ $^1$HNMR (DMSO-$d_6$, TFA): 1.66 (m, 2H); 2.02 (m, 2H); 2.16 (m, 1H); 2.76 (s, 3H); 3.03 (t, 2H); 3.45 (d, 2H); 3.97 (s, 3H); 4.03 (s, 2H); 4.08 (d, 2); 6.90 (dd, 1H); 7.38 (m, 2H); 7.39 (s, 1H); 7.87 (s, 1H); 9.05 (s, 1H).

EXAMPLE 225

Preparation of Compound 402 in Table 15

An analogous reaction to that described in example 199 but starting with 3-fluoroaniline (47 mg, 0.42 mmol) yielded compound 402 in Table 15 (142 mg, 77%).

MS $ES^+$: 537 $(M+H)^+$ $^1$HNMR (DMSO-$d_6$, TFA): 1.62 (m, 2H); 2.03 (m, 2H); 2.15 (m, 1H); 2.78 (s, 3H); 3.02 (t, 2H); 3.49 (d, 2H); 3.98 (s, 3H); 4.0 (s, 2H); 4.1 (d, 2H); 6.9 (s, 1H); 7.35 (s, 1H); 7.36 (m, 2H); 7.62 (m, 1H); 7.64 (s, 1H); 7.9 (s, 1H); 9.08 (s, 1H).

EXAMPLE 226

Preparation of Compound 403 in Table 16

4-((2-amino-1,3-thiazol-5-yl)acetic acid)-6-methoxy-7-(3-N-methylpiperazinylpropoxy)quinazoline (142 mg, 0.3 mmol) in NMP (1.5 ml) was reacted with aniline (42 μl, 0.45 mmol) in presence of 0-(7-azabenzotriazol-1-yl)-N,N,N',N', tetramethyluronium hexafluorophosphate (173 mg, 0.45 mmol) and diisopropylethylamine (105 μl, 0.6 mmol) at 65° C. under nitrogen over night. After cooling to room temperature, the reaction mixture was diluted with dichloromethane and purified by silicagel chromatography, eluant $CH_2Cl_2$, $CH_2Cl_2$/MeOH, 9/1, $CH_2Cl_2$/MeOH sat. $NH_3$, 9/1 to give title compound (24 mg, 15%).

MS $ES^+$: 548.6 $(M+H)^+$ $^1$HNMR (DMSO-$d_6$, TFA): 2.31 (t, 2H); 2.94 (s, 3H); 3.24.2 (m, 8H); 3.45 (t, 2H); 3.99 (s, 5H); 4.30 (t, 2H); 7.08 (t, 1H); 7.31 (s, 1H); 7.33 (, 2H); 7.62 (d, 2H); 7.64 (s, 1H); 7.90 (s, 1H); 9.09 (s, 1H).

2-nitro-4-(3-N-methylpiperazinylpropoxy)-5-methoxybenzonitrile 2-nitro-4-hydroxy-5-methoxybenzonitrile (45 g, 25 mmol) in $CH_2Cl_2$ (125 ml) was reacted with ditertiobutylazodicarboxylate (6.9 g, 30 mmol) triphenylphosphine (7.86 g, 30 mmol) at room temperature for 2 hours. A solution of ether (2.3N HCl, 55 ml) was added. The solid was recovered, washed with $CH_2Cl_2$, ether. The solid was dissolved in MeOH, treated with MeOH/NH3, the solvent were evaporated, and the residue purified by silicagel chromatography eluant: $CH_2Cl_2$/AcOEt 50/50, $CH_2Cl_2$/MeOH 90/10, to give title compound (8.2 g, 98%).

MS $ES^+$: 335.6 $(M+H)^+$ $^1$HNMR (DMSO-$d_6$, TFA): 2.29 (t, 2H); 3.95 (s, 3H); 3.2–4 (m, 8H); 3.38 (t, 2H); 3.98 (s, 3H); 4.32 (t, 2H); 7.70 (s, 1H); 7.89 (s, 1H).

2-amino-4-(3-N-methylpiperazinylpropoxy)-5-methoxy-benzonitrile 2-nitro-4-(3-N-methylpiperazinylpropoxy)-5-methoxybenzonitrile (1.67 g, 5 mmol), benzyltrimethylammonium chloride (0.46 g, 2.5 mmol) in methyle chloride (40 ml) was treated with sodium hydrosulfite (4.35 g, 5 mmol) in water (40 ml) at room temperature for 1 hour. HCl (6N, 28 ml) was added to the mixture which was heated at 60° C. for 2.5 hours. The mixture was cooled, extracted with ethylacetate. The aqueous phase was treated with $Na_2CO_3$ (solid), extracted with ethylacetate. The organic phase was dried over $MgSO_4$, concentrated to give title compound (0.93 g, 61%).

MS $ES^+$: 305.7 $(M+H)^+$ $^1$HNMR (DMSO-$d_6$, TFA): 2.18 (t, 2H); 2.93 (s, 3H); 3.1–4.1 (m, 8H); 3.39 (t, 2H); 3.66 (s, 3H); 4.05 (t, 2H); 6.54 (s, 1H); 7.00 (s, 1H).

N'-(2-cyano-4-methoxy-5-(3-N-methylpiperazinylpropoxy)phenyl)-N,N-dimethylimidoformamide 2-amino-4-(3-N-methylpiperazinylporpoxy)-5-methoxybenzonitrile (16.4 g, 54 mmol) was reacted with dimethylformamide dimethyl acetal (12 ml, 90 mmol) in toluene (400 ml) at reflux for 4 hours. The solvent was evaporated to give title compound (19.4 g, 100%).

MS $ES^+$: 360.7 $(M+H)^+$ $^1$HNMR (DMSO-$d_6$, TFA): 2.28 (t, 2H); 2.96 (s, 3H); 3.26 (s, 3H); 3.35 (s, 3H); 3.40 (t, 2H); 3.1–4 (m, 8H); 3.88 (s, 3H); 4.21 (t, 2H); 7.32 (s, 1H); 7.53 (s, 1H); 8.56 (s, 1H).

4-(methyl(2-amino-1,3-thiazole-5-yl)acetate)-6-methoxy-4-((3-N-methylpiperazinylpropoxy) quinazoline N'-(2-cyano-4-methoxy-5-(3-N-piperazinylpropoxy) phenyl)-N,N-dimethylimidoformamide (9.7 g, 27 mmol) in acetic acid (100 ml) was reacted with methyl (2-amino-1, 3-thiazole-5-yl)acetate (5.2 g, 30 mmol) at reflux for 4 hours. The solvent was evaporated and the residue purified by silicagel chromatography, Eluant: $CH_2Cl_2$/MeOH 99/1 to 97/3 to give title compound (9.15 g, 70%).

MS $ES^+$: 487.6 $(M+H)^+$ $^1$HNMR (DMSO-$d_6$, TFA): 2.32 (t, 2H); 2.97 (s, 3H); 3.2–4.2 (m, 8H); 3.48 (t, 2H); 3.97 (s, 2H); 4.00 (s, 3H); 4.33 (t, 2H); 7.36 (s, 1H); 7.61 (s, 1H); 7.93 (s, 1H); 9.10 (s, 1H).

4-(2-amino-1,3-thiazole-5-yl)acetic acid)-6-methoxy-7-(3-(N-methylpiperazinylpropoxy) quinazoline 4-(methyl(2-amino-1,3-thiazole-5-yl)acetate)-6-methoxy-7-(3-(N-methylpiperazinylpropoxy) quinazoline (8.25 g, 17 mmol) in ethanol (80 ml) was treated with sodium hydroxyde (2N, 42.5 ml, 85 mmol) at room temperature for 1 hour. Hydrochloride acid (2N) was added to the solution (pH 3). The solution was evaporated, the residue dissolved in ethanol and N-ethyl diisopropyl amine (8.9 ml, 51 mmol). Ether was added to the solution, the solid was recovered, dried to give title compound (7.44 g, 93%).

MS $ES^+$: 473.5 $(M+H)^+$ $^1$HNMR (DMSO-$d_6$, TFA): 2.30 (t, 2H); 2.94 (s, 3H); 3.2–4.1 (m, 8H); 3.45 (t, 2H); 3.89 (s, 2H); 3.97 (s, 3H); 4.29 (t, 2H); 7.30 (s, 1H); 7.56 (s, 1H); 7.90 (s, 1H); 9.06 (s, 1H).

EXAMPLE 227

Preparation of Compound 404 in Table 16

An analogous reaction to that described in example 226 but starting with 3,4-difluoroaniline (77 mg, 0.6 mmol) yielded title compound (105 mg, 60%).

MS ES$^+$: 584.6 (M+H)$^+$ $^1$HNMR (DMSO-$d_6$, TFA): 2.32 (t, 2H); 2.94 (s, 3H); 3.2–4.1 (m, 8H); 3.44 (t, 2H); 3.99 (s, 5H); 4.30 (t, 2H); 7.32 (s, 1H); 7.32 (m, 1H); 7.40 (q, 1H); 7.65 (s, 1H); 7.81 (m, 1H); 7.91 (s, 1H); 9.09 (s, 1H).

EXAMPLE 228

Preparation of Compound 405 in Table 16

An analogous reaction to that described in example 226 but starting with 2-aminopyridine (56 mg, 0.6 mmol) yielded title compound (53 mg, 36%).

MS ES$^+$: 549.6 (M+H)$^+$ $^1$HNMR (DMSO-$d_6$, TFA): 2.30 (t, 2H); 2.94 (s, 3H); 3.14.1 (m, 8H); 3.41 (t, 2H); 3.99 (s, 3H); 4.02 (s, 2H); 4.32 (t, 2H); 7.21 (m, 1H); 7.34 (s, 1H); 7.64 (s, 1H); 7.91 (m, 2H); 8.03 (d, 1H); 8.37 (m, 1H); 9.98 (s, 1H).

EXAMPLE 229

Preparation of Compound 406 in Table 16

An analogous reaction to that described in example 226 but starting with 3-chloro-4-fluoroaniline (87 mg, 0.6 mmol) yielded title compound (134 mg, 74%).

MS ES$^+$: 600.5 (M+H)$^+$ $^1$HNMR (DMSO-$d_6$, TFA): 2.31 (t, 2H); 2.94 (s, 3H); 3.43 (t, 2H); 3.1–4.1 (m, 8H); 3.99 (s, 5H); 4.32 (t, 2H); 7.33 (s, 1H); 7.38 (t, 1H); 7.50 (m, 1H); 7.64 (s, 1H); 7.90 (s, 1H); 7.96 (m, 1H); 9.09 (s, 1H).

EXAMPLE 230

Preparation of Compound 407 in Table 16

An analogous reaction to that described in example 226 but starting with 3-chloroaniline (77 mg, 0.6 mmol) yielded title compound (46 mg, 26%).

MS ES$^+$: 582.6 (M+H)$^+$ $^1$HNMR (DMSO-$d_6$, TFA): 2.31 (t, 2H); 2.95 (s, 3H); 3.24.1 (m, 8H); 3.45 (t, 2H); 3.99 (s, 3H); 4.07 (s, 2H); 4.30 (t, 2H); 7.22 (t, 1H); 7.31 (s, 1H); 7.35 (t, 1H); 7.53 (d, 1H); 7.65 (s, 1H); 7.74 (d, 1H); 7.92 (s, 1H); 9.08 (s, 1H).

EXAMPLE 231

Preparation of Compound 408 in Table 16

An analogous reaction to that described in example 226 but starting with 4-methylaniline (64 mg, 0.6 mmol) yielded title compound (105 mg, 62%).

MS ES$^+$: 562.6 (M+H)$^+$ $^1$HNMR (DMSO-$d_6$, TFA): 2.26 (s, 3H); 2.31 (t, 2H); 2.95 (s, 3H); 3.1–4.1 (m, 8H); 3.43 (t, 2H); 3.95 (s, 2H); 3.98 (s, 3H); 4.30 (t, 2H); 7.12 (d, 2H); 7.31 (s, 1H); 7.50 (d, 2H); 7.63 (s, 1H); 7.90 (s, 1H); 9.08 (s, 1H).

EXAMPLE 232

Preparation of Compound 409 in Table 16

An analogous reaction to that described in example 226 but starting with 2-methylaniline (64 mg, 0.6 mmol) yielded title compound (127 mg, 75%).

MS ES$^+$: 562.6 (M+H)$^+$ $^1$HNMR (DMSO-$d_6$, TFA): 2.24 (s, 3H); 2.31 (t, 2H); 2.95 (s, 3H); 3.2–4.1 (m, 8H); 3.44 (t, 2H); 3.99 (s, 3H); 4.02 (s, 2H); 4.31 (t, 2H); 7.12 (t, 1H); 7.19 (t, 1H); 7.24 (d, 1H); 7.33 (s, 1H); 7.44 (d, 1H); 7.66 (s, 1H); 7.91 (s, 1H); 9.08 (s, 1H).

EXAMPLE 233

Preparation of Compound 410 in Table 16

An analogous reaction to that described in example 226 but starting with 4-chloroaniline (77 mg, 0.6 mmol) yielded title compound (101 mg, 58%).

MS ES$^+$: 582.5 (M+H)$^+$ $^1$HNMR (DMSO-$d_6$, TFA): 2.32 (t, 2H); 2.95 (s, 3H); 3.1–4.1 (m, 8H); 3.44 (t, 2H); 4.00 (s, 5H); 4.31 (t, 2H); 7.33 (s, 1H); 7.40 (d, 2H); 7.65 (s, 1H); 7.66 (d, 2H); 7.92 (s, 1H); 9.10 (s, 1H).

EXAMPLE 234

Preparation of Compound 411 in Table 16

An analogous reaction to that described in example 226 but starting with 4-fluoroaniline (67 mg, 0.6 mmol) yielded title compound (97 mg, 57%).

MS ES$^+$: 566.5 (M+H)$^+$ $^1$HNMR (DMSO-$d_6$, TFA): 2.31 (t, 2H); 2.94 (s, 3H); 3.1–4.1 (m, 8H); 3.44 (t, 2H); 3.97 (s, 2H); 3.99 (s, 3H); 4.30 (t, 2H); 7.17 (t, 2H); 7.34 (s 1H); 7.64 (m, 3H); 7.90 (s, 1H); 9.09 (s, 1H).

EXAMPLE 235

Preparation of Compound 412 in Table 16

An analogous reaction to that described in example 226 but starting with 2-amino-6-methylpyridine (65 mg, 0.6 mmol) yielded title compound (70 mg, 42%).

MS ES$^+$: 563.6 (M+H)$^+$ $^1$HNMR (DMSO-$d_6$, TFA): 2.30 (t, 2H); 2.46 (s, 3H); 2.94 (s, 3H); 3.10–4.10 (m, 8H); 3.43 (t, 2H); 3.98 (s, 3H); 4.06 (s, 2H); 4.30 (t, 2H); 7.08 (d, 1H); 7.32 (s, 1H); 7.63 (s, 1H); 7.79 (t, 1H); 7.88 (d, 1H); 7.91 (s, 1H); 9.09 (s, 1H).

EXAMPLE 236

Preparation of Compound 413 in Table 16

An analogous reaction to that described in example 226 but starting with 2-methoxyaniline (74 mg, 0.6 mmol) yielded title compound (99 mg, 57%).

MS ES$^+$: 578.6 (M+H)$^+$ $^1$HNMR (DMSO-$d_6$, TFA): 2.30 (t, 2H); 2.94 (s, 3H); 3.1–4.1 (m, 8H); 3.43 (t, 2H); 3.74 (s, 3H); 3.97 (s, 2H); 3.99 (s, 3H); 4.30 (t, 2H); 6.67 (d, 1H); 7.15 (d, 1H); 7.24 (t, 1H); 7.33 (s, 2H); 7.64 (s, 1H); 7.90 (s, 1H); 9.09 (s, 1H).

EXAMPLE 237

Preparation of Compound 414 in Table 16

An analogous reaction to that described in example 226 but starting with 2-amino-5-chloropyridine (77 mg, 0.6 mmol) yielded title compound (23 mg, 13%).

MS $ES^+$: 583.5 $(M+H)^+$ $^1$HNMR (DMSO-$d_6$, TFA): 2.30 (t, 2H); 2.94 (s, 3H); 3.10–4.10 (m, 8H); 3.45 (t, 2H); 3.98 (s, 3H); 4.06 (s, 2H); 4.30 (t, 2H); 7.31 (s, 1H); 7.63 (s, 1H); 7.90 (s, 1H); 7.91 (dd, 1H) 8.11 (d, 1H); 8.40 (d, 1H); 9.09 (s, 1H).

EXAMPLE 238

Preparation of Compound 415 in Table 16

An analogous reaction to that described in example 226 but starting with 3-chloroaniline (77 mg, 0.6 mmol) yielded title compound (96 mg, 55%).

MS $ES^+$: 582.5 $(M+H)^+$ $^1$HNMR (DMSO-$d_6$, TFA): 2.31 (t, 2H); 2.94 (s, 3H); 3.2–4.2 (m, 8H); 3.45 (t, 2H); 3.98 (s, 5H); 4.28 (t, 2H); 7.12 (d, 1H); 7.31 (s, 1H); 7.34 (t, 1H); 7.46 (d, 1H); 7.62 (s, 1H); 7.85 (s, 1H); 7.91 (s, 1H); 9.07 (s, 1H).

EXAMPLE 239

Preparation of Compound 416 in Table 16

An analogous reaction to that described in example 226 but starting with 2-fluoroaniline (67 mg, 0.6 mmol) yielded title compound (68 mg, 40%).

MS $ES^+$: 596.6 $(M+H)^+$ $^1$HNMR (DMSO-$d_6$, TFA): 2.28 (t, 2H); 2.91 (s, 3H); 3.1–4.1 (m, 8H); 3.40 (t, 2H); 3.95 (s, 3H); 4.03 (s, 2H); 4.26 (t, 2H); 7.13 (m, 2H); 7.25 (m, 2H); 7.28 (s, 1H); 7.60 (s, 1H); 7.87 (s, 1H); 9.05 (s, 1H).

EXAMPLE 240

Preparation of Compound 417 in Table 16

An analogous reaction to that described in example 226 but starting with 3-cyanoaniline (71 mg, 0.6 mmol) yielded title compound (101 mg, 63%).

MS $ES^+$: 573.6 $(M+H)^+$ $^1$HNMR (DMSO-$d_6$, TFA): 2.31 (t, 2H); 2.95 (s, 3H); 3.1–4.1 (m, 8H); 3.45 (t, 2H); 4.00 (s, 3H); 4.04 (s, 2H); 4.31 (t, 2H); 7.33 (s, 1H); 7.56 (s, 1H); 7.57 (m, 1H); 7.66 (s, 1H); 7.82 (m, 1H); 7.92 (s, 1H); 8.15 (s, 1H); 9.10 (s, 1H).

EXAMPLE 241

Preparation of Compound 418 in Table 16

An analogous reaction to that described in example 226 but starting with 2-fluoro-4-methylaniline (75 mg, 0.6 mmol) yielded title compound (109 mg, 63%).

MS $ES^+$: 580.6 $(M+H)^+$ $^1$HNMR (DMSO-$d_6$, TFA): 2.29 (m, 5H); 2.94 (s, 3H); 3.14.1 (m, 8H); 3.44 (t, 2H); 3.98 (s, 3H); 4.03 (s, 2H); 4.30 (t, 2H); 6.98 (d, 1H); 7.09 (d, 1H); 7.32 (s, 1H); 7.63 (s, 1H); 7.74 (t, 1H); 7.90 (s, 1H); 9.08 (s, 1H).

EXAMPLE 242

Preparation of Compound 419 in Table 16

An analogous reaction to that described in example 226 but starting with 3-fluoro-4-methoxyaniline (85 mg, 0.6 mmol) yielded title compound (121 mg, 68%).

MS $ES^+$: 596.6 (M+H)+

$^1$HNMR (DMSO-$d_6$, TFA): 2.31 (t, 2H); 2.95 (s, 3H); 3.1–4.1 (m, 8H); 3.44 (t, 2H); 3.81 (s, 3H); 3.95 (s, 2H); 3.99 (s, 3H); 4.30 (t, 2H); 7.13 (t, 1H); 7.27 (m, 1H); 7.31 (s, 1H); 7.60 (m, 1H); 7.64 (s, 1H); 7.90 (s, 1H); 9.09 (s, 1H).

EXAMPLE 243

Preparation of Compound 420 in Table 16

An analogous reaction to that described in example 226 but starting with 2-methyl-4-fluoroaniline (75 mg, 0.6 mmol) yielded title compound (130 mg, 75%).

MS $ES^+$: 580.6 $(M+H)^+$ $^1$HNMR (DMSO-$d_6$, TFA) 2.23 (s, 3H); 2.29 (t, 2H); 2.95 (s, 3H); 3.1–4.1 (m, 8H); 3.44 (t, 2H); 3.99 (s, 3H); 4.00 (s, 2H); 4.30 (t, 2H); 7.01 (m, 1H); 7.09 (dd, 1H); 7.32 (s, 1H); 7.40 (m, 1H); 7.65 (s, 1H); 7.91 (s, 1H); 9.08 (s, 1H).

EXAMPLE 244

Preparation of Compound 421 in Table 16

An analogous reaction to that described in example 226 but starting with 2-amino-4-methylpyridine (65 mg, 0.6 mmol) yielded title compound (87 mg, 52%).

MS $ES^+$: 563.6 $(M+H)^+$ $^1$HNMR (DMSO-$d_6$, TFA): 2.29 (t, 2H); 2.45 (s, 3H); 2.94 (s, 3H); 3.1–4.1 (m, 8H); 3.44 (t, 2H); 3.99 (s, 3H); 4.15 (s, 2H); 4.30 (t, 2H); 7.24 (d, 1H); 7.37 (s, 1H); 7.67 (s, 1H); 7.72 (s, 1H); 7.92 (s, 1H); 8.29 (d, 1H); 9.08 (s, 1H);

EXAMPLE 245

Preparation of Compound 422 in Table 16

An analogous reaction to that described in example 226 but starting with 2,5-difluoroaniline (77 mg, 0.6 mmol) yielded title compound (56 mg, 32%).

MS $ES^+$: 584.6 $(M+H)^+$ $^1$HNMR (DMSO-$d_6$, TFA): 2.30 (t, 2H); 2.94 (s, 3H); 3.1–4.1 (m, 8H); 3.43 (t, 2H); 3.98 (s, 3H); 4.10 (s, 2H); 4.30 (t, 2H); 7.0 (m, 1H); 7.32 (s, 1H); 7.33 (m, 1H); 7.64 (s, 1H); 7.91 (m, 2H); 9.09 (s, 1H).

EXAMPLE 246

Preparation of Compound 423 in Table 16

An analogous reaction to that described in example 226 but starting with 2-fluoro-4-chloroaniline (87 mg, 0.6 mmol) yielded title compound (69 mg, 38%).

MS $ES^+$: 600.6 $(M+H)^+$ $^1$HNMR (DMSO-$d_6$, TFA): 2.32 (t, 2H); 2.94 (s, 3H); 3.2–4.2 (m, 8H); 3.44 (t, 2H); 3.99 (s, 3H); 4.07 (s, 2H); 4.30 (t, 2H); 7.20 (dd, 1H); 7.33 (s, 1H); 7.51 (dd, 1H); 7.64 (s, 1H); 7.91 (s, 1H); 7.97 (t, 1H); 9.09 (s, 1H).

EXAMPLE 247

Preparation of Compound 424 in Table 16

An analogous reaction to that described in example 226 but starting with 2-fluoro-5-methylaniline (75 mg, 0.6 mmol) yielded title compound (81 mg, 46%).

MS $ES^+$: 580.6 $(M+H)^+$ $^1$HNMR (DMSO-$d_6$, TFA): 2.27 (s, 3H); 2.32 (t, 2H); 2.94 (s, 3H); 3.1–4.1 (m, 8H); 3.44 (t, 2H); 3.99 (s, 3H); 4.05 (s, 2H); 4.30 (t, 2H); 6.97 (m, 1H); 7.13 (dd, 1H); 7.34 (s, 1H); 7.63 (s, 1H); 7.74 (d, 1H); 7.91 (s, 1H); 9.08 (s, 1H).

EXAMPLE 248

Preparation of Compound 425 in Table 16

An analogous reaction to that described in example 226 but starting with 3-methylaniline (64 mg, 0.6 mmol) yielded title compound (116 mg, 69%).

MS ES$^+$: 584.6 (M+H)$^+$ $^1$HNMR (DMSO-$d_6$, TFA): 2.28 (s, 3H); 2.31 (t, 2H); 2.95 (s, 3H); 3.14.1 (m, 8H); 3.45 (t, 2H); 3.96 (s, 2H); 3.98 (s, 3H); 4.30 (t, 2H); 6.88 (d, 1H); 7.19 (t, 1H); 7.30 (s, 1H); 7.39 (d, 1H); 7.47 (s, 1H); 7.62 (s, 1H); 7.91 (s, 1H); 9.08 (s, 1H).

EXAMPLE 249

Preparation of Compound 426 in Table 16

An analogous reaction to that described in example 226 but starting with 2,4-difluoroaniline (77 mg, 0.6 mmol) yielded title compound (84 mg, 48%).

MS ES$^+$: 584.6 (M+H)$^+$ $^1$HNMR (DMSO-$d_6$, TFA): 2.31 (t, 2H); 2.95 (s, 3H); 3.1–4.1 (in, 8H); 3.99 (s, 3H); 4.05 (s, 2H); 4.30 (t, 2H); 7.07 (t, 1H); 7.32 (in, 2H); 7.64 (s, 1H); 7.86 (m, 1H); 7.91 (s, 1H); 9.08 (s, 1H).

EXAMPLE 250

Preparation of Compound 427 in Table 16

An analogous reaction to that described in example 226 but starting with 2-methyl-5-fluoroaniline (75 mg, 0.6 mmol) yielded title compound (98 mg, 57%).

MS ES$^+$: 580.6 (M+H)$^+$ $^1$HNMR (DMSO-$d_6$, TFA): 2.23 (s, 3H); 2.31 (t, 2H); 2.94 (s, 3H); 3.1–4.1 (in, 8H); 3.43 (t, 2H); 3.98 (s, 3H); 4.05 (s, 2H); 4.30 (t, 2H); 6.91 (m, 1H); 7.25 (t, 1H); 7.32 (s, 1H); 7.44 (dd, 1H); 7.65 (s, 1H); 7.91 (s, 1H); 9.08 (s, 1H).

EXAMPLE 251

Preparation of Compound 428 in Table 16

An analogous reaction to that described in example 226 but starting with 3,5-difluoroaniline (77 mg, 0.6 mmol) yielded title compound (54 mg, 31%).

MS ES$^+$: 584.6 (M+H)$^+$ $^1$HNMR (DMSO-$d_6$, TFA): 2.31 (t, 2H); 2.95 (s, 3H); 3.1–4.1 (m, 8H); 3.45 (t, 2H); 3.99 (s, 3H); 4.02 (s, 2H); 4.31 (t, 2H); 6.92 (m, 1H); 7.33 (s, 1H); 7.35 (in, 2H); 7.66 (s, 1H); 7.92 (s, 1H); 9.10 (s, 1H).

EXAMPLE 252

Preparation of Compound 429 in Table 16

An analogous reaction to that described in example 226 but starting with 3-fluoroaniline (67 mg, 0.6 mmol) yielded title compound (120 mg, 70%).

MS ES$^+$: 566.6 (M+H)$^+$ $^1$HNMR (DMSO-$d_6$, TFA): 2.31 (t, 2H); 2.94 (s, 3H); 3.2–4.2 (m, 5H); 3.44 (t, 2H); 3.98 (s, 3H); 3.99 (s, 2H); 4.30 (t, 2H); 6.90 (s, 1H); 7.34 (s, 1H); 7.36 (m, 2H); 7.61 (m, 1H); 7.64 (s, 1H); 7.90 (s, 1H); 9.09 (s, 1H).

EXAMPLE 253

Preparation of Compound 430 in Table 17

N-(3-chlorophenyl)-2-(2-(7-(3-chloropropoxy)-6-methoxyquinazoline-4-yl-amino)1,3-thiazole-5-yl) acetamide (141 mg, 0.22 mmol) in acetonitrile (2 ml) was reacted with pyrrolidine (3.3 mmol) in presence of potassium iodide (100 mg, 0.6 mmol) at 80° C. for 15 h/30 hours. When the reaction was completed (tic) DMF (2 ml), silicagel (2 g) was added, the mixture evaporated, and the residue was purified by silica gel chromatography, eluant: $CH_2Cl_2$/MeOH 95/5, $CH_2Cl_2$/MeOH sat. $NH_3$ 90/10 to give title compound (81 mg, 29%).

MS ES$^+$: 553.4, 554.4 (M+H)$^+$ $^1$HNMR (DMSO-$d_6$, TFA): 1.90 (m, 2H); 2.06 (m, 2H); 2.26 (t, 2H); 3.09 (m, 2H); 3.36 (t, 2H); 3.67 (m, 2H); 3.99 (s, 3H); 4.00 (s, 2H); 4.29 (t, 2H); 7.14 (d, 1H); 7.30 (s, 1H); 7.37 (t, 1H); 7.47 (d, 1H); 7.65 (s, 1H); 7.85 (s, 1H); 7.91 (s, 1H); 9.09 (s, 1H).

3-methoxy-4-benzyloxybenzonitrile 3-methoxy-4-benzyloxybenzoldehyde (4.87 g, 20 mmol) in acetic acid (25 ml) was treated with hydroxylamine HCl (2.8 g, 40 mmol), sodium acetate (3.3 g, 40 mmol) at reflux for 6 hours. The mixture was cooled, extracted with water and methylenechloride, dried over $MgSO_4$, evaporated, to give title compound (4.8 g, 100%).

$^1$HNMR (DMSO-$d_6$, TFA): 3.72 (s, 3H); 5.15 (s, 2H); 7.18 (d, 1H); 7.39 (m, 7H).

2-nitro-4-benzyloxy-5-methoxybenzonitrile 3-methoxy-4-benzyloxybenzonitrile (4.78 g, 20 mmol) in acetic acid (10 ml) was slowly added to nitric acid (d=1.42, 25 ml) at 20–30° with cooling in an ice bath. The mixture was then stirred at room temperature for 6 hours. The reaction mixture was treated with potassium hydroxyde (10N) at 0° C. The basic mixture (pH 10) was extracted with $CH_2Cl_2$, the organic phase was dried over $MgSO_4$, concentrated to give title compound (3.62 g, 64%).

MS ES$^+$: 285 (M+H)$^+$ $^1$HNMR (DMSO-$d_6$, TFA): 3.97 (s, 3H); 5.33 (s, 2H); 7.42 (m, 5H); 7.70 (s, 1H); 8.03 (s, 1H).

2-amino-4-benzyloxy-5-methoxybenzonitrile 2-nitro-4-benzyloxy-5-methoxybenzonitrile (40 g, 125 mmol) tetrabutylammonium chloride (21 g, 75 mmol) in methylenechloride (500 ml) was treated with $Na_2S_2O_4$ (180 g, 87.9 mmol) in $H_2O$ (700 ml), sodium hydrosulfite was added over 45 minutes, and the mixture was stirred for 2 hours at room temperature. Sodium hydroxyde was added (pH 8.2) the mixture was extracted with methylene chloride. The organic phase was made acidic with HCl-ether (2.3N, 250 ml), the solid was recovered, suspended in methanol (250 ml) and treated with a saturated solution of sodium bicarbonate (pH 8.1). The solid was recovered, washed with water, ether to give title compound (30.7 g, 97%).

$^1$HNMR (DMSO-$d_6$): 3.65 (s, 3H); 5.04 (s, 2H); 5.61 (s, 2H); 6.51 (s, 1H); 6.91 (s, 1H); 7.40 (m, 5H).

N'-(2-cyano-4-methoxy-5-benzyloxyphenyl)-N,N-dimethylimidoformamide 2-amino-4-benzyloxy-5-methoxy benzonitrile (102 g, 400 mmol) in toluene (1.51) was reacted with DMF-DMA (110 ml, 780 mmol) at reflux for 5 hours. The solvent was evaporated, the residue triturated with ether to give title compound as yellow solid.

$^1$HNMR (DMSO-$d_6$): 2.96 (s, 3H); 3.06 (s, 3H); 3.73 (s, 3H); 5.15 (s, 2H); 6.87 (s, 1H); 7.11 (s, 1H); 7.40 (m, 5H); 7.89 (s, 1H).

N'-2-cyano-4-methoxy-5-hydroxyphenyl)-N,N-dimethylimidoformamide

N'-(2-cyano-4-methoxy-5-benzyloxyphenyl)-N,N-dimethylimidoformamide (15.45 g, 50 mmol) in TFA (200 ml) was irradiated in a microwave oven at 75° C. for 45 minutes. The solvent was evaporated, the residue dissolved in dichloromethane washed with sodium bicarbonate, dried over magnesiumsulfate, evaporated to give a pale yellow solid (10.26 g, 94%).

$^1$HNMR (DMSO-$d_6$, TFA): 3.24 (s, 3H); 3.34 (s, 3H); 3.87 (s, 3H); 7.02 (s, 1H); 7.49 (s, 1H); 8.56 (s, 1H).

N'-(2-cyano-4-methoxy-5-(3-chloropropoxyphenyl)-N,N-dimethylimidoformamide

N'-(2-cyano-4-methoxy-5-hydroxyphenyl)-N,N-dimethylimidoformamide (439 mg, 2 mmol) in acetonitrile (5 ml) was reacted with 1-bromo-3-chloropropane (0.22 ml, 2.2 mmol) and cesium carbonate (1.95 g, 5.98 mmol) at 85° C. for 0.5 hour. The reaction mixture was evaporated, taken up in methylene chloride water, extracted with $CH_2Cl_2$, dried over $MgSO_4$, evaporated to give title compound as a pale yellow solid (450 mg, 76%).

MS ES$^+$: 296.6 (M+H)$^+$ $^1$HNMR (DMSO-$d_6$, TFA): 2.26 (t, 2H); 3.26 (s, 3H); 3.37 (s, 3H); 3.81 (t, 2H); 3.87 (s, 3H); 4.23 (t, 2H); 7.34 (s, 1H); 7.53 (s, 1H); 8.56 (s, 1H)

g) N-(3-chlorophenyl)-2-(2-(7-(3-chloropropoxy)-6-methoxyquinazoline-4-ylamino)1,3-thiazol-5-yl) acetamide N'-(2-cyano-4-methoxy-5-(3-chloropropoxyphenyl)-N, N-dimethylimidoformamide (296 mg, 1 mmol) and 2-(2-amino-1,3-thiazol-5-yl)-N-(3-chlorophenyl)acetamide (268 mg, 1 mmol) in AcOH (1.5 ml, was irradiated in a microwave oven at 120° C. for 40 minutes. The mixture was cooled, the solid was filtered to give title compound (445 mg, 72%).

$^1$HNMR (DMSO-$d_6$, TFA): 2.31 (t, 2H); 3.84 (t, 2H); 3.98 (s, 3H); 3.99 (s, 2H); 4.32 (t, 2H) 7.13 (d, 1H); 7.29 (s, 1H); 7.36 (t, 1H); 7.46 (d, 1H); 7.63 (s, 1H); 7.85 (s, 1H); 7.88 (s, 1H); 9.07 (s, 1H).

EXAMPLE 254

Preparation of Compound 431 in Table 17

An analogous reaction to that described in example 253 but starting with N-(3,4-difluorophenyl)-2-(2-(7-(3-chloropropoxy)-6-methoxyquinazoline-4-yl-amino)1,3-thiazole-5-yl)acetamide (52 mg, 0.1 mmol) and pyrrolidine (150 μl, 1.8 mmol) yielded title compound (26 mg, 47%).

$^1$HNMR (DMSO-$d_6$, TFA): 1.91 (m, 2H); 2.07 (m, 2H); 2.28 (t, 2H); 3.10 (m, 2H); 3.37 (t, 2H); 3.67 (m, 2H); 3.99 (s, 5H); 4.30 (t, 2H); 7.30 (s, 1H); 7.33 (m, 1H); 7.40 (q, 1H) 7.65 (s, 1H); 7.91 (s, 1H); 9.09 (s, 1H).

Starting material N-(3,4-difluorophenyl)-2-(2-(7-(3-chloropropoxy)-6-methoxy quinazoline-4-yl-amino)1,3-thiazole-5-yl)acetamide was obtained by an analogous reaction to that described in example 130 but starting with 2-(2-amino-1,3-thiazol-5-yl)-N-(3,4-difluorophenyl) acetamide (540 mg, 2 mmol) to give title compound (980 mg, 78%).

MS ES$^+$: 520.4, 522.4 (M+H)$^+$ $^1$HNMR (DMSO-$d_6$): 1.26 (t, 2H); 3.82 (t, 2H); 3.88 (s, 2H); 3.97 (s, 3H); 4.29 (t, 2H); 7.29 (s, 1H); 7.32 (m, 1H); 7.36 (s, 1H); 7.39 (t, 1H); 7.80 (m, 1H); 8.12 (s, 1H); 8.68 (s, 1H).

EXAMPLE 255

Preparation of Compound 432 in Table 17

An analogous reaction to that described in example 253 but starting with N-(3,5-difluorophenyl)-2-(2-(7-(3-chloropropoxy)-6-methoxyquinazoline-4-yl-amino)1,3-thiazole-5-yl)acetamide (138 mg, 0.22 mmol) and dimethylamine (3.6 M in $CH_2Cl_2$, 3 ml, 3.6 mmol) yielded title compound (47 mg, 40%).

MS ES$^+$: 529.5 (M+H)$^+$ $^1$HNMR (DMSO-$d_6$, TFA): 2.25 (t, 2H); 3.28 (t, 2H); 3.99 (s, 3H); 4.01 (s, 2H); 4.28 (t, 2H) 6.93 (m, 1H); 7.30 (s, 1H); 7.34 (m, 2H); 7.65 (s, 1H); 7.90 (s, 1H); 9.09 (s, 1H).

Starting material N-(3,5-difluorophenyl)-2-(2-(7-(3-chloropropoxy)$_6$-methoxyquinazoline-4-yl-amino)1,3-thiazole-5-yl)acetamide was obtained by an analogous reaction to that described in example 130 but starting with 2-(2-amino-1,3-thiazole-5-yl)-N-(3,5-difluorophenyl) acetamide (810 mg, 3 mmol) to give title compound (630 mg, 40%).

MS ES$^+$: 520.4, 522.4 (M+H)$^+$ $^1$HNMR (DMSO-$d_6$): 2.26 (t, 2H); 3.84 (t, 2H); 3.92 (s, 2H); 3.98 (s, 3H); 4.30 (t, 2H); 6.94 (m, 1H); 7.30 (s, 1H); 7.35 (m, 2H); 7.40 (s, 1H); 8.14 (s, 1H); 8.69 (s, 1H); 10.64 (s, 1H).

EXAMPLE 256

Preparation of Compound 433 in Table 17

An analogous reaction to that described in example 253 but starting with N-(3-chloro-4-fluorophenyl)-2-(2-(7-(3-chloropropoxy)-6-methoxyquinazoline-4-yl-amino)1,3-thiazole-5-yl)acetamide (123 mg, 0.22 mmol) and 2-amino-2-methyl-1-propanol (89.1 mg, 3.3 mmol) yielded title compound (6 mg, 5%).

MS ES$^+$: 589.4 (M+H)$^+$ $^1$HNMR (DMSO-$d_6$, TFA): 1.24 (s, 6H); 2.22 (t, 2H); 3.10 (t, 2H); 3.45 (s, 2H); 3.98 (s, 3H); 4.31 (t, 2H); 7.29 (s, 1H); 7.38 (t, 1H); 7.50 (m, 1H); 7.64 (s, 1H); 7.91 (s, 1H); 7.97 (s, 1H); 9.09 (s, 1H).

Starting material N-(3-chloro-4-fluorophenyl)-2-(2-(7-(3-chloropropoxy)-6-methoxyquinazoline-4-yl-amino)1,3-thiazole-5-yl)acetamide was obtained by an analogous reaction to that described in example 130 but starting with 2-(2-amino-1,3-thiazole-5-yl)-N-(3-chloro-4-fluorophenyl) acetamide (2.29 g, 8.0 mmol) to give title compound (3.62 g, 84%).

MS ES$^+$: 536.3, 538.3 (M+H)$^+$ $^1$HNMR (DMSO-$d_6$): 2.26 (t, 2H); 3.82 (t, 2H); 3.88 (s, 2H); 3.96 (s, 3H); 4.29 (t, 2H); 7.28 (s, 1H); 7.38 (t, 1H); 7.39 (s, 1H); 7.48 (m, 1H); 7.93 (m, 1H); 8.12 (s, 1H); 8.67 (s, 1H); 10.47 (s, 1H).

EXAMPLE 257

Preparation of Compound 434 in Table 17

An analogous reaction to that described in example 253, but starting with N-(3-fluorophenyl)-2-(2-(7-(3-chloropropoxy)$_6$-methoxyquinazoline-4-yl-amino) 1,3-thiazole-5-yl)acetamide (116 mg, 0.22 mmol) and 2-amino-2-methyl-1-propanol (89 mg, 3.3 mmol) yielded title compound (40 mg, 33%).

MS ES$^+$: 555.5 (M+H)$^+$ $^1$HNMR (DMSO-$d_6$, TFA): 2.22 (t, 2H); 3.09 (t, 2H); 3.16 (s, 2H); 3.97 (s, 3H); 4.30 (t, 2H); 6.86 (t, 1H); 7.28 (s, 1H); 7.33 (m, 2H); 7.58 (m, 1H); 7.62 (s, 1H); 7.91 (s, 1H); 9.07 (s, 1H).

Starting material N-(3-fluorophenyl)-2-(2-(7-(3-chloropropoxy)-6-methoxyquinazoline-4-yl-amino)1,3- thiazole-5-yl)acetamide was obtained by an analogous reaction to that described in example 253 but starting with 2-(2-amino-1,3-thiazole-5-yl)-N-(3-fluorophenyl)acetamide (2.01 g, 8 mmol) to give title compound (3.08 g, 77%).

MS $ES^+$: 502.4, 504.4 $(M+H)^+$ $^1$HNMR (DMSO-$d_6$): 2.28 (t, 2H); 3.84 (t, 2H); 3.90 (s, 2H); 3.98 (s, 3H); 4.31 (t, 2H); 6.91 (t, 1H); 7.30 (s, 1H); 7.35 (m, 2H); 7.39 (s, 1H); 7.63 (d, 1H); 8.14 (s, 1H); 8.69 (s, 1H); 10.48 (s, 1H).

EXAMPLE 258

Preparation of Compound 435 in Table 17

An analogous reaction to that described in example 254 but starting with 4-hydroxyperidine (405 mg, 4.0 mmol) yielded compound 435 in Table 17 (82 mg, 70%).

MS $ES^+$: 585.5 $(M+H)^+$ $^1$HNMR (DMSO-$d_6$): 1.43 (m, 2H); 1.73 (m, 2H); 1.95 (m, 2H); 2.03 (t, 2H); 2.44 (t, 2H); 2.74 (m, 2H); 3.38 (m, 1H); 3.90 (s, 2H); 3.97 (s, 3H); 4.20 (t, 2H); 4.53 (d, 1H); 7.26 (s, 1H); 7.31 (m, 1H); 7.39 (s, 1H); 7.42 (ddd, 1H); 7.83 (m, 1H); 8.12 (s, 1H); 8.68 (s, 1H); 10.50 (s, 1H).

EXAMPLE 259

Preparation of Compound 436 in Table 17

An analogous reaction to that described in example 254 but starting with N,N-dimethylenediamine (0.44 ml, 4.0 mmol) yielded compound 436 in Table 17 (40 mg, 35%).

MS $ES^+$: 572.5 ($(M+H)^+$ $^1$HNMR (DMSO-$d_6$): 1.95 (m, 2H); 2.14 (s, 6H); 2.33 (t, 2H); 2.63 (t, 2H); 2.73 (t, 2H); 3.89 (s, 2H); 3.97 (s, 3H); 4.22 (t, 2H); 7.26 (s, 1H); 7.34 (m, 1H); 7.38 (s, 1H); 7.41 (ddd, 1H); 7.82 (m, 1H); 8.11 (s, 1H); 8.67 (s, 1H); 10.50 (s, 1H).

EXAMPLE 260

Preparation of Compound 437 in Table 17

An analogous reaction to that described in example 254 but starting with piperidine (0.4 ml, 3.0 mmol) yielded compound 437 in Table 17 (67 mg, 59%).

MS $ES^+$: 569.5 $(M+H)^+$ $^1$HNMR (DMSO-$d_6$): 1.40 (m, 2H); 1.52 (m, 4H); 1.95 (m, 2H); 2.42 (m, 4H); 2.48 (t, 2H); 3.89 (s, 2H); 3.97 (s, 3H); 4.20 (t, 2H); 7.25 (s, 1H); 7.33 (m, 1H); 7.39 (s, 1H); 7.41 (ddd, 1H); 7.82 (m, 1H); 8.11 (s, 1H); 8.68 (s, 1H); 10.51 (s, 1H).

EXAMPLE 261

Preparation of Compound 438 in Table 17

An analogous reaction to that described in example 254 but starting with 2-methylaminoethanol (248 mg, 3.3 mmol) yielded compound 438 in Table 17 (23 mg, 19%).

MS $ES^+$: 559 $(M+H)^+$ $^1$HNMR (DMSO-$d_6$): 1.95 (m, 2H); 2.23 (s, 3H); 2.47 (m, 2H); 3.32 (m, 2H); 3.49 (m, 2H); 3.90 (s, 2H; 3.98 (s, 3H); 4.21 (t, 2H); 4.37 (m, 1H); 7.27 (s, 1H); 7.34 (m, 1H); 7.38 (s, 1H); 7.40 (dd, 1); 7.82 (ddd, 1H); 8.13 (brs, 1H); 8.68 (s, 1H); 10.50 (s, 1H).

EXAMPLE 262

Preparation of Compound 439 in Table 17

An analogous reaction to that described in example 254 but starting with 1,2-diamino-2-methylpropane (291 mg, 3.3 mmol) yielded compound 439 in Table 17 (16 mg, 13%).

MS $ES^+$: 572 $(M+H)^+$ $^1$HNMR (DMSO-$d_6$): 1.10 (s, 6H); 1.96 (m, 2H); 2.48 (s, 2H); 2.75 (t, 2H); 3.89 (s, 2H); 3.97 (s, 3H); 4.26 (t, 2H); 7.27 (s, 1H); 7.34 (m, 1H); 7.37 (s, 1H); 7.42 (dd, 1H); 7.83 (ddd, 1H); 8.10 (s, 1H); 8.66 (s, 1H); 10.50 (s, 1H).

EXAMPLE 263

Preparation of Compound 440 in Table 17

An analogous reaction to that described in example 254 but starting with cyclohexylamine (327 mg, 3.3 mmol) yielded compound 440 in Table 17 (70 mg, 55%).

MS $ES^+$: 583 $(M+H)^+$ $^1$HNMR (DMSO-$d_6$): 1.12 (m, 1H); 1.27 (m, 4H); 1.63 (brd, 1H); 1.78 (m, 2H); 2.04 (m, 2H); 2.16 (m, 2H); 3.03 (m, 1H); 3.16 (t, 2H); 3.90 (s, 2H); 3.98 (s, 3H); 4.29 (t, 2H); 7.31 (s, 1H); 7.34 (m, 1H); 7.40 (s, 1H); 7.42 (dd, 1H); 7.82 (ddd, 1H); 8.16 (brs, 1H); 8.70 (s, 1H); 10.51 (s, 1H).

EXAMPLE 264

Preparation of Compound 441 in Table 17

An analogous reaction to that described in example 254 but starting with N,N,N'-trimethylethylenediamine (337 mg, 3.3 mmol) yielded compound 441 in Table 17 (63 mg, 49

MS $ES^+$: 587 $(M+H)^+$ $^1$HNMR (DMSO-$d_6$, TFA) 2.33 (m, 2H); 2.88 (s, 6H); 2.93 (s, 3H); 3.38 (m, 2H); 3.56 (m, 4H); 3.98 (s, 5H); 4.30 (t, 2H); 7.29 (m, 1H); 7.33 (s, 1H); 7.35 (dd, 1H); 7.63 (s, 1H); 7.80 (ddd, 1H); 7.91 (s, 1H); 9.09 (s, 1H).

EXAMPLE 265

Preparation of Compound 442 in Table 17

An analogous reaction to that described in example 254 but starting with (R)(−)-2-pyrrolidinemethanol (334 mg, 3.3 mmol) yielded compound 442 in Table 17 (90 mg, 70%).

MS $ES^+$: 585 $(M+H)^+$ $^1$HNMR (DMSO-$d_6$, TFA): 1.79 (m, 1H); 1.91 (m, 1H); 2.03 (m, 1H); 2.11 (m, 1H); 2.29 (m, 2H); 3.21 (in, 2H); 3.62 (m, 4H); 3.77 (m, 1H); 3.98 (s, 5H); 4.29 (t, 2H); 7.30 (s, 1H); 7.32 (m, 1H); 7.39 (dd, 1H); 7.64 (s, 1H); 7.80 (ddd, 1H); 7.90 (s, 1H); 9.08 (s, 1H).

EXAMPLE 266

Preparation of Compound 443 in Table 17

An analogous reaction to that described in example 254 but starting with (S)-(+)-2-pyrrolidinemethanol (334 mg, 3.3 mmol) yielded compound 443 in Table 17 (82 mg, 63%).

MS $ES^+$: 585 $(M+H)^+$ $^1$HNMR (DMSO-$d_6$, TFA): 1.76 (m, 1H); 1.88 (m, 1H); 2.01 (m, 1H); 2.10 (m, 1H); 2.26 (m, 2H); 3.21 (m, 2H); 3.59 (m, 4H); 3.74 (dd, 1H); 3.95 (s, 5H); 4.27 (t, 2H); 7.27 (s, 1H); 7.28 (m, 1H); 7.34 (dd, 1H); 7.60 (s, 1H); 7.77 (ddd, 1H); 7.88 (s, 1H); 9.05 (s, 1H).

EXAMPLE 267

Preparation of Compound 444 in Table 17

An analogous reaction to that described in example 254 but starting with 3-pyrrolidinol (288 mg, 3.3 mmol) yielded compound 444 in Table 17 (15 mg, 12%).

MS $ES^+$: 571 $(M+H)^+$

$^1$HNMR (DMSO-$d_6$, TFA): 1.85–2.04 (m, 2H); 2.28 (m, 2H); 3.03–3.54 (m, 4H); 3.75 (m, 2H); 3.99 (s, 5H); 4.28 (m, 2H); 4.40–4.52 (m, 1H); 7.29 (s, 1H); 7.33 (m, 1H); 7.39 (dd, 1H); 7.64 (s, 1H); 7.81 (ddd, 1H); 7.91 (s, 1H); 9.08 (s, 1H).

EXAMPLE 268

Preparation of Compound 445 in Table 17

An analogous reaction to that described in example 254 but starting with 1-(2-aminoethyl)pyrrolidine (377 mg, 3.3 mmol) yielded compound 445 in Table 17 (20 mg, 15%).

MS ES$^+$: 598 $(M+H)^+$

$^1$HNMR (DMSO-$d_6$, TFA): 1.92 (m, 2H); 2.06 (m, 2H); 2.24 (m, 2H); 3.11 (m, 2H); 3.23 (t, 2H); 3.42 (m, 2H); 3.49 (m, 2H); 3.52 (m, 2H); 4.00 (s, 5H); 4.32 (t, 2H); 7.32 (s, 1H); 7.33 (m, 1H); 7.39 (dd, 1H); 7.65 (s, 1H); 7.81 (ddd, 1H); 7.92 (s, 1H); 9.10 (s, 1H).

EXAMPLE 269

Preparation of Compound 446 in Table 17

An analogous reaction to that described in example 254 but starting with I-acetylpiperazine (423 mg, 3.3 mmol) yielded compound 446 in Table 17 (100 mg, 74%).

MS ES$^+$: 612 $(M+H)^+$

$^1$HNMR (DMSO-$d_6$): 2.00 (s, 5H); 2.35 (m, 2H); 2.42 (m, 2H); 3.92–3.06 (m, 1H); 3.45 (m, 4H); 3.56 (t, 1H); 3.90 (s, 2H); 3.98 (s, 3H); 4.23 (t, 2H); 7.28 (s, 1H); 7.34 (m, 1H); 7.40 (s, 1H); 7.42 (dd, 1H); 7.83 (ddd, 1H); 8.13 (brs, 1H); 8.69 (s, 1H).

EXAMPLE 270

Preparation of Compound 447 in Table 17

An analogous reaction to that described in example 254 but starting with 1-(2-morpholinoethyl)-piperazine (658 mg, 3.3 mmol) yielded compound 447 in Table 17 (44 mg, 29%).

MS ES$^+$: 683 $(M+H)^+$

$^1$HNMR (DMSO-$d_6$): 1.98 (m, 2H); 2.30–2.70 (m, 18H); 3.58 (m, 4H); 3.90 (s, 2H); 3.97 (s, 3H); 4.21 (t, 2H); 7.26 (s, 1H); 7.33 (m, 1H); 7.40 (s, 1H); 7.41 (dd, 1H); 7.82 (ddd, 1H); 8.13 (brs, 1H); 8.69 (s, 1H); 10.54 (s, 1H).

EXAMPLE 271

Preparation of Compound 448 in Table 17

An analogous reaction to that described in example 254 but starting with 2-piperidineethanol (426 mg, 3.3 mmol) yielded compound 448 in Table 17 (19 mg, 14%).

MS ES$^+$: 613 $(M+H)^+$

$^1$HNMR (DMSO-$d_6$, TFA): 1.45–1.92 (m, 7H); 2.00–2.15 (m, 1H); 2.20–2.40 (m, 2H); 3.10–3.70 (m, 7H); 3.99 (s, 5H); 4.30 (m, 2H); 7.30 (s, 1H); 7.34 (m, 1H); 7.40 (dd, 1H); 7.64 (s, 1H); 7.81 (ddd, 1H); 7.91 (s, 1H); 9.09 (s, 1H).

EXAMPLE 272

Preparation of Compound 449 in Table 17

An analogous reaction to that described in example 254 but starting with 1-(2-hydroxyethyl)piperazine (430 mg, 3.3 mmol) yielded compound 449 in Table 17 (90 mg, 66%).

MS ES$^+$: 614 $(M+H)^+$

$^1$HNMR (DMSO-$d_6$): 1.96 (m, 2H); 2.35–2.47 (m, 12H); 3.49 (q, 2H); 3.90 (s, 2H); 3.97 (s, 3H); 4.20 (t, 1H); 4.37 (t, 1H); 7.25 (s, 1H) 7.33 (m, 1H); 7.39 (s, 1H); 7.41 (dd, 1H); 7.81 (ddd, 1H); 8.12 (brs, 1H); 8.68 (s, 1H); 10.50 (s, 1H); 12.03 (brs, 1H).

EXAMPLE 273

Preparation of Compound 450 in Table 17

An analogous reaction to that described in example 254 but starting with cyclopentylamine (281 mg, 3.3 mmol) yielded compound 450 in Table 17 (43 mg, 34%).

MS ES$^+$: 614 $(M+H)^+$

$^1$HNMR (DMSO-$d_6$): 1.53 (m, 4H); 1.69 (m, 2H); 1.93 (m, 2H); 2.10 (m, 2H); 3.00 (m, 2H); 3.38 (m, 2H); 3.90 (s, 2H); 3.98 (s, 3H); 4.28 (t, 2H); 7.30 (s, 1H); 7.32 (m, 1H); 7.42 (dd, 1H); 7.81 (ddd, 1H); 8.15 (brs, 1H); 8.70 (s, 1H); 10.51 (s, 1H).

EXAMPLE 274

Preparation of Compound 451 in Table 17

An analogous reaction to that described in example 254 but starting with 4-(2-hydroxyethyl)piperidine (426 mg, 3.3 mmol) yielded compound 451 IN Table 17 (53 mg, 39%).

MS ES$^+$: 613 $(M+H)^+$

$^1$HNMR (DMSO-$d_6$): 1.14 (m, 2H); 1.36 (in, 3H); 1.63 (brd, 2H); 1.87 (m, 2H); 1.95 (m, 2H); 2.45 (m, 1H); 2.86 (in, 2H); 3.44 (in, 2H); 3.90 (s, 2H); 3.97 (s, 3H); 4.20 (t, 2H); 4.32 (t, 1H); 7.26 (s, 1H); 7.31 (m, 1H); 7.40 (s, 1H); 7.42 (dd, 1H); 7.82 (ddd, 1H); 8.13 (brs, 1H); 8.68 (s, 1H); 10.50 (s, 1H); 12.02 (brs, 1H).

EXAMPLE 275

Preparation of Compound 452 in Table 17

An analogous reaction to that described in example 254 but starting with L-alanine-T-butylester hydrochloride (599 mg, 3.3 mmol) and treating the crude reaction mixture with a 1:1 solution of $CH_2Cl_2$-TFA (4 ml) yielded compound 452 in Table 17 (75 mg, 60%).

MS ES$^+$: (573 $(M+H)^+$

$^1$HNMR (DMSO-$d_6$, TFA): 1.48 (d, 3H); 2.24 (in, 2H); 3.22 (in, 2H); 3.97 (s, 5H); 4.15 (q, 1H); 4.30 (in, 2H); 7.30 (s, 1H); 7.34 (m, 1H); 7.40 (dd, 1H); 7.64 (s, 1H); 7.81 (ddd, 1H); 7.90 (s, 1H); 9.08 (s, 1H); 10.60 (s, 1H).

EXAMPLE 276

Preparation of Compound 453 in Table 17

An analogous reaction to that described in example 254 but starting with 3-hydroxypiperidine (334 mg, 3.3 mmol) yielded compound 453 in Table 17 (84 mg, 65%).

MS ES$^+$: 585 $(M+H)^+$

$^1$HNMR (DMSO-$d_6$): 1.07 (m, 1H); 1.41 (m, 1H); 1.62 (m, 1H); 1.76 (m, 2H); 1.87 (m, 1H) 1.95 (m, 2H); 2.47 (m, 2H); 2.68 (m, 1H); 2.85 (m, 1H); 3.48 (m, 1H); 3.90 (s, 2H); 3.98 (s, 3H); 4.20 (t, 2H); 4.59 (d, 1H); 7.26 (s, 1H); 7.31 (m, 1H); 7.39 (s, 1H); 7.42 (dd, 1H); 7.81 (ddd, 1H); 8.12 (brs, 1H); 8.68 (s, 1H); 10.50 (s, 1H); 12.02 (brs, 1H).

EXAMPLE 277

Preparation of Compound 454 in Table 17

An analogous reaction to that described in example 254 but starting with 4-hydroxymethylpiperidine (380 mg, 3.3 mmol) yielded compound 454 in Table 17 (42 mg, 32%).

MS ES$^+$: 599 $(M+H)^+$ $^1$HNMR (DMSO-$d_6$): 1.13 (m, 2H); 1.33 (m, 1H); 1.62 (brd, 2H); 1.90 (m, 2H); 1.95 (m, 2H); 2.44 (m, 2H); 2.88 (m, 2H); 3.22 (t, 2H); 3.86 (s, 2H); 3.93 (s, 3H); 4.17 (t, 2H); 4.38 (t, 1H); 7.22 (s, 1H); 7.31 (m, 1H); 7.36 (s, 1H); 7.38 (dd, 1H); 7.80 (ddd, 1H); 8.09 (brs, 1H); 8.65 (s, 1H); 10.46 (s, 1H); 12.00 (brs, 1H).

EXAMPLE 278

Preparation of Compound 455 in Table 17

An analogous reaction to that described in example 254 but starting with 1-amino-2-propanol (248 mg, 3.3 mmol) yielded compound 455 in Table 17 (52 mg, 42%).

MS ES$^+$: 573 $(M+H)^+$ $^1$HNMR (DMSO-$d_6$): 1.06 (d, 3H); 1.95 (m, 2H); 2.48 (m, 2H); 2.72 (t, 2H); 3.68 (m, 1H); 3.89 (s, 2H); 3.97 (s, 3H); 4.23 (t, 2H); 4.46 (m, 1H); 7.26 (s, 1H); 7.32 (m, 1H); 7.38 (s, 1H); 7.41 (dd, 1H); 7.81 (ddd, 1H); 8.11 (s, 1H); 8.67 (s, 1H); 10.49 (s, 1H).

EXAMPLE 279

Preparation of Compound 456 in Table 17

An analogous reaction to that described in example 253 but starting with L-alamine-t-butylester hydrochloride (599 mg, 3.3 mmol) and treating the crude reaction mixture with $CH_2Cl_2$-TFA (1/1, 4 ml) yielded compound 456 in Table 17 (106 mg, 84%).

MS ES$^+$: 571 $(M+H)^+$ $^1$HNMR (DMSO-$d_6$, TFA): 1.40 (d, 3H); 2.25 (m, 2H); 3.20 (m, 2H); 3.98 (s, 3H); 4.00 (s, 2H); 4.14 (m, 1H); 4.31 (t, 2H); 7.13 (dd, 1H); 7.32 (s, 1H); 7.35 (t, 1H); 7.47 (dd, 1H); 7.63 (s, 1H); 7.86 (t, 1H); 7.90 (s, 1H); 8.30 (m, 1H); 9.08 (s, 1H); 10.60 (s, 1H).

EXAMPLE 280

Preparation of Compound 457 in Table 17

An analogous reaction to that described in example 253 but starting with 2-methylaminoethanol (248 mg, 3.3 mmol) yielded compound 457 in Table 17 (86 mg, 70%).

MS ES$^+$: 557 $(M+H)^+$ $^1$HNMR (DMSO-$d_6$): 1.93 (in, 2H); 2.20 (s, 3H); 2.43 (t, 2H); 2.48 (m, 1H); 2.55 (m, 1H); 3.47 (dd, 2H); 3.89 (s, 2H); 3.96 (s, 3H); 4.19 (t, 2H); 4.34 (t, 1H); 7.13 (brd, 1H); 7.25 (s, 1H); 7.35 (t, 1H); 7.38 (s, 1H); 7.47 (s, 1H); 7.84 (s, 1H); 8.11 (dd, 1H); 8.66 (s, 1H); 10.44 (s, 1H); 12.00 (dd, 1H).

EXAMPLE 281

Preparation of Compound 458 in Table 17

An analogous reaction to that described in example 253 but starting with 1,2-diamino-2-methylpropane (291 mg, 3.3 mmol) yielded compound 458 in Table 17 (21 mg, 17%).

MS ES$^+$: 570 $(M+H)^+$ $^1$HNMR (DMSO-$d_6$, TFA): 1.39 (s, 1H); 2.28 (in, 2H); 3.23 (in, 4H); 3.98 (s, 3H); 4.00 (s, 2H); 4.32 (m, 2H); 7.14 (ddd, 1H); 7.31 (s, 1H); 7.36 (t, 1H); 7.47 (ddd, 1H); 7.64 (s, 1H) 7.86 (t, 1H); 7.91 (s, 1H); 9.09 (s, 1H).

EXAMPLE 282

Preparation of Compound 459 in Table 17

An analogous reaction to that described in example 253 but starting with cyclohexylamine (327 mg, 3.3 mmol) yielded compound 459 in Table 17–85 mg, 66%).

MS ES$^+$: 581 $(M+H)^+$ $^1$HNMR (DMSO-$d_6$): 1.13 (m, 1H); 1.26 (in, 4H); 1.62 (brd, 1H); 1.77 (in, 2H); 2.03 (m, 2H); 2.15 (in, 2H); 3.07 (m, 1H); 3.14 (t, 2H); 3.90 (s, 2H); 3.97 (s, 3H); 4.29 (t, 2H); 7.13 (brd, 1H); 7.29 (s, 1H); 7.36 (t, 1H); 7.39 (s, 1H); 7.46 (dd, 1H); 8.16 (dd, 1H); 8.26 (brs, 1H); 8.69 (s, 1H); 10.45 (s, 1H).

EXAMPLE 283

Preparation of Compound 460 in Table 17

An analogous reaction to that described in example 253 but starting with N,N-dimethylethylenediamine (291 mg, 3.3 mmol) yielded compound 460 in Table 17 (41 mg, 32%).

MS ES$^+$: 570 $(M+H)^+$ $^1$HNMR (DMSO-$d_6$): 2.00 (m, 1H); 2.17 (s, 6H); 2.38 (t, 2H); 2.72 (t, 2H); 2.81 (t, 2H); 3.91 (s, 2H); 3.98 (s, 3H); 4.24 (t, 2H); 7.14 (dd, 1H); 7.27 (s, 1H); 7.37 (t, 1H); 7.40 (s, 1H); 7.49 (dd, 1H); 7.86 (t, 1H); 8.13 (s, 1H); 8.69 (s, 1H); 10.50 (s, 1H).

EXAMPLE 284

Preparation of Compound 461 in Table 17

An analogous reaction to that described in example 253 but starting with N,N,N'-trimethylethylenediamine (337 mg, 3.3 mmol) yielded compound 461 in Table 17 (11 mg, 8

MS ES$^+$: 584 $(M+H)^+$ $^1$HNMR (DMSO-$d_6$): 1.91 (m, 2H); 2.12 (s, 6H); 2.20 (s, 3H); 2.33 (m, 3H); 2.42 (m, 3H); 3.76 (s, 2H); 3.91 (s, 3H); 4.12 (t, 2H); 6.98 (s, 1H); 7.11 (dd, 1H); 7.16 (s, 4H); 7.35 (t, 1H); 7.52 (dd, 1H); 7.83 (s, 1H); 7.88 (t, 1H); 8.37 (s, 1H); 10.56 (s, 1H).

EXAMPLE 285

Preparation of Compound 462 in Table 17

An analogous reaction to that described in example 253 but starting with (R)-(−)-2-pyrrolidinemethanol (334 mg, 3.3 mmol) yielded compound 462 in Table 17 (76 mg, 59%).

MS ES$^+$: 583 $((M+H)^+$ $^1$HNMR (DMSO-$d_6$, TFA): 1.77 (m, 1H); 1.89 (m, 1H); 2.02 (m, 1H); 2.4 (m, 1H); 2.29 (m, 2H); 3.21 (m, 2H); 3.62 (m, 4H); 3.76 (m, 1H); 3.98 (s, 3H); 3.99 (s, 2H); 4.29 (t, 2H); 7.13 (dd, 1H); 7.29 (s, 1H); 7.35 (t, 1H); 7.46 (dd, 1H); 7.63 (s, 1H); 7.85 (t, 1H); 7.90 (s, 1H); 9.08 (s, 1H).

EXAMPLE 286

Preparation of Compound 463 in Table 17

An analogous reaction to that described in example 253 but starting with (S)-(+)-2-pyrrolidinemethanol (334 mg, 3.3 mmol) yielded compound 463 in Table 17 (72 mg, 56%).

MS ES$^+$: 583 $(M+H)^+$ $^1$HNMR (DMSO-$d_6$, TFA): 1.78 (m, 1H); 1.90 (m, 1H); 2.03 (m, 1H); 2.13 (m, 1H); 2.30 (m, 2H); 3.23 (m, 2H); 3.62 (m, 4H); 3.77 (m, 1H); 3.98 (s, 3H); 4.00 (s, 2H); 4.30 (t, 2H); 7.14 (dd, 1H); 7.30 (s, 1H); 7.36 (t, 1H); 7.46 (dd, 1H); 7.64 (s, 1H); 7.85 (s, 1H); 7.90 (s, 1H); 9.09 (s, 1H).

EXAMPLE 287

Preparation of Compound 464 in Table 17

An analogous reaction to that described in example 253 but starting with 4-hydroxypiperidine (334 mg, 3.3 mmol) yielded compound 464 in Table 17 (63 mg, 49%).

MS ES$^+$: 583 $(M+H)^+$ $^1$HNMR (DMSO-$d_6$): 1.41 (m, 2H); 1.73 (m, 2H); 1.96 (m, 2H); 2.04 (m, 2H); 2.74 (m, 2H) 2.50 (m, 2H); 3.43 (s, 1H); 3.91 (s, 2H); 3.97 (s, 3H); 4.20 (t, 2H); 4.54 (d, 1H); 7.14 (d, 1H); 7.26 (s, 1H); 7.37 (t, 1H); 7.40 (s, 1H); 7.49 (d, 1H); 7.86 (t, 1H); 8.13 (brs, 1H); 8.69 (s, 1H); 10.46 (s, 1H).

EXAMPLE 288

Preparation of Compound 465 in Table 17

An analogous reaction to that described in example 253 but starting with 3-pyrrolidinol (288 mg, 3.3 mmol) yielded compound 465 in Table 17 (57 mg, 45%).

MS ES$^+$: 569 $(M+H)^+$ $^1$HNMR (DMSO-$d_6$): 1.56 (m, 1H); 1.99 (m, 4H) 2.36 (m, 1H); 2.56 (m, 4H); 2.74 (m, 1H); 3.91 (s, 2H); 3.98 (s, 3H); 4.21 (t, 2H); 4.70 (d, 1H); 7.14 (dd, 1H); 7.26 (s, 1H); 7.37 (t, 1H); 7.40 (s, 1H); 7.49 (dd, 1H); 7.86 (t, 1H); 8.12 (s, 1H); 8.68 (s, 1H); 10.47 (s, 1H); 12.03 (brs, 1H).

EXAMPLE 289

Preparation of Compound 466 in Table 17

An analogous reaction to that described in example 253 but starting with 1-(2-aminoethyl)pyrrolidine (377 mg, 3.3 mmol) yielded compound 466 in Table 17 (39 mg, 29%).

MS ES$^+$: 596 $(M+H)^+$ $^1$HNMR (DMSO-$d_6$, TFA): 1.91 (m, 2H); 2.06 (m, 2H); 2.24 (m, 2H); 3.11 (m, 2H); 3.23 (t, 2H); 3.42 (m, 2H); 3.48 (m, 2H); 3.67 (m, 2H); 3.98 (s, 3H); 3.99 (s, 2H); 4.31 (t, 2H); 7.14 (d, 1H); 7.31 (s, 1H); 7.35 (t, 1H); 7.47 (d, 1H); 7.64 (s, 1H); 7.85 (t, 1H); 7.91 (s, 1H); 9.09 (s, 1H).

EXAMPLE 290

Preparation of Compound 467 in Table 17

An analogous reaction to that described in example 253 but starting with 4-hydroxymethylpiperidine (380 mg, 3.3 mmol) yielded compound 467 in Table 17 (64 mg, 49%).

MS ES$^+$: 597 $(M+H)^+$ $^1$HNMR (DMSO-$d_6$): 1.14 (m, 2H); 1.35 (m, 1H); 1.65 (brd, 2H); 1.88 (m, 2H); 1.97 (m, 2H); 2.47 (m, 2H); 2.90 (brd, 2H); 3.25 (t, 2H); 3.91 (s, 2H); 3.97 (s, 3H); 4.20 (t, 2H); 4.41 (t, 1H); 7.14 (d, 1H); 7.25 (s, 1H); 7.37 (t, 1H); 7.39 (s, 1H); 7.48 (s, 1H); 7.86 (s, 1H); 8.12 (brs, 1H); 8.68 (s, 1H); 10.46 (s, 1H); 12.03 (s, 1H).

EXAMPLE 291

Preparation of Compound 468 in Table 17

An analogous reaction to that described in example 253 but starting with 1-(2-hydroxyethyl)piperazine (430 mg, 3.3 mmol) yielded compound 468 in Table 17 (63 mg, 47

MS ES$^+$: 612 $(M+H)^+$ $^1$HNMR (DMSO-$d_6$): 1.96 (m, 2H); 2.41 (m, 12H); 3.50 (q, 2H); 3.91 (s, 2H); 3.97 (s, 3H); 4.20 (t, 2H); 4.37 (t, 1H); 7.14 (dd, 1H); 7.25 (s, 1H); 7.37 (t, 1H); 7.39 (s, 1H); 7.48 (d, 1H); 7.86 (t, 1H); 8.12 (brs, 1H); 8.68 (s, 1H); 10.46 (s, 1H); 12.04 (s, 1H).

EXAMPLE 292

Preparation of Compound 469 in Table 17

An analogous reaction to that described in example 253 but starting with cyclopentylamine 281 mg, 3.3 mmol) yielded compound 469 in Table 17 (77 mg, 61%).

MS ES$^+$: 567 $(M+H)^+$ $^1$HNMR (DMSO-$d_6$): 1.58 (m, 4H); 1.73 (m, 2H); 2.00 (m, 2H); 2.17 (m, 2H); 3.12 (t, 2H); 3.56 (m, 1H); 3.92 (s, 3H); 3.99 (s, 31); 4.31 (t, 2H); 7.15 (d, 1H); 7.31 (s, 1H); 7.37 (t, 1H); 7.41 (s, 1H); 7.48 (d, 1H); 7.86 (s, 1H); 8.16 (brs, 1H); 8.71 's, 1H); 10.47 (s, 1H) 12.03 (brs, 1H).

EXAMPLE 293

Preparation of Compound 470 in Table 17

An analogous reaction to that described in example 253 but starting with 4-(2-hydroxyethyl)piperidine (426 mg, 3.3 mmol) yielded compound 470 in Table 17 (78 mg, 58%).

MS ES$^+$: 611 $(M+H)^+$ $^1$HNMR (DMSO-$d_6$): 1.16 (m, 2H); 1.36 (m, 3H); 1.63 (d, 2H); 1.88 (t, 2H); 1.96 (m, 2H); 2.44 (t, 2H); 2.87 (d, 2H); 3.44 (m, 2H); 3.9 (s, 2H); 3.97 (s, 3H); 4.20 (t, 2H); 4.33 (t, 1H) 7.14 (d, 1H); 7.25 (s, 1H); 7.37 (t, 1H); 7.40 (s, 1H); 7.49 (d, 1H); 7.86 (t, 1H); 8.12 (brs, 1H); 8.68 (s, 1H); 10.46 (s, 1H); 12.04 (s, 1H).

EXAMPLE 294

Preparation of Compound 471 in Table 17

An analogous reaction to that described in example 253 but starting with 3-hydroxypiperidine (339 mg, 3.3 mmol) yielded compound 471 in Table 17 (117 mg, 91%).

MS ES$^+$: 583 $(M+H)^+$ $^1$HNMR (DMSO-$d_6$): 1.07 (m, 1H); 1.41 (m, 1H); 1.62 (m, 1H); 1.70–1.90 (m, 3H); 1.95 (m, 2H); 2.46 (m, 2H); 2.67 (m, 1H); 2.83 (brd, 1H); 3.47 (m, 1H); 3.89 (s, 2H); 3.96 (s, 3H); 4.20 (t, 2H); 4.57 (d, 1H); 7.13 (ddd, 1H); 7.24 (s, 1H); 7.36 (t, 1H); 7.38 (s, 1H); 7.47 (d, 1H); 7.84 (t, 1H); 8.11 (brs, 1H); 8.67 (s, 1H); 10.46 (s, 1H); 12.00 (brs, 1H).

EXAMPLE 295

Preparation of Compound 472 in Table 17

An analogous reaction to that described in example 253 but starting with (S)-1-amino-2-propanol (248 mg, 3.3 mmol) yielded compound 472 in Table 17 (55 mg, 45%).

MS ES$^+$: 557 $(M+H)^+$ $^1$HNMR (DMSO-$d_6$): 1.06 (d, 3H); 1.96 (m, 2H); 2.48 (m, 2H); 2.73 (t, 2H); 3.70 (m, 1H); 3.91 (s, 2H); 3.97 (s, 3H); 4.24 (t, 2H); 4.48 (brs, 1H); 7.14 (d, 1H); 7.27 (s, 1H); 7.37 (t, 1H); 7.39 (s, 1H); 7.49 (d, 1H); 7.86 (t, 1H); 8.12 (s, 1H); 8.68 (s, 1H); 10.46 (s, 1H).

EXAMPLE 296

Preparation of Compound 473 in Table 17

An analogous reaction to that described in example 253 but starting with (R)-1-amino-2-propanol (248 mg, 3.3 mmol) yielded compound 473 in Table 17 (84 mg, 68%).

MS ES$^+$: 557 $(M+H)^+$ $^1$HNMR (DMSO-$d_6$): 1.04 (d, 3H); 1.93 (m, 2H); 2.45 (m, 2H); 2.70 (t, 2H); 3.67 (m, 1H); 3.88 (s, 2H); 3.95 (s, 3H); 4.21 (t, 2H); 4.46 (brs, 1H); 7.12 (d, 1H); 7.24 (s, 1H); 7.35 (t, 1H); 7.37 (s, 1H); 7.47 (d, 1H); 7.84 (t, 1H); 8.09 (s, 1H); 8.65 (s, 1H); 10.45 (s, 1H).

EXAMPLE 297

Preparation of Compound 474 in Table 17

An analogous reaction to that described in example 253 but starting with tert-butyl-1-piperazinecarboxylate (615 mg, 3.3 mmol) and treating the crude reaction mixture with hydrochloric acid in 1,4 dioxane (4.0 M, 2 ml) yielded compound 474 (3 HCl) in Table 17 (89 mg, 61%.

MS $ES^+$: 568 $(M+H)^+$ $^1$HNMR (DMSO-$d_6$, TFA): 2.34 (m, 2H); 3.25–3.68 (m, 1H); 3.99 (s, 3H); 4.01 (s, 2H); 4.33 (t, 2H); 7.14 (dd, 1H); 7.35 (s, 1H); 7.37 (t, 1H); 7.49 (d, 1H); 7.65 (s, 1H); 7.86 (t, 1H); 7.91 (s, 1H); 9.09 (s, 1H); 10.66 (s, 1H).

EXAMPLE 298

Preparation of Compound 475 in Table 17

An analogous reaction to that described in example 253 but starting with 2-(2-hydroxyethyl)piperidine (426 mg, 3.3 mmol) yielded compound 475 in Table 17 (29 mg, 22%).

MS $ES^+$: 611 $(M+H)^+$ $^1$HNMR (DMSO-$d_6$): 1.30 (m, 2H); 1.48 (m, 4H); 1.60 (m, 2H); 1.76 (m, 1H); 1.93 (m, 2H); 2.26 (m, 1H); 2.48 (m, 1H); 2.79 (m, 2H); 3.46 (m, 2H); 3.89 (s, 2H); 3.96 (s, 3H); 4.18 (t, 2H); 4.40 (brs, 1H); 7.13 (d, 1H); 7.24 (s, 1H); 7.35 (t, 1H); 7.38 (s, 1H); 7.47 (d, 1H) 7.84 (s, 1H); 8.11 (brs, 1H); 8.67 (s, 1H); 10.44 (s, 1H).

EXAMPLE 299

Preparation of Compound 476 in Table 17

An analogous reaction to that described in example 253 but starting with 2-amino-2-methyl-1-propanol (294 mg, 3.3 mmol) yielded compound 476 in Table 17 (49 mg, 39%).

MS $ES^+$: 571 $(M+H)^+$ $^1$HNMR (DMSO-$d_6$, TFA): 1.25 (s, 6H); 2.22 (m, 2H); 3.10 (m, 2H); 3.46 (s, 2H); 3.99 (s, 3H); 4.00 (s, 2H); 4.32 (t, 2H); 7.15 (d, 1H); 7.30 (s, 1H); 7.37 (t, 1H); 7.47 (d, 1H); 7.65 (s, 1H); 7.86 (s, 1H); 7.91 (s, 1H); 9.09 (s, 4H); 10.56 (s, 1H).

EXAMPLE 300

Preparation of Compound 477 in Table 17

An analogous reaction to that described in example 253 but starting with 142-dimethylaminoethylpiperazine (519 mg, 3.3 mmol) yielded compound 477 in Table 17 (19 mg, 15%).

MS $ES^+$: 639 $(M+H)^+$ $^1$HNMR (DMSO-$d_6$): 1.96 (m, 2H); 2.13 (s, 6H); 2.30–2.52 (m, 14H); 3.89 (s, 2H); 3.95 (s, 3H); 4.18 (t, 2H); 7.13 (d, 1H); 7.23 (s, 1H); 7.35 (t, 1H); 7.38 (s, 1H); 7.84 (t, 1H); 8.10 (s, 1H); 8.67 (s, 1H); 10.45 (s, 1H).

EXAMPLE 301

Preparation of Compound 478 in Table 17

An analogous reaction to that described in example 253 but starting with a solution of dimethylamine in chloroform (3,6 M, 3 ml, 3.6 mmol) yielded compound 478 in Table 17 (44 mg, 34%)

MS $ES^+$: 527 $(M+H)^+$ $^1$HNMR (DMSO-$d_6$): 1.95 (m, 2H); 2.17 (s, 6H); 2.41 (t, 2H); 3.89 (s, 2H); 3.96 (s, 3H); 4.18 (t, 2H); 7.12 (d, 1H); 7.23 (s, 1H); 7.35 (t, 1H); 7.38 (s, 1H); 7.47 (d, 1H); 7.84 (t, 1H); 8.11 (s, 1H); 8.67 (s, 1H); 10.45 (s, 1H).

EXAMPLE 302

Preparation of Compound 479 in Table 17

An analogous reaction to that described in example 253 but starting with aminomethylcyclopropane (234 mg, 3.3 mmol) yielded compound 479 in Table 17 (88 mg, 65

MS $ES^+$: 553 $(M+H)^+$ $^1$HNMR (DMSO-$d_6$): 0.18 (m, 2H); 0.46 (m, 2H); 0.94 (m, 1H); 2.01 (m, 2H); 2.51 (d, 2H); 2.79 (t, 2H); 3.94 (s, 2H); 4.01 (s, 3H); 4.28 (t, 2H); 7.18 (d, 1H); 7.31 (s, 1H); 7.41 (t, 1H); 7.43 (s, 1H); 7.53 (d, 1H); 7.90 (s, 1H); 8.16 (s, 1H) 8.72 (s, 1H); 10.53 (s, 1H).

EXAMPLE 303

Preparation of Compound 480 in Table 17

An analogous reaction to that described in example 253 but starting with piperidine (344 mg, 4.0 mmol) yielded compound 480 in Table 17 (52 mg, 40%).

MS ES–: 565 $(M-H)^+$ $^1$HNMR (DMSO-$d_6$, TFA): 1.43 (m, 1H); 1.69 (m, 3H); 1.87 (d, 2H); 2.30 (m, 2H); 2.96 (t, 2H); 3.27 (t, 2H); 3.55 (d, 2H); 3.99 (s, 3H); 4.00 (s, 2H); 4.31 (t, 2H); 7.15 (d, 1H); 7.31 (s, 1H); 7.37 (t, 1H); 7.47 (d, 1H); 7.65 (s, 1H); 7.86 (s, 1H); 7.91 (s, 1H); 9.09 (s, 1H) 10.56 (s, 1H).

EXAMPLE 304

Preparation of Compound 481 in Table 17

An analogous reaction to that described in example 255 but starting with 1-(2-dimethylaminomethyl)piperazine (281 mg, 3.3 mmol) yielded compound 481 in Table 17 (81 mg, 64%).

MS $ES^+$: 641 $(M+H)^+$ $^1$HNMR (DMSO-$d_6$, TFA): 2.33 (m, 2H); 2.80–3.70 (m, 14H); 2.84 (s, 6H); 3.98 (s, 3H); 4.01 (s, 2H); 4.30 (brt, 1H); 6.90 (m, 1H); 7.32 (s, 2H); 7.35 (dd, 1H); 7.64 (s, 1H); 7.91 (s, 1H); 9.09 (s, 1H).

EXAMPLE 305

Preparation of Compound 482 in Table 17

An analogous reaction to that described in example 255 but starting with (S)-(+)-2-pyrrolidinemethanol (334 mg, 3.3 mmol) yielded compound 482 in Table 17 (58 mg, 45%).

MS $ES^+$: 585 $(M+H)^+$ $^1$HNMR (DMSO$d_6$, TFA): 1.79 (m, 1H); 1.90 (m, 1H); 2.02 (m, 1H); 2.13 (m, 1H); 2.30 (m, 2H); 3.33 (m, 2H); 3.62 (m, 4H); 3.77 (dd, 1H); 3.99 (s, 3H); 4.01 (s, 2H); 4.30 (brt, 2H); 6.91 (t, 1H); 7.30 (s, 1H); 7.35 (dd, 2H); 7.64 (s, 1H); 7.91 (s, 1H); 9.09 (s, 1H).

EXAMPLE 306

Preparation of Compound 483 in Table 17

An analogous reaction to that described in example 255 but starting with 4-hydroxypiperidine (334 mg, 3.3 mmol) yielded compound 483 in Table 17 (28 mg, 22%).

MS $ES^+$: 585 $(M+H)^+$ $^1$HNMR (DMSO-$d_6$): 1.40 (m, 2H); 1.73 (m, 2H); 1.96 (m, 2H); 2.03 (m, 2H); 2.45 (m, 2H) 2.74 (m, 2H); 3.45 (m, 1H); 3.92 (s, 2H); 3.97 (s, 3H); 3.97 (t, 2H); 4.54 (d, 1H); 6.95 (m, 1H); 7.26 (s, 1H); 7.36 (dd, 2H); 7.40 (s, 1H); 8.14 (brs, 1H); 8.68 (s, 1H); 10.65 (s, 1H); 12.04 (brs, 1H).

EXAMPLE 307

Preparation of Compound 484 in Table 17

An analogous reaction to that described in example 255 but starting with 3-pyrrolidinol (288 mg, 3.3 mmol) yielded compound 484 in Table 17 (30 mg, 23%).

MS ES$^+$: 571 (M+H)$^+$ $^1$HNMR (DMSO-$d_6$): 1.57 (m, 1H); 1.97 'm, 4H); 2.37 (m, 1H); 2.58 (m, 4H); 2.74 (m, 1H) 3.92 (s, 2H); 3.98 (s 3H); 4.22 (brt, 2H); 4.72 (brs, 1H); 6.95 (m, 1H); 7.26 (s, 1H); 7.36 (dd, 2H); 7.40 (s, 1H); 8.13 (brs, 1H); 8.69 (s, 1H); 10.65 (s, 1H); 12.04 (brs, 1H).

EXAMPLE 308

Preparation of Compound 485 in Table 17

An analogous reaction to that described in example 255 but starting with 1-(2-aminoethyl)pyrrolidine (377 mg, 3.3 mmol) yielded compound 485 in Table 17 (25 mg, 19

MS ES$^+$: 598 (M+H)$^+$ $^1$HNMR (DMSO-$d_6$, TFA): 1.91 (m, 2H); 2.06 (m, 2H); 2.24 (m, 2H); 3.11 (m, 2H); 3.23 (t, 2H); 3.41 (m, 2H); 3.49 (m, 2H); 3.67 (m, 2H); 3.99 (s, 3H); 4.01 (s, 2H); 4.31 (t, 2H); 6.89 (t, 1H); 7.32 (s, 1H); 7.34 (d, 2H); 7.64 (s, 1H); 7.92 (s, 1H); 9.09 (s, 1H).

EXAMPLE 309

Preparation of Compound 486 in Table 17

An analogous reaction to that described in example 255 but starting with 4-hydroxymethylpyperidine (380 mg, 3.3 mmol) yielded compound 486 in Table 17 (62 mg, 47%).

MS ES$^+$: 599 (M+H)$^+$ $^1$HNMR (DMSO-$d_6$): 1.14 (m, 2H); 1.34 (m, 1H); 1.65 (d, 2H); 1.88 (t, 2H); 1.96 (m, 2H); 2.45 (t, 2H); 2.90 (d, 2H); 3.25 (t, 2H); 3.92 (s, 2H); 3.97 (s, 3H); 4.20 (t, 2H); 4.41 (t, 1H); 6.94 (m, 1H); 7.26 (s, 1H); 7.36 (dd, 2H); 7.40 (s, 1H); 8.13 (brs, 1H); 8.68 (s, 1H); 10.64 (s, 1H); 12.07 (brs, 1H).

EXAMPLE 310

Preparation of Compound 487 in Table 17

An analogous reaction to that described in example ~255 but starting with 2-(2-hydroxyethyl)piperidine (426 mg, 3.3 mmol) yielded compound 487 in Table 17 (61 mg, 45%).

MS ES$^+$: 613 (M+H)$^+$ $^1$HNMR (DMSO-$d_6$, TFA): 1.47–1.90 (m, 7H); 2.09 (m, 1H); 2.27 (m, 2H); 3.08–3.70 (m, 7H); 3.99 (s, 3H); 4.00 (s, 2H); 4.30 (m, 2H); 6.84 (m, 1H); 7.29 (d, 1H); 7.34 (dd, 1H); 7.62 (s, 1H); 7.92 (s, 1H); 9.08 (s, 1H).

EXAMPLE 311

Preparation of Compound 488 in Table 17

An analogous reaction to that described in example 255 but starting with 1-(2-hydroxyethyl)piperazine (430 mg, 3.3 mmol) yielded compound 488 in Table 17 (124 mg, 92%).

MS ES$^+$: 614 (M+H)$^+$ $^1$HNMR (DMSO-$d_6$, TFA): 1.96 (m, 2H); 2.40 (m, 12H); 2.70 (m, 1H); 3.48 (m, 2H); 3.90 (s, 2H); 3.95 (s, 3H); 4.18 (t, 2H); 4.35 (brt, 1H); 6.43 (m, 1H); 7.23 (s, 1H); 7.34 (dd, 2H) 7.38 (s, 1H); 8.10 (s, 1H); 8.66 (s, 1H); 10.63 (s, 1H).

EXAMPLE 312

Preparation of Compound 489 in Table 17

An analogous reaction to that described in example 255 but starting with 4-(2-hydroxyethyl)piperidine (426 mg, 3.3 mmol) yielded compound 489 in Table 17 (54 mg, 40

MS ES$^+$: 613 (M+H)$^+$ $^1$HNMR (DMSO-$d_6$): 1.15 (m, 2H); 1.36 (m, 3H); 1.63 (brd, 2H); 1.88 (m, 2H); 1.96 (m, 2H); 2.44 (m, 2H); 2.87 (brd, 2H); 3.44 (m, 2H); 3.92 (s, 2H); 3.97 (s, 3H); 4.20 (t, 2H); 4.33 (t, 1H); 6.95 (m, 1H); 7.26 (s, 1H); 7.36 (dd, 2H); 7.40 (s, 1H); 8.13 (brs, 1H); 8.68 (s, 1H); 10.64 (s, 1H); 12.04 (brs, 1H).

EXAMPLE 313

Preparation of Compound 490 in Table 17

An analogous reaction to that described in example 255 but starting with 3-hydroxypiperidine (334 mg, 3.3 mmol) yielded compound 490 in Table 17 (53 mg, 41%).

MS ES$^+$: 559 (M+H)$^+$ $^1$HNMR (DMSO-$d_6$): 1.09 (m, 1H); 1.43 (m, 1H); 1.64 (m, 1H); 1.79 (m, 2H); 1.87 (m, 1H); 1.96 (m, 2H); 2.47 (m, 2H); 2.69 (m, 2H); 2.85 (m, 2H); 3.49 (m, 1H); 3.92 (s, 2H); 3.98 (s, 3H); 4.21 (t, 2H); 4.60 (d, 1H); 6.95 (t, 10H); 7.26 (s, 1H); 7.36 (d, 2H); 7.40 (s, 1H); 8.13 (brs, 1H); 8.69 (s, 1H); 10.65 (s, 1H); 12.04 (brs, 1H).

EXAMPLE 314

Preparation of Compound 491 in Table 17

An analogous reaction to that described in example 255 but starting with N,N,N'-trimethylethylenediamine (337 mg, 3.3 mmol) yielded compound 491 in Table 17 (54 mg, 42%).

MS ES$^+$: 586 (M+H)$^+$ $^1$HNMR (DMSO-$d_6$, TFA) 2.32 (m, 1H); 2.34 (m, 1H); 2.88 (s, 6H); 2.93 (s, 3H); 3.39 (m, 2H); 3.56 (m, 4H); 3.99 (s, 3H); 4.01 (s, 2H); 4.30 (t, 2H); 6.91 (m, 1H); 7.33 (s, 1H); 7.35 (dd, 2H); 7.64 (s, 1H); 7.91 (s, 1H); 9.09 (s, 1H).

EXAMPLE 315

Preparation of Compound 492 in Table 17

An analogous reaction to that described in example 255 but starting with piperidine (281 mg, 3.3 mmol) yielded compound 492 in Table 17 (81 mg, 64%).

MS ES$^+$: 569 (M+H)$^+$ $^1$HNMR (DMSO-$d_6$): 1.38 (m, 2H); 1.50 (m, 4H); 2.34 (brs, 4H); 2.41 (t, 2H); 3.90 (s, 2H) 3.96 (s, 3H); 4.19 (t, 2H); 6.93 (t, 1H); 7.24 (s, 1H); 7.34 (d, 2H); 7.38 (s, 1H); 8.11 (brs, 1H); 8.67 (s, 1H); 10.63 (s, 1H); 11.98 (brs, 1H).

EXAMPLE 316

Preparation of Compound 493 in Table 17

An analogous reaction to that described in example 255 but starting with pyrrolidine (235 mg, 3.3 mmol) yielded compound 493 in Table 17 (66 mg, 54%).

MS ES$^+$: 555 (M+H)$^+$ $^1$HNMR (DMSO-$d_6$, TFA): 1.90 (m, 2H); 2.06 (m, 2H); 2.28 (m, 2H); 3.09 (m, 2H); 3.36 (m, 2H); 3.68 (m, 2H); 3.99 (s, 3H); 4.01 (s, 2H); 4.29 (t, 2H); 6.93 (m, 1H); 7.30 (s, 1H); 7.34 (dd, 2H); 7.65 (s, 1H); 7.91 (s, 1H); 9.09 (s, 1H).

EXAMPLE 317

Preparation of Compound 494 in Table 17

An analogous reaction to that described in example 255 but starting with 2-amino-2-methyl-1-propanol (294 mg, 3.3 mmol) yielded compound 494 in Table 17 (28 mg, 22%).

MS ES$^+$: 573 (M+H)$^+$ $^1$HNMR (DMSO-$d_6$, TFA): 1.24 (s, 6H); 2.23 (m, 2H); 3.10 (t, 2H); 3.45 (s, 2H); 3.99 (s, 3H); 4.01 (s, 2H); 4.31 (t, 2H); 6.91 (m, 1H); 7.30 (s, 1H); 7.34 (dd, 2H); 7.64 (s, 1H) 7.91 (s, 1H); 9.09 (s, 1H).

EXAMPLE 318

Preparation of Compound 495 in Table 17

An analogous reaction to that described in example 255 but starting with 2-methylaminoethanol (248 mg, 3.3 mmol) yielded compound 495 in Table 17 (33 mg, 27%).

MS ES$^+$: 559 (M+H)$^+$ $^1$HNMR (DMSO-$d_6$): 1.95 (m, 2H); 2.24 (s, 3H); 2.48 (m, 2H); 2.45 (m, 2H); 3.49 (m, 2H) 3.93 (s, 2H); 3.98 (s, 3H); 4.21 (t, 2H); 4.38 (m, 1H); 6.95 (m, 1H); 7.27 (s, 1H); 7.36 (dd, 2H); 7.40 (s, 1H); 8.13 (brs, 1H); 8.69 (s, 1H); 10.65 (s, 1H); 12.04 (brs, 1H).

EXAMPLE 319

Preparation of Compound 496 in Table 17

An analogous reaction to that described in example 255 but starting with N,N-dimethylethylenediamine (291 mg, 3.3 mmol) yielded compound 496 in Table 17 (22 mg, 17%).

MS ES$^+$: 572 (M+H)$^+$ $^1$HNMR (DMSO-$d_6$, TFA): 2.23 (m, 2H); 2.89 (s, 6H); 3.22 (m, 2H); 3.41 (s, 4H); 3.96 (s, 3H); 4.01 (s, 2H); 4.31 (t, 2H); 6.92 (m, 1H); 7.31 (s, 1H); 7.35 (dd, 2H); 7.64 (s, 1H); 7.91 (s, 1H); 9.09 (s, 1H).

EXAMPLE 320

Preparation of Compound 497 in Table 17

An analogous reaction to that described in example 255 but starting with (S(-(+)-1-amino-2-propanol (248 mg, 3.3 mmol) yielded compound 497 in Table 17 (32 Mg, 26%).

MS ES$^+$: 559 (M+H)$^+$ $^1$HNMR (DMSO-$d_6$, TFA): 1.15 (d, 3H); 2.24 (m, 2H); 2.83 (dd, 1H); 3.06 (dd, 1H); 3.15 (t, 2H); 3.95 (m, 1H); 3.99 (s, 3H); 4.01 (s, 3H); 4.29 (t, 1H); 6.92 (m, 1H); 7.28 (s, 1H); 7.34 (dd, 2H); 7.65 (s, 1H); 7.91 (s, 1H); 9.09 (s, 1H).

EXAMPLE 321

Preparation of Compound 498 in Table 17

An analogous reaction to that described in example 255 but starting with (R)-(−)-1-amino-2-propanol (248 mg, 3.3 mmol) yielded compound 498 in Table 17 (40 mg, 32%).

MS ES$^+$: 559 (M+H)$^+$ $^1$HNMR (DMSO-$d_6$, TFA): 1.15 (d, 3H); 2.24 (m, 2H); 2.83 (dd, 1H); 3.06 (dd, 1H); 3.15 (t, 2H); 3.95 (m, 1H); 3.99 (s, 3H); 4.01 (s, 3H); 4.29 (t, 1H); 6.90 (m, 1H); 7.28 (s, 1H) 7.34 (dd, 2H); 7.64 (s, 1H); 7.91 (s, 1H); 9.09 (s, 1H).

EXAMPLE 322

Preparation of Compound 499 in Table 17

An analogous reaction to that described in example 255 but starting with tert-butyl-1-piperazine carboxylate (615 mg, 3.3 mmol) and treating the crude reaction mixture with hydrochloric acid in 1,4-dioxane (4M, 2 ml) yielded compound 499 in Table 17 (66 mg, 45%, 3 HCl).

MS ES$^+$: 570 (M+H)$^+$ $^1$HNMR (DMSO-$d_6$, TFA) 2.35 (m, 2H); 3.20–3.94 (m, 1H); 3.99 (s, 3H); 4.03 (s, 2H); 4.33 (t, 2H); 6.93 (m, 1H); 7.36 (s, 1H); 7.37 (dd, 2H); 7.65 (s, 1H); 7.91 (s, 1H); 9.09 (s, 1H).

EXAMPLE 323

Preparation of Compound 500 in Table 17

An analogous reaction to that described in example 255 but starting with N-allylpiperazine (416 mg, 3.3 mmol) yielded compound 500 in Table 17 (33 mg, 25%).

MS ES$^+$: 610 (M+H)$^+$ $^1$HNMR (DMSO-$d_6$): 1.96 (m, 2H); 2.30–2.50 (m, 1H); 2.93 (d, 2H); 3.92 (s, 2H); 3.97 (s, 3H); 4.20 (t, 2H); 5.12 (d, 1H); 5.18 (d, 1H); 5.82 (m, 1H); 6.95 (m, 1H); 7.25 (s, 1H); 7.35 (dd, 2H); 7.40 (s, 1H); 8:12 (s, 1H); 8.68 (s, 1H); 10.64 (s, 1H); 11.99 (brs, 1H).

EXAMPLE 324

Preparation of Compound 501 in Table 17

An analogous reaction to that described in example 255 but starting with (R)-(−)-2-pyrrolidinemethanol (334 mg, 3.3 mol) yielded compound 501 in Table 17 (51 mg, 40%).

MS ES$^+$: 585 (M+H)$^+$ $^1$HNMR (DMSO-$d_6$, TFA)-1.57 (m, 1H); 1.67 (m, 2H); 1.82 (m, 1H); 1.96 (m, 2H); 2.18 (q, 1H); 2.45 (m, 3H); 2.98 (m, 1H); 3.10 (m, 1H); 3.20 (m, 1H); 3.92 (s, 2H); 3.98 (s, 3); 4.22 (t, 2H); 4.35 (brs, 1H); 6.95 (m, 1H); 7.27 (s, 1H); 7.36 (dd, 2H); 7.40 (s, 1H); 8.13 (s, 1H); 8.68 (s, 1H); 10.66 (s, 1H); 12.00 (brs, 1H).

EXAMPLE 325

Preparation of Compound 502 in Table 17

An analogous reaction to that described in example 255 but starting with cyclopentylamine (281 mg, 3.3 mmol) yielded compound 502 in Table 17 (28 mg, 22%).

MS ES$^+$: 569 (M+H)$^+$ $^1$HNMR (DMSO-$d_6$): 1.31 (m, 2H); 1.47 (m, 2H); 1.62 (m, 2H); 1.73 (m, 2H); 1.93 (m, 2H); 2.70 (t, 2H); 3.03 (m, 1H); 3.92 (s, 2H); 3.97 (s, 3H); 4.23 (t, 2H); 6.94 (m, 1H); 7.26 (s, 1H); 7.36 (dd, 2H); 7.39 (s, 1H); 8.11 (s, 1H); 8.67 (s, 1H); 10.66 (s, 1H).

EXAMPLE 326

Preparation of Compound 503 in Table 17

An analogous reaction to that described in example 256 but starting with 2-methylaminoethanol (248 mg, 3.3 mmol) yielded compound 503 in Table 17 (31 mg, 24%).

MS ES$^+$: 575 (M+H)$^+$ $^1$HNMR (DMSO$d_6$, TFA): 2.31 (m, 2H); 2.88 (s, 3H); 3.16–3.45 (m, 4H); 3.77 (t, 2H); 3.99 (s, 5H); 4.29 (t, 2H); 7.30 (s, 1H); 7.38 (t, 1H); 7.50 (m, 1H); 7.64 (s, 1H); 7.91 (s, 1H); 7.97 (dd, 1H); 9.09 (s, 1H).

EXAMPLE 327

Preparation of Compound 504 in Table 17

An analogous reaction to that described in example 256 but starting with N,N,N'-trimethylethylenediamine (337 mg, 3.3 mmol) yielded compound 504 in Table 17 (28 mg, 21%).

MS ES$^+$: 602 (M+H)$^+$ $^1$HNMR (DMSO$d_6$, TFA): 2.32 (m, 2H); 2.89 (s, 6H); 2.93 (s, 3H); 3.38 (m, 2H); 3.56 (brs, 4H); 3.99 (s, 5H); 4.30 (t, 2H); 7.35 (s, 1H); 7.39 (t, 1H); 7.50 (m, 1H); 7.65 (s, 1H); 7.91 (s, 1H); 7.97 (dd, 1H); 9.09 (s, 1H).

EXAMPLE 328

Preparation of Compound 505 in Table 17

An analogous reaction to that described in example 256 but starting with N-allylpyperazine (416 mg, 3.3 mmol) yielded compound 505 in Table 17 (42 mg, 30%).

MS ES$^+$: 626 (M+H)$^+$ $^1$HNMR (DMSOd$_6$, TFA): 2.33 (m, 2H); 3.20–3.80 (m, 1H); 3.91 (d, 2H); 3.99 (s, 5H); 4.32 (t, 2H); 5.60 (m, 2H); 5.94 (m, 1H); 7.33 (s, 1H); 7.39 (t, 1H); 7.50 (m, 1H); 7.65 (s, 1H); 7.91 (s, 1H); 7.97 (dd, 1H); 9.09 (s, 1H).

EXAMPLE 329

Preparation of Compound 506 in Table 17

An analogous reaction to that described in example 256 but starting with 4-hydroxypiperidine (334 mg, 3.3 mmol) yielded compound 506 in Table 17 (32 mg, 25%).

MS ES$^+$: 601 (M+H)$^+$ $^1$HNMR (DMSOd$_6$): 1.41 (m, 2H); 1.73 (m, 2H); 1.96 (m, 2H); 2.03 (m, 2H); 2.45 (m, 2H); 2.74 (m, 2H); 3.46 (m, 1H); 3.90 (s, 2H); 3.98 (s, 3H); 4.21 (t, 2H); 4.55 (brs, 1H); 7.26 (s, 1H); 7.40 (s, 1H); 7.41 (t, 1H); 7.51 (m, 1H); 7.97 (dd, 1H); 8.13 (brs, 1H); 8.69 (s, 1H); 10.49 (s, 1H); 12.03 (brs, 1H).

EXAMPLE 330

Preparation of Compound 507 in Table 17

An analogous reaction to that described in example 256 but starting with 3-pyrrolidinol (288 mg, 3.3 mmol) yielded compound 507 in Table 17 (24 mg, 19%).

MS ES$^+$: 587 (M+H)$^+$ $^1$HNMR (DMSOd$_6$): 1.57 (m, 1H); 1.98 (m, 3H); 2.30–2.81 (m, 6H); 3.38 (m, 1H); 3.90 (s, 2H); 3.98 (s, 3H); 4.22 (t, 2H); 4.74 (brs, 1H); 7.27 (s, 1H); 7.39 (s, 1H); 7.40 (t, 1H); 7.50 (m, 1H); 7.96 (dd, 1H); 8.13 (brs, 1H); 8.69 (s, 1H); 10.49 (s, 1H); 12.05 (brs, 1H).

EXAMPLE 331

Preparation of Compound 508 in Table 17

An analogous reaction to that described in example 256 but starting with 1-(2-aminoethyl)pyrrolidine (377 mg, 3.3 mmol) yielded compound 508 in Table 17 (18 mg, 13%).

MS ES$^+$: 614 (M+H)$^+$ $^1$HNMR (DMSOd$_6$, TFA): 1.91 (m, 2H); 2.06 (m, 2H); 2.23 (m, 2H); 3.11 (m, 2H); 3.22 (t, 2H); 3.41 (m, 2H); 3.47 (m, 2H); 3.67 (m, 2H); 3.98 (s, 5H); 4.30 (t, 2H); 7.30 (s, 1H); 7.36 (t, 1H); 7.49 (m, 1H); 7.63 (s, 1H); 7.91 (s, 1H). 7.95 (dd, 1H); 9.09 (s, 1H).

EXAMPLE 332

Preparation of Compound 509 in Table 17

An analogous reaction to that described in example 256 but starting with N-acetylpiperazine (423 mg, 3.3 mmol) yielded compound 509 in Table 17 (113 mg, 82%).

MS ES$^+$: 628 (M+H)$^+$ $^1$HNMR (DMSOd$_6$): 1.98 (m, 2H); 2.00 (s, 3H); 2.36 (t, 2H); 2.42 (t, 2H); 2.92 (t, 0.5H); 2.99 (t, 0.5H); 3.45 (m, 4H); 3.55 (t, 1H); 3.90 (s, 2H); 3.98 (s, 3H); 4.23 (t, 2H); 7.27 (s, 1H); 7.40 (s, 1H); 7.41 (t, 1H); 7.52 (m, 1H); 7.97 (dd, 1H); 8.13 (s, 1H); 8.69 (s, 1H); 10.51 (s, 1H).

EXAMPLE 333

Preparation of Compound 510 in Table 17

An analogous reaction to that described in example 256 but starting with 2-(2-hydroxyethyl)piperidine (426 mg, 3.3 mmol) yielded compound 510 in Table 17 (34 mg, 24%).

MS ES$^+$: 629 (M+H)$^+$ $^1$HNMR (DMSOd$_6$, TFA): 1.48–1.90 (m, 7H); 2.08 (m, 1H); 2.27 (m, 2H); 3.09–3.69 (m, 7H); 3.99 (s, 5H); 4.30 (m, 2H); 7.30 (d, 1H); 7.38 (t, 1H); 7.50 (m, 1H); 7.64 (s, 1H); 7.91 (s, 1H); 7.97 (dd, 1H); 9.09 (s, 1H).

EXAMPLE 334

Preparation of Compound 511 in Table 17

An analogous reaction to that described in example 256 but starting with 2-(2-hydroxyethyl)piperazine (430 mg, 3.3 mmol) yielded compound 511 in Table 17 (80 mg, 58%).

MS ES$^+$: 630 (M+H)$^+$ $^1$HNMR (DMSOd$_6$): 1.96 (m, 2H); 2.42 (m, 12H); 3.49 (dd, 2H); 3.90 (s, 2H); 3.97 (s, 3H); 4.20 (t, 2H); 4.37 (t, 1H); 7.25 (s, 1H); 7.39 (s, 1H); 7.40 (t, 1H); 7.51 (m, 1H); 7.97 (dd, 1H); 8.12 (s, 1H); 8.68 (s, 1H); 10.42 (s, 1H); 12.02 (brs, 1H).

EXAMPLE 335

Preparation of Compound 512 in Table 17

An analogous reaction to that described in example 256 but starting with cyclopentylamine (281 mg, 3.3 mmol) yielded compound 512 in Table 17 (12 mg, 9%).

MS ES$^+$: 585 (M+H)$^+$ $^1$HNMR (DMSOd$_6$, TFA): 1.59 (m, 4H); 1.73 (m, 2H); 2.00 (m, 2H); 2.21 (m, 2H); 3.13 (t, 2H); 3.56 (m, 1H); 3.99 (s, 5H); 4.31 (t, 2H); 7.29 (s, 1H); 7.37 (t, 1H); 7.49 (m, 1H); 7.64 (s, 1H); 7.92 (s, 1H); 7.96 (dd, 1H); 9.09 (s, 1H).

EXAMPLE 336

Preparation of Compound 513 in Table 17

An analogous reaction to that described in example 256 but starting with 4-(2-hydroxyethyl)piperidine (426 mg, 3.3 mmol) yielded compound 513 in Table 17 (54 mg, 39%).

MS ES$^+$: 629 (M+H)$^+$ $^1$HNMR (DMSOd$_6$): 1.15 (m, 2H); 1.36 (m, 3H); 1.63 (d, 2H); 1.88 (t, 2H); 1.96 (m, 2H); 2.44 (t, 2H); 2.87 (d, 2H); 3.44 (m, 2H); 3.90 (s, 2H); 3.97 (s, 3H); 4.20 (t, 2H); 4.33 (t, 1H); 7.25 (s, 1H); 7.40 (s, 1H); 7.41 (t, 1H); 7.51 (m, 1H); 7.97 (dd, 1H); 8.12 (s, 1H); 8.68 (s, 1H); 10.48 (s, 1H); 12.03 (brs, 1H).

EXAMPLE 337

Preparation of Compound 514 in Table 17

An analogous reaction to that described in example 256 but starting with 3-hydroxypiperidine (334 mg, 3.3 mmol) yielded compound 514 in Table 17 (96 mg, 73%).

MS ES$^+$: 601 (M+H)$^+$ $^1$HNMR (DMSOd$_6$): 1.09 (m, 1H); 1.43 (m, 1H); 1.63 (m, 1H); 1.78 (m, 2H); 1.87 (m, 1H); 1.96 (m, 2H); 2.47 (m, 2H); 2.68 (m, 1H); 2.84 (brd, 1H); 3.50 (m, 1H); 3.90 (s, 2H); 3.98 (s, 3H); 4.20 (t, 2H); 4.59 (d, 1H); 7.26 (s, 1H); 7.40 (s, 1H); 7.41 (t, 1H); 7.51 (m, 1H); 7.97 (dd, 1H); 8.13 (brs, 1H); 8.68 (s, 1H); 10.48 (s, 1H); 12.03 (brs, 1H).

EXAMPLE 338

Preparation of Compound 515 in Table 17

An analogous reaction to that described in example 256 but starting with 4-hydroxymethylpyperidine (380 mg, 3.3 mmol) yielded compound 515 in Table 17 (18 mg, 13).

MS $ES^+$: 615 $(M+H)^+$ $^1$HNMR ($DMSOd_6$): 1:15 (m, 2H); 1.35 (m, 1H); 1.65 (d, 2H); 1.88 (m, 2H); 1.97 (m, 2H); 2.46 (m, 2H); 2.91 (m, 2H); 3.25 (t, 2H); 3.90 (s, 2H); 3.97 (s, 3H); 4.21 (t, 2H); 4.41 (t, 1H); 7.26 (s, 1H); 7.40 (s, 1H); 7.41 (t, 1H); 7.50 (m, 1H); 7.97 (dd, 1H); 8.13 (brs, 1H); 8.68 (s, 1H); 10.49 (s, 1H); 12.03 (brs, 1H).

EXAMPLE 339

Preparation of Compound 516 in Table 17

An analogous reaction to that described in example 256 but starting with 1-amino-2-propanol (248 mg, 3.3 mmol) yielded compound 516 in Table 17 (14 mg, 11%).

MS $ES^+$: 575 $(M+H)^+$ $^1$HNMR ($DMSOd_6$): 1.06 (d, 3H); 1.96 (m, 2H); 2.49 (m, 2H); 2.74 (t, 2H); 3.71 (m, 2H); 3.90 (s, 2H); 3.98 (s, 3H); 4.24 (t, 2H); 4.50 (brs, 1H); 7.27 (s, 1H); 7.39 (s, 1H); 7.41 (t, 1H); 7.51 (m, 1H); 7.97 (dd, 1H); 8.12 (s, 1H); 8.68 (s, 1H); 10.49 (s, 1H).

EXAMPLE 340

Preparation of Compound 517 in Table 17

An analogous reaction to that described in example 256 but starting with tert-butyl-1-piperazinecarboxylate (615 mg, 3.3 mmol) and treating the crude reaction mixture with hydrochloric acid in 1,4-dioxane (4. M, 2 ml) yielded compound 517 in Table 17 (61 mg, 47%).

MS $ES^+$: 586 $(M+H)^+$ $^1$HNMR ($DMSOd_6$, TFA): 2.31 (m, 2H); 3.00–3.95 (m, 1H); 3.99 (s, 5H); 4.31 (t, 2H); 7.32 (s, 1H); 7.39 (t, 1H); 7.50 (m, 1H); 7.65 (s, 1H); 7.91 (s, 1H); 7.97 (dd, 1H); 9.10 (s, 1H).

EXAMPLE 341

Preparation of Compound 518 in Table 17

An analogous reaction to that described in example 256 but starting with 1-(2-morpholinoethyl)piperazine (519 mg, 3.3 mmol) yielded compound 518 in Table 17 (69 mg, 48%).

MS $ES^+$: 699 $(M+H)^+$ $^1$HNMR ($DMSOd_6$, TFA): 2.31 (m, 2H); 2.98 (m, 2H); 3.10–37.5 (m, 16H); 3.86 (m, 4H); 3.99 (s, 5H); 4.31 (t, 2H); 7.33 (s, 1H); 7.39 (t, 1H); 7.50 (m, 1H); 7.65 (s, 1H); 7.92 (s, 1H); 7.97 (dd, 1H); 9.10 (s, 1H).

EXAMPLE 342

Preparation of Compound 519 in Table 17

An analogous reaction to that described in example 256 but starting with pyrrolidine (235 mg, 3.3 mmol) yielded compound 519 in Table 17 (55 mg, 44%).

MS $ES^+$: 571 $(M+H)^+$ $^1$HNMR ($DMSOd_6$, TFA): 1.90 (m, 2H); 2.06 (m, 2H); 2.27 (m, 2H); 3.09 (m, 2H); 3.36 (t, 2H); 3.66 (m, 2H); 3.98 's, 5H); 4.29 (t, 2H); 7.29 (s, 1H); 7.39 (t, 1H); 7.50 (m, 1H); 7.64 (s, 1H); 7.90 (s, 1H); 7.96 (dd, 1H); 9.09 (s, 1H).

EXAMPLE 343

Preparation of Compound 520 in Table 17

An analogous reaction to that described in example 257 but starting with 2-methylaminoethanol (248 mg, 3.3 mmol) yielded compound 520 in Table 17 (34 mg, 29%).

MS $ES^+$: 541 $(M+H)^+$ $^1$HNMR ($DMSOd_6$, TFA): 2.30 (m, 2H); 3.57 (s, 3H); 3.16–3.45 (m, 4H); 3.75 (t, 2H); 3.98 (s, 3H); 3.99 (s, 2H); 4.29 (t, 2H); 6.89 (t, 1H); 7.29 (s, 1H); 7.30–7.40 (m, 2H); 7.62 (d, 1H); 7.63 (s, 1H); 7.91 (s, 1H); 9.08 (s, 1H).

EXAMPLE 344

Preparation of Compound 521 in Table 17

An analogous reaction to that described in example 257 but starting with 1,2-diamino-2-methylpropane (291 mg, 3.3 mmol) yielded compound 521 in Table 17 (10 mg, 8%).

MS $ES^+$: 554 $(M+H)^+$ $^1$HNMR ($DMSOd_6$, TFA): 1.39 (s, 6H); 2.27 (m, 2H); 3.22 (m, 4H); 3.97 (s, 3H); 3.98 (s, 2H); 4.32 (t, 2H); 6.89 (m, 1H); 7.29–7.39 (m, 3H); 7.62 (d, 1H); 7.63 (s, 1H); 7.92 (s, 1H); 9.08 (s, 1H).

EXAMPLE 345

Preparation of Compound 522 in Table 17

An analogous reaction to that described in example 257 but starting with N,N-dimethylethylenediamine (291 mg, 3.3 mmol) yielded compound 522 in Table 17 (26 mg, 22%).

MS $ES^+$: 554 $(M+H)^+$ $^1$HNMR ($DMSOd_6$)): 1.95 (m, 2H); 2.15 (s, 6H); 2.33 (t, 2H); 2.63 (t, 2H); 2.73 (t, 2H); 3.90 (s, 2H); 3.97 (s, 3H); 4.23 (t, 2H); 6.91 (m, 1H); 7.26 (s, 1H); 7.31–7.42 (m, 2H) 7.39 (s, 1H); 7.64 (d, 1H) 8.11 (s, 1H); 8.68 (s, 1H); 10.48 (s, 1H).

EXAMPLE 346

Preparation of Compound 523 in Table 17

An analogous reaction to that described in example 257 but starting with N,N,N'-trimethylethylenediamine (337 mg, 3.3 mmol) yielded compound 523 in Table 17 (37 mg, 30%).

MS $ES^+$: 568 $(M+H)^+$ $^1$HNMR ($DMSOd_6$, TFA): 2.34 (m, 2H); 2.88 (s, 6H); 2.93 (s, 3H); 3.38 (m, 2H); 3.55 (m, 4H); 3.98 (s, 3H); 3.99 (s, 2H); 4.29 (t, 2H); 6.89 (m, 1H); 7.29–7.41 (m, 2H); 7.33 (s, 1H) 7.63 (d, 1H); 7.64 (s, 1H); 7.91 (s, 1H); 9.09 (s, 1H).

EXAMPLE 347

Preparation of Compound 524 in Table 17

An analogous reaction to that described in example 257 but starting with N-allylpiperazine (416 mg, 3.3 mmol) yielded compound 524 in Table 17 (77 mg, 59%).

MS $ES^+$: 592 $(M+H)^+$ $^1$HNMR ($DMSOd_6$, TFA): 2.34 (m, 2H); 3.00–3.08 (m, 8H); 2.86 (d, 2H); 3.92 (m, 2H); 3.98 (s, 3H); 3.99 (s, 2H); 4.31 (t, 2H); 5.53–5.66 (m, 2H); 5.60–5.87 (m, 1H); 6.89 (m, 1H) 7.31–7.40 (m, 3H); 7.62 (d, 1H); 7.63 (s, 1H); 7.91 (s, 1H); 9.09 (s, 1H).

EXAMPLE 348

Preparation of Compound 525 in Table 17

An analogous reaction to that described in example 257 but starting with 4-hydroxypyperidine (334 mg, 3.3 mmol) yielded compound 525 in Table 17 (21 mg, 17%).

MS ES$^+$: 567 (M+H)$^+$ $^1$HNMR (DMSOd$_6$, TFA): 1.59 (m, 1H); 1.85 (m, 2H); 2.01 (d, 1H); 2.28 (m, 2H); 3.03 (t, 1H); 3.21 (m, 1H); 3.28 (m, 2H); 3.40 (m, 1H); 3.57 (d, 1H); 3.68 (m, 1H); 3.98 (s, 3H); 3.99 (s, 2H); 4.28 (t, 2H), 6.90 (t, 1H); 7.29 (s, 1H); 7.30–7.40 (m, 2H); 7.63 (d, 1H); 7.64 (s, 1H), 7.91 (s, 1H); 9.09 (s, 1H).

EXAMPLE 349

Preparation of Compound 526 in Table 17

An analogous reaction to that described in example 257 but starting with 3-pyrrolidinol (288 mg, 3.3 mmol) yielded compound 526 in Table 17 (18 mg, 15%).

MS ES$^+$: 553 (M+H)$^+$ $^1$HNMR (DMSOd$_6$, TFA): 1.84–2.03 (m, 2H); 2.27 (m, 2H); 3.02–3.79 (m, 6H); 3.99 (s, 3H) 4.00 (s, 2H); 4.29 (m, 2H); 4.41–4.51 (m, 1H); 6.91 (m, 1H); 7.28 (d, 1H); 7.31–7.41 (m, 2H); 7.63 (d, 1H); 7.64 (s, 1H); 7.91 (s, 1H); 9.09 (s, 1H).

EXAMPLE 350

Preparation of Compound 527 in Table 17

An analogous reaction to that described in example 257 but starting with 1-(aminoethyl)pyrrolidine (377 mg, 3.3 mmol) yielded compound 527 in Table 17 (34 mg, 27%).

MS ES$^+$: 580 (M+H)$^+$ $^1$HNMR (DMSOd$_6$): 1.68 (m, 4H); 1.97 (m, 2H); 2.47 (m, 6H); 2.70 (t, 2H); 2.77 (t, 2H); 3.91 (s, 2H); 3.97 (s, 3H); 4.24 (t, 2H); 6.91 (m, 1H); 7.27 (s, 1H); 7.30–7.42 (m, 2H); 7.39 (s, 1H); 7.64 (d, 1H), 8.12 (s, 1H); 8.68 (s, 1H); 10.49 (s, 1H).

EXAMPLE 351

Preparation of Compound 528 in Table 17

An analogous reaction to that described in example 257 but starting with N-acetylpiperazine (423 mg, 3.3 mmol) yielded compound 528 in Table 17 (93 mg, 71%).

MS ES$^+$: 594 (M+H)$^+$ $^1$HNMR (DMSOd$_6$): 1.99 (m, 2H); 2.00 (s, 3H); 2.35 (t, 2H); 2.41 (t, 2H); 2.49 (m, 2H); 3.45 (m, 4H); 3.91 (s, 2H); 3.97 (s, 3H); 4.23 (t, 2H); 6.92 (m, 1H); 7.27 (s, 1H); 7.32–7.42 (m, 2H); 7.40 (s, 1H); 7.63 (d, 1H); 8.13 (brs, 1H); 8.69 (s, 1H); 10.48 (s, 1H).

EXAMPLE 352

Preparation of Compound 529 in Table 17

An analogous reaction to that described in example 257 but starting with 1-(2-hydroxyethyl)piperazine (430 mg, 3.3 mmol) yielded compound 529 in Table 17 (91 mg, 69%).

MS ES$^+$: 596 (M+H)$^+$ $^1$HNMR (DMSOd$_6$): 1.96 (m, 2H); 2.41 (m, 12H); 3.50 (q, 2H); 3.91 (s, 2H); 3.97 (s, 3H); 4.20 (t, 2H); 4.37 (t, 1H); 6.91 (t, 1); 7.25 (s, 1H); 7.32–7.42 (m, 2H); 7.39 (s, 1H); 7.65 (d, 1H); 8.12 (s, 1H); 8.68 (s, 1H); 10.48 (s, 1H); 12.04 (brs, 1H).

EXAMPLE 353

Preparation of Compound 530 in Table 17

An analogous reaction to that described in example 257 but starting cyclopentylamine (281 mg, 3.3 mmol) yielded compound 530 in Table 17 (47 mg, 39%).

MS ES$^+$: 551 (M+H)$^+$ $^1$HNMR (DMSOd$_6$): 1.39 (m, 2H); 1.50 (m, 2H); 1.65 (m, 2H); 1.80 (m, 2H); 2.00 (m, 2H); 2.80 (t, 2H); 3.16 (m, 1H); 3.91 (s, 2H); 3.98 (s, 3H); 4.25 (t, 2H); 6.98 (t, 1H); 7.28 (s, 1H); 7.31–7.42 (m, 2H); 7.40 (s, 1H); 7.64 (d, 1H); 8.13 (s, 1H); 8.69 (s, 1H); 10.49 (s, 1H).

EXAMPLE 354

Preparation of Compound 531 in Table 17

An analogous reaction to that described in example 257 but starting with 4-(2-hydroxyethyl)piperidine (426 mg, 3.3 mmol) yielded compound 531 in Table 17 (65 mg, 50%).

MS ES$^+$: 595 (M+H)$^+$ $^1$HNMR (DMSOd$_6$): 1.15 (m, 2H); 1.36 (m, 3H); 1.63 (d, 2H); 1.88 (m, 2H); 1.96 (m, 2H); 2.44 (m, 2H); 2.87 (d, 2H); 3.44 (m, 2H); 3.91 (s, 2H); 3.97 (s, 3H); 4.20 (t, 2H); 4.33 (t, 1H); 6.91 (t, 1H); 7.25 (s, 1H); 7.32–7.42 (m, 2H); 7.40 (s, 1H); 7.63 (d, 1H); 8.12 (brs, 1H); 8.68 (s, 1H); 10.48 (s, 1H); 12.03 (s, 1H).

EXAMPLE 355

Preparation of Compound 532 in Table 17

An analogous reaction to that described in example 257 but starting with 3-hydroxypiperidine (334 mg, 3.3 mmol) yielded compound 532 in Table 17 (72 mg, 58%).

MS ES$^+$: 567 (M+H)$^+$ $^1$HNMR (DMSOd$_6$): 1.09 (m, 1H); 1.43 (m, 1H); 1.63 (m, 1H); 1.78 (m, 2H); 1.87 (m, 1H) 1.96 (t, 2H); 2.47 (m, 2H); 2.69 (m, 1H); 2.85 (brd, 1H); 3.49 (m, 1H); 3.91 (s, 2H); 3.98 (s, 3H); 4.20 (t, 2H); 4.60 (d, 1H), 6.91 (t, 1H); 7.26 (s, 1H); 7.31–7.42 (m, 2H); 7.40 (s, 1H); 7.64 (d, 1H); 8.13 (brs, 1H); 8.68 (s, 1H); 10.48 (s, 1H); 12.02 (brs, 1H).

EXAMPLE 356

Preparation of Compound 533 in Table 17

An analogous reaction to that described in example 257 but starting with 4-hydroxymethylpyperidine (380 mg, 3.3 mmol) yielded compound 533 in Table 17 (56 mg, 44%).

MS ES$^+$: 581 (M+H)$^+$ $^1$HNMR (DMSOd$_6$): 1.14 (m, 2H); 1.34 (m, 1H); 1.65 (d, 2H); 1.88 (t, 2H); 1.97 (m, 2H); 2.45 (t, 2H); 2.90 (d, 2H); 3.25 (t, 2H); 3.91 (s, 2H); 3.97 (s, 3H); 4.20 (t, 2H); 4.41 (t, 1H); 6.93 (t, 1H); 7.25 (s, 1H); 7.32–7.42 (m, 2H); 7.40 (s, 1H); 7.63 (d, 1H); 8.12 (brs, 1H); 8.68 (s, 1H); 10.48 (s, 1H); 12.03 (brs, 1H).

EXAMPLE 357

Preparation of Compound 534 in Table 17

An analogous reaction to that described in example 257 but starting with 1-amino-2-propanol (248 mg, 3.3 mmol) yielded compound 534 in Table 17 (36 mg, 30%).

MS ES$^+$: 541 (M+H)$^+$ $^1$HNMR (DMSOd$_6$): 1.06 (d, 3H); 1.95 (m, 2H); 2.48 (m, 2H); 2.72 (t, 2H); 3.69 (m, 1H); 3.90 (s, 2H); 3.97 (s, 3H); 4.23 (t, 2H); 4.47 (brs, 1H); 6.91 (t, 1H); 7.26 (s, 1H); 7.32–7.41 (m, 2H); 7.39 (s, 1H); 7.63 (d, 1H); 8.11 (s, 1H); 8.67 (s, 1H); 10.48 (s, 1H).

EXAMPLE 358

Preparation of Compound 535 in Table 17

An analogous reaction to that described in example 257 but starting with (R)-(−)-2-pyrrolidinemethanol (334 mg, 3.3 mmol) yielded compound 535 in Table 17 (66 mg, 53%).

MS $ES^+$: 567 $(M+H)^+$ $^1$HNMR ($DMSOd_6$): 1.57 (m, 1H); 1.67 (m, 2H); 2.82 (m, 1H); 1.96 (m, 2H); 2.18 (m, 1H); 2.45 (m, 2H); 2.98 (m, 1H); 3.10 (m, 1H); 3.20 (m, 1H); 3.41 (m, 1H); 3.91 (s, 2H); 3.98 (s, 3H); 4.22 (t, 2H); 4.35 (brs, 1H); 6.91 (t, 1H); 7.26 (s, 1H); 7.31–7.42 (m, 2H); 7.39 (s, 1H); 7.64 (d, 1H); 8.13 (s, 1H); 8.68 (s, 1H); 10.48 (s, 1H); 12.01 (brs, 1H).

EXAMPLE 359

Preparation of Compound 536 in Table 17

An analogous reaction to that described in example 257 but starting with (S)-(+)-2-pyrrolidinemethanol (334 mg, 3.3 mmol) yielded compound 536 in Table 17 (59 mg, 48%).

MS $ES^+$: 567 $(M+H)^+$ $^1$HNMR ($DMSOd_6$, TFA): 1.78 (m, 1H); 1.90 (m, 1H); 2.03 (m, 1H); 2.13 (m, 1H); 2.31 (m, 2H); 3.23 (m, 2H); 3.61 (m, 4H); 3.77 (q, 1H); 3.98 (s, 3H); 3.99 (s, 2H); 4.29 (t, 2H); 6.89 (t, 1H); 7.29 (s, 1H); 7.30–7.40 (m, 2H); 7.63 (d, 1H); 7.64 (s, 1H); 7.91 (s, 1H); 9.08 (s, 1H).

EXAMPLE 360

Preparation of Compound 537 in Table 17

An analogous reaction to that described in example 257 but starting with t-butyl-1-pyperazinecarboxylate (615 mg, 3.3 mmol) and treating the crude reaction mixture with hydrochloric acid in 1,4-dioxane (4M, 2 ml) yielded compound 537 in Table 17 (35 mg, 27%).

MS $ES^+$: 552 $(M+H)^+$ $^1$HNMR ($DMSOd_6$): 1.96 (m, 2H); 2.33 (brs, 4H); 2.42 (t, 2H); 2.73 (t, 4H); 3.89 (s, 2H); 3.95 (s, 3H); 4.19 (t, 2H); 6.89 (t, 1H); 7.24 (s, 1H); 7.32–7.42 (m, 2H); 7.37 (s, 1H); 7.62 (d, 1H); 8.10 (s, 1H); 8.66 (s, 1H); 10.47 (s, 1H).

EXAMPLE 361

Preparation of Compound 538 in Table 17

An analogous reaction to that described in example 257 but starting with 1-(2-morpholinoethyl)piperazine (519 mg, 3.3 mmol) yielded compound 538 in Table 17 (50 mg, 37%).

MS $ES^+$: 665 $(M+H)^+$ $^1$HNMR ($DMSOd_6$, TFA): 2.33 (m, 2H); 2.99 (t, 2H); 3.05–3.75 (m, 16H); 3.86 (brs, 4H); 3.99 (s, 3H); 4.00 (s, 2H); 4.29 (t, 2H); 6.90 (t, 1H); 7.32 (s, 1H); 7.41–7.31 (m, 2H); 7.62 (d, 1H); 7.64 (s, 1H); 7.92 (s, 1H); 9.09 (s, 1H).

EXAMPLE 362

Preparation of Compound 539 in Table 17

An analogous reaction to that described in example 257 but starting with 2-amino-2-methyl-1-propanol (294 mg, 3.3 mmol) yielded compound 539 in Table 17 (40 mg, 33%).

MS $ES^+$: 555 $(M+H)^+$ $^1$HNMR ($DMSOd_6$): 0.96 (s, 6H); 1.91 (m, 2H); 2.67 (t, 2H); 3.19 (s, 2H); 3.90 (s, 2H) 3.97 (s, 3H); 4.24 (t, 2H); 4.53 (brs, 1H); 6.91 (m, 1H); 7.26 (s, 1H); 7.36 (m, 2H); 7.38 (s, 1H); 7.63 (d, 1H); 8.11 (s, 1H); 8.67 (s, 1H); 10.48 (s, 1H).

EXAMPLE 363

Preparation of Compound 540 in Table 18

4-((2-amino-1,3-thiazole-5-yl)acetic acid)-6-methoxy-7-(3-morpholinopropoxy)quinazoline (125 mg, 0.27 mmol) in DMF (2.5 ml) was reacted with N-ethylaniline (84.3 μl, 0.707 mmol) in presence of O-(7-azabenzotriazol-1-yl)-N,N,N',N'-tetramethyluronium hexafluorophosphate (136 mg, 0.37 mmol) and DIEA (95 μl, 0.54 mmol) at 50° C. for 18 hours. The reaction mixture was cooled, sodium bicarbonate (sat., 1 ml) 3 g alumina were added, the mixture was evaporated to dryness, and the residue purified by chromatography over alumina, Eluant $CH_2Cl_2$, $CH_2Cl_2$/MeOH 99/1 to 95/5 to give title compound (68 mg, 44%).

MS $ES^+$: 563.6 $(M+H)^+$ $^1$H NMR ($DMSOd_6$, TFA): 1.05 (t, 3H); 2.31 (t, 2H); 3.15 (t, 2H); 3.35 (t, 2H); 3.54 (d, 2H); 3.65 (m, 6H); 3.97 (s, 3H); 4.03 (d, 2H); 4.29 (t, 2H); 7.31 (s, 1H); 7.38 (s, 1H); 7.40 (m, 2H); 7.46 (m, 1H); 7.53 (m, 2H); 7.87 (s, 1H); 9.06 (s, 1H).

EXAMPLE 364

Preparation of Compound 541 in Table 18

An analogous reaction to that described in example 363 but starting with 3-chloro-4-fluoro-N-methylaniline (97 mg, 0.35 mmol) yielded title compound (98 mg, 60%).

MS $ES^+$: 601.5, 603.5 $(M+H)^+$ $^1$H NMR ($DMSOd_6$, TFA): 2.31 (t, 2H); 3.15 (t, 2H); 3.21 (s, 3H); 3.35 (t, 2H); 3.54 (d, 2H); 3.7 (m, 4H); 3.97 (s, 3H); 4.03 (d, 2H); 4.29 (t, 2H); 7.31 (s, 1H); 7.41 (s, 1H); 7.50 (m, 2H); 7.80 (m, 1H); 7.87 (s, 1H); 9.06 (s, 1H).

N-(tert-butyloxycarbonyl)-3-chloro-4-fluoroaniline 3-chloro-4-fluoroaniline (2 g, 13.7 mmol) in THF (12.5 ml) under argon, was treated with NaHMDS (1 M, 27.5 ml, 27.5 mmol) at room temperature for 15 minutes. Di-tert-butyl dicarbonate in THF (10 ml) was slowly added to the reaction mixture, and the mixture stirred at room temperature for 45 minutes. The solvent was evaporated, diluted HCl (0.1N) was added, and the mixture extracted with ethylacetate, dried, purified by silica gel chromatography, ether/petroleum ether 10–20/90-80 to give title compound (2.77 g, 82%).

$^1$H NMR ($CDCl_3$): 1.49 (s, 9H); 6.42 (s, 1H); 7.01 (t, 1H); 7.01 (m, 1H); 7.54 (m, 1H).

3-chloro-4-fluoro-N-methylaniline

To a solution of N-(tert-butyloxycarbonyl)$_3$-chloro-4-fluoroaniline (250 mg, 1.02 mmol) in THF (4 ml) at 0° C. was added sodium hydride (60%, 45 mg, 1.12 mmol), and the mixture was stirred for 20 minutes. Methyl iodide (70 μl, 1.12 mmol) was added to the mixture which was stirred at room temperature for 4 hours. The solvent was evaporated, a saturated solution of sodium chloride was added, and the mixture was extracted with $CH_2Cl_2$, dried, and purified by silica gel chromatography, ether/petroleum ether, 8/2 to give compound (235 mg). This compound was dissolved in $CH_2Cl_2$ (2 ml) and TFA (2 ml), $H_2O$ (200 μl) was added, the mixture was stirred for 1 hour at room temperature, the solvent was evaporated, to give title compound (256 mg, 89%).

$^1$HNMR ($CDCl_3$): 2.98 (s, 3H); 7.3 (m, 3H).

EXAMPLE 365

Preparation of Compound 542 in Table 18

An analogous reaction to that described in example 363 but starting with ethyl-2-(3-chloro-4-fluoroaniline)acetate (151 mg, 0.65 mmol) yielded title compound (10 mg, 4.5%).

MS $ES^+$: 673.6 $(M+H)^+$ $^1H$ NMR ($DMSOd_6$, TFA): 1.18 (t, 3H); 2.30 (t, 2H); 3.16 (t, 2H); 3.35 (t, 2H); 3.54 (d, 2H); 3.68 (t, 2H); 3.83 (s, 1H); 3.97 (s, 3H); 4.03 (m, 4H); 4.13 (s, 2H); 4.29 (t, 2H); 4.41 (s, 1H); 7.30 (s, 1H); 7.44 (s, 1H); 7.55 (m, 2H); 7.78 (m, 1H); 7.87 (s, 1H); 9.06 (s, 1H).

EXAMPLE 366

Preparation of Compound 543 in Table 18

An analogous reaction to that described in example 363 but starting with 2-anilinoacetonitrile (371 mg, 2.72 mmol) yielded title compound (110 mg, 18%).

MS $ES^+$: 574.6 $(M+H)^+$ $^1H$ NMR ($DMSOd_6$, TFA): 2.31 (t, 2H); 3.16 (t, 2H); 3.35 (t, 2H); 3.55 (d, 2H); 3.68 (t, 2H) 3.77 (s, 1H); 3.97 (s, 3H); 4.04 (d, 2H); 4.30 (t, 2H); 4.81 (s, 2H); 7.31 (s, 1H); 7.43 (s, 1H); 7.57 (m, 5H); 7.88 (s, 1H); 9.09 (s, 1H).

EXAMPLE 367

Preparation of Compound 544 in Table 18

An analogous reaction to that described in example 363 but starting with 3-anilinoacetonitrile (335 mg, 2.18 mmol) yielded title compound (100 mg, 18%).

MS $ES^+$: 588.6 $(M+H)^+$ $^1H$ NMR ($DMSOd_6$, TFA): 2.29 (t, 2H); 2.75 (t, 2H); 3.16 (t, 2H); 3.35 (t, 2H); 3.55 (d, 2H); 3.68 (m, 4H); 3.95 (t, 2H); 3.97 (s, 3H); 4.04 (d, 2H); 4.29 (t, 2H); 7.29 (s, 1H); 7.42 (s, 1H); 7.48 (m, 3H); 7.55 (m, 2H); 7.87 (s, 1H); 9.08 (s, 1H).

EXAMPLE 368

Preparation of Compound 545 in Table 18

An analogous reaction to that described in example 363 but starting with N-(2-tert-butylethyl)-3-chloro-4-fluoroaniline (346 mg, 1.42 mmol) yielded title compound (147 mg, 30%).

MS $ES^+$: 687.6 $(M+H)^+$ $^1H$ NMR ($DMSOd_6$, TFA): 1.08 (s, 9H); 2.31 (t, 2H); 3.14 (t, 2H); 4.34.5 (m, 4H); 3.55 (d, 2H); 3.68 (m, 6H); 3.97 (s, 3H); 4.03 (d, 2H); 4.29 (t, 2H); 7.30 (s, 1H); 7.41 (s, 1H); 7.51 (m, 2H); 7.78 (m, 1H); 7.87 (s, 1H); 9.06 (s, 1H).

N-(2-hydroxyethyl)$_3$-chloro-4-fluoroaniline ethyl-2-(3-chloro-4-fluoroanilino)acetate (J. Med. Chem. 1965, 405–407) (2 g, 8.6 mmol) in THF (15 ml) ether (10 ml) was treated with Li Al H4 (460 mg, 12.1 mmol) at 40° C. for 4 hours. The mixture was then poured onto ice, treated with NaOH (2N, 10 ml), extracted with ethyl acetate, dried, evaporated to give title compound (1.48 g, 90%).

$^1H$ NMR ($CDCl_3$): 1.67 (s, 1H); 3.24 (t, 2H); 3.84 (t, 2H); 3.92 (s, 1H); 6.47 (m, 1H); 6.64 (m, 1H); 6.95 (t, 1H).

N-(2-tert-butoxyethyl)$_3$-chloro-4-fluoroaniline

N-2-hydroxyethyl-3-chloro-4-fluoroaniline (1.48 g, 7.81 mmol) in $CH_2Cl_2$ (20 ml) was reacted with N,N-diisopropyl O-tert-butyl-isourea (6.25 g, 31.2 mmol) at room temperature over night. The product was purified by silicagel chromatography, Eluant, ether/petroleum ether 5/95, 10/90 to give title compound (1.15 g, 60%).

$^1H$ NMR ($CDCl_3$): 1.20 (s, 9H); 3.18 (t, 2H); 3.55 (t, 2H); 4.00 (s, 1H); 6.44 (m, 1H); 6.62 (m, 1H); 6.93 (t, 1H).

EXAMPLE 369

Preparation of Compound 546 in Table 18

An analogous reaction to that described in example 363 but starting with N-allylaniline (0.3 ml, 2.18 mmol) yielded title compound (252 mg, 50%).

MS $ES^+$: 575.7 $(M+H)^+$ $^1H$ NMR ($DMSOd_6$, TFA): 2.31 (t, 2H); 3.15 (t, 2H); 3.35 (t, 2H); 3.55 (d, 2H); 3.68 (m, 4H); 3.97 (s, 3H); 4.03 (d, 2H); 4.28 (m, 4H); 5.12 (m, 2H); 5.82 (m, 1H); 7.30 (s, 1H); 7.38 (m, 3H); 7.40 (s, 1H); 7.51 (m, 2H); 7.87 (s, 1H); 9.07 (s, 1H).

EXAMPLE 370

Preparation of Compound 547 in Table 18

An analogous reaction to that described in example 363 but starting with N-ethyl-3,4-(methylenedioxy)aniline (320 μl, 2.18 mmol) yielded title compound (351 mg, 66%).

MS $ES^+$: 607.7 $(M+H)^+$ $^1H$ NMR ($DMSOd_6$, TFA): 1.04 (t, 3H); 2.31 (t, 2H); 3.16 (t, 2H); 3.34 (t, 2H); 3.54 (d, 2H); 3.68 (m, 6H); 3.97 (s, 3H); 4.09 (d, 2H); 4.29 (t, 2H); 6.12 (s, 2H); 6.83 (d, 1H); 7.02 (m, 2H); 7.30 (s, 1H); 7.42 (s, 1H); 7.86 (s, 1H); 9.06 (s, 1H).

EXAMPLE 371

Preparation of Compound 548 in Table 18

An analogous reaction to that described in example 363 but starting with ethyl-4-(N-butylamino)benzoate (482 mg, 2.18 mmol) yielded title compound (58 mg, 10%).

MS $ES^+$: 663.7 $(M+H)^+$ $^1H$ NMR ($DMSOd_6$, TFA): 0.85 (t, 3H); 1.32 (m, 7H); 2.31 (t, 2H); 3.16 (t, 2H); 3.35 (t, 2H); 3.54 (d, 2H); 3.70 (m, 6H); 3.97 (s, 3H); 4.04 (d, 2H); 4.29 (t, 2H); 4.35 (s, 2H); 7.30 (s, 1H); 7.41 (s, 1H); 7.54 (d, 2H); 7.87 (s, 1H); 8.07 (d, 2H); 9.07 (s, 1H).

EXAMPLE 372

Preparation of Compound 549 in Table 18

An analogous reaction to that described in example 363 but starting with N-ethyl-m-toluidine (294 mg, 2.18 mmol) yielded title compound (294 mg, 58%).

MS $ES^+$: 577.7 $(M+H)^+$ $^1H$ NMR ($DMSOd_6$, TFA): 1.05 (t, 9H); 2.31 (t, 2H); 2.38 (s, 3H); 3.16 (t, 2H); 3.35 (t, 2H); 3.54 (d, 2H); 3.67 (m, 6H); 3.97 (s, 3H); 4.04 (d, 2H); 4.29 (t, 2H); 7.18 (m, 2H); 7.28 (d, 1H); 7.30 (s, 1H); 7.39 (s, 1H); 7.42 (d, 1H); 7.86 (s, 1H); 9.07 (s, 1H).

EXAMPLE 373

Preparation of Compound 550 in Table 18

Compound 545 (120 mg) in $CH_2Cl_2$ (2 ml) was treated with TFA (3 ml) and $H_2O$ (200 μl) at room temperature for 3 hours. The solvent was evaporated to give title compound (45 mg, 41%).

MS $ES^+$: 631.6 $(M+H)^+$ $^1H$ NMR ($DMSOd_6$, TFA): 2.29 (t, 2H); 3.16 (t, 2H); 3.35 (t, 2H); 3.51 (t, 2H); 3.54 (d, 2H); 3.70 (m, 6H); 3.97 (s, 3H); 4.03 (d, 2H); 4.30 (t, 2H); 7.30 (s, 1H); 7.42 (s, 1H); 7.54 (m, 2H); 7.78 (d, 1H); 7.87 (s, 1H); 9.06 (s, 1H).

EXAMPLE 374

Preparation of Compound 551 in Table 19

4-((2-amino-4-methyl-1,3-thiazole-5-yl)acetic acid)-6-methoxy-7-(3-morpholinopropoxy)quinazoline (118 mg, 0.25 mmol) in DMF (1.5 ml) was reacted with aniline (32 mg, 0.35 mmol) in presence of 0-(7-azabenzotriazol-1-yl)-N,N,N',N'-tetramethyluronium hexafluorophosphate (142 mg, 0.375 mmol) and DIEA (65 mg, 0.5 mmol) at 65° over night. The mixture was cooled, sodium bicarbonate was added, and the resulting mixture was evaporated. The residue was dissolved in $CH_2Cl_2$/MeOH 92/8 and purified by chromatography over alumina, Eluant $CH_2Cl_2$, $CH_2Cl_2$/MeOH 98/2 to 95/5 a second purification over silicagel was performed, Eluant $CH_2Cl_2$/MeOH 95/5 to 90/10 to give title compound (86 mg, 62%).

MS ES$^+$: 549.6 (M+H)$^+$ $^1$H NMR (DMSOd$_6$, TFA): 2.31 (t, 2H); 2.34 (s, 3H); 3.15 (t, 2H); 3.34 (t, 2H); 3.54 (d, 2H); 3.72 (t, 2H); 3.90 (s, 2H); 3.98 (s, 3H); (4.03); (d, 2H); 4.30 (t, 2H); 7.08 (t, 2H); 7.29 (s, 1H); 7.31 (t, 2H); 7.62 (d, 2H); 7.85 (s, 1H); 9.05 (s, 1H).

4-(ethyl(2-amino-4-methyl-1,3-thiazole-5-yl) acetate)-6-methoxy-7-(3-morpholinopropoxy) quinazoline N'-(2-cyano-4-methoxy-5-(3-morpholinopropoxy) phenyl)-N,N-dimethylimidoformamide (1.38 g, 4 mmol) in acetic acid was reacted with ethyl-2-amino-4-methyl-1,3-thiazole-5-yl)acetate at reflux for 3.5 hours. The mixture was cooled, evaporated, HCl (1N) was added and the mixture extracted with ethylacetate. Sodium bicarbonate was cautiously added to the aqueous phase, which was extracted with ethylacetate. The organic fractions were dried, evaporated, the residue was purified by chromatography over alumina, Eluant $CH_2Cl_2$, $CH_2Cl_2$/AcOEt 1/1, $CH_2Cl_2$/AcOEt/MeOH 50/45/5 to give starting material as a yellow solid. (1.12 g, 52%).

MS ES$^+$: 502.6 (M+H)$^+$ $^1$H NMR (DMSOd$_6$, TFA): 1.24 (t, 3H); 2.28 (m, 5H); 3.15 (t, 2H); 3.36 (t 2H); 3.55 (d, 2H); 3.69 (t, 2H); 3.92 (s, 2H); 3.98 (s, 3H) 4.04 (d, 2H); 4.15 (q, 2H); 4.30 (t, 2H); 7.30 (s, 1H); 7.86 (s, 1H); 9.05 (s, 1H).

4-(2-amino-4-methyl-1,3-thiazole-5-yl)acetic acid)-6-methoxy-7-(3-morpholinopropoxy)quinazoline 4-(ethyl(2-amino-4-methyl-1,3-thiazole-5-yl)acetate)-6-methoxy-7-(3-morpholinopropoxy)quinazoline (1.1 g, 2.2 mmol) in ethanol (11 ml) was treated with NaOH (2N, 5.5 ml, 11 mmol) at room temperature for 1 hour. The mixture was then acidified with HCl (2N) to pH 3. The solution was evaporated, the solid suspended in $CH_2Cl_2$ (8 ml) MeOH (6 ml), and DIEA was added (852 mg, 6.6 mmol). The mixture was stirred for 10 minutes, filtered. The filtrate was concentrated, ethanol was added and the solid recovered to give title compound (980 mg, 94%).

MS ES$^+$: 474.5 (M+H)$^+$ $^1$H NMR (DMSOd$_6$, TFA): 2.28 (m, 5H); 3.16 (t, 2H); 3.36 (t, 2H); 3.55 (d, 2H); 3.70 (t, 2H); 3.83 (s, 2H); 3.98 (s, 3H); 4.04 (d, 2H); 4.30 (t, 2H); 7.30 (s, 1H); 7.86 (s, 1H); 9.05 (s, 1H).

EXAMPLE 375

Preparation of Compound 552 in Table 19

An analogous reaction to that described in example 374 but starting with 3-chloro-4-fluoroaniline (51 mg, 0.35 mmol) yielded the title compound (60 mg, 40%).

MS ES$^+$: 601.5 (M+H)$^+$ $^1$H NMR (DMSOd$_6$, TFA): 2.30 (t, 2H); 2.33 (s, 3H); 3.16 (t, 2H); 3.36 (t, 2H); (3.55) (d, 2H); 3.69 (t, 2H); 3.90 (s, 2H); 3.98 (s, 3H); 4.04 (d, 2H); 4.30 (t, 2H); 7.28 (s, 1H); 7.39 (t, 1H); 7.49 (m, 1H); 7.86 (s, 1H); 7.96 (m, 1H); 9.05 (s, 1H).

EXAMPLE 376

Preparation of Compound 553 in Table 19

An analogous reaction to that described in example 374 but starting with 2-aminopyridine (33 mg, 0.35 mmol) yielded the title compound (45 mg, 32%).

MS ES$^{30}$ : 550.6 (M+H)$^+$ $^1$H NMR (DMSOd$_6$, TFA): 2.31 (t, 2H); 2.35 (s, 3H); 3.16 (t, 2H); 3.36 (t, 2H); 3.55 (d, 2H); 3.69 (t, 2H); 3.98 (s, 3H); 4.04 (m, 4H); 4.30 (t, 2H); 7.30 (m, 2H); 7.87 (s, 1H); 7.95 (d, 1H); 8.05 (m, 1H); 8.40 (d, 1H); 9.04 (s, 1H).

EXAMPLE 377

Preparation of Compound 554 in Table 19

An analogous reaction to that described in example 374 but starting with 3,4 difluoroaniline (50 mg, 0.39 mmol) yielded the title compound (120 mg, 74%).

MS ES$^+$: 585.6 (M+H)$^+$ $^1$H NMR (DMSOd$_6$, TFA): 2.30 (t, 2H); 2.33 (s, 3H); 3.16 (t, 2H); 3.36 (t, 2H); 3.55 (d, 2H); 3.67 (t, 2H); 3.90 (s, 2H); 3.98 (s, 3H); 4.05 (d, 2H); 4.31 (t, 2H); 7.28 (s, 1H); 7.32 (m, 1H); 7.40 (q, 1H); 7.80 (m, 1H); 7.86 (s, 1H); 9.05 (s, 1H).

EXAMPLE 378

Preparation of Compound 555 in Table 20

N'-(2-cyano-5-((2S)-2-hydroxy-3-piperidinylpropoxy)-4-methoxyphenyl)-N,N-dimethylimidoformamide (381 mg, 0.96 mmol) in acetic acid (6 ml) was irradiated in a microwave oven in presence of N-(4-fluoro-3-chlorophenyl)-2-(2-amino-1,3-thiazole-5-yl)acetamide (275 mg, 0.96 mmol) at reflux for 0.5 hour. The solvent was evaporated, and the residue purified by silica gel chromatography, eluant $CH_2Cl_2$/MeOH sat. $NH_3$ 95/5 to 93/7 to give title compound (230 mg, 40%).

MS ES$^+$: 601.5 (M+H)$^+$ $^1$HNMR (DMSOd$_6$, TFA): 1.42 (m, 1H); 1.6–1.9 (m, 5H); 3.02 (m, 2H); 3.28 (m, 2H); 3.52 (m, 2H); 3.99 (s, 5H); 4.19 (d, 2H); 4.43 (m, 1H); 7.35 (s, 1H); 7.40 (t, 1H); 7.48 (m, 1H); 7.64 (s, 1H); 7.91 (s, 1H); 7.95 (m, 1H); 9.08 (s, 1H).

N'-(2-cyano-5-((2S)-2-hydroxy-3-piperidinylpropoxy)-4-methoxyphenyl)-N,N,-dimethylimidoformamide N'-(2-cyano-5-(2S)-oxiranylmethoxy-4-methoxyphenyl)-N,N-dimethylimidoformamide (850 mg, 3.09 mmol) in chloroform (6 ml) and ethanol (12 ml) was irradiated with piperidine (0.46 ml, 4.6 mmol) in a microwave oven at reflux for 10 minutes. The solvent was evaporated and the residue was purified by silica gel chromatography, eluant $CH_2Cl_2$/MeOH 90/10 to give title compound (954 mg, 86%).

MS ES$^+$: 361.6 (M+H)$^+$ $^1$HNMR (DMSOd$_6$): 1.43 (m, 6H); 2.4 (m, 6H); 2.97 (s, 3H); 3.06 (s, 3H); 3.75 (s, 3H); 3.95 (d, 2H); 4.03 (m, 1H); 4.83 (s, 1H); 6.75 (s, 1H); 7.10 (s, 1H); 7.90 (s, 1H).

N'-(2-cyano-5-(2S)-oxiranylmethoxy-4-methoxyphenyl)-N,N-dimethylimidoformamide

N'-(2-cyano-4-methoxy-5-hydroxyphenyl)-N,N-dimethyl-imidoformamide (1 g, 4.57 mmol) in DMF (25 ml)

was reacted with (2S) glycidyl toxylate (1.15 g, 5.02 mmol) in presence of cesium carbonate (5.95 g, 18.3 mmol) at 60° C. under argon for 2 hours. The solvent was evaporated, water was added, and the mixture was extracted with ethylacetate, dried, concentrated and purified by silica gel chromatography, eluant $CH_2Cl_2$/AcOEt 80/20 to 70/30 to give title compound (1.18 g, 94%).

MS ES$^+$: 276.6 (M+H)$^+$ $^1$HNMR (DMSOd$_6$): 2.70 (m, 1H); 2.86 (m, 1H); 2.95 (s, 3H); 3.01 (s, 3H); 3.35 (m, 1H); 3.75 (s, 3H); 3.90 (m, 1H); 4.37 (m, 1H); 6.75 (s, 1H); 7.11 (s, 1H); 7.89 (s, 1H).

methyl-(2-tritylamino-1,3-thiazole-5-yl)acetate

Methyl-(2-amino-1,3-thiazole-5-yl)acetate (1 g, 5.8 mmol) in $CH_2Cl_2$ (15 ml) was reacted with triphenylmethyl chloride (1.73 g, 6.2 mmol) and triethylamine (0.89 ml, 6.4 mmol) at 0° C. for 1.5 hour. Water was added to the mixture which was extracted with ethyl acetate, dried, purified by silica gel chromatography to give title compound (2.21 g, 91%).

$^1$HNMR (DMSOd$_6$): 3.58 (s, 3H); 3.59 (s, 2H); 6.57 (s, 1H); 7.23 (m, 1H); 8.40 (s, 1H).

(2-tritylamino-1,3-thiazol-5-yl)acetic acid

Methyl(2-tritylamino-1,3-thiazole-5-yl)acetate (2 g, 4.8 mmol) in THF (10 ml) and ethanol (10 ml) was reacted with sodium hydroxyde (1N, 7.2 ml, 7.2 mmol) at room temperature for 1.5 hour. The solvent was evaporated, HCl (6N) was added, the solid recovered by filtration to give title compound (1.96 g).

$^1$HNMR (DMSOd$_6$): 3.63 (s, 2H); 5.70 (s, 1H); 7.32 (m, 15H).

N-(4-fluoro-3-chlorophenyl)-2-tritylamino-1,3-thiazole-5-yl)acetamide (2-tritylamino-1,3-thiazol-5-yl)acetic acid (1.96 g, 4.9 mmol) in DMF (25 ml) was reacted with 3-chloro-4-fluoroaniline (1.07 g, 7.3 mmol) in presence of 0-(7-azabenzotriazol-1-yl)-N,N,N',N'-tetramethyluronium hexafluorophosphate (2.42 g, 6.37 mmol) and DIEA (1.7 ml, 9.8 mmol) at 50° C. for 18 hours. DMF was evaporated, the residue taken up in $CH_2Cl_2$/EtOAc, washed with a saturated solution of sodium bicarbonate. The solid precipitating in the organic phase was recovered, the organic phase was evaporated, MeOH was added to the residue to give a solid, a second crop of title compound was thus recovered to give together (1.38 g, 53%).

$^1$HNMR (DMSOd$_6$): 3.56 (s, 2H); 6.61 (s, 1H); 7.28 (m, 17H); 7.88 (m, 1H); 8.41 (s, 1H).

N-(4-fluoro-3-chlorophenyl)-2-(2-amino-1,3-thiazole-5-yl)acetamide

N-(4-fluoro-3-chlorophenyl)-2-(2-tritylamino-1,3-thiazole-5-yl)acetamide (12.28 g, 23 mmol) was dissolved in TFA (100 ml) and water (10 ml). The mixture was stirred at room temperature for 45 minutes. Water (300 ml) was added to the reaction mixture, a solid was recovered by filtration, washed with water and ether. The solid was dissolved in MeOH, and the solution treated with ammonia (pH 8), MeOH was then partially evaporated, water (300 ml) was added and a precipitate of title compound recovered, dried (5.37 g, 81%).

$^1$HNMR (DMSOd$_6$): 3.64 (s, 2H); 6.76 (m, 3H); 7.38 (t, 1H); 7.48 (m, 1H); 7.92 (m, 1H).

EXAMPLE 379

Preparation of Compound 556 in Table 20

An analogous reaction to that described in example 378 but starting with N'-(2-cyano-5-((2S)-2-hydroxy-3-pyrrolidinylpropoxy)$_4$-methoxyphenyl)-N,N,-dimethylimido-formamide (267 mg, 0.77 mmol) yielded title compound (213 mg, 52%).

MS ES$^+$: 587.5 (M+H)$^+$ $^1$HNMR (DMSOd$_6$): 1.68 (m, 4H); 2.5 (m, 5H); 2.66 (m, 1H); 3.88 (s, 2H); 3.96 (s, 3H); 4.00 (m, 1H); 4.07 (m, 1H); 4.20 (m, 1H); 4.95 (m, 1H); 7.26 (s, 1H); 7.36 (s, 1H); 7.37 (m, 1H); 7.47 (m, 1H); 7.95 (m, 1H); 8.11 (s, 1H); 8.66 (s, 1H).

N'-(2-cyano-5-((2S)-2-hydroxy-3-pyrrolinylpropoxy)-4-methoxyphenyl)-N,N-dimethylimidoformamide An analogous reaction to that described in example 378, but starting with pyrrolidine (1.4 ml, 16 mmol) yielded title compound (2.8 g, 74%).

MS ES$^+$: 347.6 (M+H)$^+$ $^1$HNMR (DMSOd$_6$): 1.67 (m, 4H); 1.45 (m, 4H); 1.63 (m, 2H); 2.95 (s, 3H); 3.05 (s, 3H); 3.73 (s, 3H); 3.95 (m, 2H); 4.04 (m, 1H); 4.93 (m, 1H); 6.73 (s, 1H); 7.08 (s, 1H); 7.89 (s, 1H).

EXAMPLE 380

Preparation of Compound 557 in Table 20

An analogous reaction to that described in example 378 but starting with N'-(2-cyano-5-((2S)-2-hydroxy-3-(4-hydroxypiperidinyl)propoxy)$_4$-methoxy-phenyl)-N,N-dimethylimidoformamide (195 mg, 0.52 mmol) yielded title compound (88 mg, 30%).

MS ES$^+$: 617.5, 619.5 (M+H)$^+$ $^1$HNMR (DMSOd$_6$): 1.40 (m, 2H); 1.70 (m, 2H); 2.13 (m, 2H); 2.43 (m, 2H); 2.77 (m, 2H); 3.43 (m, 1H); 3.88 (s, 2H); 3.96 (s, 3H); 4.03 (m, 2H); 4.19 (m, 1H); 4.52 (d, 1H); 4.87 (m, 1H); 7.27 (s, 1H); 7.39 (m, 2H); 7.49 (m, 1H); 7.99 (m, 1H); 8.67 (s, 1H).

N'-(2-cyano-5-((2S)-2-hydroxy-3-(4-hydroxypiperidinyl)propoxy)-4-methoxyphenyl)-N,N'-dimethylimidoformamide An analogous reaction to that described in example 378, but starting with 4-hydroxypiperidine (131 mg, 1.27 mmol) yielded title compound (200 mg, 58%).

MS ES$^+$: 377.6 (M+H)$^+$ $^1$HNMR (DMSOd$_6$): 1.39 (m, 2H); 1.68 (m, 2H); 2.10 (m, 2H); 2.40 (m, 2H); 2.75 (m, 2H); 2.95 (s, 3H); 3.05 (s, 3H); 3.21 (s, 3H); 3.31 (m, 1H); 3.95 (m, 2H); 4.00 (m, 1H); 4.52 (m, 1H); 4.82 (m, 1H); 6.73 (s, 1H); 7.08 (s, 1H); 7.88 (s, 1H).

EXAMPLE 381

Preparation of Compound 558 in Table 20

An analogous reaction to that described in example 378, but starting with N'-(2-cyano-5-((2S)-2-hydroxy-3-(4-tert-butyloxycarbonylpiperazinyl)propoxy)-4-methoxtphenyl)-N,N-dimethylimidoformamide (355 mg, 0.77 mmol) yielded title compound (70 mg, 17%).

MS ES$^+$: 602.4 (M+H)$^+$ $^1$HNMR ($DMSOd_6$): 2.42 (m, 6H); 2.73 (d, 4H); 3.88 (s, 2H); 3.96 (s, 3H); 4.04 (m, 2H); 4.19 (m, 1H); 4.90 (m, 1H); 7.28 (s, 1H); 7.37 (m, 2H); 7.47 (m, 1H); 7.94 (m, 1H); 8.11 (s, 1H); 8.66 (s, 1H).

N'-(2-cyano-5-((2S)-2-hydroxy-3-(4-tert-butyloxycarbonylpiperazinyl)propoxy)-4-methoxyphenyl)-N,N-dimethylimidoformamide An analogous reaction to that described in example 378, but starting with tert-butyloxycarbonylpiperazine (284 mg, 1.53 mmol) yielded title compound (444 mg, 88%).

MS $ES^+$: 462.6 $(M+H)^+$ $^1$HNMR ($DMSOd_6$): 1.39 (s, 9H); 2.40 (m, 6H); 2.95 (s, 3H); 3.04 (s, 3H); 3.30 (m, 4H); 3.72 (s, 3H); 3.95 (m, 2H); 4.02 (m, 1H); 4.91 (d, 1H); 6.74 (s, 1H); 7.09 (s, 1H); 7.88 (s, 1H).

EXAMPLE 382

Preparation of Compound 559 in Table 20

An analogous reaction to that described in example 378, but starting with N'-(2-cyano-5-((2S)-2-hydroxy-3-cyclopentylaminopropoxy)-4-methoxyphenyl)-N,N-dimethylimidoformamide (290 mg, 0.77 mmol) yielded title compound (226 mg, 54%)

MS $ES^+$: 601.4 $(M+H)^+$ $^1$HNMR ($DMSOd_6$): 1.32 (m, 2H), 1.48 (m, 2H); 1.62 (m, 2H); 1.73 (m, 2H); 2.63 (m, 1H) 2.71 (m, 1H); 3.05 (m, 1H); 3.89 (s, 2H); 3.98 (m, 4H); 4.09 (m, 1H); 4.17 (m, 1H); 5.03 (m, 1H); 7.27 (s, 1H); 7.40 (m, 2H); 7.51 (m, 1H); 7.97 (m, 1H); 8.12 (s, 1H); 8.67 (s, 1H).

N'-(2-cyano-5-((2S)-2-hydroxy-3-cyclopentylaminopropoxy)-4-methoxyphenyl)-N,N-dimethylimidoformamide An analogous reaction to that described in example 378, but starting with cyclopentylamine (2.7 ml, 27 mmol) yielded title compound (1.6 g, 82%)

MS $ES^+$: 361.6 $(M+H)^+$ $^1$HNMR ($DMSOd_6$): 1.30 (m, 2H); 1.48 (m, 2H); 1.60 (m, 2H); 1.72 (m, 2H); 2.56 (m, 1H); 2.67 (m, 1H); 2.97 (s, 3H); 3.01 (m, 1H); 3.07 (s, 3H); 3.75 (s, 3H); 3.89 (m, 1H); 4.00 (m, 2H); 5.01 (m, 1H); 6.75 (s, 1H); 7.10 (s, 1H); 7.91 (s, 1H).

EXAMPLE 383

Preparation of Compound 560 in Table 20

An analogous reaction to that described in example 378, but starting with N'-(2-cyano-5-((2S)-2-hydroxy-3-((2-hydroxy-1,1-dimethylethyl)amino)propoxy-4-methoxyphenyl)-N,N-dimethylimidoformamide (350 mg, 0.77 mmol) yielded title compound (147 mg, 34%)

MS $ES^+$: 305.4 $(M+H)^+$ $^1$HNMR ($DMSOd_6$): 0.97 (s, 3H); 0.98 (s, 3H); 2.63 (m, 2H); 3.19 (dd, 2H); 3.89 (m, 3H); 3.98 (s, 3H); 4.10 (m, 1H); 4.18 (m, 1H); 4.56 (m, 1H); 7.29 (s, 1H); 7.39 (m, 2H); 7.50 (m, 1H); 7.97 (m, 1H); 8.13 (s, 1H); 8.68 (s, 1H).

N'-(2-cyano-5-((2S)-2-hydroxy-3-(2-hydroxy-1,1-dimethylethyl)amino)propoxy)-4-methoxyphenyl)-N,N-dimethylimidoformamide An analogous reaction to that described in example 378, but starting with 2-amino-2-methyl-1-propanol (1.8 ml, 18.2 mmol) yielded title compound (1.25 g, 93%).

$^1$HNMR ($DMSOd_6$): 0.93 (s, 3H); 0.94 (s, 3H); 2.58 (m, 2H); 3.19 (m, 2H); 3.73 (s, 3H); 3.80 (m, 1H); 3.97 (m, 1H); 4.03 (m, 1H); 4.50 (m, 1H); 4.95 (m, 1H); 6.75 (s, 1H); 7.10 (s, 1H); 7.91 (s, 1H).

EXAMPLE 384

Preparation of Compound 561 in Table 20

An analogous reaction to that described in example 378, but starting with N-(3,4-difluorophenyl)-2-(2-amino-1,3-thiazole-5-yl)acetamide (200 mg, 0.74 mmol) and acetic acid (3 ml) yielded title compound (263 mg, 60%).

MS $ES^+$: 585.5 $(M+H)^+$ $^1$HNMR ($DMSOd_6$): 1.37 (m, 2H); 1.50 (m, 4H); 2.41 (m, 6H); 3.88 (s, 2H); 3.96 (s, 3H); 4.03 (m, 2H); 4.18 (d, 1H); 4.88 (m, 1H); 7.28 (s, 1H); 7.40 (s, 1H); 7.40 (m, 2H); 7.80 (m, 1H); 8.11 (s, 1H); 8.66 (s, 1H).

N-(3,4-difluorophenyl)-2-(2-amino-1,3-thiazole-5-yl)acetamide

An analogous reaction to that described in example 378, but starting with N-(3,4-difluorophenyl)-2-(2-tritylamino-1,3-thiazole-5-yl)acetamide (1,75 g, 3.42 mmol) yielded title compound (642 mg, 70%).

$^1$HNMR ($DMSOd_6$): 3.62 (s, 2H); 6.73 (s, 1H); 6.74 (s, 2H); 7.28 (m, 1H); 7.37 (q, 1H); 7.77 (m, 1H).

N-(3,4-difluorophenyl)-2-(2-tritylamino-1,3-thiazole-5-yl)acetamide

An analogous reaction to that described in example 378, but starting with 3,4-difluoroaniline (0.97 ml, 9.75 mmol) yielded title compound (1.75 g, 46%).

MS $ES^+$: 512.5 $(M+H)^+$ $^1$HNMR ($DMSOd_6$): 3.54 (s, 2H); 6.58 (s, 1H); 7.25 (m, 17H); 7.71 (m, 1H); 8.39 (s, 1H).

EXAMPLE 385

Preparation of Compound 562 in Table 20

An analogous reaction to that described in example 379 but starting with N-(3,4-difluorophenyl)-2-(2-amino-1,3-thiazole-5-yl)acetamide (200 mg, 0.74 mmol) yielded title compound (226 mg, 53%).

MS $ES^+$: 571.5 $(M+H)^+$ $^1$HNMR ($DMSOd_6$): 1.70 (m, 4H); 2.52 (m, 5H); 2.68 (m, 1H); 3.89 (s, 2H); 3.98 (s, 3H); 4.06 (m, 2H); 4.21 (m, 1H); 4.95 (m, 1H); 7.28 (s, 1H); 7.33 (m, 1H); 7.39 (s, 1H); 7.40 (m, 1H); 7.81 (m, 1H); 8.12 (s, 1H); 8.68 (s, 1H).

EXAMPLE 386

Preparation of Compound 563 in Table 20

An analogous reaction to that described in example 380, but starting with N-(3,4-difluorophenyl)-2-(2-amino-1,3-thiazole-5-yl)acetamide (200 mg, 0.74 mmol) yielded title compound (220 mg, 49%).

MS $ES^+$: 601.5 $(M+H)^+$ $^1$HNMR ($DMSOd_6$): 1.40 (m, 2H); 1.70 (m, 2H); 2.12 (m, 2H); 2.40 (m, 2H); 2.78 (m, 2H) 3.43 (m, 1H); 3.88 (s, 2H); 3.96 (s, 3H); 4.03 (m, 2H); 4.18 (m, 1H); 4.51 (d, 1H); 4.87 (m, 1H); 7.27 (s, 1H); 7.32 (m, 1H); 7.38 (s, 1H); 7.40 (m, 1H); 7.80 (m, 1H); 8.11 (s, 1H); 8.67 (s, 1H).

EXAMPLE 387

Preparation of Compound 565 in Table 20

An analogous reaction to that described in example 382, but starting with N-(3,4-difluorophenyl)-2-(2(amino-1,3- thiazole-5-yl)acetamide (200 mg, 0.74 mmol) yielded title compound (233 mg, 53%).

MS $ES^+$: 585.5 $(M+H)^+$ $^1$HNMR ($DMSOd_6$): 1.32 (m, 2H); 1.47 (m, 2H); 1.61 (m, 2H); 1.72 (m, 2H); 2.63 (m, 1H) 2.72 (m, 1H); 3.05 (m, 1H); 3.89 (s, 2H); 3.97 (m, 4H); 4.09 (m, 1H); 4.16 (m, 1H); 5.05 (m, 1H); 7.27 (s, 1H); 7.34 (m, 1H); 7.38 (s, 1H); 7.42 (m, 1H); 7.82 (m, 1H); 8.12 (s, 1H) 8.67 (s, 1H).

EXAMPLE 388

Preparation of Compound 566 in Table 20

An analogous reaction to that described in example 379 but starting with N-(3-chlorophenyl) 2-(2-amino-1,3-thiazole-5-yl)acetamide (200 mg, 0.74 mmol) yielded title compound (238 mg, 56%).

MS $ES^+$: 569.5 $(M+H)^+$ $^1$HNMR ($DMSOd_6$): 1.70 (s, 1H); 2.52 (m, 5H); 2.68 (m, 1H); 3.90 (s, 2H); 3.98 (s, 3H); 4.06 (m, 2H); 4.21 (m, 1H); 4.97 (m, 1H); 7.14 (d, 1H); 7.27 (s, 1H); 7.37 (m, 2H); 7.48 (d, 1H); 7.85 (m, 1H); 8.12 (s, 1H); 8.68 (s, 1H).

N-(3-chlorophenyl)-2-(2-amino-1,3-thiazole-5-yl) acetamide

An analogous reaction to that described in example 378, but starting with N-(3-chlorophenyl)-2-(2-tritylamino-1,3-thiazole-5-yl)acetamide (3.62 g, 7.1 mmol) yielded title compound (1.6 g, 84%).

$^1$HNMR ($DMSOd_6$): 3.63 (s, 2H); 6.74 (m, 3H); 7.11 (m, 1H); 7.33 (t, 1H); 7.42 (d, 1H); 7.79 (m, 1H).

N-(3-chlorophenyl)-2-(2-tritylamino-1,3-thiazole-5-yl)acetamide

An analogous reaction to that described in example 378, but starting with 3-chloroaniline (1.4 ml, 13 mmol) yielded title compound (3.62 g, 71%).

$^1$HNMR ($DMSOd_6$): 3.55 (s, 2H); 6.59 (s, 1H); 7.21 (m, 18H); 7.76 (m, 1H); 8.39 (s, 1H).

EXAMPLE 389

Preparation of Compound 567 in Table 20

An analogous reaction to that described in example 380, but starting with N-(3-chlorophenyl)-2-(2-amino-1,3-thiazole-5-yl)acetamide (200 mg, 0.75 mmol) yielded title compound (156 mg, 35%).

MS $ES^+$: 599.4, 601.4 $(M+H)^+$ $^1$HNMR ($DMSOd_6$): 1.40 (m, 2H); 1.70 (m, 2H); 2.12 (m, 2H); 2.42 (m, 2H); 2.77 (m, 2H) 3.42 (m, 1H); 3.89 (s, 2H); 3.96 (s, 3H); 4.02 (m, 2H); 4.18 (m, 1H); 4.52 (d, 1H); 4.89 (m, 1H); 7.12 (d, 1H); 7.26 (s, 1H); 7.35 (t, 1H); 7.38 (s, 1H); 7.46 (d, 1H); 7.84 (m, 1H); 8.11 (s, 1H); 8.67 (s, 1H).

EXAMPLE 390

Preparation of Compound 568 in Table 20

An analogous reaction to that described in example 382, but starting with N-(3-chlorophenyl)-2-(2-amino-1,3-thiazole-5-yl)acetamide (200 mg, 0.75 mmol) yielded title compound (255 mg, 58%).

MS $ES^+$: 583.5, 585.5 $(M+H)^+$ $^1$HNMR ($DMSOd_6$): 1.32 (m, 2H); 1.48 (m, 2H); 1.62 (m, 2H); 1.73 (m, 2H); 2.63 (m, 1H) 2.72 (m, 1H); 3.04 (m, 1H); 3.90 (s, 2H); 3.97 (m, 4H); 4.09 (m, 1H); 4.16 (m, 1H); 5.05 (m, 1H); 7.12 (d, 1H); 7.27 (s, 1H); 7.37 (t, 1H); 7.39 (s, 1H); 7.48 (m, 1H); 8.12 (s, 1H) 8.68 (s, 1H).

EXAMPLE 391

Preparation of Compound 569 in Table 20

An analogous reaction to that described in example 383, but starting with N-(3-chlorophenyl)-2-(2-amino-1,3-thiazole-5-yl)acetamide (200 mg, 0.74 mmol) yielded title compound (130 mg, 30%).

MS $ES^+$: 587.5, 589.5 $(M+H)^+$ $^1$HNMR ($DMSOd_6$): 0.97 (s, 6H); 2.63 (m, 2H); 3.19 (m, 2H); 3.90 (m, 3H); 3.98 (s, 3H); 4.10 (m, 1H); 4.18 (m, 1H); 4.55 (m, 1H); 5.03 (m, 1H); 7.13 (d, 1H); 7.29 (s, 1H); 7.37 (t, 1H); 7.39 (s, 1H); 7.48 (d, 1H); 7.86 (m, 1H); 8.13 (s, 1H); 8.68 (s, 1H).

EXAMPLE 392

Preparation of Compound 570 in Table 20

An analogous reaction to that described in example 381, but starting with N-(3-chlorophenyl)-2-(2-amino-1,3-thiazole-5-yl)acetamide (200 mg, 0.75 mmol) yielded title compound (211 mg, 48%).

MS $ES^+$: 584.4 $(M+H)^+$ $^1$HNMR ($DMSOd_6$): 2.37 (m, 6H); 2.70 (m, 4H); 3.89 (s, 2H); 3.96 (s, 3H); 4.05 (m, 2H); 4.19 (m, 1H); 4.90 (m, 1H); 7.12 (d, 1H); 7.27 (s, 1H); 7.35 (t, 1H); 7.37 (s, 1H); 7.47 (d, 1H); 7.84 (m, 1H); 8.10 (s, 1H); 8.66 (s, 1H).

EXAMPLE 393

Preparation of Compound 571 in Table 20

An analogous reaction to that described in example 388, but starting with N'-(2-cyano-5-((2S)-2-hydroxy-3-methoxy)propoxy-4-methoxyphenyl)-N,N-dimethyl imidoformamide (252 mg, 0.82 mmol) yielded title compound (200 mg, 50%).

MS $ES^+$: 530.4, 532.4 $(M+H)^+$ $^1$HNMR ($DMSOd_6$): 3.22 (s, 3H); 3.42 (m, 2H); 3.91 (s, 2H); 3.98 (s, 2H); 4.10 (m, 3H); 5.21 (d, 1H); 7.13 (d, 1H); 7.26 (s, 1H); 7.37 (t, 1H); 7.39 (s, 1H); 7.48 (d, 1H); 7.85 (m, 1H); 8.13 (m, 1H); 8.69 (s, 1H).

N'-(2-cyano-5-((2S)-2-hydroxy-3-methoxy)propoxy-4-methoxy-phenyl)-N,N-dimethylimidoformamide N'-(2-cyano-5-(2S)-oxiranylmethoxy-4-(methoxyphenyl)-N,N-dimethylimidoformamide (1 g, 3.6 mmol) in methanol (80 ml) was treated with sodium methoxide (10 g, 218 mmol) at reflux in a microwave oven for 0.5 hour. The solvent was evaporated and the mixture purified by silica gel chromatography, Eluant $CH_2Cl_2$/MeOH 95/5 to give title compound (896 mg, 80

$^1$HNMR ($DMSOd_6$): 2.97 (s, 1H); 3.07 (s, 1H); 3.29 (s, 1H); 3.38 (m, 2H); 3.75 (s, 3H); 3.98 (m, 3H); 5.16 (d, 1H); 6.75 (s, 1H); 7.10 (s, 1H); 7.93 (s, 1H).

EXAMPLE 394

Preparation of Compound 572 in Table 20

An analogous reaction to that described in example 378, but starting with N-(3-chlorophenyl)-2-(2-amino-1,3-thiazole-5-yl)acetamide (200 mg, 0.75 mmol) yielded title compound (268 mg, 61%).

MS $ES^+$: 583.5 $(M+H)^+$ $^1$HNMR (DMSO$d_6$): 1.38 (m, 2H); 1.50 (m, 4H); 2.43 (m, 6H); 3.91 (s, 2H); 3.98 (s, 3H); 4.05 (m, 2H); 4.21 (m, 1H); 4.88 (m, 1H); 7.14 (d, 1H); 7.29 (s, 1H); 7.37 (t, 1H); 7.39 (s, 1H); 7.48 (d, 1H); 7.85 (m, 1H); 8.12 (s, 1H); 8.68 (s, 1H).

EXAMPLE 395

Preparation of Compound 573 in Table 20

An analogous reaction to that described in example 378, but starting with N-(3,5-difluorophenyl)-2-(2-amino-1,3-thiazole-5-yl)acetamide (200 mg, 0.74 mmol) yielded title compound (157 mg, 36%).

MS $ES^+$: 585.5 $(M+H)^+$ $^1$HNMR (DMSO$d_6$): 1.37 (m, 2H); 1.50 (m, 4H); 2.40 (m, 6H); 3.90 (s, 2H); 3.96 (s, 3H); 4.05 (m, 2H); 4.19 (m, 1H); 4.88 (m, 1H); 6.92 (m, 1H); 7.28 (s, 1H); 7.34 (m, 2H); 7.38 (s, 1H); 8.11 (s, 1H); 8.67 (s, 1H).

N-(3,5-difluorophenyl)-2-(2-amino-1,3-thiazole-5-yl) acetamide

An analogous reaction to that described in example 378, but starting with N-(3,5-difluorophenyl)-2-(2-tritylamino-1,3-thiazole-5-yl)acetamide (11.4 g, 28.5 mmol) yielded title compound (4.75 g, 62%).

$^1$HNMR (DMSO$d_6$) 3.64 (s, 2H); 6.74 (s, 1H); 6.76 (s, 2H); 6.89 (m, 1H); 7.29 (m, 2H).

N-(3,5-difluorophenyl)-2-(2-tritylamino-1,3-thiazole-5-yl)acetamide

An analogous reaction to that described in example 378, but starting with 3,5-difluoroaniline (1.68 g, 13 mmol) yielded title compound (3.53 g, 69%).

$^1$HNMR (DMSO$d_6$: 3.56 (s, 2H); 6.59 (s, 1H); 6.90 (m, 1H); 7.28 (m, 17H); 8.40 (s, 1H).

EXAMPLE 396

Preparation of Compound 574 in Table 20

An analogous reaction to that described in example 379 but starting with N-(3,5-difluorophenyl)-2-(2-amino-1,3-thiazole-5-yl)acetamide (200 mg, 0.74 mmol) yielded title compound (200 mg, 47%)

MS $ES^+$: 571.5 $(M+H)^+$ $^1$HNMR (DMSO$d_6$: 1.65 (m, 4H); 2.50 (m, 5H); 2.65 (m, 1H); 3.91 (s, 1H); 3.96 (s, 3H); 4.04 (m, 2H); 4.20 (m, 1H); 4.95 (m, 1H); 6.92 (m, 1H); 7.26 (s, 1H); 7.34 (m, 2H); 7.38 (s, 1H); 8.1 (s, 1H); 8.66 (s, 1H).

EXAMPLE 397

Preparation of Compound 575 in Table 20

An analogous reaction to that described in example 383 but starting with N-(3,5-difluorophenyl)-2-(2-amino-1,3-thiazole-5-yl)acetamide (200 mg, 0.74 mmol) yielded title compound (177 mg, 40%).

MS $ES^+$: 589.4 $(M+H)^+$ $^1$HNMR (DMSO$d_6$: 0.96 (s, 3H); 0.97 (s, 3H); 2.64 (m, 2H); 3.19 (dd, 2H); 3.92 (m, 3H); 3.98 (s, 3H); 4.09 (m, 1H); 4.20 (m, 1H); 4.56 (m, 1H); 5.05 (m, 1H); 6.94 (m, 1H); 7.29 (s, 1H); 7.35 (m, 2H); 7.39 (s, 1H); 8.12 (s, 1H); 8.68 (s, 1H).

EXAMPLE 398

Preparation of Compound 576 in Table 20

An analogous reaction to that described in example 381 but starting with N-(3,5-difluorophenyl)-2-(2-amino-1,3-thiazole-5-yl)acetamide (200 mg, 0.74 mmol) yielded title compound (40 mg, 9%).

MS $ES^+$: 628.5 $(M+H)^+$ $^1$HNMR (DMSO$d_6$: 2.05 (s, 3H); 2.40 (m, 4H); 2.57 (m, 2H); 2.69 (m, 4H); 3.91 (s, 2H); 3.97 (s, 3H); 4.35 (m, 2H); 5.31 (m, 1H); 6.93 (m, 1H); 7.33 (s, 1H); 7.35 (m, 2H); 7.39 (s, 1H); 8.13 (s, 1H); 8.68 (s, 1H).

EXAMPLE 399

Preparation of Compound 577 in Table 20

An analogous reaction to that described in example 381 but starting with N-(3,5-difluorophenyl)-2-(2-amino-1,3-thiazole-5-yl)acetamide (200 mg, 0.74 mmol) yielded title compound (192 mg, 44%).

MS $ES^+$: 586.5 $(M+H)^+$ $^1$HNMR (DMSO$d_6$: 2.42 (m, 6H); 2.74 (m, 4H); 3.92 (s, 2H); 3.98 (s, 3H); 4.09 (m, 2H); 4.20 (m, 1H); 4.92 (m, 1H); 6.93 (m, 1H); 7.29 (s, 1H); 7.35 (m, 2H); 7.39 (s, 1H); 8.12 (s, 1H); 8.68 (s, 1H).

EXAMPLE 400

Preparation of Compound 578 in Table 20

An analogous reaction to that described in example 379 but starting with N-(3-fluorophenyl) 2-(2-amino-1,3-thiazole-5-yl)acetamide (200 mg, 0.8 mmol) yielded title compound (156 mg, 35%).

MS $ES^+$: 553.5 $(M+H)^+$ $^1$HNMR (DMSO$d_6$: 1.70 (m, 4H); 2.5 (m, 5H); 2.67 (m, 1H); 3.90 (s, 2H); 3.98 (s, 3H); 4.06 (m, 2H); 4.20 (m, 1H); 4.97 (m, 1H); 6.92 (m, 1H); 7.28 (m, 1H); 7.35 (m, 2H); 7.39 (s, 1H); 7.63 (m, 1H); 8.12 (s, 1H); 8.68 (s, 1H).

N-(3-fluorophenyl)-2-(2-amino-1,3-thiazole-5-yl) acetamide

An analogous reaction to that described in example 378 but starting with N-(3-fluorophenyl)-2-(2-tritylamino-1,3-thiazole-5-yl)acetamide (14.6 g, 38.4 mmol) yielded title compound (6.21 g, 65%).

$^1$HNMR (DMSO$d_6$: 3.65 (s, 2H); 6.76 (m, 3H); 6.89 (t, 1H); 7.35 (m, 2H); 7.59 (d, 1H).

N-(3-fluorophenyl)$_2$-(2-tritylamino-1,3-thiazole-5-yl)acetamide

An analogous reaction to that described in example 378 but starting with 3-fluoroaniline yielded title compound (14.6 g, 79%).

$^1$HNMR (DMSO$d_6$: 3.56 (s, 2H); 6.61 (s, 1H); 6.89 (t, 1H); 7.25 (m, 17H); 7.56 (d, 1H); 8.41 (s, 1H).

EXAMPLE 401

Preparation of Compound 579 in Table 20

An analogous reaction to that described in example 378 but starting with N-(3-fluororphenyl)-2-(2-amino-1,3-thiazole-5-yl)acetamide (200 mg, 0.8 mmol) yielded title compound (214 mg, 47%).

MS $ES^+$: 567.6 $(M+H)^+$ $^1$HNMR (DMSO$d_6$): 1.38 (m, 2H); 1.52 (m, 4H); 2.42 (m, 6H); 3.91 (s, 2H); 3.98 (s, 3H); 4.04 (m, 2H); 4.20 (m, 1H); 4.89 (m, 1H); 6.91 (m, 1H); 7.29 (s, 1H); 7.37 (m, 1H); 7.39 (s, 1H); 7.63 (m, 1H); 8.13 (s, 1H); 8.68 (s, 1H).

EXAMPLE 402

Preparation of Compound 580 in Table 20

An analogous reaction to that described in example 381 but starting with N-(3-fluorophenyl)-2-(2-amino-1,3-thiazole-5-yl)acetamide (200 mg, 0.8 mmol) yielded title compound (210 mg, 46%).

MS $ES^+$: 568.5 $(M+H)^+$ $^1$HNMR (DMSO$d_6$: 2.38 (m, 6H); 2.70 (m, 4H); 3.89 (s, 2H); 3.96 (s, 3H); 4.02 (m, 2H); 4.19 (m, 1H); 4.98 (m, 1H); 6.89 (m, 1H); 7.27 (s, 1H); 7.32 (m, 2H); 7.37 (s, 1H); 7.61 (m, 1H); 8.10 (s, 1H); 8.66 (s, 1H).

EXAMPLE 403

Preparation of Compound 581 in Table 20

An analogous reaction to that described in example 381 but starting with N-(3-fluorophenyl)-2-(2-amino-1,3-thiazole-5-yl)acetamide (200 mg, 0.8 mmol) yielded title compound (35 mg, 7%).

MS $ES^+$: 610.5 $(M+H)^+$ $^1$HNMR (DMSO$d_6$: 2.03 (s, 3H); 2.38 (m, 4H); 2.57 (m, 2H); 2.69 (m, 4H); 3.88 (s, 2H); 3.95 (s, 3H); 4.34 (m, 2H); 5.30 (m, 1H); 6.89 (m, 1H); 7.31 (s, 1H); 7.34 (m, 2H); 7.37 (s, 1H); 7.62 (m, 1H); 8.11 (s, 1H); 8.66 (s, 1H).

EXAMPLE 404

Preparation of Compound 582 in Table 20

An analogous reaction to that described in example 382 but starting with N-(3-fluorophenyl)-2-(2-amino-1,3-thiazole-5-yl)acetamide (200 mg, 0.8 mmol) yielded title compound (196 mg, 43%).

MS $ES^+$: 567.5 $(M+H)^+$ $^1$HNMR (DMSO$d_6$): 1.30 (m, 2H); 1.47 (m, 2H); 1.61 (m, 2H); 1.73 (m, 3H); 2.62 (m, 1H) 2.71 (m, 1H); 3.0 (m, 1H); 3.89 (m, 1H); 3.97 (s, 3H); 4.07 (m, 1H); 4.13 (m, 1H); 5.03 (m, 1H); 6.90 (m, 1H); 7.25 (s, 1H); 7.35 (m, 2H); 7.37 (s, 1H); 7.62 (m, 1H); 8.10 (s, 1H); 8.66 (s, 1H).

EXAMPLE 405

Preparation of Compound 583 in Table 21

4-((2-amino-1,3-thiazole-5-yl)acetic acid)-6,7-dimethoxyquinazoline (173 mg, 0.5 mmol) in NMP (2 ml) was reacted with 3,5-difluoroaniline (98 mg, 0.75 mmol) in the presence of 0-(7-azabenzotriazol-1-yl)-N,N,N',N'-tetramethyluronium hexafluorophosphate (285 mg, 0.75 mmol) and DIEA (130 μl, 0.75 mmol) at 50° C. for 20 hours. The mixture was cooled, dimethylamine (2M MeOH, 2 ml) was added, and the resulting solution was stirred at room temperature for 15 hours, MeOH was evaporated, and water (20 ml) added to the mixture, the precipitate was recovered, washed with water, and purified by silicagel chromatography, eluant $CH_2Cl_2$/MeOH 50/40/10 to give title compound (22 mg, 10%).

$^1$HNMR (DMSO$d_6$): 3.90 (s, 2H); 3.95 (s, 6H); 6.93 (t, 1H); 7.26 (s, 1H); 7.34 (d, 2H); 7.39 (s, 1H); 8.12 (s, 1H); 8.68 (s, 1H).

4-((2-amino-1,3-thiazole-5-yl)acetic acid)-6,7-dimethoxyquinazoline 4-(methyl(2-amino-1,3-thiazole-5-yl)acetate)-6,7-dimethoxyquinazoline (3.92 g, 10.9 mmol) in ethanol 50 ml was treated with sodium hydroxyde (2N, 27 ml, 54.5 mmol) for 45 minutes. The solvent was evaporated, the residue dissolved in $CH_2Cl_2$/MeOH triethylamine (3 eq.) was added the solid removed by filtration, the filtrate was evaporated and triturated with ethanol to give title compound as a solid (1.88 g, 50%).

$^1$HNMR (DMSO$d_6$): 3.83 (s, 2H); 3.96 (s, 6H); 7.27 (s, 1H); 7.35 (s, 1H); 8.13 (s, 1H) 8.69 (s, 1H).

4-(methyl(2-amino-1,3-thiazole-5-yl)acetate)-6,7-dimethoxyquinazoline

N'-(2-cyano-4,5-dimethoxyphenyl)-N,N-dimethylimidoformamide (3.5 g, 15 mmol) in acetic acid (35 ml) was reacted with methyl (2-amino-1,3-thiazole-5-yl) acetate (3.22 g, 18.7 mmol) at reflux for 4 hours. The solvent was evaporated and the residue purified by silicagel chromatography, Eluant $CH_2Cl_2$/MeOH 95/5 to give title compound (3.92 g, 73%).

$^1$HNMR (DMSO$d_6$): 3.69 (s, 3H); 3.95 (s, 2H); 3.96 (s, 6H); 7.27 (s, 1H); 7.38 (s, 1H); 8.12 (s, 1H); 8.69 (s, 1H).

EXAMPLE 406

Preparation of Compound 584 in Table 21

An analogous reaction to that described in example 405 but starting with 3-chloroaniline (80 μl, 0.75 mmol) yielded title compound (81 mg, 26%).

MS $ES^+$: 456.4,458.4 $(M+H)^+$ $^1$HNMR (DMSO$d_6$): 3.91 (s, 2H); 3.96 (s, 6H); 7.14 (d, 1H); 7.28 (s, 1H); 7.37 (t, 1H); 7.48 (d, 1H); 7.85 (m, 1H); 8.13 (s, 1H); 8.69 (s, 1H).

EXAMPLE 407

Preparation of Compound 585 in Table 21

An analogous reaction to that described in example 405 but starting 3-chloro-4-fluoroaniline (110 mg, 0.75 mmol) yielded title compound (93.7 mg, 40%).

MS $ES^+$: 474.4, 476.4 $(M+H)^{+1}$NMR: 3.90 (s, 2H); 3.97 (s, 3H); 7.28 (s, 1H); 7.40 (m, 1H); 7.40 (s, 1H); 7.50 (m, 1H) 7.96 (m, 1H); 8.14 (s, 1H); 8.70 (s, 1H).

EXAMPLE 408

Preparation of Compound 586 in Table 21

An analogous reaction to that described in example 405 but starting 3,4-difluoroaniline (75 mg, 0.75 mmol) yielded title compound (130 mg, 60%).

MS $ES^+$: 458.5 $(M+H)^+$ $^1$HNMR: 3.89 (s, 2H); 3.97 (s, 6H); 7.28 (s, 1H); 7.33 (m, 1H); 7.40 (s, 1H); 7.41 (m, 1H); 7.82 (m, 1H); 8.14 (s, 1H); 8.69 (s, 1H).

EXAMPLE 409

Preparation of Compound 587 in Table 22

4-((2-amino-1,3-thiazole-5-yl)(hydroxy)acetic acid)-6-methoxy-7-(3-morpholinopropoxy)quinazoline (143 mg, 0.3 mmol) in DMF (4 ml) was reacted with aniline 30 (36 mg, 0.39 mmol) 1-(3-dimethylaminopropyl)-3-ethylcarbodiimide hydrochloride (63 mg, 0.33 mmol), 2-hydroxypyridine N-oxyde (33 mg, 0.3 mmol) and DIEA (36 mg, 0.3 mmol) at 90° C. for 1 hour. The mixture was cooled, diluted with $CH_2Cl_2$ (8 ml) and purified by silica gel chromatography, Eluant $CH_2Cl_2$/MeOH 90/10 to 85/15. The combined fractions containing product were evaporated, the residue was dissolved in MeOH, water was added and the precipitate recovered, dissolved in MeOH/$CH_2Cl_2$, dried, concentrated to give title compound (145 mg, 88%).

MS $ES^+$: 551.6 $(M+H)^+$ $^1$HNMR ($DMSOd_6$, TFA): 2.31 (t, 2H); 3.15 (t, 2H); 3.34 (t, 2H); 3.55 (d, 2H); 3.71 (t, 2H) 3.98 (s, 3H); 4.03 (d, 2H); 4.31 (t, 2H); 5.47 (s, 1H); 7.11 (t, 1H); 7.31 (s, 1H); 7.33 (t, 2H); 7.70 (s, 1H); 7.73 (d, 21); 7.92 (s, 1H); 9.12 (s, 1H).

4-(2-amino-1,3-thiazole-5-yl)-6-methoxy-7-(3-morpholinopropoxy)quinazoline

N'-(2-cyano-4-methoxy-5-(3-morpholinopropoxy) phenyl)-N,N-dimethylimidoformamide (692 mg, 2 mmol) was reacted with amino-1,3-thiazole (240 mg, 2.4 mmol) in acetic acid (6.9 ml) at reflux for 4 hours. The mixture was concentrated, the residue dissolved in AcOEt, washed with aqueous sodium bicarbonate, the organic phase was dried, concentrated, the residual oil triturated in ether to give a solid (560 mg, 70%).

MS $ES^+$: 402.6 $(M+H)^+$ $^1$HNMR ($DMSOd_6$, TFA): 2.29 (t, 2H); 3.16 (t, 2H); 3.36 (t, 2H); 3.56 (d, 2H); 3.69 (t, 2H); 3.99 (s, 3H); 4.04 (d, 2H); 4.31 (t, 2H); 7.32 (s, 1H); 7.47 (d, 1H); 7.75 ((d, 1H); 7.95 (s, 1H); 9.11 (s, 1H).

4-((2-amino-1,3-thiazole-5-yl)(hydroxy)acetic acid)-6-methoxy-7-(3-morpholinopropoxy)quinazoline 4-(2-amino-1,3-thiazole-5-yl)-6-methoxy-7-(3-morpholinopropoxy)quinazoline (1.6 g, 4 mmol) in water (16 ml), MeOH (16 ml), was reacted with glyoxylic acid (740 mg, 8 mmol) at pH 11.5 (NaOH 6N) and 45–50° C. for 6 hours. Methanol was evaporated, and the pH of the aqueous phase adjusted to 3 (HCl 6N), and the solution poured on a strong cation exchanger (isolute®) column, washed with water (120 ml), methanol (120 ml) and eluted with $CH_2Cl_2$/MeOH, $NH_3$ (3N) 1/1 200 ml to give title compound (1.58 g, 83%).

$^1$HNMR ($DMSOd_6$, TFA): 2.31 (t, 2H); 3.15 (t, 2H); 3.35 (t, 2H); 3.54 (d, 2H); 3.68 (t, 2H); 3.98 (s, 3H); 4.03 (d, 2H); 4.30 (t, 2H); 5.38 (s, 1H); 7.32 (s, 1H); 7.68 (s, 1H); 7.91 (s, 1H); 9.12 (s, 1H).

EXAMPLE 410

Preparation of Compound 588 in Table 22

An analogous reaction to that described in example 409 but starting with 3,4(difluoroaniline (34 mg, 0.26 mmol) yielded title compound (30 mg, 26%).

MS $ES^+$: 587.5 $(M+H)^+$ $^1$HNMR ($DMSOd_6$, TFA): 2.31 (t, 2H); 3.16 (t, 2H); 3.35 (t, 2H); 3.54 (d, 2H); 3.69 (t, 2H) 3.98 (s, 3H); 4.04 (d, 2H); 4.30 (t, 2H); 5.48 (s, 1H); 7.32 (s, 1H); 7.40 (q, 1H); 7.57 (m, 1H); 7.70 (s, 1H); 7.92 (m, 2H); 9.12 (s, 1H).

EXAMPLE 411

Preparation of Compound 589 in Table 22

N'-(2-cyano-4-methoxy-5-(3-N-methylpiperazinylpropoxy)$_4$-methoxyphenyl)-N,N-dimethylimidoformamide (144 mg, 0.4 mmol) was reacted with N-(3,4-difluorophenyl)-2-(2-amino-1,3-thiazole-5-yl)-2-hydroxyacetamide (137 mg, 0.4 mmol) in acetic acid (350 μl) at reflux for 40 minutes. The solvent was removed, and the residue purified by silica gel chromatography, Eluant $CH_2Cl_2$/MeOH/Et3N, 90.10.1 to give title compound (180 mg, 37%).

MS $ES^+$: 600.5 $(M+H)^+$ $^1$HNMR ($DMSOd_6$, TFA): 2.30 (t, 2H); 2.94 (s, 3H); 3.1–4.1 (m, 8H); 3.44 (t, 2H); 3.99 (s, 3H); 4.30 (t, 2H); 5.48 (s, 1H); 7.32 (s, 1H); 7.40 (q, 1H); 7.57 (m, 1H); 7.70 (s, 1H); 7.92 (m, 2H); 9.12 (s, 1H).

Methyl(2-tert-butoxycarbonylamino-1,3-thiazole-5-yl)acetate

Methyl(2-amino-1,3-thiazol-5-yl)acetate (4.3 g, 25 mmol) was reacted with di-tert-butyl dicarbonate (10.9 g, 50 mmol) neat, at 100° C. for 2 hours. The cold mixture was triturated in ether to give title compound as a solid (4.3 g, 63%).

$^1$HNMR ($DMSOd_6$): 1.48 (s, 9H); 3.66 (s, 3H); 3.86 (s, 2H); 7.17 (s, 1H).

Methyl(2-tert-butoxycarbonylamino-1,3-thiazole-5-yl)(oxo)acetate

Methyl(2-tert-butoxycarbonylamino 1,3-thiazole-5-yl) acetate (4.08 g, 15 mmol) in dioxane (60 ml) was reacted with selenium dioxide (4 g, 36 mmol) at reflux for 45 minutes. The mixture was cooled, $CH_2Cl_2$/MeOH 8/2 (150 ml) was added, the insoluble material was filtered, the organic phase was washed with a saturated solution of sodium bicarbonate, and extracted with $CH_2Cl_2$, dried, purified by chromatography over alumina, eluant $CH_2Cl_2$/MeOH 9/1 to give title compound (1 g, 23%).

$^1$HNMR ($DMSOd_6$): 1.57 (s, 9H); 3.94 (s, 3H); 8.48 (s, 1H).

(2-tert-butoxycarbonylamino-1,3-thiazole-5-yl)(oxo) acetic acid

Methyl(2-tert-butoxycarbonylamino-1,3-thiazole-5-yl) (oxo)acetate (1.14 g, 4 mmol) in ethanol (10 ml) was treated with sodium hydroxyde (2N, 4 ml, 8 mmol) for 3M minutes at room temperature. Ethanol was removed, the aqueous solution was acidified (pH 3). The solid was recovered, dried to give title product (900 mg, 82%).

$^1$HNMR ($DMSOd_6$): 1.53 (s, 9H); 8.41 (s, 1H).

N-(3,4-difluorophenyl)-2-(2-tert-butoxycarbonylamino-1,3-thiazole-5-yl)(oxo) acetamide 2-tert-butoxycarbonylamino-1,3-thiazole-5-yl)(oxo) acetic acid (136 mg, 0.5 mmol) in DMF (2 ml) was reacted with 3,4-difluoroaniline (77 mg, 0.6 mmol) in presence of 0-(7-azabenzotriazol-1-yl)-N,N,N',N'-tetramethyluronium hexafluorophosphate (203 mg, 0.55 mmol) and DIEA (77 mg, 0.6 mmol) for 15 minutes. The mixture was diluted with water, the solid was filtered, washed with water, dried, to give title compound (162 mg, 84%).

$^1$HNMR ($DMSOd_6$): 1.53 (s, 9H); 7.48 (q, 1H); 7.68 (m, 1H); 7.98 (m, 1H); 8.61 (s, 1H).

N-(3,4-difluorophenyl)-2-(2-tert-butoxycarbonylamino-1,3-thiazole-5-yl)-2-hydroxyacetamide N-(3,4-difluorophenyl)-2-(2-tert-butoxycarbonylamino-1,3-thiazole-5-yl) (oxo)acetamide (938 mg, 2.4 mmol) in THF (50 ml) and MeOH (10 ml) was treated with sodium borohydride (93 mg, 2.4 mmol) for 30 minutes. The mixture was evaporated, the residue dissolved in ethanol (3 ml) water (25 ml) was added, and the pH adjusted to 6, more water was added, a solid was recovered, dried, recristalized in ether/petroleum ether to give title compound (850 mg, 90%).

$^1$HNMR ($DMSOd_6$): 1.48 (s, 9H); 5.34 (d, 1H); 6.78 (d, 1H); 7.33 (s, 1H); 7.40 (s, 1H) 7.56 (m, 1H); 7.90 (m, 1H).

N-(3,4-difluorophenyl)-2-(2-tert-butoxycarbonylamino-1,3-thiazole-5-yl)-2-hydroxyacetamide (847 mg, 2.2 mmol) in $CH_2Cl_2$ (12 ml) and TFA (4 ml) was stirred at room temperature for 3 hours. The solvent was evaporated, the residue dissolved in $MeOH/H_2O$, the pH adjusted to 7 and the mixture was extracted with ethyl acetate. The organic layer was dried, evaporated, the residue was triturated in ether, the solid filtered to give title compound (515 mg, 82%).

$^1$HNMR ($DMSOd_6$): 5.17 (d, 1H); 6.51 (d, 1H); 6.91 (m, 3H); 7.39 (s, 1H); 7.52 (m, 1H); 7.87 (m, 1H).

EXAMPLE 412

Preparation of Compound 590 in Table 22

N'-(2-cyano-4-methoxy-5-(3-piperidinylpropoxy)$_4$-methoxyphenyl)-N,N-dimethylimidoformamide (100 mg, 0.29 mmol) was reacted with N-(3-fluorophenyl)-2-(2-amino-1,3-thiazole-5-yl)-2-hydroxyacetamide (82 mg, 0.3 mmol) in acetic acid (260 mg) at 105° C. for 40 minutes. The mixture was evaporated and purified by silica gel chromatography, eluant $CH_2Cl_2$/MeOH($NH_3$ 3N) 9/1 to give title compound (42 mg, 26%).

MS ES$^+$: 567.5 (M+H)$^+$ $^1$HNMR ($DMSOd_6$): 1.4 (m, 2H); 1.51 (m, 4H); 1.95 (t, 2H); 2.40 (m, 6H); 3.95 (s, 3H); 4.19 (t, 2H); 5.41 (d, 1H); 6.78 (d, 1H); 6.91 'm, 1H); 7.25 (s, 1H); 7.35 (q, 1H); 7.50 (s, 1H); 7.55 (d, 1H); 7.71 (m, 1H); 8.10 (s, 1H); 8.68 (s, 1H).

N'-(2-cyano-4-methoxy-5-(3-piperidinylpropoxy)-4-methoxyphenyl)-N,N-dimethylimidoformamide N'-(2-cyano-4-methoxy-5-(3-chloropropoxy)$_4$-methoxyphenyl)-N,N-dimethylimidoformamide (3 g, 10 mmol) in acetonitrile (50 ml) was reacted with piperidine (10 ml, 100 mmol) in presence of KI (300 mg, 1.8 mmol) and $K_2CO_3$ (2.1 g, 0.015 mmol) at 75° C. under argon for 3 hours. The solvent was evaporated, and the residue purified by silica gel chromatography, Eluant $CH_2Cl_2$/MeOH, $NH_3$ 3N 95/5 to give title compound (3.48 g, 100%).

MS ES$^+$: 345.6 (M+H)$^+$ $^1$HNMR ($DMSOd_6$): 1.4 (m, 2H); 1.50 (m, 4H); 1.88 (m, 2H); 2.35 (m, 6H); 2.95 (s, 3H); 3.05 (s, 3H); 3.72 (s, 3H); 4.05 (t, 2H); 6.72 (s, 1H); 7.07 (s, 1H); 7.89 (s, 1H).

N-3-fluorophenyl)-2-(2-amino-1,3-thiazole-5-yl)-2-hydroxyacetomide

An analogous reaction to that described in example 411, but starting with N-(3-fluorobenzyl)-2-(2-tert-butoxycarbonylamino-1,3-thiazole-5-yl)-2-hydroxyacetamide (2.55 g, 0.69 mmol) yielded title compound (1.37 g, 75%).

MS ES$^+$: 268.5 (M+H)$^+$ $^1$HNMR ($DMSOd_6$): 5.16 (d, 1H); 6.45 (d, 1H); 6.90 (m, 4H); 7.34 (q, 1H); 7.49 (d, 1H); 7.70 (m, 1H).

N-(3-fluorophenyl)-2-(2-tert-butoxycarbonylamino-1,3-thiazole-5-yl)-2-hydroxyacetamide An analogous reaction to that described in example 411, but starting with N-(3-fluorophenyl)-2-(2-tert-butoxycarbonylamino-1,3-thiazole-5-yl)(oxo)acetamide (2.92 g, 8 mmol) yielded title compound (2.59 g, 88%).

$^1$HNMR ($DMSOd_6$): 1.48 (s, 9H); 5.34 (d, 1H); 6.74 (d, 1H); 6.90 (m, 1H); 7.33 (m, 2H); 7.54 (d, 1H); 7.70 (m, 1H).

N-(3-fluorophenyl)-2-(2-tert-butoxycarbonylamino-1,3-thiazole-5-yl) (oxo)acetamide An analogous reaction to that described in example 411, but starting with 3-fluoroaniline (1.6 g, 14.4 mmol) yielded title compound (4.06 g, 93%).

$^1$HNMR ($DMSOd_6$): 1.54 (s, 9H); 7.01 (m, 1H); 7.42 (m, 1H); 7.69 (m, 1H); 7.80 (m, 1H); 8.6 (s, 1H).

EXAMPLE 413

Preparation of Compound 591 in Table 22

An analogous reaction to that described in example 412, but starting with N-(3-chlorophenyl)-2-(2-amino-1,3-thiazole-5-yl)-2-hydroxyacetamide (99 mg, 0.35 mmol) yielded title compound (47 mg, 23%).

MS ES$^+$: 583.4 (M+H)$^+$ $^1$HNMR ($DMSOd_6$): 1.38 (m, 2H); 1.51 (m, 4H); 1.95 (m, 2H); 2.38 (m, 6H); 3.95 (s, 3H) 4.19 (t, 2H); 5.40 (d, 1H); 6.79 (d, 1H); 7.14 (d, 1H); 7.24 (s, 1H); 7.35 (t, 1H); 7.50 (s, 1H); 7.67 (d, 1H); 7.95 (s, 1H); 8.10 (s, 1H); 8.68 (s, 1H).

N-(3-chlorophenyl)-2-(2-amino-1,3-thiazole-5-yl)-2-hydroxyacetamide

An analogous reaction to that described in example 412, but starting with N-3-chlorophenyl)-2-(2-tert-butoxycarbonylamino-1,3-thiazole-5-yl)-2-hydroxyacetamide (2.13 g, 5.5 mmol) yielded title compound (1.02 g, 65%).

$^1$HNMR ($DMSOd_6$): 5.15 (d, 1H); 6.45 (d, 1H); 6.90 (m, 3H); 7.12 (dd, 1H); 7.33 (t, 1H); 7.62 (d, 1H); 7.89 (m, 1H).

N-(3-chlorophenyl)-2-(2-tert-butoxycarbonylamino 1,3-thiazole-5-yl)-2-hydroxyacetamide An analogous reaction to that described in example 412, but starting with N-(3-chlorophenyl)-2-(2-tert-butoxycarbonylamino-1,3-thiazole-5-yl) (oxo)acetamide (2.5 g, 6.5 mmol) yielded title compound (2.23 g, 89%).

$^1$HNMR ($DMSOd_6$): 1.48 (s, 9H); 5.34 (d, 1H); 6.74 (d, 1H); 7.14 (m, 1H); 7.34 (m, 2H); 7.65 (m, 1H); 7.92 (m, 1H).

N-(3-chlorophenyl)-2-(2-tert-butoxycarbonylamino-1,3-thiazole-5-yl) (oxo)acetamide An analogous reaction to that described in example 412, but starting with 3-chloroaniline (1.84 g, 14 mmol) yielded title compound (3.6 g, 79%).

$^1$HNMR ($DMSOd_6$): 1.54 (s, 9H); 7.24 (d, 1H); 7.43 (t, 1H); 7.79 (d, 1H); 8.03 (s, 1H); 8.61 (s, 1H).

EXAMPLE 414

Preparation of Compound 592 in Table 22

N'-(2(cyano-4-methoxy-5-(N-methyl-3-piperazinylpropoxyphenyl)-N,N-dimethylimidoformamide (140 mg, 0.39 mmol) in acetic acid (0.5 ml) in presence of N-(3,4-difluorophenyl)-2-(2-amino-1,3-thiazole-5-yl)-2-(hydroxyimino)acetamide (116 mg, 0.39 mmol) was heated at 110° C. for 16 hours. The mixture was concentrated and purified by silica gel chromatography, Eluant $CH_2Cl_2$/MeOH, $HN_3$ 3N 95/5 to 90/10, to give title compound (23 mg, 10%).

MS $ES^+$: 613.5 $(M+H)^+$ $^1$HNMR ($DMSOd_6$): 2.0 (m, 2H); 2.22 (s, 3H); 2.47 (m, 1H); 4.0 (s, 3H); 4.22 (t, 2H); 7.29 (m, 1H); 7.47 (m, 1H); 7.57 (m, 1H); 7.97 (m, 1H); 8.2 (s, 1H); 8.38 (s, 1H); 8.80 (s, 1H).

N-(3,4-difluorophenyl)-2-(2-amino-1,3-thiazol-5-yl)-2-(hydroxyimino)acetamide

N-(3,4-difluorophenyl)-2-(2-tert-butoxycarbonyl-amino-1,3-thiazol-5-yl)-2-(hydroxyimino)acetamide (600 mg, 1.5 mmol) in $CH_2Cl_2$ (12 ml) and TFA (4 ml) was stirred at room temperature for 2 hours. The mixture was evaporated, dissolved in methanol, the pH adjusted to 6 with sodium bicarbonate, water was added, the precipitate recovered, dried to give title compound (388 mg, 86%).

MS $ES^+$: 299.4 $(M+H)^+$ $^1$HNMR ($DMSOd_6$) mixture of isomers 7.05, 7.8 (2s, 1H); 7.43 (m, 4H); 7.88 (m, 1H).

N-3,4-difluorophenyl)-2-(2-tert-butoxycarbonyl-amino-1,3-thiazole-5-yl)-2-(hydroxyimino) acetamide N-(3,4-difluorophenyl)-2-(2-tert-butoxycarbonyl-amino-1,3-thiazole-5-yl) (oxo)acetamide (100 mg, 0.26 mmol) in pyridine (8 ml) was reacted with hydroxylamine hydrochloride (27 mg, 0.39 mmol) at 70° C. for 15 hours. The solvent was evaporated, water was added to the residue, the solid was filtered, washed with water, dried to give title compound (84 mg, 81%).

$^1$HNMR ($DMSOd_6$) mixture of isomers 7.41, 8.18 (2s, 1H); 7.50 (m, 2H); 7.90 (m, 1H).

EXAMPLE 415

Preparation of Compound 593 in Table 23

5-((6-methoxy-7-(3-morpholinopropoxy)quinazolin-4-yl) amino)thiophene-2-carboxylic acid (80 mg, 0.18 mmol) in DMF (2 ml) was reacted with 2-aminopyridine (17 mg, 0.18 mmol) in presence of 0-(7-azabenzotriazol-1-yl)-N,N,N',N'-tetramethyluronium hexafluorophosphate (70 mg, 0.18 mmol) and DIEA (80 $\mu$l, 0.46 mmol), at 50° C. for 6 hours. A saturated solution of sodium bicarbonate (2 ml) was added and the mixture stirred for 0.5 hour. A solid is recovered by filtration, washed with water, dried to give title compound (15 mg, 16%).

MS $ES^+$: 521 $(M+H)^+$ $^1$HNMR ($DMSOd_6$, TFA): 2.31 (m, 2H); 3.16 (t, 2H); 3.36 (t, 2H); 3.55 (d, 2H); 3.69 (t, 2H); 4.03 (d, 2H); 4.05 (s, 3H); 4.32 (t, 2H); 7.43 (m, 2H); 7.53 (t, 1H); 7.94 (d, 1H); 8.21 (m, 2H); 8.35 (t, 1H); 8.49 (d, 1H); 9.30 (s, 1H).

EXAMPLE 416

Preparation of Compound 594 in Table 23

An analogous reaction to that described in example 415, but starting with 4-methylaniline (19 mg, 0.18 mmol) yielded title compound (69 mg, 72%).

MS $ES^+$: 535 $(M+H)^+$ $^1$HNMR ($DMSOd_6$, TFA): 2.34 (s, 3H); 2.40 (t, 2H); 3.11 (t, 2H); 3.38 (t, 2H); 3.60 (d, 2H) 3.90 (t, 2H); 4.03 (d, 2H); 4.05 (s, 3H); 4.35 (t, 2H); 7.15 (d, 2H); 7.27 (d, 1H); 7.52 (s, 1H); 7.62 (d, 2H); 7.85 (d, 1H); 8.15 (s, 1H); 8.87 (s, 1H).

EXAMPLE 417

Preparation of Compound 595 in Table 23

An analogous reaction to that described in example 415, but starting 2-methylaniline (19 mg, 0.18 mmol) yielded title compound (28 mg, 29%).

MS $ES^+$: 535 $(M+H)^+$ $^1$HNMR ($DMSOd_6$, TFA): 2/28 (s, 3H); 2.32 (t, 2H); 3.18 (t, 2H); 3.37 (t, 2H); 3.56 (d, 2H); 3.70 (t, 2H); 4.05 (d, 2H); 4.07 (s, 3H); 7.30 (m, 4H); 7.35 (d, 1H); 7.41 (s, 1H); 7.96 (d, 1H); 8.22 (s, 1H); 9.26 (s, 1H).

EXAMPLE 418

Preparation of Compound 596 in Table 23

An analogous reaction to that described in example 415, but starting 3-methoxyaniline (22 mg, 0.18 mmol) yielded title compound (14 mg, 14%).

MS $ES^+$: 550.6 $(M+H)^+$ $^1$HNMR ($DMSOd_6$, TFA): 2.32 (t, 2H); 3.17 (t, 2H); 3.37 (t, 2H); 3.57 (d, 2H); 3.70 (t, 2H); 3.78 (s, 3H); 4.04 (d, 2H); 4.06 (s, 3H); 4.33 (t, 2H); 6.7 (d, 1H); 7.28 (s, 1H); 7.35 (s, 1H); 7.36 (d, 1H); 7.41 (s, 1H); 7.45 (s, 1H); 8.01 (d, 1H); 8.22 (s, 1H); 9.27 (s, 1H).

EXAMPLE 419

Preparation of Compound 597 in Table 23

An analogous reaction to that described in example 415, but starting 2-hydroxymethyl-aniline (22 mg, 0.18 mmol) yielded title compound (7 mg, 7%).

MS $ES^+$: 550.6 $(M+H)^+$ $^1$HNMR ($DMSOd_6$, TFA): 2.31 (m, 2H); 3.18 (t, 2H); 3.36 (t, 2H); 3.56 (d, 2H); 3.69 (t, 2H); 4.06 (m, 5H); 4.32 (t, 2H); 4.65 (s, 2H); 7.22 (t, 1H); 7.32 (t, 1H); 7.37 (d, 1H); 7.40 (s, 1H); 7.46 (d, 1H); 7.72 (d, 1H); 7.81 (d, 1H); 8.22 (s, 1H); 9.27 (s, 1H).

EXAMPLE 420

Preparation of Compound 598 in Table 23

An analogous reaction to that described in example 415, but starting 3-nitroaniline (25 mg, 0.18 mmol) yielded title compound (6 mg, 6%).

MS $ES^+$: 565.6 $(M+H)^+$ $^1$HNMR ($DMSOd_6$, TFA): 2.32 (t, 2H); 3.18 (t, 2H); 3.38 (t, 2H); 3.58 (d, 2H); 3.70 (t, 2H) 4.05 (d, 2H); 4.07 (s, 3H); 4.33 (t, 2H); 7.39 (d, 1H); 7.42 (s, 1H); 7.68 (t, 1H); 7.98 (d, 1H); 8.08 (d, 1H); 8.20 (m, 1H); 8.23 (s, 1H); 8.77 (s, 1H); 9.3 (s, 1H).

EXAMPLE 421

Preparation of Compound 599 in Table 23

An analogous reaction to that described in example 415, but starting 4-trifluoromethylaniline (29 mg, 0.18 mmol) yielded title compound (8 mg, 8%).

MS $ES^+$: 588.6 $(M+H)^+$ $^1$HNMR ($DMSOd_6$, TFA): 2.33 (m, 2H); 3.19 (t, 2H); 3.41 (t, 2H); 3.61 (d, 2H); 3.75 (t, 2H); 4.05 (d, 2H); 4.08 (s, 1H); 4.37 (t, 2H); 7.39 (d, 1H); 7.43 (s, 1H); 7.72 (d, 2H); 8.03 (d, 2H); 8.10 (d, 1H); 8.23 (s, 1H); 9.29 (s, 1H).

EXAMPLE 422

Preparation of Compound 600 in Table 23

An analogous reaction to that described in example 415, but starting 3-chloroaniline (23 mg, 0.18 mmol) yielded title compound (21 mg, 21%).

$^1$HNMR ($DMSOd_6$, TFA): 2.32 (m, 2H); 3.19 (t, 2H); 3.37 (t, 2H); 3.57 (d, 2H); 3.70 (t, 2H); 4.03 (d, 2H); 4.07 (s,

3H); 4.34 (t, 2H); 7.17 (d, 1H); 7.37 (t, 1H); 7.40 (m, 2H); 7.70 (d, 1H); 7.95 (m, 1H); 8.02 (d, 1H); 8.22 (s, 1H); 9.29 (s, 1H).

EXAMPLE 423

Preparation of Compound 601 in Table 23

An analogous reaction to that described in example 415, but starting 2-methoxyaniline (22 mg, 0.18 mmol) yielded title compound (32 mg, 32%).

$^1$HNMR (DMSOd$_6$, TFA): 2.35 (t, 2H); 3.18 (t, 2H); 3.37 (t, 2H); 3.56 (d, 2H); 3.70 (t, 2H); 3.87 (s, 3H); 4.05 (d, 2H); 4.06 (s, 3H); 4.34 (t, 2H); 6.99 (t, 1H); 7.11 (d, 1H); 7.20 (s, 1H); 7.33 (d, 1H); 7.40 (s, 1H); 7.73 (dd, 1H); 7.97 (d, 1H); 8.22 (s, 1H); 9.27 (s, 1H).

EXAMPLE 424

Preparation of Compound 602 in Table 23

An analogous reaction to that described in example 415, but starting 3-(2-hydroxyethyl) aniline (25 mg, 0.18 mmol) yielded title compound (27 mg, 26%).

MS ES$^+$: 564.7 (M+H)$^+$ $^1$HNMR (DMSOd$_6$, TFA): 1.37 (d, 3H); 2.32 (t, 2H); 3.19 (t, 2H); 3.38 (t, 2H); 3.58 (d, 2H) 3.62 (t, 2H); 4.06 (d, 2H); 4.08 (s, 3H); 4.36 (t, 2H); 4.76 (q, 1H); 7.08 (d, 1H); 7.29 (t, 1H); 7.35 (d, 1H); 7.42 (s, 1H); 7.70 (d, 1H); 7.76 (s, 1H); 8.05 (d, 1H); 8.23 (s, 1H); 9.28 (s, 1H).

EXAMPLE 425

Preparation of Compound 603 in Table 23

An analogous reaction to that described in example 415, but starting 3-fluoro-4-methoxyaniline (25 mg, 0.18 mmol) yielded title compound (14 mg, 14%).

MS ES$^+$: 568.6 (M+H)$^+$ $^1$HNMR (DMSOd$_6$, TFA): 2.32 (t, 2H); 3.19 (t, 2H); 3.38 (t, 2H); 3.57 (d, 2H); 3.72 (t, 2H); 3.85 (s, 3H); 4.04 (d, 2H); 4.07 (s, 3H); 4.35 (t, 2H); 7.17 (t, 1H); 7.36 (d, 1H); 7.42 (s, 1H); 7.47 (dd, 1H); 7.73 (dd, 1H); 7.98 (d, 1H); 8.24 (s, 1H); 9.27 (s, 1H).

EXAMPLE 426

Preparation of Compound 604 in Table 23

An analogous reaction to that described in example 415, but starting 2-methyl-4-fluoroaniline (23 mg, 0.18 mmol) yielded title compound (27 mg, 27%).

MS ES$^+$: 552.6 (M+H)$^+$ $^1$ HNMR (DMSOd$_6$, TFA): 2.28 (s, 3H); 2.31 (t, 2H); 3.18 (t, 2H); 3.38 (t, 2H); 3.57 (d, 2H); 3.71 (t, 2H); 4.05 (d, 2H); 4.07 (s, 3H); 7.07 (dt, 1H); 7.15 (dd, 1H); 7.35 (d, 1H); 7.36 (m, 1H); 7.41 (s, 1H); 7.95 (d, 1H); 8.23 (s, 1H); 9.26 (s, 1H).

EXAMPLE 427

Preparation of Compound 605 in Table 23

An analogous reaction to that described in example 415, but starting 2-fluoro-5-methylaniline (23 mg, 0.18 mmol) yielded title compound (9 mg, 9%).

MS ES$^+$: 552.6 (M+H)$^+$ $^1$HNMR (DMSOd$_6$, TFA): 2.33 (m, 5H); 3.19 (t, 2H); 3.38 (t, 2H); 3.56 (d, 2H); 3.71 (t, 2H); 4.04 (d, 2H); 4.07 (s, 3H); 4.35 (t, 2H); 7.09 (m, 1H); 7.18 (m, 1H); 7.35 (d, 1H) 7.40 (s, 1H); 7.41 (m, 1H); 8.0 (d, 1H); 8.23 (s, 1H); 9.27 (s, 1H).

EXAMPLE 428

Preparation of Compound 606 in Table 23

An analogous reaction to that described in example 415, but starting 3-cyanoaniline (21 mg, 0.18 mmol) yielded title compound (9 mg, 9%).

MS ES$^+$: 545.6 (M+I)+

$^1$HNMR (DMSOd$_6$) TFA): 2.33 (t, 2H); 3.21 (t, 2H); 3.39 (t, 2H); 3.60 (d, 2H); 3.72 (t, 2H); 4.07 (d, 2H); 4.10 (s, 3H); 4.37 (t, 2H); 7.40 (d, 1H); 7.44 (s, 1H); 7.62 (s, 1H); 7.63 (m, 1H); 8.06 (m, 1H); 8.06 (d, 1H); 8.26 (s, 1H); 8.30 (s, 1H); 9.32 (s, 1H).

EXAMPLE 429

Preparation of Compound 607 in Table 23

An analogous reaction to that described in example 415, but starting isoamylamine (16 mg, 0.18 mmol) yielded title compound (15 mg, 17%).

MS ES$^+$: 514.7 (M+H)$^+$ $^1$HNMR ($CDCl_3$): 0.96 (d, 6H); 1.77 (m, 5H); 2.11 (m, 2H); 2.5 (m, 4H); 2.56 (t, 2H); 3.73 (m, 4H); 4.03 (s, 3H); 4.22 (t, 2H); 6.05 (t, 1H); 6.88 (d, 1H); 7.24 (s, 1H); 7.39 (d, 1H); 7.58 (s, 1H); 8.70 (s, 1H).

EXAMPLE 430

Preparation of Compound 608 in Table 23

An analogous reaction to that described in example 415, but starting 2-chloroaniline (23 mg, 0.18 mmol) yielded title compound (5 mg, 5%).

MS ES$^+$: 554.5, 556.5 (M+H)$^+$ $^1$HNMR (DMSOd$_6$, TFA): 2.32 (t, 2H); 3.19 (t, 2H); 3.39 (t, 2H); 3.57 (d, 2H); 3.70 (t, 2H); 4.04 (d, 2H); 4.07 (s, 3H); 4.34 (t, 2H); 7.32 (t, 1H); 7.36 (d, 1H); 7.41 (s, 1H); 7.41 (t, 1H); 7.57 (d, 1H); 7.63 (d, 1H); 8.0 (d, 1H); 8.23 (s, 1H); 9.27 (s, 1H).

EXAMPLE 431

Preparation of Compound 609 in Table 24

An analogous reaction to that described in example 415, but starting with 5-((6-methox-7-(3-morpholinopropoxy) quinazolin-4-yl)amino)thiophene-3-carboxylic acid (80 mg, 0.18 mmol) and aniline (20 μl, 0.22 mmol) yielded title compound (28 mg, 30%).

MS ES$^+$: 520 (M+H)$^+$ $^1$HNMR (DMSOd$_6$, TFA): 2.32 (t, 2H); 3.18 (t, 2H); 3.38 (t, 2H); 3.56 (d, 2H); 3.71 (t, 2H) 4.05 (d, 2H); 4.06 (s, 3H); 4.34 (t, 2H); 7.12 (t, 1H); 7.37 (t, 2H); 7.40 (s, 1H); 7.76 (d, 1H); 7.79 (d, 2H); 8.18 (s, 1H); 8.21 (d, 1H); 9.17 (s, 1H).

5-((6-methoxy-7-(3-morpholinopropoxy)quinazolin-4-yl)amino)thiophene-3-carboxylic acid Ethyl-5-((6-methoxy-7-(3-morpholinopropoxy) quinazolin-4-yl)amino thiophene-3-carboxylate (1.05 g, 2.2 mmol) in methanol (10 ml) was treated with sodium hydroxyde (2N, 10 ml) at 75° C. for 1.5 hour. Methanol was evaporated, HCl (2N) was added (pH 3) the solid filtered, redissolved in $CH_2Cl_2$/MeOH 1/1, DIEA (1.5 ml, 8.8 mmol)

was added the solid removed by filtration, the filtrate was concentrated, and the residue dissolved in ethanol, title material was obtained as a solid (0.7 g, 71%).

MS $ES^+$: 445 $(M+H)^+$ $^1$HNMR ($DMSOd_6$, TFA): 2.36 (t, 2H); 3.17 (t, 2H); 3.36 (t, 2H); 3.56 (d, 2H); 3.79 (t, 2H); 4.03 (d, 2H); 4.08 (s, 3H); 4.35 (t, 2H); 7.45 (s, 1H); 7.81 (s, 1H); 8.03 (s, 1H); 8.50 (s, 1H); 9.15 (s, 1H).

Ethyl-5-((6-methoxy-7-(3-morpholinopropoxy) quinazolin-4-yl)aminothiophene-3-carboxylate 4-chloro-6-methoxy-7-(3-morpholinopropoxy) quinazoline (1 g, 3 mmol) in isopropanol (25 ml) and isopropanol HCl (0.5 ml) was reacted with ethyl 5-aminothiophene-3-carboxylate (0.6 g, 3.3 mmol) at 110° C. for 1 hour. The mixture was cooled, diluted with EtOAc, filtered to give title compound (1.58 g, 99%).

MS $ES^+$: 473 $(M+H)^+$ $^1$HNMR ($DMSOd_6$, TFA): 1.33 (t, 3H); 2.33 (t, 2H); 3.17 (t, 2H); 3.35 (t, 2H); 3.54 (d, 2H); 3.75 (t, 2H); 4.03 (d, 2H); 4.06 (s, 3H); 4.30 (q, 2H); 4.33 (t, 2H); 7.42 (s, 1H); 7.73 (s, 1H); 8.09 (s, 1H); 8.35 (s, 1H); 9.15 (s, 1H).

EXAMPLE 432

Preparation of Compound 610 in Table 24

An analogous reaction to that described in example 431, but starting with 4-fluoroaniline (24 mg, 0.18 mmol) yielded title compound (20 mg, 22%).

MS $ES^+$: 538.5 $(M+H)^+$ $^1$HNMR ($DMSOd_6$, TFA): 2.32 (t, 2H); 3.20 (t, 2H); 3.40 (t, 2H); 3.60 (d, 2H); 3.72 (t, 2H) 4.04 (d, 2H); 4.07 (s, 3H); 4.34 (t, 2H); 7.9 (s, 1H); 7.20 (m, 2H); 7.41 (s, 1H); 7.76 (d, 1H); 7.82 (m, 1H); 8.19 (s, 1H); 8.21 (d, 1H); 9.17 (s, 1H).

EXAMPLE 433

Preparation of Compound 611 in Table 24

An analogous reaction to that described in example 431, but starting with 3-hydroxyaniline (24 mg, 0.18 mmol) yielded title compound (15 mg, 17%).

MS $ES^+$: 536.6 $(M+H)^+$

EXAMPLE 434

Preparation of Compound 612 in Table 24

An analogous reaction to that described in example 431, but starting with 3-(methylthio)aniline (30 mg, 0.18 mmol) yielded title compound (23 mg, 24%).

$^1$HNMR ($DMSOd_6$, TFA): 2.31 (t, 2H); 3.17 (t, 2H); 3.36 (t, 2H); 3.56 (d, 2H); 3.69 (t, 2H); 4.04 (m, 5H); 4.33 (t, 2H); 7.24 (t, 1H); 7.32 (t, 1H); 7.41 (s, 1H); 7.43 (m, 2H); 7.72 (d, 2H); 8.16 (m, 2H); 9.17 (s, 1H).

EXAMPLE 435

Preparation of Compound 613 in Table 24

An analogous reaction to that described in example 431, but starting with 4-fluoro-3-chloroaniline (32 mg, 0.18 mmol) yielded title compound (21 mg, 21%).

MS $ES^+$: 577 $(M+H)^+$ $^1$HNMR ($DMSOd_6$, TFA): 2.32 (t, 2H); 3.19 (t, 2H); 3.37 (t, 2H); 3.57 (d, 2H); 3.71 (t, 2H); 4.06 (m, 5H); 4.34 (t, 2H); 7.41 (m, 2H); 7.75 (m, 2H); 8.11 (m, 1H); 8.18 (s, 1H); 8.21 B(s, 1H); 9.18 (s, 1H).

EXAMPLE 436

Preparation of Compound 614 in Table 24

An analogous reaction to that described in example 431, but starting with 2,4-difluorobenzylamine (31 mg, 0.18 mmol) yielded title compound (22 mg, 22%).

MS $ES^+$: 570.5 $(M+H)^+$ $^1$HNMR ($DMSOd_6$, TFA): 2.34 (t, 2H); 3.19 (t, 2H); 3.39 (t, 2H); 3.58 (d, 2H); 3.72 (t, 2H); 4.06 (m, 5H); 4.34 (t, 2H); 4.51 (s, 2H); 7.06 (t, 1H); 7.15 (t, 1H); 7.40 (s, 1H); 7.48 (m, 1H); 7.69 (d, 1H); 8.03 (d, 1H); 8.17 (s, 1H); 9.14 (s, 1H).

EXAMPLE 437

Preparation of Compound 615 in Table 24

An analogous reaction to that described in example 431, but starting with 3-fluoroaniline (24 mg, 0.18 mmol) yielded title compound (27 mg, 29%).

MS $ES^+$: 538.6 $(M+H)^+$ $^1$HNMR ($DMSOd_6$, TFA): 2.33 (t, 2H); 3.18 (t, 2H); 3.38 (t, 2H); 3.58 (d, 2H); 3.72 (d, 2H); 4.04 (d, 2H); 4.07 (s, 3H); 4.35 (t, 2H); 6.91 (m, 1H); 7.42 (m, 2H); 7.59 (d, 1H); 7.78 (d, 1H); 7.79 (m, 1H); 8.19 (s, 1H); 8.24 (d, 1H); 9.18 (s, 1H).

EXAMPLE 438

Preparation of Compound 616 in Table 25

2-((6-methoxy-7-(3-morpholinopropoxy)quinazolin-4-yl) amino)imidazole-5-carboxylic acid (200 mg, 0.47 mmol) in DMF (3 ml) was reacted with aniline (43 μl, 0.47 mmol) in presence of 0-(7-azabenzotriazol-1-yl)N,N,N',N'-tetramethyluronium hexafluorophosphate (178 mg, 0.47 mmol) and DIEA (120 μl, 0.7 mmol) at 40° C. for 3 hours. A solution of dimethylamine in methanol (2M, 1 ml) was added and stirring was carried on for 3 hours. The solvent was evaporated, and the mixture was purified by silica gel chromatography, Eluant $CH_2Cl_2$/MeOH $NH_3$ (sat.) 95/5 to give title compound (80 mg, 34%).

MS $ES^+$: 504.1 $(M+H)^+$ $^1$HNMR ($DMSOd_6$) TFA): 2.29 (t, 2H); 3.18 (t, 2H); 3.35 (t, 2H); 3.56 (d, 2H); 3.69 (t, 2H); 3.96 (s, 3H); 4.04 (d, 2H); 4.27 (t, 2H); 7.15 (t, 1H); 7.25 (s, 1H); 7.40 (t, 2H); 7.74 (d, 2H); 7.81 (s, 1H); 8.09 (s, 1H); 8.75 (s, 1H).

EXAMPLE 439

Preparation of Compound 617 in Table 25

An analogous reaction to that described in example 438, but starting with 4-fluoroaniline (60 μl, 0.58 mmol) yielded title compound (120 mg, 39%).

MS $ES^+$: 522.1 $(M+H)^+$ $^1$HNMR ($DMSOd_6$, TFA): 2.29 (t, 2H); 3.17 (t, 2H); 3.36 (t, 2H); 3.55 (d, 1H); 3.69 (t, 2H); 3.96 (s, 3H); 4.04 (d, 2H); 4.27 (t, 2H); 7.22 (m, 3H); 7.74 (m, 2H); 7.82 (s, 1H); 8.07 (s, 1H); 8.76 (s, 1H).

EXAMPLE 440

Preparation of Compound 618 in Table 25

An analogous reaction to that described in example 438, but starting with allylamine 50 μl, 0.7 mmol) yielded title compound (133 mg, 40%).

MS $ES^+$: 468.1 $(M+H)^+$ $^1$HNMR ($DMSOd_6$, TFA): 2.28 (t, 2H); 3.15 (t, 2H); 3.35 (t, 2H); 3.54 (d, 2H); 3.68 (t, 2H) 3.94 (m, 5H); 4.04 (d, 2H); 4.26 (t, 2H); 5.14 (dd, 1H); 5.23 (dd, 1H); 5.88 (m, 1H); 7.23 (s, 1H); 7.77 (s, 1H); 7.86 (s, 1H); 8.71 (s, 1H).

2-((6-methoxy-7-(3-morpholinoporpoxy)quinazolin-4-yl)amino)imidazole-5-carboxylic acid ethyl-2((4-imino-6-methoxy-7-(3-morpholinopropoxy) quinazolin-3-(4H)-yl)imidazole-5-carboxylate (650 mg, 1.42 mmol) in methanol (14 ml) was treated with sodium hydroxyde (2N, 14 ml) at 80° C. for 1.5 hour. Methanol was evaporated, hydrochloric acid (6N) was added (pH 2.5), the precipitate was recovered by filtration, dried to give title compound (650 mg, 100%).

$^1$HNMR ($DMSOd_6$, TFA): 2.35 (t, 2H); 3.13 (t, 2H); 3.32 (t, 2H); 3.5 (d, 2H); 3.95 (m, 7H) 4.28 (t, 2H); 7.42 (s, 1H); 7.8 (s, 1H); 7.86 (s, 1H); 8.72 (s, 1H).

EXAMPLE 441

Preparation of Compound 619 in Table 26

4-chloro-6-methoxy-7-(3-morpholinopropoxy) quinazoline (265 mg, 0.79 mmol) in 2-propanol (14 ml) was reacted with 4-amino-N-phenylthiophene-3-carboxamide hydrochloride (210 mg, 0.82 mmol) at 100° C. for 2 hours. The solvent was evaporated and the residue purified by silica gel chromatography, eluent $CH_2Cl_2$/MeOH, $NH_3$ sat. 95/5 to give title compound (330 mg, 81%).

MS $ES^+$: 520.6 $(M+H)^+$ $^1$HNMR ($DMSOd_6$, TFA): 2.30 (t, 2H); 3.15 (t, 2H); 3.35 (t, 2H); 3.54 (d, 2H); 3.68 (t, 2H) 4.03 (s, 3H); 4.04 (d, 2H); 4.32 (t, 2H); 7.13 (t, 1H); 7.35 (t, 2H); 7.39 (s, 1H); 7.69 (d, 2H); 7.79 (s, 1H); 8.13 (d, 1H); 8.58 (d, 1H); 8.95 (s, 1H).

4-(tert-butoxycarbotylamino-N-phenylthiophene-3-carboxamide 4-(tert-butoxycarbonylamino)thiophene-3-carboxylic acid obtained by a literature procedure, Tetrahedron Letters 1997, 2637, (385 mg, 1.58 mmol) in DMF (5 ml) was reacted with aniline (140 μl, 1.58 mmol) in presence of O-(7-azabenzotriazol-1-yl)-N,N,N',N'-tetramethyluronium hexafluorophosphate (602 mg, 1.58 mmol) at 40° C. for 7 hours. The solvent was evaporated, and the residue purified by silica gel chromatography, Eluant petroleum ether/AcOEt: 80/20 to give title compound (348 mg, 70%).

$^1$HNMR ($CDCl_3$): 1.50 (s, 9H); 7.19 (t, 1H); 7.39 (t, 2H); 7.54 (d, 2H); 7.69 (s, 2H); 7.71 (s, 1H); 9.45 (s, 1H).

4-amino-N-phenylthiophene-3-carboxamide 4-(tert-butoxycarbonylamino)-N-phenylthiophene-3-carboxamide (300 mg, 0.94 mmol) in $CH_2Cl_2$ (3 ml) was treated with TFA (0.36 ml, 4.71 mmol) at room temperature for 2.5 hours. The solvent was evaporated, the residue was dissolved in methanol/HCl, ether was added to the solution, the precipitate was recovered to give title compound (210 mg, 87%) which was used as is in the next step.

EXAMPLE 442

Preparation of Compound 620 in Table 26

An analogous reaction to that described in example 441, but starting with 4-amino-N-allylthiophene-3-carboxamide (218 mg, 1.06 mmol) yielded title compound (366 mg, 75%).

MS $ES^+$: 484.6 $(M+H)^+$ $^1$HNMR ($DMSOd_6$, TFA): 2.28 (t, 2H); 3.15 (t, 2H); 3.35 (t, 2H); 3.54 (d, 2H); 3.68 (t, 2H); 3.95 (d, 2H); 4.03 (m, 5H); 4.32 (t, 2H); 5.14 (dd, 1H); 5.24 (dd, 1H); 5.91 (m, 1H); 7.41 (s, 1H); 7.59 (s, 1H); 8.28 (d, 1H); 8.51 (d, 1H); 9.04 (s, 1H).

4-tert-butoxycarbonylamino)-N-allylthiophene-3-carboxamide

An analogous reaction to that described in example 319, but starting with allylamine (150 μl, 2.06 mmol) yielded title compound (385 mg, 66%).

$^1$HNMR ($CDCl_3$): 1.51 (s, 9H); 4.04 (m, 2H); 5.21 (dd, 1H); 5.29 (dd, 1H); 5.92 (m, 1H); 6.1 (m, 1H); 7.54 (d, 1H); 7.64 (m, 1H); 9.64 (s, 1H).

4-amino-N-allylthiophene-3-carboxamide

An analogous reaction to that described in example 441, but starting with 4-tert-butoxycarboxylamino-N-allyl-thiophene-3-carboxamide (320 mg, 1.13 mmol) yielded title compound (218 mg, 94%) which was used as is in the next step.

EXAMPLE 443

Preparation of Compound 621 in Table 27

4-chloro-6-methoxy-7-(3-morpholinopropoxy) quinzaoline (100 mg, 0.29 mmol) in isopropanol (5 ml) was reacted with methyl-4-amino-thiophene-4-carboxylate hydrochloride (63.6 mg, 0.33 mmol) at reflux for 1 hour. Ethyl acetate was added to the reaction mixture, the solid was recovered by filtration, dried, to give title compound (140 mg, 89%).

MS $ES^+$: 459.1 $(M+H)^+$ $^1$HNMR ($DMSOd_6$, TFA): 2.39 (t, 2H); 3.19 (t, 2H); 3.40 (t, 2H); 3.58 (d, 2H); 3.77 (m, 5H); 4.06 (m, 5H); 4.37 (t, 2H); 7.42 (s, 1H); 7.95 (s, 1H); 8.01 (d, 1H); 8.49 (d, 1H); 8.93 (s, 1H).

EXAMPLE 444

Preparation of Compound 622 in Table 28

4-chloro-6-methoxy-7-(3-morpholinopropoxy) quinazoline (110 mg, 0.3 mmol) in 2-pentanol (5 ml) and isopropanol/HCl (55 μl) was reacted with 2-amino-5-isopropylthiophene-3-carboxamide (60 mg, 0.33 mmol) at 100° C. for 1 hour, ether and ethylacetate was added to the mixture, the precipitate was filtered to give title compound (155 mg, 93%).

MS $ES^+$: 486.6 $(M+H)^+$ $^1$HNMR ($DMSOd_6$, TFA); 1.38 (d, 6H); 2.38 (t, 2H); 3.20 (m, 3H); 3.38 (t, 2H); 3.57 (d, 2H); 3.82 (t, 2H); 4.05 (d, 2H); 4.08 (s, 3H); 4.39 (t, 2H); 7.40 (s, 1H); 7.47 (s, 1H); 7.52 (s, 1H); 9.23 (s, 1H).

EXAMPLE 445

Preparation of Compound 623 in Table 28

An analogous reaction to that described in example 444 but starting with allyl-5-aminothiophene-2-carboxylate (67 mg, 0.33 mmol) at 100° C. for 2 hours yielded title compound (151 mg, 85%).

MS $ES^+$: 485.6 $(M+H)^+$ $^1$HNMR ($DMSOd_6$) TFA): 2.38 (t, 2H); 3.18 (t, 2H); 3.38 (t, 2H); 3.57 (d, 2H); 3.80 (t, 2H) 4.06 (d, 2H); 4.12 (s, 3H);

4.38 (t, 2H); 4.84 (d, 2H); 5.33 (d, 1H); 5.45 (d, 1H); 6.10 (m, 1H); 7.48 (s, 1H); 7.65 (d, 1H); 7.84 (d, 1H); 8.64 (s, 1H); 9.30 (s, 1H).

EXAMPLE 446

Preparation of Compound 624 in Table 28

An analogous reaction to that described in example 444 but starting with 2-aminothiophene-3-carboxamide (46 mg, 0.33 mmol) yielded title compound (154 mg, 99%).

MS $ES^+$: 444.6 $(M+H)^+$ $^1$HNMR ($DMSOd_6$, TFA): 2.34 (t, 2H); 3.15 (t, 2H); 3.36 (t, 2H); 3.54 (d, 2H); 3.76 (t, 2H) 4.02 (d, 2H); 4.05 (s, 3H); 4.36 (t, 2H); 7.32 (d, 1H); 7.41 (s, 1H); 7.48 (s, 1H); 7.66 (d, 1H); 9.23 (s, 1H).

EXAMPLE 447

Preparation of Compound 625 in Table 28

An analogous reaction to that described in example 444 but starting with 2-amino-5-ethylthiophene-3-carboxamide (55 mg, 0.33 mmol) yielded title compound (147 mg, 90%).

MS $ES^+$: 472.5 $(M+H)^+$ $^1$HNMR ($DMSOd_6$, TFA): 1.34 (t, 3H); 2.38 (t, 2H); 2.86 (q, 2H); 3.18 (t, 2H); 3.38 (t, 2H); 3.57 (d, 2H); 3.80 (t, 2H); 4.05 (d, 2H); 4.07 (s, 3H); 4.38 (t, 2H); 7.40 (s, 1H); 7.43 (s, 1H); 7.52 (s, 1H); 9.21 (s, 1H).

EXAMPLE 448

Preparation of Compound 626 in Table 29

Methyl-2-cyano-4-methoxy-5-(3-morpholinopropoxy) phenylimidoformate (100 mg; 0.3 mmol) in DMF (1.5 ml) was reacted with 2-amino-4-phenyl-1,3-thiazole (58 mg; 0.33 mmol) in presence of sodium hydride (13.2 mg; 0.33 mmol) at 75° C. for 1.5 h. Acetic acid (1.5 eq.) was added and the solvent was evaporated to give 6-methoxy-7-(3-morpholinopropoxy)-3-(4-phenyl-1,3-thiazol-2-yl) quinazolin-4(3H)-imine as an intermediate which was redissolved in DMF (1.5 ml) and ammonium acetate (95 mg; 0.9 mmol) added. The mixture was stirred at 75° C. for 1 h, the solvent was evaporated and the residue purified by silica gel chromatography, $CH_2Cl_2$/MeOH 95/5→90/10 to give title compound (44 mg, 31%).

$^1$HNMR ($DMSOd_6$, TFA): 2.30 (t, 2H); 3.17 (t, 2H); 3.36 (t, 2H); 3.56 (d, 2H); 3.70 (t, 2H); 4.05 (m, 5H); 4.33 (t, 2H); 7.42 (m, 2H); 7.51 (t, 2H); 7.90 (s, 1H); 8.00 (d, 2H); 8.35 (s, 1H); 9.27 (s, 1H).

EXAMPLE 449

Preparation of Compound 627 in Table 29

An analogous reaction to that described in example 448 but starting with 2-amino-4-methyl-5-acetyl-1,3-thiazole (103 mg, 0.66 mmol), heating at 75° C. for 1 h in the first step, and stirring the intermediate in the above conditions at room temperature for 1 h, gave title compound (71 mg, 52%).

MS $ES^+$: 458 $(M+H)^+$ $^1$HNMR ($DMSOd_6$, TFA): 2.32 (t, 2H); 2.55 (s, 3H); 2.67 (s, 3H); 3.16 (t, 2H); 3.36 (t, 2H); 3.56 (d, 2H); 3.69 (t, 2H); 4.0 (s, 3H); 4.03 (d, 2H); 4.32 (t, 2H); 7.37 (s, 1H); 7.99 (s, 1H); 9.26 (s, 1H).

EXAMPLE 450

Preparation of Compound 628 in Table 29

An analogous reaction to that described in example 448 but starting with ethyl-2-amino-4-trifluoromethyl-1,3-thiazole-5-carboxylate (79 mg, 0.33 mmol) yielded title compound (81 mg, 50%).

MS $ES^+$: 542 $(M+H)^+$ $^1$HNMR ($DMSOd_6$, TFA): 1.34 (t, 3H); 2.32 (t, 2H); 3.17 (t, 2H); 3.36 (t, 2H); 3.55 (d, 2H); 3.69 (t, 2H); 4.03 (s, 3H); 4.04 (d, 2H); 4.36 (m, 4H); 7.47 (s, 1H); 8.41 (s, 1H); 9.34 (s, 1H).

EXAMPLE 451

Preparation of Compound 629 in Table 29

An analogous reaction to that described in example 448 but starting with ethyl-2-amino-4-phenyl-1,3-thiazole-5-carboxylate (82 mg, 0.33 mmol) yielded title compound (133 mg, 81%).

MS $ES^+$: 550 $(M+H)^+$ $^1$HNMR ($DMSOd_6$, TFA): 1.25 (t, 2H); 2.32 (t, 2H); 3.16 (t, 2H); 3.36 (t, 2H); 3.56 (d, 2H); 3.69 (t, 2H); 4.02 (s, 1H); 4.04 (d, 2H); 4.26 (q, 2H); 4.35 (t, 2H); 7.45 (s, 1H); 7.50 (m, 3H); 7.79 (m, 2H); 8.33 (s, 1H); 9.37 (s, 1H).

EXAMPLE 452

Preparation of Compound 630 in Table 29

An analogous reaction to that described in example 448 but starting with 4,5,6,7-tetrahydro-1,3-benzothiazole-2-amine (51 mg, 0.33 mmol) yielded title compound (97 mg, 71%).

MS $ES^+$: 456 $(M+H)^+$ $^1$HNMR ($DMSOd_6$, TFA): 1.83 (m, 4H); 2.29 (t, 2H); 2.61 (m, 2H); 2.67 (m, 2H); 3.15 (t, 2H); 3.35 (t, 2H); 3.55 (d, 2H); 3.68 (t, 2H); 3.97 (s, 3H); 4.04 (d, 2H); 4.29 (t, 2H); 7.28 (s, 1H); 7.84 (s, 1H); 9.0 (s, 1H).

EXAMPLE 453

Preparation of Compound 631 in Table 29

An analogous reaction to that described in example 448 but starting with N-(4-(2-amino-1,3-thiazol-4-yl)phenyl) acetamide (77 mg, 0.33 mmol) yielded title compound (58 mg, 36%).

MS $ES^+$: 535 $(M+H)^+$ $^1$HNMR ($DMSOd_6$, TFA): 2.09 (s, 3H); 2.32 (t, 2H); 3.17 (t, 2H); 3.37 (t, 2H); 3.56 (d, 2H); 3.70 (t, 2H); 4.05 (s, 3H); 4.06 (d, 2H); 4.35 (t, 2H); 7.40 (s, 1H); 7.72 (d, 2H); 7.77 (s, 1H); 7.92 (d, 2H); 8.33 (s, 1H); 9.25 (s, 1H).

EXAMPLE 454

Preparation of Compound 632 in Table 29

An analogous reaction to that described in example 448 but starting with 5-phenyl-4-(trifluoromethyl)-1,3-thiazole-2-amine (81 mg, 0.33 mmol) yielded title compound (144 mg, 88%).

MS $ES^+$: 546 $(M+H)^+$ $^1$HNMR ($DMSOd_6$, TFA): 2.32 (t, 2H); 3.16 (t, 2H); 3.36 (t, 2H); 3.56 (d, 2H); 3.69 (t, 2H) 4.04 (d, 2H); 4.05 (s, 3H); 4.36 (t, 2H); 7.49 (s, 1H); 7.54 (s, 5H); 8.46 (s, 1H); 9.30 (s, 1H).

EXAMPLE 455

Preparation of Compound 633 in Table 29

An analogous reaction to that described in example 448 but starting with 4-(trifluoromethyl)-1,3-thiazole-2-amine (55 mg, 0.33 mmol) yielded title compound (62 mg, 44%).

MS ES$^+$: 470 (M+H)$^+$ $^1$HNMR (DMSOd$_6$, TFA): 2.32 (t, 2H); 3.17 (t, 2H); 3.37 (t, 2H); 3.56 (d, 2H); 3.69 (t, 2H) 4.04 (s, 3H); 4.05 (d, 2H); 4.36 (t, 2H); 7.49 (s, 1H); 8.23 (s, 1H); 8.44 (s, 1H); 9.34 (s, 1H).

EXAMPLE 456

Preparation of Compound 634 in Table 29

An analogous reaction to that described in example 448 but starting with 4-tert-butyl-1,3-thiazole-2-amine (52 mg, 0.33 mmol) yielded title compound (90 mg, 65%).

MS ES$^+$: 458 (M+H)$^+$ $^1$HNMR (DMSOd$_6$, TFA): 1.46 (s, 9H); 2.32 (t, 2H); 3.16 (t, 2H); 3.36 (t, 2H); 3.55 (d, 2H); 3.69 (t, 2H); 4.00 (s, 3H); 4.03 (d, 2H); 4.32 (d, 2H); 7.38 (s, 1H); 7.95 (s, 1H); 9.18 (s, 1H).

EXAMPLE 457

Preparation of Compound 635 in Table 29

An analogous reaction to that described in example 448 but starting with 4,5-dimethyl-1,3-thiazole-2-amine (42 mg, 0.33 mmol) yielded title compound (61 mg, 47%).

MS ES$^+$: 430 (M+H)$^+$ $^1$HNMR (DMSOd$_6$, TFA): 2.25 (s, 3H); 2.30 (m, 5H); 3.15 (t, 2H); 3.35 (t, 2H); 3.55 (d, 2H); 3.68 (t, 2H); 3.96 (s, 3H); 4.04 (d, 2H); 4.28 (t, 1H); 7.28 (s, 1H); 7.82 (s, 1H); 8.98 (s, 1H).

EXAMPLE 458

Preparation of Compound 636 in Table 29

An analogous reaction to that described in example 448 but starting with 4-methyl-1,3-thiazole-2-amine (38 mg, 0.33 mmol) yielded title compound (40 mg, 32%).

MS ES$^+$: 415 (M+H)$^+$ $^1$HNMR (DMSOd$_6$, TFA) 2.31 (t, 2H); 2.34 (s, 3H); 3.15 (t, 2H); 3.37 (t, 2H); 3.55 (d, 2H); 3.69 (t, 2H); 3.99 (s, 3H); 4.04 (d, 2H); 4.29 (t, 2H); 7.03 (s, 1H); 7.29 (s, 1H); 7.87 (s, 1H); 9.05 (s, 1H).

EXAMPLE 459

Preparation of Compound 637 in Table 29

1-(2-((6-methoxy-7-(3-morpholinopropoxy)quinazolin-4-yl)amino)-4-methyl-1,3-thiazole-5-yl)ethanone (50 mg, 0.11 mmol) in ethanol (4 ml) and pyridine (1 ml) was reacted with hydroxylamine hydrochloride (19.5 mg, 0.27 mmol) at reflux for 3 h. The solvent was evaporated, water was added to the residue and a solid was recovered, washed with water to give title compound (14 mg, 27%)

MS ES$^+$: 473 (M+H)$^+$ $^1$HNMR (DMSOd$_6$, TFA): 2.25 (s, 3H); 2.30 (t, 2H); 2.53 (s, 3H); 3.17 (t, 2H); 3.38 (t, 2H); 3.56 (d, 2H); 3.69 (t, 2H); 3.99 (s, 3H); 4.05 (d, 2H); 4.32 (t, 2H); 7.32 (s, 1H); 7.88 (s, 1H); 9.12 (s, 1H).

EXAMPLE 460

Preparation of Compound 638 in Table 29

2-((6-methoxy-7-(3-morpholinopropoxy)quinazolin-4-yl) amino)-1,3-thiazole-5-carboxylic acid (89 mg, 0.2 mmol) in DMF (1.5 ml) was treated with diphenylphosporyl azide (66 mg, 0.24 mmol) and triethylamine (26 mg, 0.26 mmol). The solution was stirred at room temperature for 1 h and at 45° C. for 1 h. Tert-butanol (1 ml) was added, and the mixture heated at 90° C. for 2 h. The mixture was diluted with ethylacetate, aqueous sodium bicarbonate, the organic phase was recovered, dried over $MgSO_4$, filtered, concentrated and purified by silica gel chromatography, eluent $CH_2Cl_2$/MeOH 95/5 to 85/15 to give title compound as a yellow solid (25 mg, 24%).

MS ES$^+$: 517 (M+H)$^+$ $^1$HNMR (DMSOd$_6$, TFA): 1.50 (s, 9H); 2.31 (t, 2H); 3.15 (t, 2H); 3.35 (t, 2H); 3.55 (d, 2H); 3.69 (t, 2H); 3.97 (s, 3H); 4.04 (d, 2H); 4.29 (t, 2H); 7.13 (s, 1H); 7.26 (s, 1H); 7.94 (s, 1H); 9.11 (s, 1H).

EXAMPLE 461

Preparation of Compound 639 in Table 29

An analogous reaction to that described in example 459 but starting with O-methylhydroxylamine hydrochloride (18 mg, 0.22 mmol) and heating at reflux for 72 h yielded title compound (39 mg, 63%).

MS ES$^+$: 487 (M+H)$^+$ $^1$HNMR (DMSOd$_6$, TFA): 2.26 (s, 3H); 2.31 (t, 2H); 3.53 (s, 3H); 3.16 (t, 2H); 3.35 (t, 2H) 3.54 (d, 2H); 3.76 (s, 2H); 3.94 (s, 3H); 3.99 (s, 3H); 4.02 (d, 2H); 4.33 (t, 2H); 7.35 (s, 1H); 7.89 (s, 1H); 9.11 (s, 1H).

EXAMPLE 462

Preparation of Compound 640 in Table 29

An analogous reaction to that described in example 459 but starting with O-phenylhydroxylamine hydrochloride (32 mg, 0.22 mmol) yielded title compound (8 mg, 12

MS ES$^+$: 549 (M+H)$^+$ $^1$HNMR (DMSOd$_6$, TFA): 2.28 (t, 2H); 3.12 (t, 2H); 3.32 (t, 2H); 3.52 (d, 2H); 3.65 (t, 2H); 3.96 (s, 3H); 4.0 (d, 2H); 4.27 (t, 2H); 7.06 (t, 1H); 7.20 (d, 2H); 7.28 (s, 1H); 7.34 (t, 2H); 7.91 (s, 1H); 9.17 (s, 1H).

EXAMPLE 463

Preparation of Compound 641 in Table 29

An analogous reaction to that described in example 448 but starting with 2-amino-5-(4-methoxyphenyl)-1,3-thiazole, HBr (86 mg, 0.33 mmol) yielded title compound (105 mg, 77%).

MS ES$^+$: 508.6 (M+H)$^+$ $^1$HNMR (DMSOd$_6$, TFA): 2.33 (t, 2H); 3.20 (t, 2H); 3.40 (t, 2H); 3.60 (d, 2H); 3.73 (t, 2H); 3.86 (s, 3H); 4.08 (s, 3H); 4.09 (d, 2H); 4.36 (t, 2H); 7.10 (d, 2H); 7.44 (s, 1H); 7.76 (s, 1H); 7.96 (d, 2H); 8.33 (s, 1H); 9.26 (s, 1H).

EXAMPLE 464

Preparation of Compound 642 in Table 29

An analogous reaction to that described in example 448 but starting with 2-amino-5-phenyl)-1,3-thiazole (58 mg, 0.33 mmol) yielded title compound (120 mg, 84%).

MS ES$^+$: 478.6 (M+H)$^+$ $^1$HNMR (DMSOd$_6$, TFA): 2.31 (t, 2H); 3.17 (t, 2H); 3.37 (t, 2H); 3.56 (d, 2H); 3.70 (t, 2H); 4.01 (s, 3H); 4.05 (d, 2H); 4.32 (t, 2H); 7.34 (s, 1H); 7.41 (t, 1H); 7.51 (t, 2H); 7.72 (d, 2H); 7.97 (s, 1H); 8.24 (s, 1H); 9.16 (s, 1H).

EXAMPLE 465

Preparation of Compound 643 in Table 29

Methyl-2-cyano-4-methoxy-5-(3-morpholinopropoxy) phenyl-imidoformate (300 mg, 0.9 mmol) in DMF (4.5 ml) was reacted with 2-amino-5-ethyl-1,3-thiazole (127 mg, 0.99 mmol) in presence of sodium hydride (39.6 mg, 0.99 mmol) at 75° C. for 2 h. Acetic acid (77 μl, 1.35 mmol) was added to the mixture at room temperature, followed by MeOH/$Me_2NH$ (2M) (90 μl, 0.18 mmol) and the mixture was stirred at 75° C. for 1 h. The solvent was evaporated and the mixture was purified by silica gel chromatography, eluent $CH_2Cl_2$/MeOH 95/5→90/10 to give title compound (193 mg, 50%).

MS $ES^+$: 430.6 $(M+H)^+$ $^1$HNMR (DMSO$d_6$, TFA): 1.29 (t, 3H); 2.32 (t, 2H); 2.81 (q, 2H); 3.16 (t, 2H); 3.36 (t, 2H); 3.56 (d, 2H); 3.69 (t, 2H); 3.98 (s, 3H); 4.05 (d, 2H); 4.30 (t, 2H); 7.30 (s, 1H); 7.50 (s, 1H); 7.87 (s, 1H); 9.04 (s, 1H).

EXAMPLE 466

Preparation of Compound 644 in Table 29

An analogous reaction to that described in example 465 but starting with 2-amino-5-isopropyl)-1,3-thiazole (141 mg, 0.99 mmol) yielded title compound (107 mg, 26%).

MS $ES^+$: 444.6 $(M+H)^+$ $^1$HNMR (DMSO$d_6$, TFA): 1.33 (d, 6H); 2.32 (t, 2H); 3.17 (t, 2H); 3.36 (t, 2H); 3.55 (d, 2H); 3.69 (t, 2H); 3.98 (s, 3H); 4.04 (d, 2H); 4.30 (t, 2H); 7.29 (s, 1H); 7.49 (s, 1H); 7.87 (s, 1H); 9.05 (s, 1H).

EXAMPLE 467

Preparation of Compound 645 in Table 29

An analogous reaction to that described in example 465 but starting with 2-amino-5-benzyl)-1,3-thiazole (188 mg, 0.99 mmol) yielded title compound (370 mg, 84%).

MS $ES^+$: 492.6 $(M+H)^+$ $^1$HNMR (DMSO$d_6$, TFA): 2.31 (t, 2H); 3.16 (t, 2H); 3.35 (t, 2H); 3.55 (d, 2H); 3.69 (t, 2H); 3.98 (s, 3H); 4.04 (d, 2H); 4.18 (s, 2H); 4.29 (t, 2H); 7.27 (s, 1H); 7.28 (m, 1H); 7.35 (m, 4H); 7.61 (s, 1H); 7.88 (s, 1H); 9.02 (s, 1H).

EXAMPLE 468

Preparation of Compound 646 in Table 29

An analogous reaction to that described in example 465 but starting with 2-amino-5-methyl)-1,3-thiazole (113 mg, 0.99 mmol) yielded title compound (300 mg, 80%).

MS $ES^+$: 416.6 $(M+H)^+$ $^1$HNMR (DMSO$d_6$, TFA): 2.31 (t, 2H); 2.42 (s, 3H); 3.16 (t, 2H); 3.35 (t, 2H); 3.55 (d, 2H); 3.68 (t, 2H); 3.97 (s, 3H); 4.04 (d, 2H); 4.29 (t, 2H); 7.30 (s, 1H); 7.48 (s, 1H); 7.86 (s, 1H); 9.03 (s, 1H).

EXAMPLE 469

Preparation of Compound 647 in Table 29

An analogous reaction to that described in example 465 but starting with 2-amino-5-butyl) 1,3-thiazole (155 mg, 0.99 mmol) yielded title compound (385 mg, 93%).

MS $ES^+$: 458.6 $(M+H)^+$ $^1$HNMR (DMSO$d_6$, TFA): 0.93 (t, 3H); 1.36 (m, 2H); 1.64 (m, 2H); 2.29 (t, 2H); 2.79 (t, 2H); 3.16 (t, 2H); 3.35 (t, 2H); 3.55 (d, 2H); 3.68 (t, 2H); 3.97 (s, 3H); 4.04 (d, 2H); 4.29 (t, 2H); 7.29 (s, 1H); 7.51 (s, 1H); 7.86 (s, 1H); 9.03 (s, 1H).

EXAMPLE 470

Preparation of Compound 648 in Table 29

An analogous reaction to that described in example 465 but starting with 2-amino-5-formyl-1,3-thiazole (499.4 mg, 3.9 mmol) yielded title compound (244 mg, 39%).

MS $ES^+$: 430.6 $(M+H)^+$ $^1$HNMR (DMSO$d_6$, TFA): 2.32 (t, 2H); 3.17 (t, 2H); 3.37 (t, 2H); 3.57 (d, 2H); 3.70 (t, 2H) 4.03 (s, 3H); 4.06 (d, 2H); 4.35 (t, 2H); 7.45 (s, 1H); 8.12 (s, 1H); 8.71 (s, 1H); 9.32 (s, 1H).

EXAMPLE 471

Preparation of Compound 649 in Table 29

An analogous reaction to that described in example 459 but starting with 2-(6-methoxy-7-(3-morpholinopropoxy) quinazolin-4-yl)amino-1,3-thiazol-5-carbaldehyde (100 mg, 0.23 mmol) and heating at 80° C. for 4 h, yielded title compound (21 mg, 20%).

MS $ES^+$: 445.6 $(M+H)^+$ $^1$HNMR (DMSO$d_6$, TFA): 2.31 (t, 2H); 3.17 (t, 2H); 3.36 (t, 2H); 3.56 (d, 2H); 3.70 (t, 2H) 4.00 (s, 3H); 4.05 (d, 2H); 4.32 (t, 2H); 7.36 (s, 1H); 7.92 (s, 1H); 7.98 (s, 1H); 8.33 (s, 1H); 9.20 (s, 1H).

EXAMPLE 472

Preparation of Compound 650 in Table 30

An analogous reaction to that described in example 448, but starting with 2-amino-5-tert-butyl-1,3,4-thiadiazol (52 mg, 0.33 mmol) yielded title compound (80 mg, 58%).

MS $ES^+$: 458 $(M+H)^+$ $^1$HNMR (DMSO$d_6$, TFA): 1.45 (s, 9H); 2.32 (t, 2H); 3.16 (t, 2H); 3.36 (t, 2H); 3.56 (d, 2H); 3.69 (t, 2H); 4.00 (s, 3H); 4.03 (d, 2H); 4.32 (t, 2H); 7.38 (s, 1H); 7.95 (s, 1H); 9.18 (s, 1H).

EXAMPLE 473

Preparation of Compound 651 in Table 30

An analogous reaction to that described in example 448, but starting with 2-amino-5-cyclopropyl-1,3,4-thiadiazol (47 mg, 0.33 mmol) yielded title compound (105 mg, 83%).

MS $ES^+$: 443 $(M+H)^+$ $^1$HNMR (DMSO$d_6$, TFA): 1.08 (m, 2H); 1.23 (m, 3H); 2.32 (t, 2H); 3.15 (t, 2H); 3.35 (t, 2H); 3.55 (d, 2H); 3.68 (t, 2H); 3.99 (s, 3H); 4.04 (d, 2H); 4.32 (t, 2H); 7.38 (s, 1H); 7.93 (s, 1H); 9.14 (s, 1H).

EXAMPLE 474

Preparation of Compound 652 in Table 30

An analogous reaction to that described in example 448, but starting with 2-amino-5-ethylthio-1,3,4-thiadiazol (53 mg, 0.33 mmol) yielded title compound (103 mg, 75%).

MS $ES^+$: 463 $(M+H)^+$ $^1$HNMR (DMSO$d_6$, TFA): 1.41 (t, 3H); 2.31 (t, 2H); 3.15 (t, 2H); 3.31 (q, 2H); 3.35 (t, 2H); 3.55 (d, 2H); 3.69 (t, 2H);

4.00 (s, 3H); 4.04 (d, 2H); 4.33 (t, 2H); 7.41 (s, 1H); 8.08 (s, 1H); 9.19 (s, 1H).

EXAMPLE 475

Preparation of Compound 653 in Table 30

An analogous reaction to that described in example 448, but starting with 2-amino-5-phenyl-1,3,4-thiadiazol (91 mg, 0.33 mmol) yielded title compound (110 mg, 76%).

MS $ES^+$: 479 $(M+H)^+$ $^1$HNMR ($DMSOd_6$, TFA): 2.32 (t, 2H); 3.16 (t, 2H); 3.37 (t, 2H); 3.57 (d, 2H); 3.69 (t, 2H); 4.03 (s, 3H); 4.05 (d, 2H); 4.34 (t, 2H); 7.42 (s, 1H); 7.61 (m, 3H); 7.99 (m, 2H); 8.06 (s, 1H); 9.25 (s, 1H).

EXAMPLE 476

Preparation of Compound 654 in Table 30

An analogous reaction to that described in example 448, but starting with N-phenyl-4H-1,2,4 triazole-3,5-diamine (58 mg, 0.33 mmol) yielded title compound (70 mg, 49%).

MS $ES^+$: 477 $(M+H)^+$ $^1$HNMR ($DMSOd_6$, TFA): 2.32 (t, 2H); 3.16 (t, 2H); 3.37 (t, 2H); 3.57 (d, 2H); 3.70 (t, 2H); 4.02 (s, 3H); 4.05 (d, 2H); 4.34 (t, 2H); 6.92 (t, 1H); 7.30 (t, 1H); 7.42 (s, 1H); 7.58 (d, 2H); 8.19 (s, 1H); 8.95 (s, 1H).

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro Aurora2 Kinase Inhibition Test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into *E. coli* DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1\times10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2\times10^6$ cells $ml^{-1}$ they were infected with plaque-pure aurora2 recombinant virus at a multiplicity of infection of 1 and harvested 48 hours later. All subsequent purification steps were performed at 4° C. Frozen insect cell pellets containing a total of $2.0\times10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM $Na_3VO_4$, 1 mM PMSF (phenylmethylsulphonyl fluoride), 2 mM 2-mercaptoethanol, 2 mM imidazole, 1 $\mu$g/ml aprotinin, 1 $\mu$g/ml pepstatin, 1 $\mu$g/ml leupeptin), using 1.0 ml per $3\times10^7$ cells. Lysis was achieved using a dounce homogeniser, following which the lysate was centrifuged at 41,000 g to for 35 minutes. Aspirated supernatant was pumped onto a 5 mm diameter chromatography column containing 500 $\mu$l Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 $\mu$l of dilute enzyme is used for each assay well. Test compounds (at 10 mM in dimethylsulphoxide (DMSO)) were diluted with water & 10 $\mu$l of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM $MnCl_2$, 6.25 mM ATP, 7.5 μM peptide substrate [biotin-LRRWSLGLRRWSLGLRRWSLGLRRWSLG]) containing 0.2 μCi [$\gamma^{33}$P]ATP (Amersham Pharmacia, specific activity≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity. In this test, compound 52 in Table 2 gave 50% inhibition of enzyme activity at a concentration of 0.167 μM, and Compound 253 in Table 21 gave 50% inhibition of enzyme activity at 0.089 μM.

(a) In Vitro Cell Proliferation Assay

This assay determines the ability of a test compound to inhibit the growth of adherent mammalian cell lines, for example the human tumour cell line MCF7. MCF-7 (ATCC HTB-22) or other adherent cells were typically seeded at $1\times10^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 μl of a cell lysis/dye mixture (10 μl of 20× cell lysis buffer B, 190 μl of sterile water, 0.25 μl of CYQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compound 52 in Table 2 was effective in this test at 0.616 μM and Compound 253 in Table 20 was effective at 5.9 μM.

These values could also be used to calculate the dilution range of a test compound at which the cell density dropped below the day 1 control value. This indicates the cytotoxicity of the compound.

(a) In Vitro Cell Cycle Analysis Assay

This assay determines the ability of a test compound to arrest cells in specific phases of the cell cycle. Many different mammalian cell lines could be used in this assay and MCF7 cells are included here as an example. MCF-7 cells were seeded at $3\times10^5$ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200 μl of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 μg/ml and RNAase A (Sigma Aldrich Co.) to 100 μg/ml. The cells were then incubated at 37° C. for 30 minutes. The samples were centrifuged at 2200 rpm for 10 min, the supernatant removed and the remaining pellet (nuclei) resuspended in 200 μl of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle.

Treating MCF7 cells with 1 μM Compound 52 in Table 2 for 24 hours produced the following changes in cell cycle distribution:

| Treatment | % Cells in G2/M |
|---|---|
| DMSO (control) | 9.27% |
| 10 μM Compound 52 | >50% |

What is claimed is:

1. A compound of formula (I)

(I)

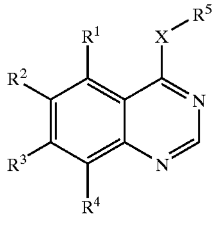

or a salt, ester, or amide thereof;

wherein X is O or NH;

$R^5$ is a substituted 5-membered heteroaromatic ring, selected from formula (a) or (b)

(a)

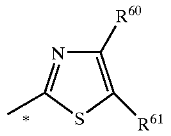

(b)

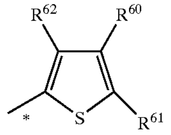

wherein any one of $R^{60}$, $R^{61}$, and $R^{62}$ is a substituent group and * indicates the point of attachment to the group X in formula (I), and the other two are each independently hydrogen or a $C_{1-3}$alkyl $R^1$, $R^2$, $R^3$, and $R^4$ are independently selected from, halo, cyano, nitro, trifluoromethyl, $C_{1-3}$alkyl, —$NR^7R^8$ (wherein $R^7$ and $R^8$, which may be the same or different, each represents hydrogen or $C_{1-3}$alkyl), or —$X^1R^9$ (wherein $X^1$ represents a direct bond, —O—, —$CH_2$—, —OCO—, carbonyl, —S—, —SO—, —$SO_2$—, —$NR^{10}$CO—, —$CONR^{11}$ —, —$SO_2NR^{12}$—, —$NR^{13}SO_2$— or —$NR^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following groups:

1) hydrogen or $C_{1-5}$alkyl which may be unsubstituted or which may be substituted with one or more groups selected from hydroxy, fluoro, or amino, 2) $C_{1-5}$alkyl$X^2COR^{15}$ (wherein $X^2$ represents —O— or —$NR^{16}$ (in which $R^{15}$ represents hydrogen, $C_{1-3}$allyl or $C_{1-3}$alkoxy$C_{2-3}$alkyl) and $R^{16}$ represents $C_{1-3}$alkyl, —$NR^{17}R^{18}$ or —$OR^{19}$ (wherein $R^{17}$, $R^{18}$ and $R^{19}$ which may be the same or different each represents hydrogen, $C_{1-3}$alkyl or $C_{1-3}$alkoxy$C_{2-3}$alkyl));

3) $C_{1-5}$alkyl$X^3R^{20}$ (wherein $X^3$ represents —O—, —S—, —SO—, —$SO_2$—, —OCO—, —$NR^{21}$CO—, —$CONR^{22}$—, —$SO_2NR^{23}$—, —$NR^{24}SO_2$— or —$NR^{25}$— (wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{26}$ (wherein $X^4$ and $X^5$ which may be the same or different are each —O—, —S—, —SO—, —$SO_2$—, —$NR^{27}$CO—, —$CONR^{28}$—, —$SO_2NR^{29}$—, —$NR^3SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5) $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6) $C_{1-5}$alkyl$R^{32}$ (wherein $R^{32}$ is as defined hereinbefore);

7) $C_{2-5}$alkenyl$R^{32}$ (wherein $R^{32}$ is as defined hereinbefore);

8) $C_{2-5}$alkynyl$R^{32}$(wherein $R^{32}$ is as defined hereinbefore);

9) $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_4$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{34}R^{15}$ and —$NR^{36}COR^{37}$ (wherein $R^{33}$, $R^{35}$, $R^{36}$ and $R^{37}$, which may be the same or different, each represents hydrogen, $C_{1-4}$alkyl or $C_{1-3}$alkoxy$C_{2-3}$alkyl));

10) $C_{1-5}$alkyl$R^{33}$ (wherein $R^{33}$ is as defined hereinbefore);

11) $C_{2-5}$alkenyl$R^{33}$ (wherein $R^{33}$ is as defined hereinbefore);

12) $C_{2-5}$alkynyl$R^{33}$ (wherein $R^{33}$ is as defined hereinbefore);

13) $C_{1-5}$alkyl$X^6R^{33}$ (wherein $X^6$ represents —O—, —S—, —SO—, —$SO_2$—, —$NR^{38}$CO—, $CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{33}$ is as defined hereinbefore);

14) $C_{2-5}$alkenyl$X^7R^{33}$ (wherein $X^7$ represents —O—, —S—, —SO—, —$SO_2$—, —$NR^{43}$CO—, —$CONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15) $C_{2-5}$alkynyl$X^8R^{33}$ (wherein $X^8$ represents —O—, —S—, —SO—, —$SO_2$—, —$NR^{48}$CO—, —$CONR^{49}$—, —$SO_2NR^{50}$—, —$NR^{51}$— or —$NR^{52}$— (wherein $R^{48}$, $R^{49}$, $R^{50}$, $R^{51'}$ and $R^{52}$ each independently represents hydrogen, $C_{1-3}$alkyl or $C_{1-3}$alkoxy$C_{2-3}$ alkyl) and $R^{33}$ is as defined hereinbefore);

16) $C_{1-3}$alkyl$X^9C_{1-3}$alkyl$R^{33}$ (wherein $X^9$ represents —O—, —S—, —SO—, —$SO_2$—, —$NR^{53}$CO—, —$CONR^{54}$—, —$SO_2NR^{55}$—, —$NR^{56}SO_2$— or —$NR^{57}$— (wherein $R^{53}$, $R^{54}$, $R^{55}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17) $C_{1-3}$alkyl$X^9C_{1-3}$alkyl $R^{32}$ (wherein $X^9$ and $R^{28}$ are as defined hereinbefore); and where any one of $R^{60}$, $R^{61}$, or $R^{62}$ is a substituent group, it is a group of sub-formula (k):

(k)

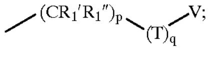

; or a group of sub-formula (II)

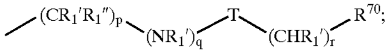; or (II)

a group of formula (VI)

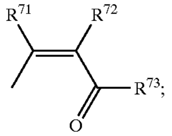; or any one of $R^{60}$, $R^{61}$, or $R^{62}$ is a functional group;

p and q are independently 0 or 1; and $R_1$' and $R_1$" are independently hydrogen, hydroxy, optionally substituted alkyl, optionally substituted cycloalkyl, halogen, cyano, optionally substituted alkyl, optionally substituted alkenyl, where the optionally substituted alkyl or alkynyl may be substituted with halo, nitro, cyano, hydroxy, trifluoromethyl, amino, carboxy, carbamoyl, mercapto, sulfamoyl, $C_{1-4}$alkyl, $C_{2-4}$alkenyl, $C_{2-4}$alkynyl, $C_{3-6}$-cycloalkyl, $C_{3-6}$cycloalkenyl, $C_{1-4}$alkoxy, $C_{1-4}$alkanoyl, $C_{1-}$alkanoyloxy, N-($C_{1-4}$alkyl), N($C_{1-4}$alkyl)$_2$, $C_{1-4}$alkanoylamino, ($C_{1-4}$alkanoyl)$_2$amino, N—($C_{1-4}$ alkyl)carbamoyl, N,N-($C_{1-4}$)$_2$carbamoyl, $C_{1-4}$)S, $C_{1-4}$S (O), ($C_{1-4}$alkyl)S(O)$_2$, ($C_4$)alkoxycarbonyl, N-($C_{1-4}$ alkyl)sulfamoyl, N,N—$C_{1-4}$alkyl)sulfamoyl, $C_{1-4}$ alkylsulfonylamino, or heterocyclyl, and wherein $R_1$' can form with $R_1$"a 3 to 6 membered ring;

T is C═O, $SO_n$, C(═NOR)CO, C(O)C(O), C═NCN, CV═NO or wherein n=0, 1 or 2;

V is independently $R^{63}$ or N($R^{63}$)$R^{64}$ wherein $R^{63}$ and $R^{64}$ are independently selected from optionally substituted hydrocarbyl or optionally substituted heterocyclyl, or $R^{63}$ and $R^{64}$ together with the nitrogen atom to which they are attached form an optionally substituted heterocyclic ring; r is 0, 1, 2, 3, or 4;

$R^{70}$ is hydrogen, hydroxy (other than where q is 0), $C_{1-6}$alkyl, $C_{1-6}$alkoxy, amino, N—$C_{1-6}$alkylamino, N,N-($C_{1-4}$alkyl)$_2$amino, hydroxy$C_{2-6}$alkoxy, $C_{1-6}$alkoxy$C_{2-6}$alkoxy, amino$C_{2-6}$alkoxy, N—$C_{1-6}$ alkylamino$C_{2-6}$alkoxy, N,N-($C_{1-6}$alkyl)$_2$amino$C_{2-6}$ alkoxy or $C_{3-7}$cycloalkyl, or $R^{70}$ is of the Formula (III):

$$—K—J \quad (III)$$

wherein J is aryl, heteroaryl or heterocyclyl and K is a bond, oxy, imino, N-($C_{1-6}$alkyl)imino, oxy$C_{1-6}$ alkylene, imino$C_{1-6}$alkylene, N-($C_{1-6}$alkyl)imino$C_{1-6}$ alkylene, —NHC(O)—, —$SO_2$NH—, —$NHSO_2$— or —NHC(O)—C-alkylene-; and any aryl, heteroaryl or heterocyclyl group in a $R^{70}$ group may be optionally substituted with one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—, $C_{1-6}$alkylS(O)$_n$— (wherein n is 0 to 2), N—$C_{1-6}$alkylamino, N,N-($C_{1-6}$ alkyl)$_2$amino, $C_{1-6}$alkoxycarbonyl, N—$C_{1-6}$ alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N—$C_{1-6}$alkylsulphamoyl, N,N-($C_{1-6}$alkyl)$_2$ sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^{70}$ group may be optionally substituted with one or more groups of the Formula (IV):

$$—B^1—(CH_2)_p—A^1 \quad (IV)$$

wherein $A^1$ is halo, hydroxy, $C_{1-6}$alkoxy, cyano, amino, N—$C_{1-6}$alkylamino, N,N-($C_{1-6}$alkyl)$_2$amino, carboxy, $C_{1-6}$alkoxycarbonyl, carbamoyl, N—$C_{1-6}$alkylcarbamoyl or N,N-($C_{1-6}$alkyl)$_2$carbamoyl, p is 1 to 6, and $B^1$ is a bond, oxy, imino, N-($C_{1-6}$alkyl)imino or —NHC(O)—, with the proviso that p is 2 or more unless $B^1$ is a bond or —NHC(O)—; or any aryl, heteroaryl or heterocyclyl group in a $R^{70}$ group may be optionally substituted with one or more groups of the Formula (V):

$$—E^1—D^1 \quad (V)$$

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$ alkyl)imino, imino$C_{1-4}$alkylene, N—$C_{1-4}$alkyl)-imino$C_{1-6}$ alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$ alkylene, —NHC(O)—, —$NHSO_2$—, —$SO_2$NH— or —NHC(O)—$C_{1-6}$alkylene-, and any aryl, heteroaryl or heterocyclyl group in a substituent on $D^1$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N-($C_{1-6}$alkyl)$_2$ carbamoyl, $C_{2-6}$alkanoyl, amino, N—$C_{1-6}$alkylamino and N,N-($C_{1-6}$alkyl)$_2$amino, and any $C_{3-7}$cycloalkyl or heterocyclyl group in a $R^{70}$ group may be optionally substituted with one or two oxo or thioxo substituents;

and any of the $R^{70}$ groups defined hereinbefore which comprises a $CH_2$ group which is attached to two carbon atoms or a $CH_3$ group which is attached to a carbon atom may optionally bear on each said $CH_2$ or $CH_3$ group a substituent selected from hydroxy, amino, $C_{1-6}$alkoxy, N—$C_{1-6}$alkylamino, N,N-($C_{1-6}$alkyl)$_2$ mino and heterocyclyl; where $R^{71}$ and $R^{72}$ are independently selected from hydrogen or $C_{1-4}$alkyl, or $R^{71}$ and $R^{72}$ together form a bond, and $R^{73}$ is a group $OR^{74}$, $NR^{75}R^{76}$ where $R^{74}$, $R^{75}$ and $R^{76}$ are independently selected from optionally substituted hydrocarbyl or optionally substituted heterocyclic groups, and $R^{75}$ and $R^{76}$ may additionally form together with the nitrogen atom to which they are attached, an aromatic or non-aromatic heterocyclic ring which may contain further heteroatoms; optional substituents for hydrocarbyl or heterocyclic groups $R^{74}$, $R^{75}$ and $R^{76}$ include functional groups as defined above, and heterocyclic groups $R^{74}$, $R^{75}$ and $R^{76}$ may further be substituted by hydrocarbyl groups;

functional group is a reactive substituent selected from nitro, cyano, halo, oxo, $═CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, $NOR^{77}—NR^{77}C(O)_xR^{78}$, $—NR^{77}CONR^{78}R^{79}$, $—N═CR^{78}R^{79}$, $S(O)_yNR^{78}R^{79}$ and $—NR^{77}S(O)\ R^{78}$ where $R^{77}$, $R^{78}$ and $R^{79}$ are independently selected from hydrogen or optionally substituted hydrocarbyl, or $R^{78}$ and $R^{79}$ together form an optionally substituted ring which optionally contains further heteroatoms integer of 1 or 2, and y is 0 or an integer of 1.

2. A compound according to claim 1, wherein any one of $R^{60}$, $R^{61}$, or $R^{62}$ is a group of sub-formula (k) and $R^{63}$ and $R^{64}$ are selected from hydrogen or $—(CH_2)_qR^{70}$.

3. A compound according to claim 1, wherein any one of $R^{63}$ or $R^{64}$ is hydrogen or methyl, ethyl, or propyl optionally substituted with hydroxy and the other is optionally substituted hydrocarbyl or optionally substituted heterocyclyl;

wherein optionally substituted hydrocarbyl for $R^{63}$ or $R^{64}$ comprises alkyl, cycloalkyl, alkenyl, or aryl, any of which is optionally substituted with a functional group, or in the case of aryl groups, with an alkyl group and in the case of alkyl group, with an aryl or heterocyclic group either of which may themselves be optionally substituted with alkyl or a functional group; or phenyl optionally substituted with one or more groups selected from methyl or ethyl (either of which may be optionally substituted with hydroxy), or a functional group selected from halo, hydroxy, alkoxy, trifluoromethyl, nitro, cyano, trifluromethoxy, $CONH_2$, $C(O)CH_3$, amino, or dimethylamino); or $C_{1-6}$alkyl, optionally substituted with one or more functional groups selected from cyano, hydroxy, alkoxy, methoxy, COOalkyl, or aryl optionally substituted with a functional group selected from cyano, hydroxy, alkoxy, methoxy, and COOalkyl, or an optionally substituted heterocyclic group; and wherein optionally substituted heterocyclyl, or $R^{63}$ and $R^{64}$ together form a heterocyclic group, with the nitrogen to which they are attached form an optionally substituted heterocyclic ring, comprise an aromatic or non-aromatic ring selected from piperidine, piperazine, morpholino, pyrrolidine, and pyridine, any of which may be optionally substituted with a functional group selected from hydroxy, alkoxy, and alkyl which may itself be substituted with a hydroxy group.

4. A compound according to claim 1, wherein any one of $R^{60}$, $R^{61}$, or $R^{62}$ is a group of sub-formula (II).

5. A compound according to claim 1, wherein $R^4$ is $X^1R^9$, $X^1$ is a direct bond, and $R^9$ is hydrogen.

6. A compound according to claim 1, wherein $R^1$ is $X^1R^9$, $X^1$ is a direct bond, and $R^9$ is hydrogen.

7. A compound according to claim 1, wherein $R^2$ is selected from halo, cyano, nitro, trifluoromethyl, $C_{1-3}$alkyl, $—NR^7R^8$ (wherein $R^1$ and $R^8$, which may be the same or different, and each is selected from hydrogen or $C_{1-3}$alkyl), or a group $—X^1R^9$, $X^1$ is oxygen and $R^9$ is selected from a group of formula (I) or (10).

8. A compound according to claim 1, wherein $R^3$ is a group $X^1R^9$, $X^1$ is oxygen and $R^9$ is selected from a group of formula (I) or (10).

9. A process for the preparation of a compound of claim 1 or a pharmaceutically acceptable salt, or an in vivo hydrolysable ester thereof, comprising (i) reacting a compound of formula (VII)

(VII)

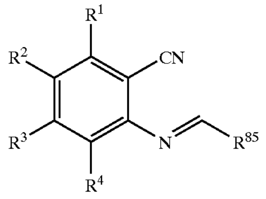

$R^1$, $R^2$, $R^3$, and $R^4$ are independently selected from, halo, cyano, nitro, trifluoromethyl, $C_{1-3}$alkyl, $—NR^7R^8$ (wherein $R^7$ and $R^8$, which may be the same or different, each represents hydrogen or $C_{1-3}$alkyl), or $—X^1R^9$ (wherein $X^1$ represents a direct bond, —O—, $—CH_2—$, —OCO—, carbonyl, —S—, —SO—, $—SO_2—$, $—NR^{10}CO—$, $—CONR^{11}—$, $—SO_2NR^{12}—$, $—NR^{13}SO_2—$ or $—NR^{14}—$ (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following groups:

1) hydrogen or $C_{1-5}$alkyl which may be unsubstituted or which may be substituted with one or more groups selected from hydroxy, fluoro or amino, 2) $C_{1-5}$alkyl$X^2COR^{15}$ (wherein $X^2$ represents —O— or $—NR_{1-6}—$(in which $R^{15}$ represents hydrogen, $C_{1-3}$alkyl or $C_{1-3}$alkoxy$C_{2-3}$alkyl) and $R^{16}$ represents $C_{1-3}$alkyl, $—NR^{17}R^{18}$ or $—OR^{19}$ (wherein $R^{17}$, $R^{18}$ and $R^{19}$ which may be the same or different each represents hydrogen, $C_{1-3}$alkyl or $C_{1-3}$alkoxy$C_{2-3}$ alkyl));

3) $C_{1-5}$alkyl$X^3R^{20}$ (wherein $X^3$ represents —O—, —S—, —SO—, $—SO_2—$, —OCO—, $—NR^{21}CO—$, $—CONR^{22}—$, $—SO_2NR^{23}—$, $—NR^{24}SO_2—$ or $—NR^{25}—$ (wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{26}$ (wherein $X^4$ and $X^5$ which may be the same or different are each —O—, —S—, —SO—, $—SO_2—$, $—NR^{27}CO—$, $—CONR^{28}—$, $—SO_2NR^{29}—$, $—NR^{30}SO_2—$ or $—NR^{31}—$ (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5) $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6) $C_{1-5}$alkyl$R^{32}$ (wherein $R^{32}$ is as defined hereinbefore);

7) $C_{2-5}$alkenyl$R^{32}$ (wherein $R^{32}$ is as defined hereinbefore);

8) $C_{2-5}$alkynyl$R^{32}$ (wherein $R^{32}$ is as defined hereinbefore);

9) $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, $—CONR^{34}R^{35}$ and $—NR^{36}COR^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$ alkyl));

10) $C_{1-5}alkylR^{33}$ (wherein $R^{33}$ is as defined hereinbefore);

11) $C_{2-5}alkenylR^{33}$ (wherein $R^{33}$ is as defined hereinbefore);

12) $C_{2-5}alkynylR^{33}$ (wherein $R^{33}$ is as defined hereinbefore);

13) $C_{1-5}alkylX^6R^{33}$ (wherein $X^6$ represents —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{41}$, $R^{41}$ and $R^{42}$ each independently represents hydrogen, $C_{1-3}alkyl$ or $C_{1-3}alkoxyC_{2-3}alkyl$) and $R^{33}$ is as defined hereinbefore);

14) $C_{2-5}alkenylX^7R^{33}$ (wherein $X^7$ represents —O—, —S—, —SO—, —$SO_2$—, —$NR^{43}CO$—, —$CONR^{44}$—, —$SO_2NR^{45}$—, —$NR^{46}SO_2$— or —$NR^{47}$— (wherein $R^{43}$, $R^{44}$, R, $R^{46}$ and $R^{47}$ each independently represents hydrogen, $C_{1-3}alkyl$ or $C_{1-3}alkoxyC_{2-3}alkyl$) and $R^{33}$ is as defined hereinbefore);

15) $C_{2-5}alkynylX^8R^{33}$ (wherein $X^8$ represents —O—, —S—, —SO—, —$SO_2$—, —$NR^{48}CO$—, —$CONR^{49}$—, $SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}alkyl$ or $C_{1-3}alkoxyC_{2-3}alkyl$) and $R^{33}$ is as defined hereinbefore);

16) $C_{1-3}alkylX^9C_{1-3}alkylR^{33}$ (wherein $X^9$ represents —O—, —S—, —SO—, —$SO_2$—, —$NR^{53}CO$—, —$CONR^{54}$—, —$SO_2NR^{55}$—, —$NR^{55}SO_2$— or —$NR^{57}$ (wherein $R^{53}$, $R^{54}$, $R^{55}$, $R^{16}$ and $R^{57}$ each independently represents hydrogen, $C_{1-3}alkyl$ or $C_{1-3}alkoxyC_{2-3}alkyl$) and $R^{33}$ is as defined hereinbefore); and 17) $C_{1-3}alkylX^9C_{1-3}alkylR^{32}$ (wherein $X^9$ and $R^{28}$ are as defined hereinbefore); and where any one of $R^{60}$, $R^{61}$ or $R^{62}$ are a substituent group, it is a group of sub-formula (k):

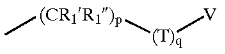

(k)

or they are a group of sub-formula (II)

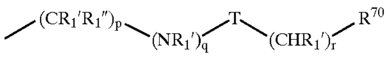

(II)

or they are a group of formula (VI)

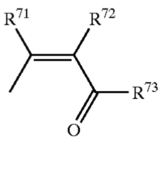

or at least one of $R^{60}$, $R^{61}$ or $R^{62}$ is a functional group;

wherein p and q are independently 0 or 1 and wherein $R_1'$ and $R_1''$ are independently hydrogen, hydroxy, optionally substituted alkyl, optionally substituted cycloalkyl, halogen, cyano, optionally substituted alkyl, optionally substituted alkyenyl, where the optionally substituted alkyl or alkynyl may be substituted with halo, nitro, cyano, hydroxy, trifluoromethyl, amino, carboxy, carbamoyl, mercapto, sulfamoyl, $C_{1-4}$ alkyl, $C_{2-4}alkenyl$, $C_{2-4}$ alkynyl, $C_{3-4}$ cycloalkyl, $C_{3-6}$ cycloalkenyl, $C_{1-4}$ alkoxy, $C_{1-4}$ alkanoyl, $C_{1-4}$ alkanoyloxy, N-($C_{1-4}$ alkyl), $N(C_{1-4}alkyl)_2$, $C_{1-4}$ alkanoylamino, $(C_{1-4}$ alkanoyl$)_2$amino, N-($C_{1-4}$alkyl) carbamoyl, N,N-$(C_{1-4})_2$carbamoyl, $C_{1-4})S$, $C_{1-4}S(O)$, $(C_{1-4}alkyl)S(O)_2$, $(C_{1-4})$ alkoxycarbonyl, N-($C_{1-4}$ alkyl)sulfamoyl, N,N—$C_{1-4}$ alkyl)sulfamoyl, $C_{1-4}$ alkylsolfonylamino, or heterocyclyl, and wherein $R_1'$ can form with $R_1''$ a 3 to 6 membered ring; wherein T is C═O, $SO_n$, C(═NOR)CO, C(O)C(O), C═NCN, CV═NO or wherein n=0, 1 or 2; V is independently $R^{63}$ or $N(R^{63})R^{64}$ wherein $R^{63}$ and $R^{64}$ are independently selected from hydrogen, optionally substituted hydrocarbyl or optionally substituted heterocyclyl, or $R^{63}$ and $R^{64}$ together with the nitrogen atom to which they are attached form an optionally substituted heterocyclic ring; r is 0, 1, 2, 3 or 4; and $R^{70}$ is hydrogen, hydroxy (other than where q is 0), $C_{1-6}alkyl$, $C_{1-6}alkoxy$, amino, N—$C_{1-6}alkylamino$, N,N-$(C_{1-6}$ alkyl$)_2$amino, hydroxy$C_{2-6}$alkoxy, $C_{1-6}alkoxyC_{2-6}$ alkoxy, amino$C_{2-6}$alkoxy, N—$C_{1-6}alkylaminoC_{2-6}$ alkoxy, N,N-$(C_{1-6}alkyl)_2aminoC_{2-6}alkoxy$ or $C_{3-7}cycloalkyl$, or $R^{70}$ is of the Formula (III):

$$—K—J \quad (III)$$

wherein J is aryl, heteroaryl or heterocyclyl and K is a bond, oxy, imino, N-($C_{1-6}$alkyl)imino, oxy$C_{1-6}$alkylene, imino$C_{1-6}$ alkylene, N-($C_{1-6}$alkyl)imino$C_{1-6}$alkylene, —NHC(O)—, —$SO_2NH$—, —$NHSO_2$— or —NHC(O)—$C_1$-alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}alkyl$, $C_{2-6}alkenyl$, $C_{2-6}alkynyl$, $C_{1-6}alkoxy$, —O—($C_{1-3}$alkyl)-O—, $C_{1-6}alkylS(O)$— (wherein n is 0–2), N—$C_{1-6}$ alkylamino, N,N-$(C_{1-6}alkyl)_2$amino, $C_{1-6}$alkoxycarbonyl, N—$C_{1-4}$alkylcarbamoyl, N,N-$(C_{1-6}alkyl)_2$carbamoyl, $C_{2-4}$alkanoyl, $C_{1-6}$alkanoyloxy, $C_{1-6}$alkanoylamino, N—$C_{1-6}$alkylsulphamoyl, N,N-$(C_{1-6}alkyl)_2$sulphamoyl, $C_{1-4}$alkylsulphonylamino and $C_{1-6}$alkylsulphonyl-N-($C_{1-6}$alkyl)amino, or any aryl, heteroaryl or heterocyclyl group in a $R^{70}$ group may be optionally substituted with one or more groups of the Formula (IV):

$$—B^1—(CH_2)_p—A^1 \quad (IV)$$

wherein $A^1$ is halo, hydroxy, $C_{1-6}alkoxy$, cyano, amino, N—$C_{1-6}$alkylamino, N,N-$(C_{1-6}alkyl)_2$amino, carboxy, $C_{1-6}$alkoxycarbonyl, carbamoyl, N—$C_{1-6}$alkylcarbamoyl or N,N-$(C_{1-6}alkyl)_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—;

or any aryl, heteroaryl or heterocyclyl group in a $R^{70}$ group may be optionally substituted with one or more groups of the Formula (V):

$$—E^1—D^1 \quad (V)$$

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$ alkyl)imino, imino$C_{1-6}$alkylene, N-($C_{1-6}$alkyl)-imino$C_{1-6}$ alkylene, $C_{1-4}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-}$ $_4$alkylene, —NHC(O)—, —$NHSO_2$—, —$SO_2NH$— or —NHC(O)—$C_{1-6}$alkylene-, and any aryl, heteroaryl or heterocyclyl group in a substituent on $D^1$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N-($C_{1-6}$alkyl)$_2$ carbamoyl, $C_{2-6}$alkanoyl, amino, N—$C_{1-6}$alkylamino and N,N—$C_{1-6}$alkyl)$_2$amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-4}$alkoxy, N—$C_{1-6}$alkylamino, N,N-($C_{1-4}$alkyl)$_2$amino and heterocyclyl; where $R^{71}$ and $R^{72}$ are independently selected from hydrogen or $C_{1-4}$alkyl, or $R^{71}$ and $R^{72}$ together form a bond, and $R^{73}$ is a group $OR^{74}$, $NR^{75}R^{76}$ where $R^{74}$, $R^{75}$ and $R^{76}$ are independently selected from optionally substituted hydrocarbyl or optionally substituted heterocyclic groups, and $R^{75}$ and $R^{76}$ may additionally form together with the nitrogen atom to which they are attached, an aromatic or non-aromatic heterocyclic ring which may contain further heteroatoms; optional substituents for hydrocarbyl or heterocyclic groups $R^{74}$, $R^{75}$ and $R^{76}$ include functional groups as defined above. Heterocyclic groups $R^{74}$, $R^{75}$ and $R^{76}$ may further be substituted by hydrocarbyl groups;

wherein functional group is a reactive substituents selected from nitro, cyano, halo, oxo, $=CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, $=NOR^{77}$, $NR^{77}C(O)_xR^{78}$, $—NR^{77}CONR^{78}R^{79}$, $—N=CR^{78}R^{79}$, $S(O)_yNR^{78}R^{79}$ and $—NR^{77}S(O)_yR^{78}$ where $R^{77}$, $R^{78}$ and $R^{79}$ are independently selected from hydrogen or optionally substituted hydrocarbyl, or $R^{78}$ and $R^{79}$ together form an optionally substituted ring which optionally contains further heteroatoms, x is an integer of 1 or 2, and y is 0 or an integer of 1;

and $R^{85}$ is a group $NR^{86}R^{78}$, wherein $R^{86}$ and $R^{87}$ are independently alkyl, with a compound of formula (VIII)

$$H_2N—R^{5'} \quad \text{(VIII)}$$

where $R^{5'}$ an optionally substituted 5-membered heteroaromatic ring, selected from a compound of formula (a) or (b)

(a)

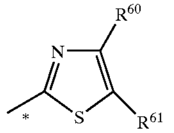

(b)

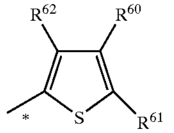

wherein where any one of $R^{60}$, $R^{61}$ and $R^{62}$ is selected from hydrogen or a substituent group, or a precursor thereof, and * indicates the point of attachment to X, and the other two are each independently hydrogen or $C_{1-3}$alkyl; and (ii) thereafter optionally converting a precursor group $R^{5'}$ to group $R^5$ and/or modifying substituents on the group $R^5$.

10. A pharmaceutical composition comprising a compound of claim 1, or a pharmaceutically acceptable salt, or an in vivo hydrolysable ester thereof.

11. A pharmaceutical composition of claim 10, further comprising a pharmaceutically acceptable carrier.

12. A method for treating colorectal or breast cancer where aurora 2 kinase is upregulated in a warm blooded animal, comprising administering a therapeutically effective amount of a compound of claim 1, or a pharmaceutically acceptable salt, or an in vivo hydrolysable ester thereof.

* * * * *